(12) United States Patent
Zhang et al.

(10) Patent No.: US 12,115,158 B2
(45) Date of Patent: Oct. 15, 2024

(54) SURVIVIN-TARGETING ANTI-TUMOR AGENTS AND USES THEREOF

(71) Applicant: Indiana University Research and Technology Corporation, Indianapolis, IN (US)

(72) Inventors: Jian-Ting Zhang, Carmel, IN (US); Jing-Yuan Liu, Indianapolis, IN (US); Mingji Dai, West Lafayette, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 370 days.

(21) Appl. No.: 17/195,166

(22) Filed: Mar. 8, 2021

(65) Prior Publication Data

US 2021/0299123 A1 Sep. 30, 2021

Related U.S. Application Data

(60) Provisional application No. 62/985,965, filed on Mar. 6, 2020.

(51) Int. Cl.
*A61K 31/4985* (2006.01)
*A61K 31/498* (2006.01)
*A61P 35/00* (2006.01)

(52) U.S. Cl.
CPC ........ *A61K 31/4985* (2013.01); *A61K 31/498* (2013.01); *A61P 35/00* (2018.01)

(58) Field of Classification Search
CPC .... A61K 31/4985; A61K 31/498; A61P 35/00
See application file for complete search history.

(56) References Cited

U.S. PATENT DOCUMENTS

| 10,517,871 B2 * | 12/2019 | Zhang | A61K 31/4985 |
| 2016/0106743 A1 * | 4/2016 | Goldfarb | A61K 45/06 |
| | | | 514/250 |
| 2018/0134729 A1 * | 5/2018 | Ji | C07D 498/14 |
| 2018/0296557 A1 * | 10/2018 | Zhang | A61P 35/02 |
| 2020/0222398 A1 * | 7/2020 | Zhang | A61P 35/02 |

OTHER PUBLICATIONS

Catrow; J. Med. Chem. 2015, 58, 4678-4692. http://dx.doi.org/10.1021/acs.jmedchem.5b00223 (Year: 2015).*
Li; J Exp Clin Cancer Res 2019, 38, 368. https://doi.org/10.1186/s13046-019-1362-1 (Year: 2019).*
Qi; Cancer Res 2016, 76, 453-462. https://doi.org/10.1158/0008-5472.CAN-15-1874 (Year: 2016).*
Peery; Drug Discovery Today 2017, 22, 1466-1477. https://doi.org/10.1016/j.drudis.2017.05.009 (Year: 2017).*
Schepetkin; European Journal of Medicinal Chemistry 2019, 161, 179-191. https://doi.org/10.1016/j.ejmech.2018.10.023 (Year: 2019).*
Xu; Biomedicine & Pharmacotherapy 2020, 121, 109679. https://doi.org/10.1016/j.biopha.2019.109679 (Year: 2020).*

* cited by examiner

*Primary Examiner* — Daniel R Carcanague
(74) *Attorney, Agent, or Firm* — Faegre Drinker Biddle & Reath LLP

(57) ABSTRACT

Methods for treating various cancers by administering one or more compounds that target the dimeric protein survivin are disclosed. Pharmaceutical compositions containing such compounds are also disclosed, along with general methods of identifying anti-cancer compounds that target oncogenic dimeric proteins. Exemplary compounds that can be used in the disclosed methods of treatment and pharmaceutical compositions have the chemical structures disclosed in the specification.

6 Claims, 145 Drawing Sheets

$^1$H NMR (500 MHz, CDCl$_3$)

7I

<sup>13</sup>C NMR (125 MHz, DMSO-*d₆*)

| Ratio ($IC_{50}$:$IC_{50}$) | CI (C4-2) | CI (PC-3) |
|---|---|---|
| 1 to 1 | 0.041 | 0.051 |
| 3 Doc:1 LQZ-7F-1 | 0.026 | 0.025 |
| 1 Doc:3 LQZ-7F-1 | 0.0273 | 0.034 |

FIG. 27F

SURVIVIN-TARGETING ANTI-TUMOR AGENTS AND USES THEREOF

PRIORITY CLAIM

This application claims the benefit of U.S. Provisional Patent Application No. 62/985,965, which was filed on Mar. 6, 2020, this provisional application in incorporated by reference in its entirety into this application.

GOVERNMENT SUPPORT CLAUSE

This invention was made with government support under GM127656 awarded by the National Institutes of Health and W81XWH-14-1-0489 awarded by the Department of Defense. The government has certain rights in the invention.

BACKGROUND AND SUMMARY OF THE APPLICATION

Survivin (BIRC5), a homodimeric protein of 16.5-kDa, is a member of the Inhibitor of Apoptosis Protein (IAP) family with a single BIR domain, a zinc-finger fold, and an extended C-terminal helical coiled coil. Ectopic overexpression of survivin inhibits both the intrinsic and extrinsic apoptosis pathways in cell lines and animal models and has been suggested to contribute to treatment resistance (Ref). Interestingly, survivin is expressed at undetectable or low levels in normal adult tissues while it has been shown to be overexpressed in almost all solid tumors. Thus, survivin has become a significant and attractive target not only due to its aberrant expression but also its dual roles in inhibition of apoptotic pathway and cell cycle progression as a member of the Chromosomal Passenger Complex.

However, survivin has been considered 'undruggable' due to lack of known enzymatic activities and the majority of drug discovery studies targeting survivin have avoided targeting the protein directly. Recently using a combination of computational analysis and in silico screening, we have identified the first direct small molecule inhibitor of survivin targeting the residues of Leu$^{98}$ and Phe$^{101}$ in the dimerization interface of survivin to inhibit survivin dimerization. The initial hit inhibitor, LQZ-7, upon binding to the survivin dimeric interface, causes exposure of the hydrophobic dimerization core and lead to protein misfolding and subsequent proteasomal degradation.

In the current study, we further investigated the scaffold of LQZ-7 and synthesized five novel analogues with a goal to improve its property. Of these 5 analogues, one compound (LQZ-7I) showed significantly improved activity. LQZ-7I is soluble in corn oil and inhibited survivin dimerization, leading to survivin degradation, and suppressed prostate cancer cell survival and growth of xenograft tumors by causing apoptosis. Thus, LQZ-7I may be developed as a potential therapeutic to overcome docetaxel resistance in prostate cancers by targeting survivin.

Embodiments of the invention include a method of treating cancer by administering to a subject in need thereof a therapeutically effective amount of a composition comprising a survivin-targeting compound and a pharmaceutically acceptable salt thereof; whereby the cancer is treated in the subject. The composition may be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery. The cancer that is treated may be breast cancer, colon cancer, lung cancer, pancreatic cancer, prostate cancer, ovarian cancer, and leukemia.

Other embodiments of the invention include a pharmaceutical composition with (a) a survivin-targeting compound and a pharmaceutically acceptable salt thereof; and (b) a pharmaceutically acceptable carrier.

Further embodiments include a survivin-targeting compound for use in treating cancer in a subject. The survivin-targeting compound may be a pharmaceutically acceptable salt thereof. The compound may be for use in treating cancer such as breast cancer, colon cancer, lung cancer, pancreatic cancer, prostate cancer, ovarian cancer, and leukemia. The survivin-targeting compound may be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

Yet other embodiments related to a survivin-targeting compound or a pharmaceutically acceptable salt thereof for use in manufacturing a medicament for treating cancer in a subject The medicament may be for treating breast cancer, colon cancer, lung cancer, pancreatic cancer, prostate cancer, ovarian cancer, or leukemia. The medicament may be designed to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

This invention is not limited to the particular methodology, protocols, cell lines and reagents described, as these may vary. The terminology used herein is only for the purpose of describing particular embodiments and is not intended to limit the scope of the present invention, which will be limited only by the appended claims.

According to an exemplary embodiment of the present disclosure, a method of treating cancer comprises administering to a subject in need thereof, a therapeutically effective amount of a composition comprising a survinin-targeting compound of the following formula

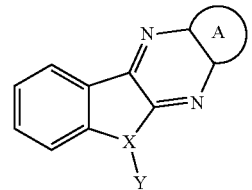

wherein A is selected from the group consisting of isoxazole, 1,2,3 oxadiazole, 1,2,5 oxadiazole, and phenyl, and A may be substituted or unsubstituted; X is carbon or nitrogen, Y comprises at least one of a hydrogen, an amine, a ketone, an alcohol, an unsubstituted alkane, and a substituted alkane, wherein the substituent on the substituted alkane comprises at least one of an ether, an alcohol, a ketone, a carboxylic acid, a tetrazole, a 1,2,5 oxadiazole, a carboxamide, an azo, an oxime, a sulfonyl, an aldoxime, an aminofurazan, an amine, and a nitro group; and a pharmaceutically acceptable salt thereof.

In a variation thereof the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery. In a further variation thereof, the subject in need thereof is selected from the group consisting subjects with at least one of the following diseases: breast cancer, colon cancer, lung cancer, pancreatic cancer, prostate cancer, ovarian cancer, and leukemia. In a still further variation thereof, the subject in need thereof has prostate cancer. In a further variation thereof, the method further comprises administering to a subject in need thereof a pharmaceutically acceptable carrier.

In yet another variation thereof, the survivin-targeting compound comprises a compound selected from the group consisting of: compounds of the following formulas

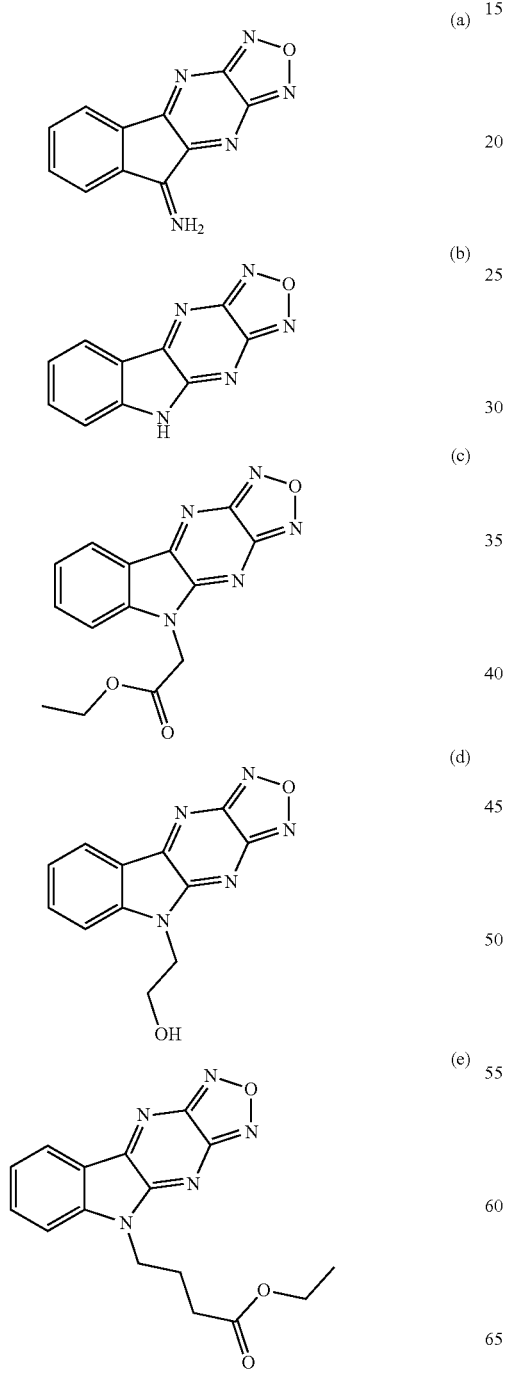

-continued

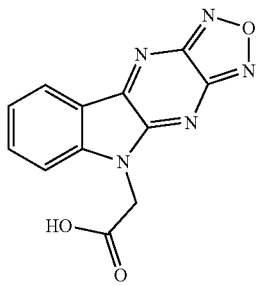

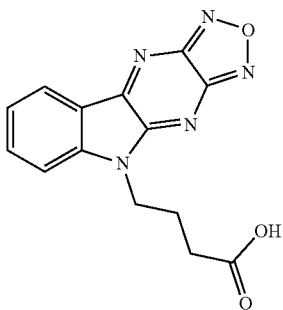

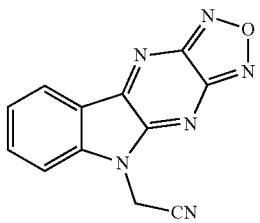

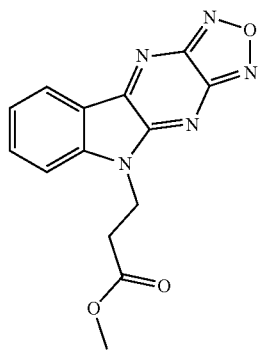

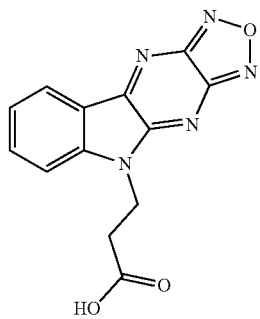

(k)
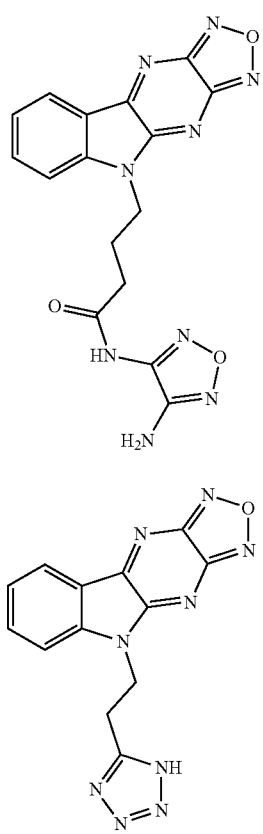
(l)
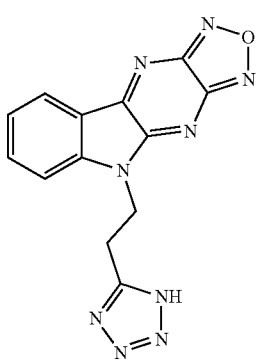
(m)
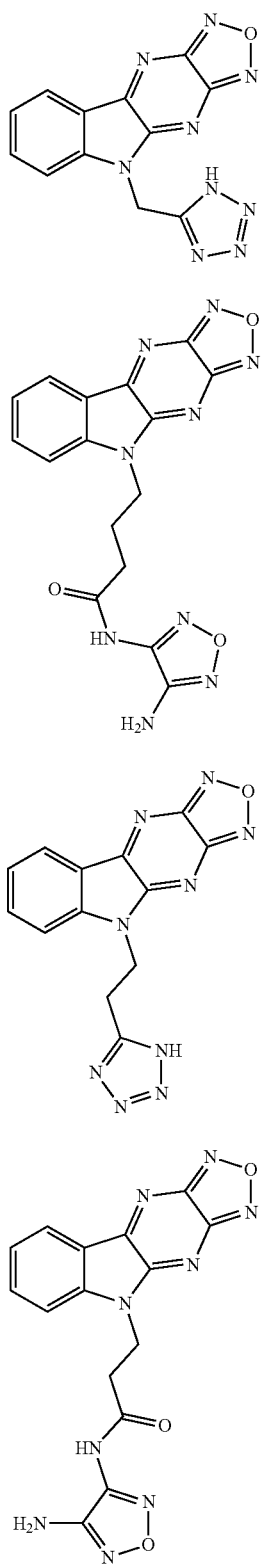
(n)
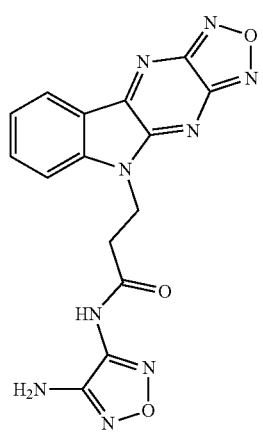
In another variation thereof, wherein the survivin-targeting compound comprises a compound selected from the group consisting of: compounds of the following formulas
(a)
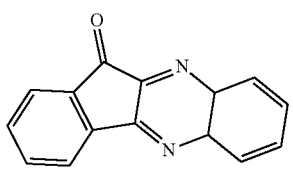
(b)
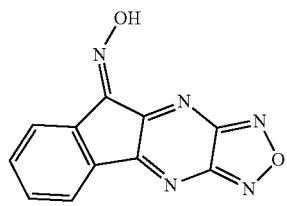
(c)
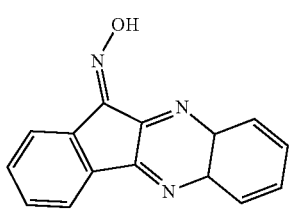
(d)
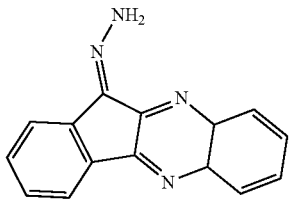
(e)
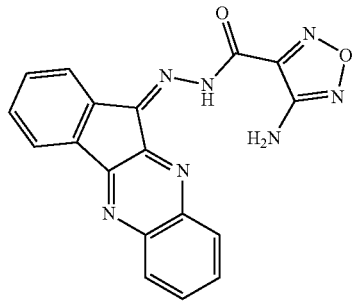
(f)
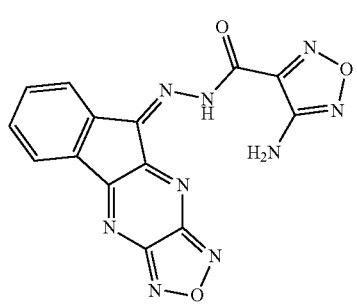
(g)
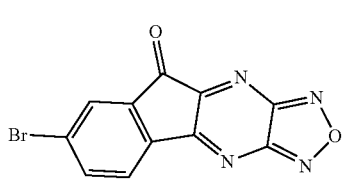

(h)

(i)

(j)

(k)

(l)

(m)

(n)

(o)

(p)

(q)

(r)
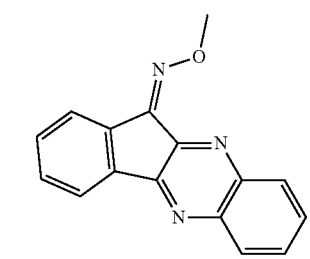
(s)
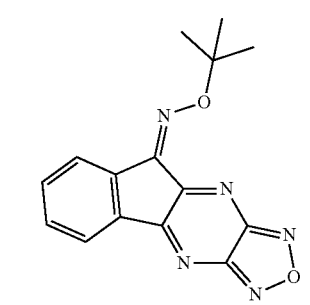
(t)
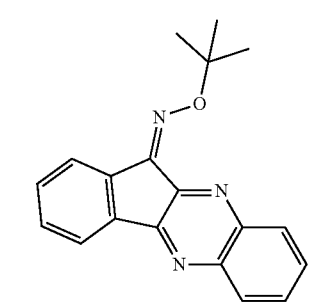
(u)
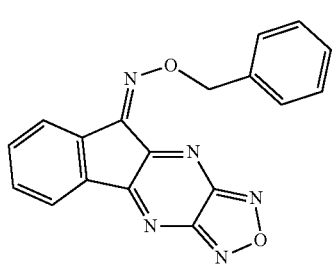
(v)
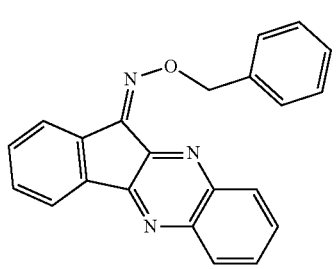
(w)
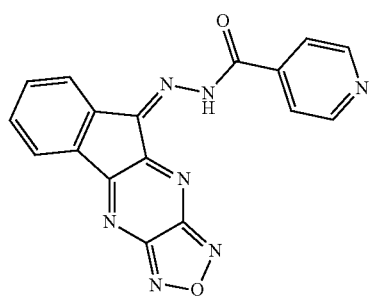
(x)
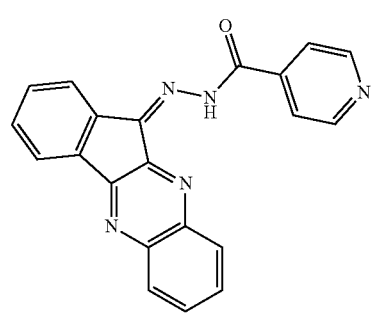
(y)
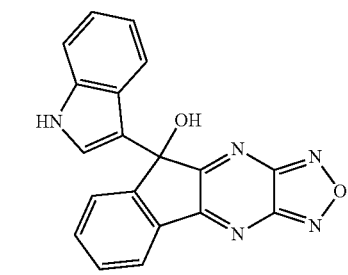
(z)
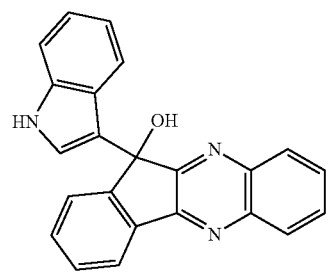
(a1)

-continued

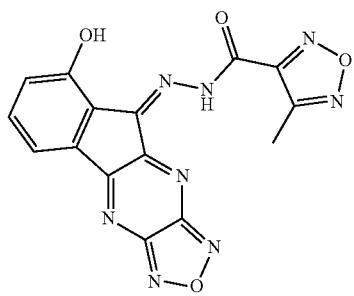

(b1)

According to another exemplary embodiment of the present disclosure, a survivin-targeting compound is provided for use in treating cancer in a subject, wherein the survivin-targeting compound is the compound of the following formula

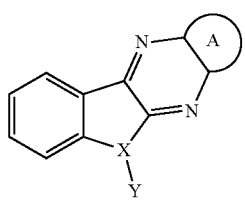

wherein A is selected from the group consisting of isoxazole, 1,2,3 oxadiazole, 1,2,5 oxadiazole, and phenyl, and A may be substituted or unsubstituted;

X is carbon or nitrogen

Y comprises at least one of a hydrogen, an amine, a ketone, an alcohol, an unsubstituted alkane, and a substituted alkane, wherein the substituent on the substituted alkane comprises at least one of an ether, an alcohol, a ketone, a carboxylic acid, a tetrazole, a 1,2,5 oxadiazole, a carboxamide, an azo, an oxime, a sulfonyl, an aldoxime, an aminofurazan, an amine, and a nitro group; and a pharmaceutically acceptable salt thereof.

In a variation thereof, the compound is for use in treating cancer that is selected from the group consisting of breast cancer, colon cancer, lung cancer, pancreatic cancer, prostate cancer, ovarian cancer, and leukemia. In another variation thereof, the compound is for use in treating prostate cancer. In a further variation thereof, the compound is to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery. In another variation thereof, the survivin-targeting compound comprises a compound selected from the group consisting of: compounds of the following formulas

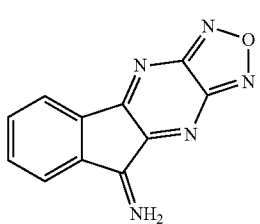

(a)

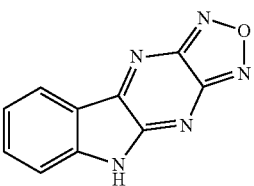

(b)

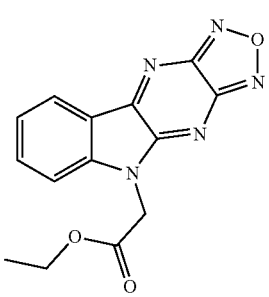

(c)

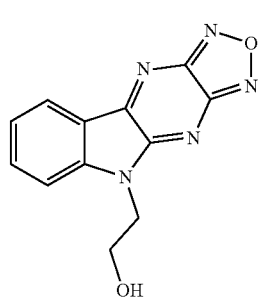

(d)

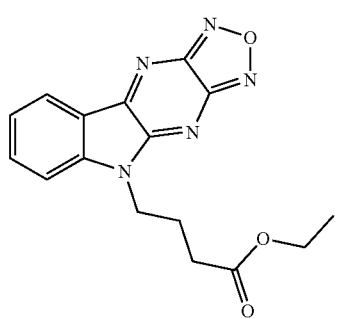

(e)

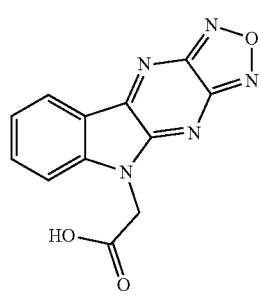

(f)

(g)
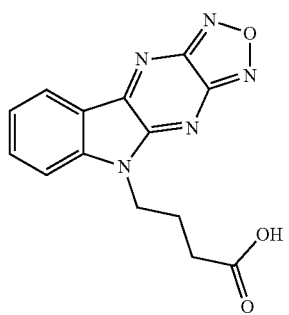
(h)
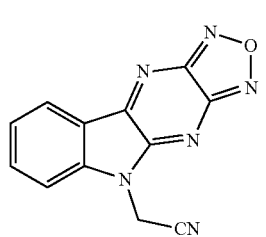
(i)
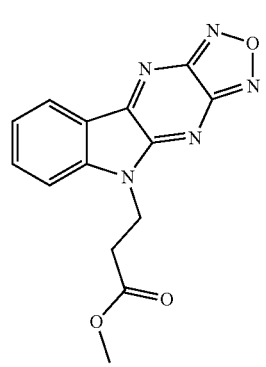
(j)
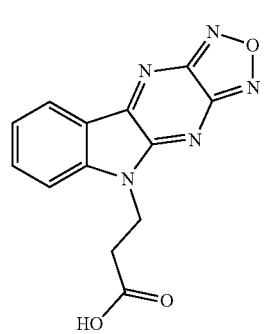
(k)
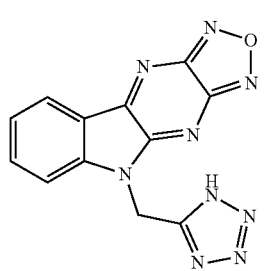
(l)
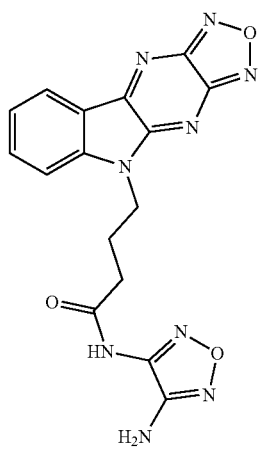
(m)
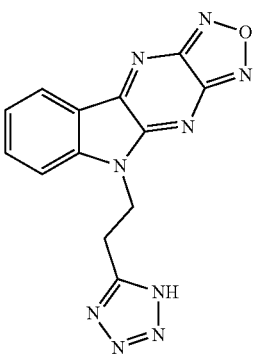
(n)
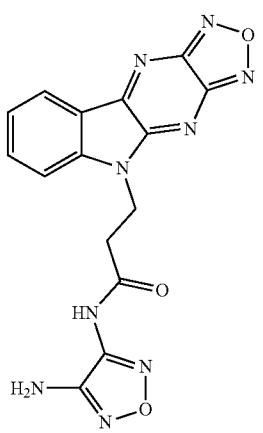
In yet another variation thereof, the survivin-targeting compound comprises a compound selected from the group consisting of: compounds of the following formulas
(a)
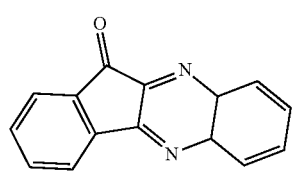

-continued
(b)
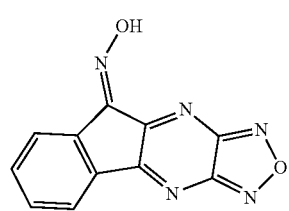
(d)
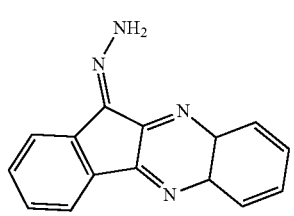
(e)
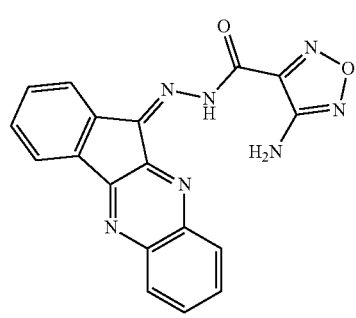
(g)
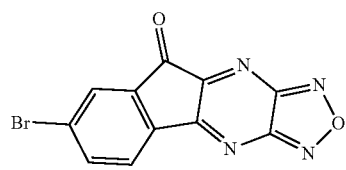
(h)
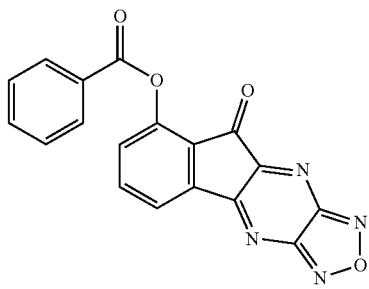
(i)
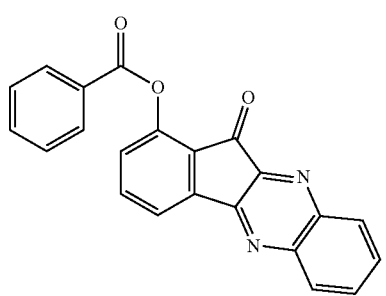
-continued
(j)
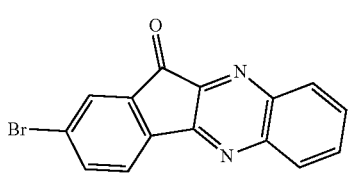
(k)
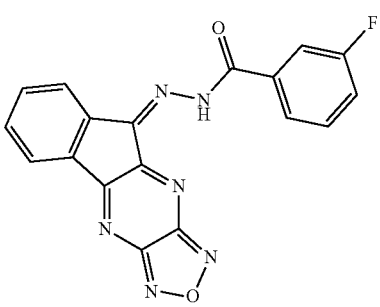
(l)
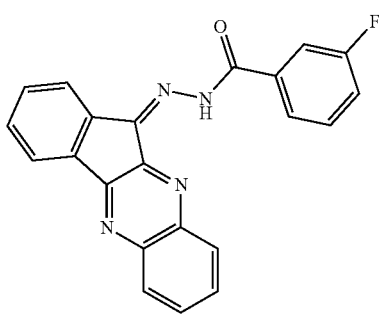
(m)
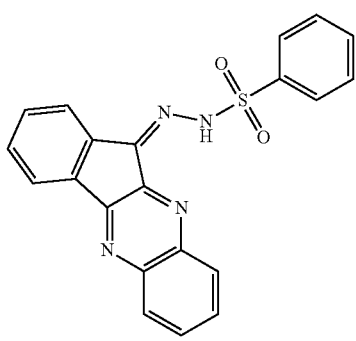
(n)
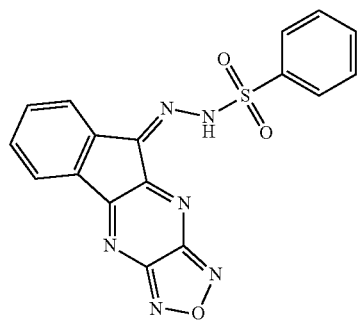

(o)
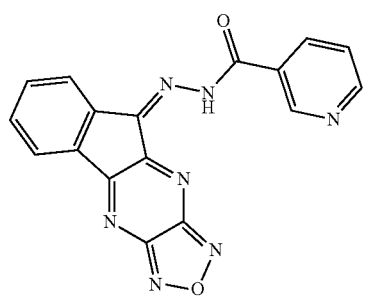
(p)
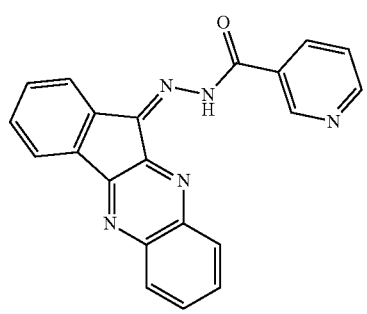
(q)
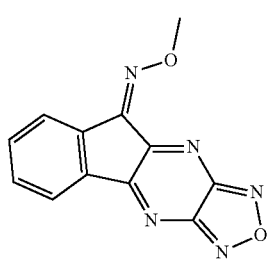
(r)
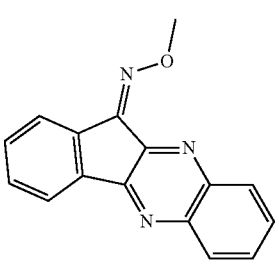
(s)
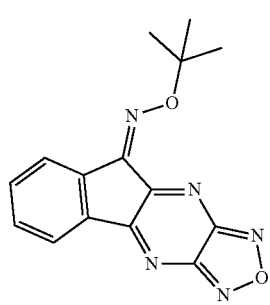
(t)
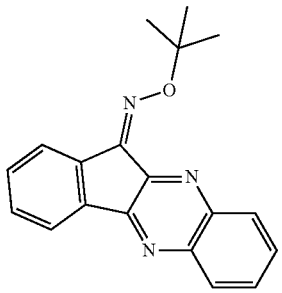
(u)
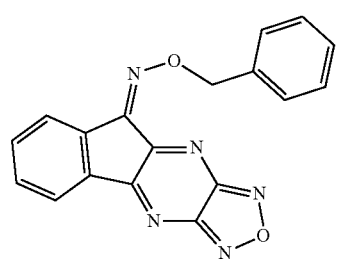
(v)
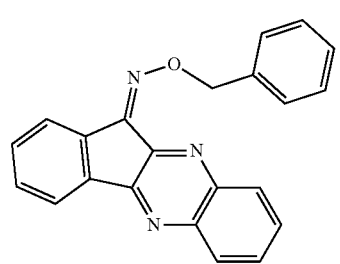
(w)
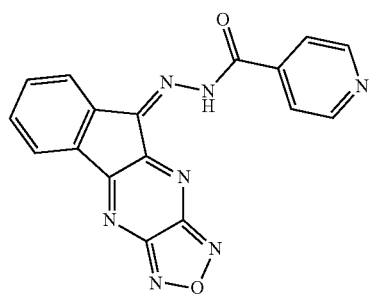
(x)
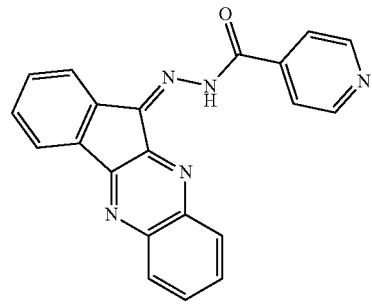

(y)

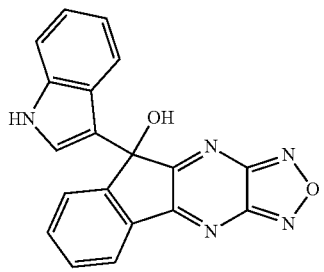

(z)

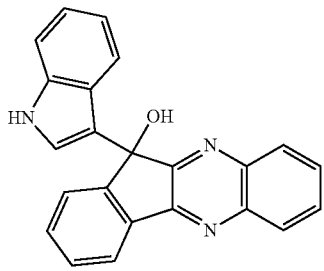

(a1)

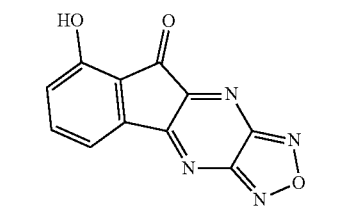

(b1)

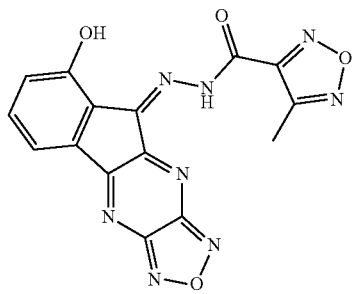

According to yet another embodiment of the present disclosure, a method of treating cancer comprises administering to a subject in need thereof, a therapeutically effective amount of a composition comprising a survivin-targeting compound of the following formula

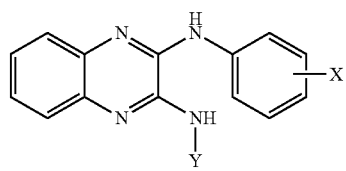

wherein X comprises at least one of a hydrogen, a halogen, a straight alkane, and a branched alkane, Y comprises at least one of a ketone, a phenyl, and a group of the following formula:

$$\left[\begin{array}{c}\text{O}\\\text{\raisebox{0pt}[0pt][0pt]{}}\end{array}\right]$$

wherein Y is substituted or unsubstituted, and the substituents comprise at least one of a halogen, a straight alkane, and a branched alkane.

In a variation thereof, the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery. In another variation thereof, the subject in need thereof is selected from the group consisting subjects with at least one of the following diseases: breast cancer, colon cancer, lung cancer, pancreatic cancer, prostate cancer, ovarian cancer, and leukemia. In still another variation thereof, the a survivin-targeting compound comprises a compound selected from the group consisting of: compounds of the following formulas (a)

(a)

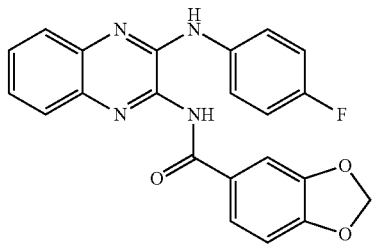

(b)

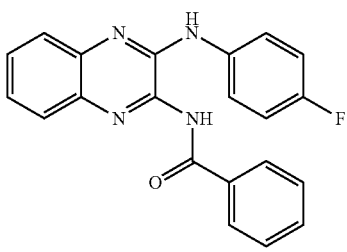

(c)

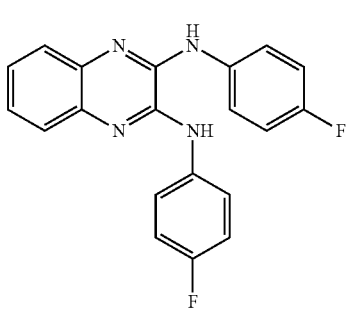

According to still another embodiment of the present disclosure, a survivin-targeting compound is provided for use in treating cancer in a subject, wherein the survivin-targeting compound is the compound of the following formula wherein X comprises at least one of a hydrogen, a halogen, a straight alkane, and a branched alkane, Y comprises at least one of a ketone, a phenyl, and a group of the following formula:

wherein Y is substituted or unsubstituted, and the substituents comprise at least one of a halogen, a straight alkane, and a branched alkane.

In a variation thereof, the a survivin-targeting compound comprises a compound selected from the group consisting of: compounds of the following formulas In another variation thereof, the compound is for use in treating cancer that is selected from the group consisting of breast cancer, colon cancer, lung cancer, pancreatic cancer, prostate cancer, ovarian cancer, and leukemia.

BRIEF DESCRIPTION OF THE FIGURES

FIGS. 27A-27F show LQZ-7F-1 synergizes with docetaxel in vitro. Methylene response curves in combination treatments of docetaxel and LQZ-7F-1 in (A) 1:1 ratio, (B) 3 Doc:1 LQZ-7F-1 ratio, (C) 1 Doc:3 LQZ-7F-1 ratio. Each data point was performed in triplicate. (D) PC-3 and (E) C4-2 cells Isobologram analysis demonstrating strong synergism between docetaxel and LQZ-7F-1 in. Each point represents the average of three independent experiments. (F) Summarized combination index (CI) value for both cell lines with different ratios tested.

DESCRIPTION

Figure 1:
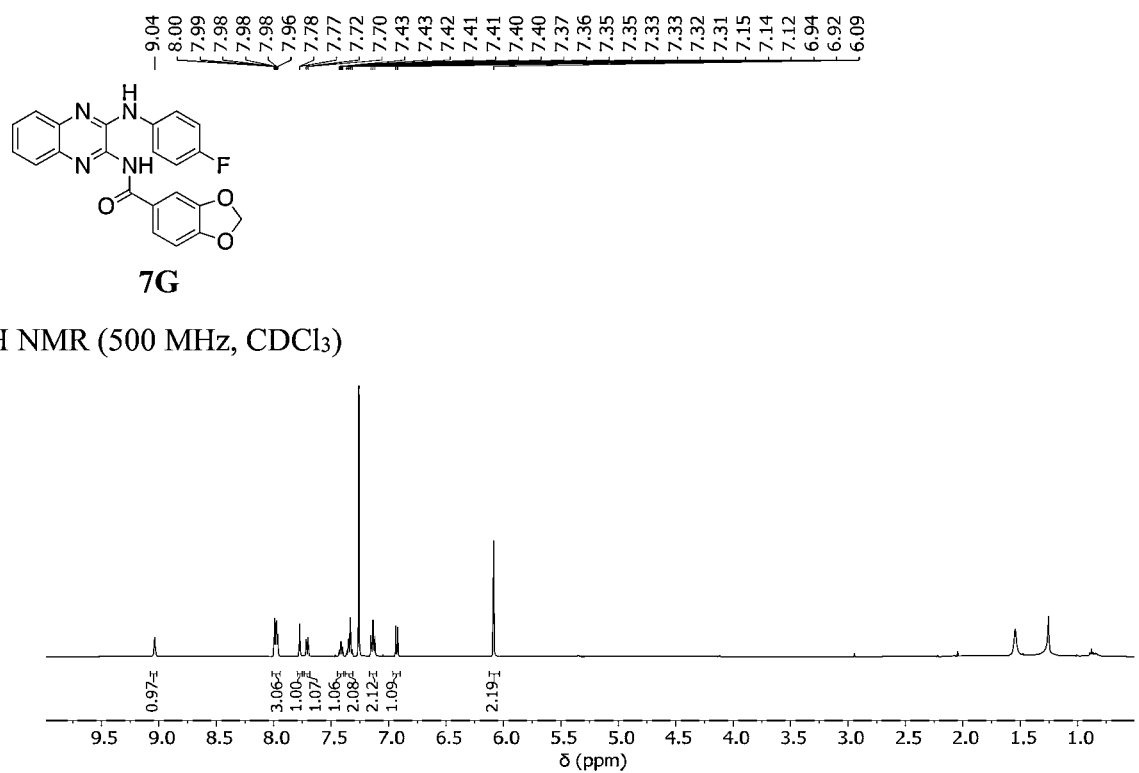
FIG. 1 shows the $^1$H or $^{13}$C NMR spectrum of the indicated compound.
Figure 2:
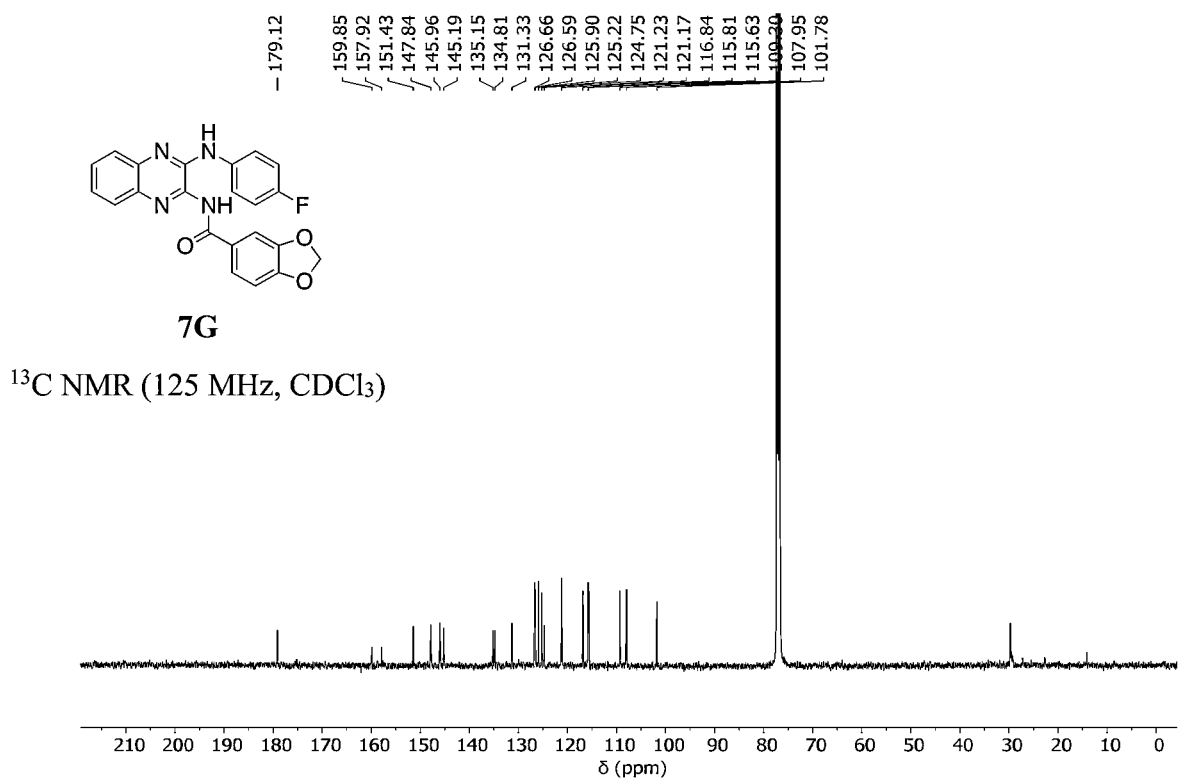
FIG. 2 shows the $^1$H or $^{13}$C NMR spectrum of the indicated compound.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. The invention encompasses the use of any optically-active, racemic, polymorphic, or stereroisomeric form, or mixtures thereof, which form possesses properties useful in the treatment of tumor-related conditions described and claimed herein.

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, such as, sodium hydroxide. Also, esters of the phenolic compounds can be made with aliphatic and aromatic carboxylic acids, such as for example, acetic acid and benzoic acid esters. As used herein, the term "pharmaceutically acceptable salt" refers to a compound formulated from a base compound that achieves substantially the same pharmaceutical effect as the base compound.

In addition, this invention further includes methods utilizing hydrates of the anti-tumor compounds. The term "hydrate" includes but is not limited to hemihydrates, monohydrates, dihydrates, trihydrates and the like.

The term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

The term "administering" refers to bringing a patient, tissue, organ or cells in contact with one or more compounds that exhibit an anti-tumor activity. As used herein, administration can be accomplished in vitro, i.e., in a test tube, or in vivo, i.e., in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor compound; or (2) is susceptible to a disorder that is preventable by administering the anti-tumor compound.

"Pharmaceutical composition" means therapeutically effective amounts of the anti-tumor compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. The optimum effective amounts can be readily determined by one of ordinary skill in the art using routine experimentation.

Pharmaceutical compositions are liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms, protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitoneally, intraventricularly, intracranially and intratumorally.

"Pharmaceutically acceptable carriers" are well known to those skilled in the art and include, but are not limited to, 0.01-0.1M and preferably a 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used. In yet another embodiment, a controlled release system can be placed in proximity to the therapeutic target, i.e., the skin, thus requiring only a fraction of the systemic dose. Other controlled release systems are understood by those skilled in the art.

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a subject by, for example, subcutaneous implantation of a pellet. In a further embodiment, a pellet provides for controlled release of anti-tumor compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating or tablet-forming processes. For oral administration, the anti-tumor compounds or their physiologically tolerated derivatives such as salts, esters, N-oxides and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin; with disintegrating agents such as cornstarch, potato starch, alginic acid; or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the anti-tumor compounds or their physiologically tolerated derivatives such as salts, esters, N-oxides and the like are converted into a solution, suspension, or expulsion, if desired, with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, such as for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides and the like are prepared and applied as solutions, suspensions, or emulsions in a physiologically acceptable diluent with or without a pharmaceutical carrier.

In another method according to the invention, the active compound can be delivered in a vesicle, in particular a liposome.

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as, for example, hydrochloric acid, sulfuric acid, methanesulphonic acid, fumaric acid, maleic acid, succinic acid, acetic acid, benzoic acid, oxalic acid, citric acid, tartaric acid, carbonic acid or phosphoric acid.

In sum, the present invention provides numerous methods and pharmaceutical compositions for the treatment, inhibition, recurrence and occurrence of cancer or cancer related conditions, including without limitation leukemia, prostate cancer, breast cancer, colon cancer, lung cancer, pancreatic cancer or ovarian cancer.

General Chemistry: All chemical reactions were performed using standard syringe techniques under argon. Starting materials and reagents were used as received from commercial suppliers. Acetonitrile ($CH_3CN$), methanol (MeOH), and toluene were purified by passing the previously degassed solvents through activated alumina columns. Dichloromethane ($CH_2Cl_2$) and tetrahydrofuran (THF) were distilled prior to use.

All compounds were purified using flash chromatography with silica gel (230-400 mesh). Thin layer chromatography (TLC) was performed using glass-backed silica plates (Silicycle). NMR spectra were recorded on a Bruker ARX-400 spectrometer or AV-500 spectrometer at room temperature. Chemical shifts $\delta$ (in ppm) are given in reference to the solvent signal. $^1H$ NMR data are reported as follows: chemical shifts ($\delta$ ppm), multiplicity (s=singlet, d=doublet, t=triplet, q=quartet, quin=quintuplet, m=multiplet, br=broad), coupling constant (Hz), and integration. $^{13}C$ NMR data are reported in terms of chemical shift and multiplicity. IR data were recorded on a Thermo Nicolet Nexus 470 FTIR. Electrospray ionization mass spectrometry data for compound characterization were determined using an Advion Expression CMS instrument.

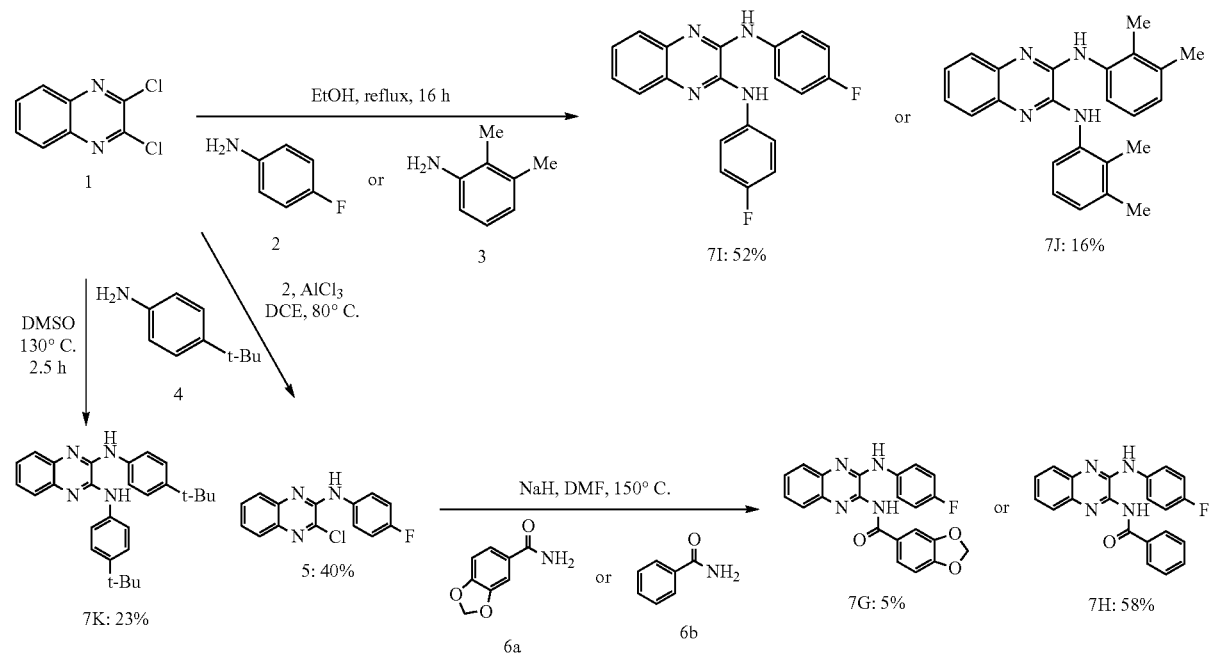

General procedure for the synthesis of quinoxaline amine (5). To a flame-dried round-bottom flask charged with a stir bar, commercially available 2,3-dichloroquinoxaline (1) (170 mg, 0.85 mmol, 1.0 equiv), 4-fluoroaniline (2) (0.081 mL, 0.85 mmol, 1.0 equiv.), $AlCl_3$ (125.3 mg, 0.94 mmol, 1.1 equiv), and DCE (4.25 mL, 0.2M) were added sequentially. The reaction mixture was then stirred at 80° C. for 16 hours. After this period, the reaction was cooled to room temperature and quenched with ice-cold water (10 mL) while stirring. Stirring was continued for an additional 10 minutes. The reaction was then extracted with EtOAc (3×), and the combined organic layers washed with ice-cold water 2×. The organics were then dried over $MgSO_4$, filtered, and concentrated under reduced pressure. The crude product was purified by column chromatography using Hexanes-EtOAc (49:1 to 20:1) to give the pure product as a yellow solid. Yield: 92.2 mg, 40%. All spectroscopic data matched that previously reported in the literature.

General procedure for the synthesis of quinoxaline amine carboxamides 7G and 7H from intermediate 5. To a suspension of NaH (60% in mineral oil, 14.4 mg, 0.36 mmol, 2.0 equiv) in 0.8 mL of DMF was added the desired benzamide (0.36 mmol, 2.0 equiv) The reaction mixture was stirred at room temperature for 1 hour. After the suspension turned lightly yellow, 3-chloro-N-(4-fluorophenyl)quinoxalin-2-amine (5) (50 mg, 0.18 mmol, 1.0 equiv.) in DMF (0.2 mL) was added slowly and the solution turned dark red instantly. The reaction mixture was then stirred at 150° C. for 4 hours, and then cooled to room temperature before it was quenched with ice-cold water (3 mL). The reaction mixture was then extracted with EtOAc (3×) and the combined organic layers were dried over anhydrous MgSO$_4$, and concentrated under reduced pressure. The crude product was then purified by column chromatography to give a bright yellow solid.

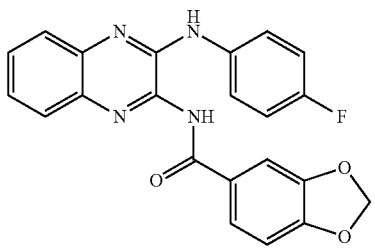

7G

N-(3-((4-fluorophenyl)amino)quinoxalin-2-yl)benzo[d][1,3]dioxole-5-carboxamide (7G). Analog 7G was synthesized from corresponding intermediate (5) (Yellow solid, 5% yield). $^1$H NMR (500 MHz, CDCl$_3$): δ=9.04 (s, 1H), 8.01-7.94 (m, 3H), 7.77 (d, J=1.6 Hz, 1H), 7.71 (d, J=8.0 Hz, 1H), 7.42 (ddd, J=8.3, 6.6, 2.1 Hz, 1H), 7.38-7.31 (m, 2H), 7.14 (t, J=8.7 Hz, 2H), 6.93 (d, J=8.2 Hz, 1H), 6.09 (s, 2H); $^{13}$C NMR: (125 MHz, CDCl$_3$): δ=179.12, 159.85, 157.92, 151.43, 147.84, 145.96, 145.19, 135.15, 134.81, 131.33, 126.66, 126.59, 125.90, 125.22, 124.75, 121.23, 116.84, 115.81, 115.63, 109.30, 107.95, 101.78; IR (neat, cm$^{-1}$): v=3319, 2921, 1593, 1546, 1506, 1483, 1437, 1382, 1356, 1292, 1255, 1209, 1192, 1156, 1104, 1038, 926, 832, 808. MS (ESI): m/z 403.1 found for $C_{22}H_{16}FN_4O_3$ [M+H]$^+$.

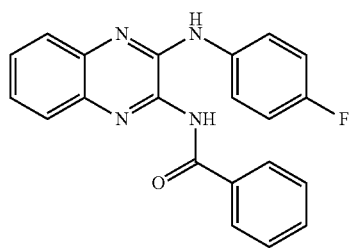

7H

N-(3-((4-fluorophenyl)amino)quinoxalin-2-yl)benzamide (7H). Analog 7H was synthesized from corresponding intermediate (5) (Yellow solid, 58% yield). $^1$H NMR (500 MHz, CDCl$_3$): δ=9.06 (s, 1H), 8.30 (d, J=7.5 Hz, 2H), 7.98-7.89 (m, 2H), 7.98-7.89 (m, 1H), 7.61-7.55 (m, 1H), 7.51 (t, J=7.5 Hz, 2H), 7.43-7.37 (m, 1H), 7.35-7.27 (m, 1H), 7.11 (t, J=8.5 Hz, 2H); $^{13}$C NMR: (125 MHz, CDCl$_3$): δ=180.15, 159.91, 157.98, 146.00, 145.41, 136.90, 135.37, 134.95, 132.64, 129.44, 128.48 (2C), 126.80, 126.76, 126.00, 124.72, 121.20, 121.14, 117.01, 115.89, 115.71. IR (neat, cm$^{-1}$): v=3316, 3066, 1592, 1551, 1506, 1483, 1448, 1413, 1385, 1356, 1314, 1291, 1210, 1156, 1124, 1100, 1068, 1024, 921, 864, 831. MS (ESI): m/z 359.2 found for $C_{21}H_{16}FN_4O$ [M+H]$^+$.

General procedures for the synthesis of quinoxaline-2,3-diamines 7I and 7J. To a flame dried round bottomed flask, commercially available 2,3-dichloroquinoxaline (1) (200 mg, 1.0 mmol, 1.0 equiv.), substituted anilines (2 or 3) (2.2 mmol, 2.2 equiv.), and ethanol (5.0 mL, 0.2M) are added sequentially. The reaction mixture is then refluxed for 16 hours. After reaching room temperature, the solvent was slowly removed under reduced pressure. The resulting solid is dissolved in EtOAc (10 mL), washed with water and brine, dried over anhydrous MgSO$_4$ and concentrated under reduced pressure to give the crude product. The crude product was then purified by column chromatography.

General procedures for the synthesis of quinoxaline-2,3-diamine 7K. A mixture of 2,3-dichloroquinoxaline (1) (50 mg, 0.25 mmol, 1.0 equiv.), 4-tert-Butylaniline (4) (1.25 mmol, 5.0 equiv.) and DMSO (2.5 mL, 0.1M) in a flame dried round-bottomed flask was heated at 130° C. for 2.5 hours. After this period, the reaction mixture is cooled to room temperature and diluted with EtOAc (2.5 mL) and poured into ice-water (10 mL). The organic phase is then washed with ice-cold water 2× and dried over MgSO$_4$, and concentrated under reduced pressure. The crude product was then purified by column chromatography using Hexanes:EtOAc (20:1) to give the pure product.

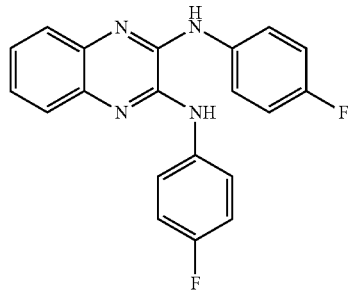

7I

N$^2$,N$^3$-bis(4-fluorophenyl)quinoxaline-2,3-diamine (7I). Analog 7I was synthesized using method A from commercially available (1) and 4-Fluoroaniline (2). Column chromatography was performed using a Hexanes:EtOAc (20:1 to 3:1) mixture to give the pure product. (Yellow solid, 52% yield). $^1$H NMR (500 MHz, DMSO-d$_6$): δ=9.06 (s, 2H), 7.95-7.75 (m, 4H), 7.53 (dd, J=6.1, 3.5 Hz, 2H), 7.33 (dd, J=6.1, 3.4 Hz, 2H), 7.24 (t, J=8.9 Hz, 4H). $^{13}$C NMR (125 MHz, DMSO-d$_6$): δ=158.74 (2C), 156.84 (2C), 141.19, 141.16, 136.49, 136.13, 125.34, 125.15, 125.11, 122.37, 122.31, 115.29 (2C), 115.26 (2C), 115.11, 115.09 (2C). IR (neat, cm$^{-1}$): v=3386, 2925, 1644, 1616, 1574, 1537, 1501, 1449, 1410, 1328, 1301, 1212, 1155, 1118, 1098, 1012, 923, 830. MS (ESI): m/z 349.2 found for $C_{20}H_{15}F_2N_4$ [M+H]$^+$.

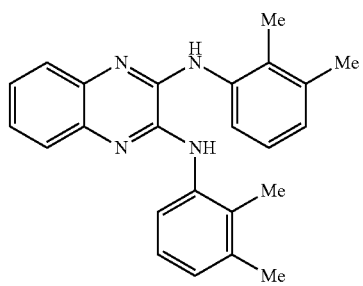

7J

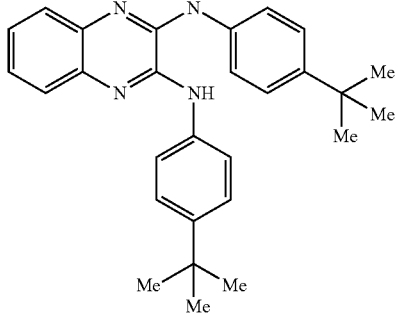

7K

N²,N³-bis(2,3-dimethylphenyl)quinoxaline-2,3-diamine (7J). Analog 7J was synthesized using method A from commercially available (1) and 2,3-Dimethylaniline (3). Column chromatography was performed using a Hexanes:EtOAc (49:1 to 20:1) mixture to give the pure product. (Light brown solid, 16% yield). ¹H NMR (500 MHz, DMSO-$d_6$): δ=8.52 (s, 2H), 7.38-7.23 (m, 4H), 7.22-7.12 (m, 4H), 7.09 (d, J=7.6 Hz, 2H), 2.32 (s, 6H), 2.11 (s, 6H). ¹³C NMR (125 MHz, DMSO-$d_6$): δ 142.59 (2C), 137.72 (2C), 137.15 (2C), 136.62 (2C), 132.27 (2C), 126.88 (2C), 125.47 (2C), 125.05 (2C), 124.30 (2C), 124.16 (2C), 20.29 (2C), 14.56 (2C). IR (neat, cm⁻¹): ν=3312, 2916, 1640, 1614, 1567, 1541, 1463, 1381, 1351, 1324, 1258, 1215, 1181, 1119, 1089, 1060, 990, 927, 896, 779. MS (ESI): m/z 369.2 found for $C_{24}H_{25}N_4$ [M+H]⁺.

N²,N³-bis(4-(tert-butyl)phenyl)quinoxaline-2,3-diamine (7K). Analog 7K was synthesized using method B from commercially available (1) and 4-tert-Butylaniline (4). Column chromatography was performed using a Hexanes:EtOAc (20:1) mixture to give the pure product. (Light brown oil, 23% yield). ¹H NMR (500 MHz, DMSO-$d_6$): δ=8.97 (s, 2H), 7.82 (d, J=8.7 Hz, 4H), 7.52 (dd, J=6.1, 3.4 Hz, 2H), 7.42 (d, J=8.7 Hz, 4H), 7.32 (dd, J=6.1, 3.4 Hz, 2H), 1.32 (s, 18H). ¹³C NMR (125 MHz, DMSO-$d_6$): δ 144.96 (2C), 141.12 (2), 137.55 (2C), 136.19 (2C), 125.24 (4C), 124.93 (4C), 120.35 (4C), 34.06 (2C), 31.31 (6C). IR (neat, cm⁻¹): ν=3385, 2958, 2902, 2865, 1640, 1613, 1586, 1570, 1513, 1450, 1408, 1361, 1330, 1315, 1294, 1266, 1245, 1191, 1144, 1111, 1016, 940, 858, 831. MS (ESI): m/z 425.3 found for $C_{28}H_{33}N_4$ [M+H]⁺.

TABLE 1

| Name | Structure | IC50 (μm) PC-3 | IC50 (μm) C4-2 | Dimerization Inhibition | Survivin Degradation |
|---|---|---|---|---|---|
| LQZ-7[b] | 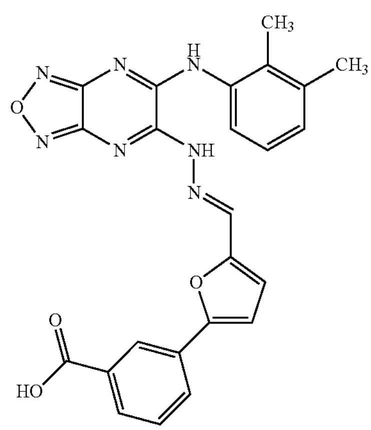 [SMILES: Cc1cccc(Nc2nc3nonc3nc2N/N=C/c2ccc(-c3cccc(C(=O)O)c3)o2)c1C] | 8.1 | 9.1 | + | + |

TABLE 1-continued
| Name | Structure | IC50 (μm) PC-3 | C4-2 | Dimerization Inhibition | Survivin Degradation |
|---|---|---|---|---|---|
| LQZ-7A[a] | 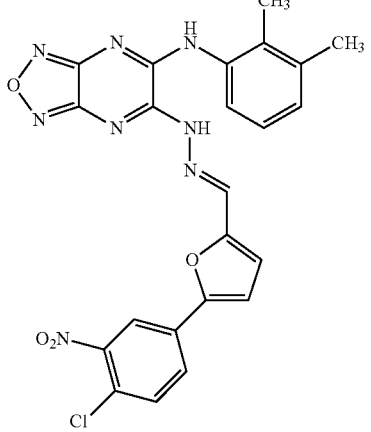 | 7.2 ± 2.7 | | ND | − |
| LQZ-7B[a] | 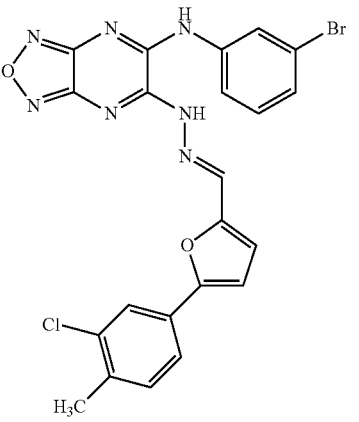 [SMILES: Cc1ccc(-c2ccc(/C=N/Nc3nc4nonc4nc3Nc3cccc(Br)c3)o2)cc1Cl] | 3.3 ± 0.2 | | ND | + |
| LQZ-7C[a] | 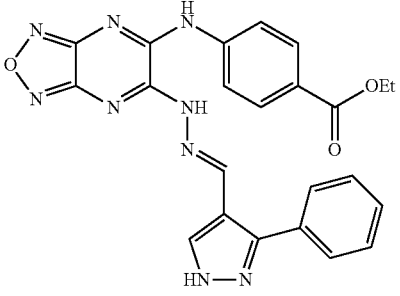 [SMILES: CCOC(=O)c1ccc(Nc2nc3nonc3nc2N/N=C/c2c[nH]nc2-c2ccccc2)cc1] | 3.5 ± 0.0 | | ND | + |
| LQZ-7D[a] | 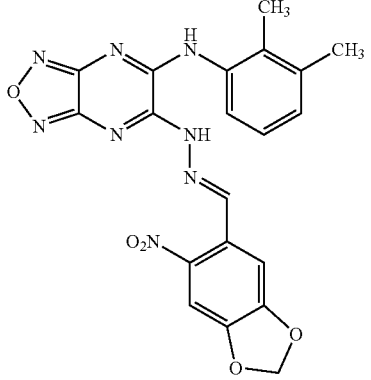 [SMILES: Cc1cccc(Nc2nc3nonc3nc2N/N=C/c2cc3c(cc2[N+](=O)[O-])OCO3)c1C] | 2.6 ± 0.3 | | ND | − |

TABLE 1-continued

| Name | Structure | IC50 (μm) PC-3 | C4-2 | Dimerization Inhibition | Survivin Degradation |
|---|---|---|---|---|---|
| LQZ-7E[a] | 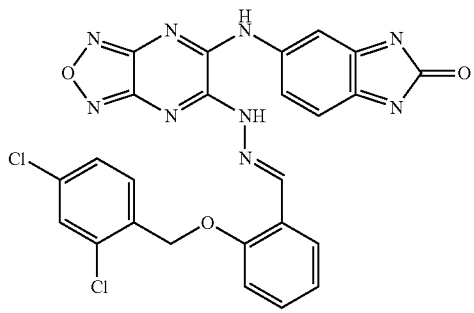 | 60.3 ± 1.0 | | ND | – |
| LQZ-7G[b] | 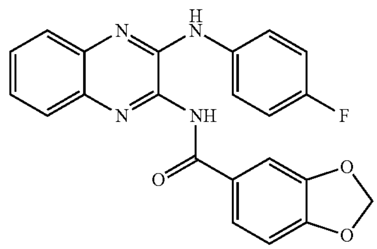 [SMILES: O=C(Nc1nc2ccccc2nc1Nc1ccc(F)cc1)c1ccc2c(c1)OCO2] | 20.7 | 14.3 | – | ND |
| LQZ-7H[b] | 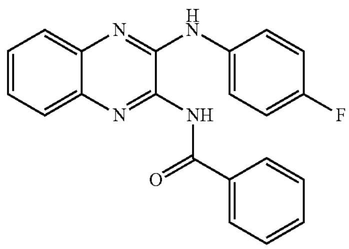 [SMILES: O=C(Nc1nc2ccccc2nc1Nc1ccc(F)cc1)c1ccccc1] | 19.7 | 12.7 | – | ND |
| LQZ-7I[b] | 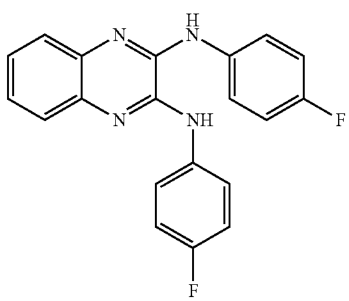 [SMILES: Fc1ccc(Nc2nc3ccccc3nc2Nc2ccc(F)cc2)cc1] | 4.8 | 3.1 | + | + |
| LQZ-7J[b] | 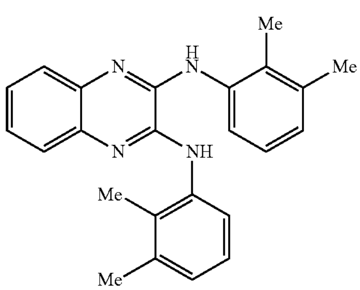 [SMILES: Cc1cccc(Nc2nc3ccccc3nc2Nc2cccc(C)c2C)c1C] | 24.8 | 17.6 | – | ND |

[a] The data for LQZ-7A-E were from the previous study [12]. The IC50 was determined using MTT assay.
[b] The data for the LQZ-7G-K were from this study. The IC50 was determined using methylene blue assay.
[c] ND = not determined.

Antibodies against FLAG tag (F3165) and b-actin (A5316) were obtained from Sigma-Aldrich. The antibody against survivin (2808), the Annexin V-FITC apoptosis kit, and the Metafectene Pro transfection reagent were purchased from Cell Signaling Technology, MilliporeSigma, and Bion-tex, respectively. The enhanced chemiluminescence reagent was from GE Healthcare. The matchmaker mammalian two hybrid assay kit and the Great Escape SEAP Chemiluminesence assay kit were purchased from Clontech. Cell culture media and fetal bovine serum were from Corning and Applied Biosystems-Life Technologies, respectively. All other chemicals were purchased from Sigma or Fisher Scientific.

Cell lines. The human cancer cell lines C4-2, PC-3, Du145, LNCAP, and 22Rv1 were purchased from and authenticated by the ATCC (Manassas, Va.). E7 prostate epithelial cells were a generous gift from Dr. Travis Jerde (Indiana University School of Medicine). All cell lines were maintained at 37° C. in 5% $CO_2$ and grown in RPMI (Corning: Manassas, Va.) with 10% Fetal Bovine Serum (Gibco by Life Sciences: Mexico).

Methylene blue survival assay. Prostate cancer cells were seeded 2000-3500 per well (cell line dependent) and treated with LQZ-7-3 for 72 hours. After 72 hours, media was then removed and cells were fixed with methanol for 30 minutes and subsequently stained with 100 μL of 1% methylene blue (diluted in 10 mM borate buffer) for 1 hour. The cells were then washed 3× with 10 mM borate buffer and then allowed to air dry for 30 minutes. 100 μL of 100% ethanol:0.1 M HCl (1:1) was added to each well to dissolve the methylene blue stain and absorbance was measured via spectrometry at 650 nM. After normalization to DMSO controls, the percent viabilities were graphed and IC50 concentrations were determined using Prism. DMSO control did not show a difference from media alone cells.

Survivin mammalian two hybrid assay. The mammalian two hybrid assay was performed utilizing the ClonTech Matchmaker Mammalian Two Hybrid Assay kit [13]. Briefly, the coding region (~400 bp) of survivin was cloned in to two different plasmids, the pM plasmid containing the GAL4-DNA Binding Domain and the pVP16 plasmid containing an activation domain. Correct orientation and sequence was validated by sequencing using forward and reverse primers to survivin. These two plasmids (0.45 ug/well) along with the pGSEAP reporter plasmid (0.09 ug/well) and firefly luciferase plasmid (30 ng/well) were co-transfected in to $1 \times 10^5$ Du145 cells per well in a 12 well plate. Each condition was tested in triplicate. For experiments utilizing LQZ-7-3 the cells were seeded then 24 hours later the transfection was performed. 48 hours later the media was changed and cells were treated with DMSO or LQZ-7-3 for 24 hours. SEAP was detected utilizing the Takara ClonTech SEAP Great Escape chemiluminescence assay kit 2.0 and cells were lysed and luciferase was measured to control for transfection efficiency. IAP family member degradation assay. For this experiment C4-2 or PC-3 cells were plated in a 10 cm dish at $1 \times 10^6$ cells per dish. 24 hours later the media was changed and cells were treated with DMO or LQZ-7-3. After 48 hours the cells were harvested, washed in PBS, and IAP family members level were evaluated using specific antibodies and Western Blotting.

Survivin Cycloheximide Half-Life Assay. The effect of LQZ-7-3 on survivin half-life was performed as previously described. Briefly, PC-3 or C4-2 cells were pretreated with 10 μmol/L cycloheximide for 1 hour followed by incubation with or without LQZ-7-3 10 uM for different times (0-6 hours). The cells were then harvested for Western Blot analysis for survivin. Apoptosis Assay. The apoptosis assay was performed as detailed in the Anenxin V-FITC kit from BioVision. Briefly, apoptosis was induced by treatment with LQZ-7-3 and cells were collected by centrifugation. Cells were resuspended in 500 ul of 1× binding buffer and 5 ul of annexin V-FITC and 5 ul of propidium iodide (50 ug/ml) was added to the cells. The cells were incubated at room temperature for 5 minutes in the dark then subjected to quantification by flow cytometry.

Proteasome Inhibitors Study. For the proteasome inhibitor rescue experiment, PC3 and C4-2 cells were seeded in 10-cm dishes at $8 \times 10^5$ cells/dish and cultured for 48 hours followed by replacement with fresh media containing DMSO control, 7 μmol/L MG132, or 70 nmol/L bortezomib and incubation for 2 hours. LQZ-7-3 was then added to the culture to final concentrations of 10 uM respectively and incubated for additional 24 hours. The cells were then harvested used for Western blot analysis of survivin.

PC-3 Xenograft Model. For the in vivo efficacy study, $3 \times 10^6$ PC-3 cells in media were implanted in to the hind flanks of 6 week old NSG male mice. After the tumor volume reached approximately 100 $m^3$ in volume, the mice were randomized in to two groups (5 mice/group). The mice were either given 200 uL vehicle (90% corn oil/10% DMSO) or LQZ-7-3 100 mg/kg vial oral gavage every other day for a total of ten treatments. Before each treatment mouse bodyweight and tumor volume by caliper was measured. At the end of the study mice were sacrificed, and tumors were extracted for western blot analysis and H&E staining of survivin.

Figure 11A:
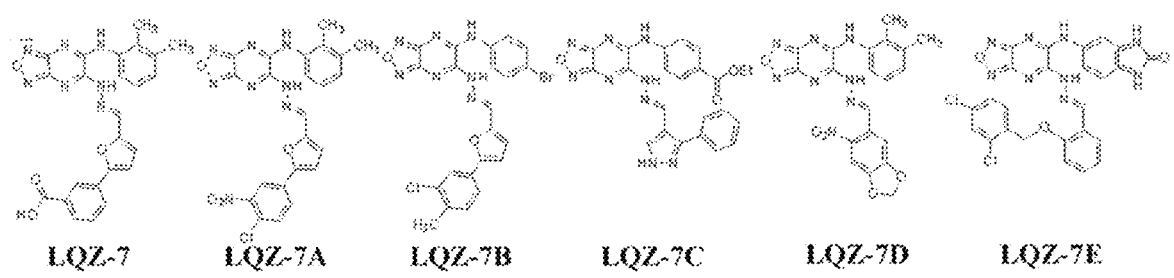
FIGS. 11A-11C show LQZ-7 has important interactions with survivin.
Figure 11B:
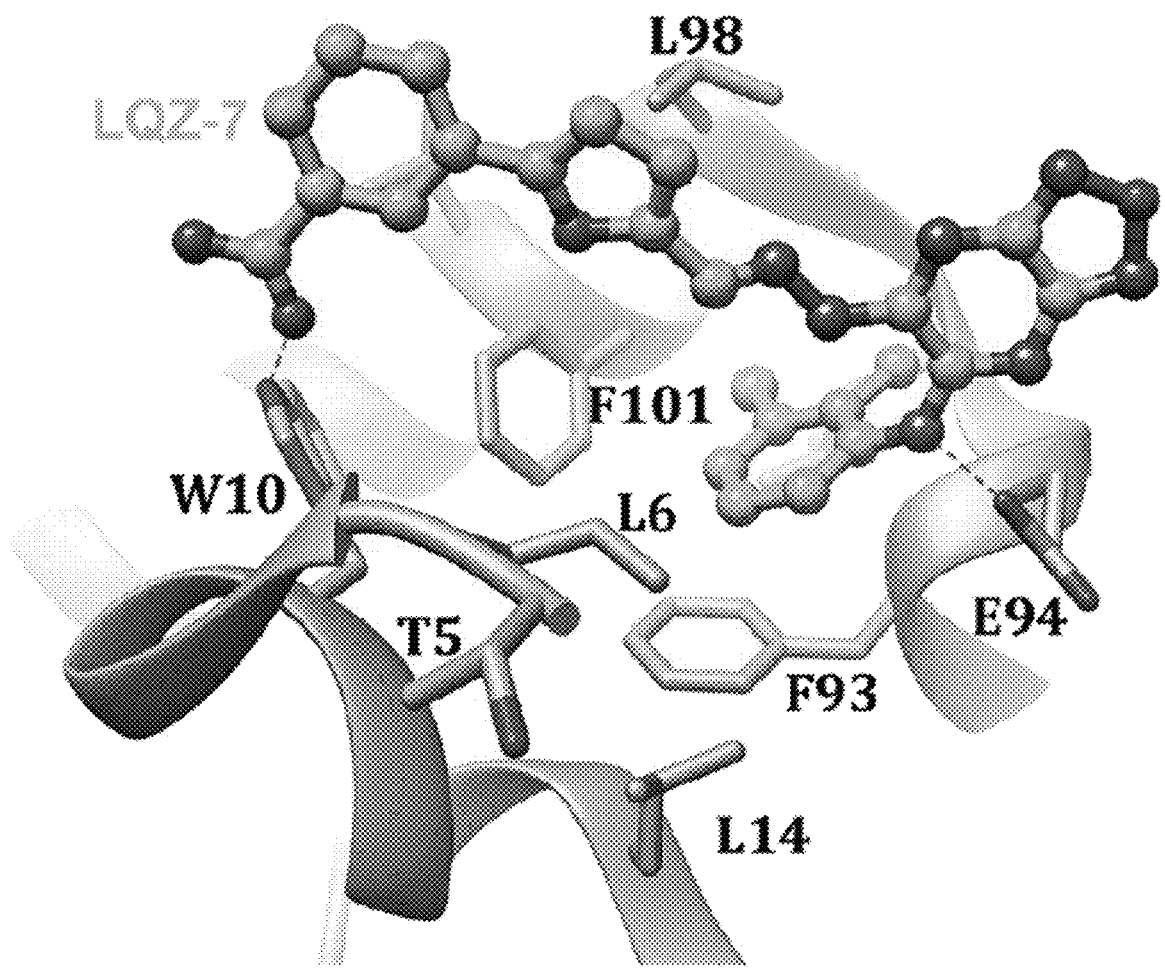
Figure 11B:
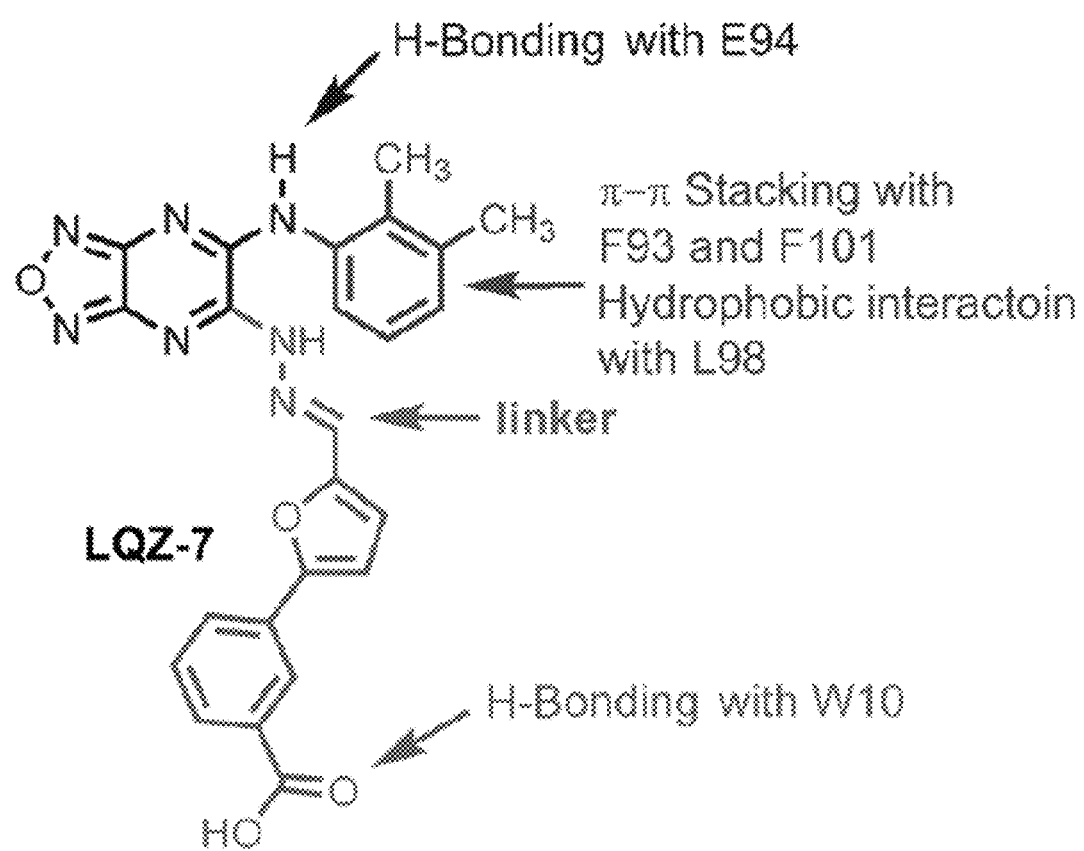
Figure 11C:
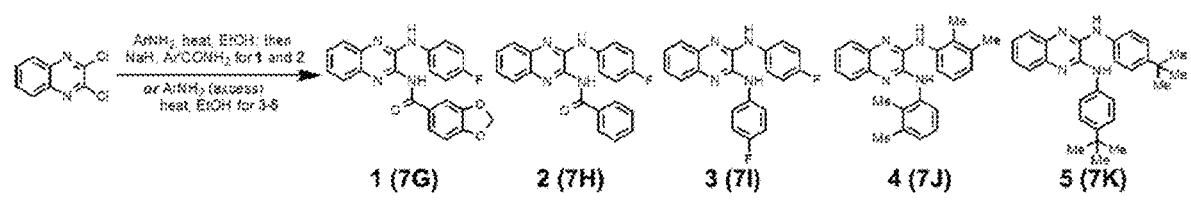

Design and synthesis of novel LQZ-7 analogs. To investigate the structure-activity relationship of LQZ-7 for optimization and creation of better and novel survivin inhibitors, we first performed molecular dynamic simulation analysis of LQZ-7 bound to the dimeric interface of survivin. As shown in FIG. 11B-C, LQZ-7 has three important interactions with survivin: (a) H-bond between an aniline NH group of LQZ-7 and Glu94 of survivin; (b) interaction between the substituted aniline in LQZ-7 and Phe93, Phe101, and Leu98 in the hydrophobic pocket of survivin via π-π stacking and hydrophobic interaction; and (c) H-bond between the carboxylic acid of LQZ-7 and Trp10 of survivin. This analysis shows clearly that the furazanopyrazine ring did not contribute to the binding to survivin. It is also noteworthy that LQZ-7 has a labile hydrazone linker, which is undesirable. Thus, for the new synthesis, we attempted to remove the hydrazone linker and replaced the furazanopyrazine with an aniline ring. To this end, five analogues were synthesized by two nucleophilic aromatic substitutions of the amine/amide nucleophiles with dichloroquinoxaline (FIG. 11D). All five analogues (LQZ-7G to LQZ-7K) retain the two predicted critical interactions with survivin and have the labile hydrazone linker replaced.

Figure 12A:
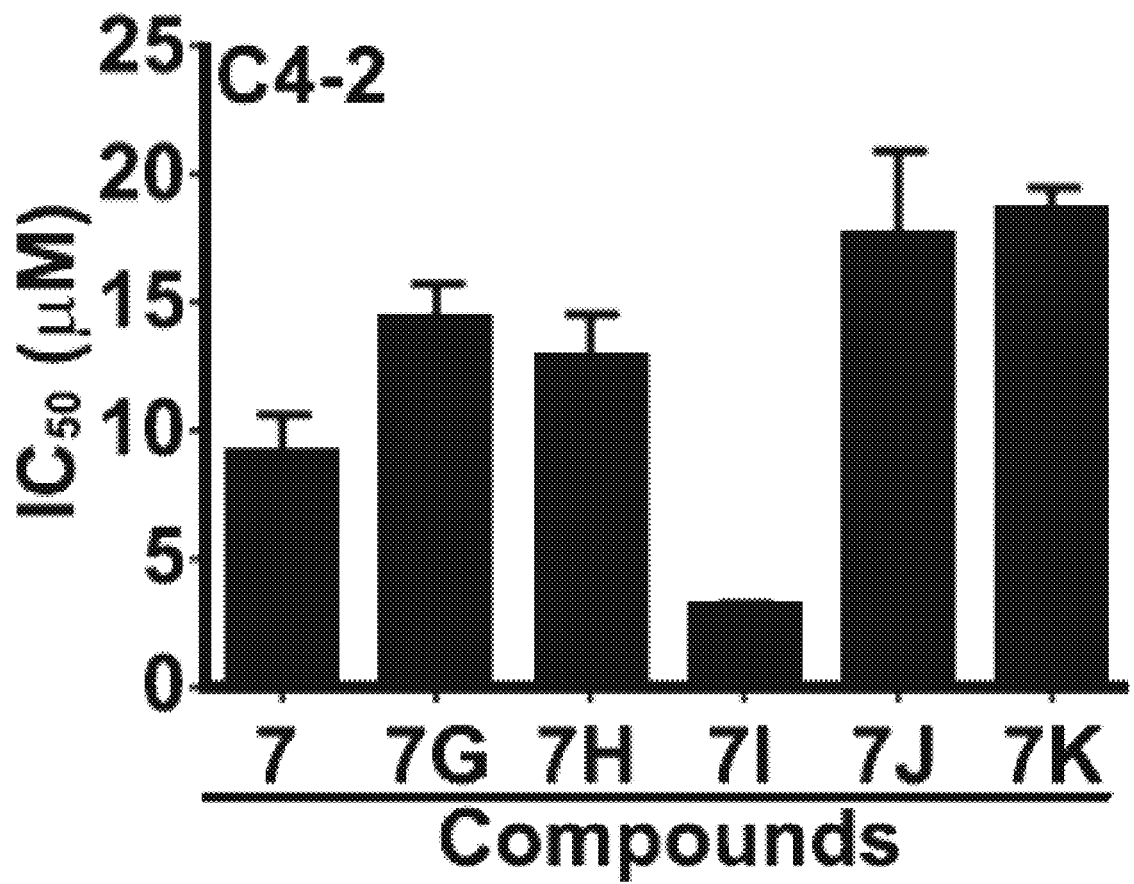
FIGS. 12A-12D show LQZ-7I has enhanced cytotoxicity compared to the parent compound LQZ-7.
Figure 12B:
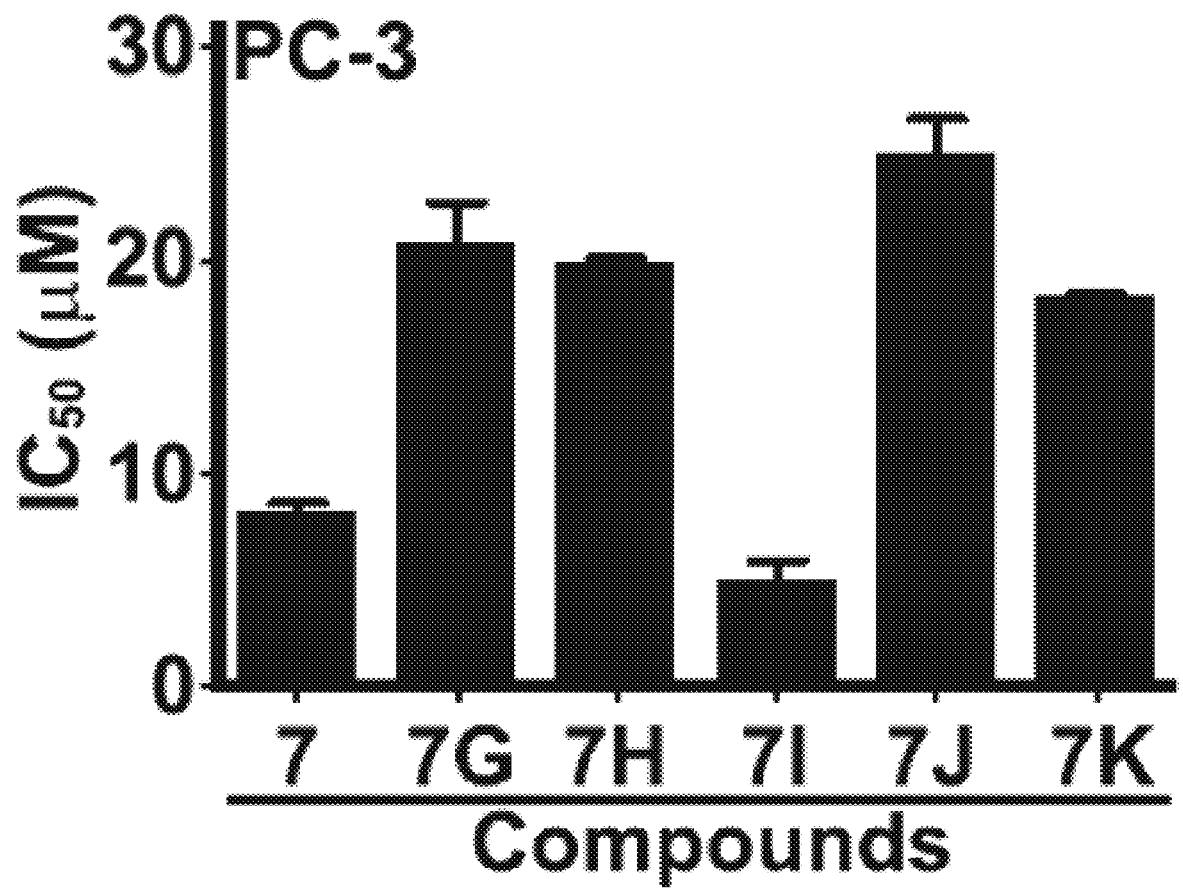

LQZ-7I has enhanced cytotoxicity compared to the parent compound LQZ-7. These five newly synthesized LQZ-7 analogs were first tested for their cytotoxicity against prostate cancer cell lines C4-2 and PC-3 in comparison with their parent compound LQZ-7 using methylene blue assay. Dose response survival curves were generated following 72-hr treatments (FIG. 32), which were used to derive their IC50. As shown in FIG. 12A-B, the compound 7I has improved cytotoxicity with an IC50 of 3.1 μM against C4-2 cells and 4.8 μM against PC-3 cells compared with the parent compound LQZ-7, which has an IC50 of 9.1 and 8.1 μM, respectively. The other compounds performed worse with higher IC50 compared with LQZ-7.

Figure 7:
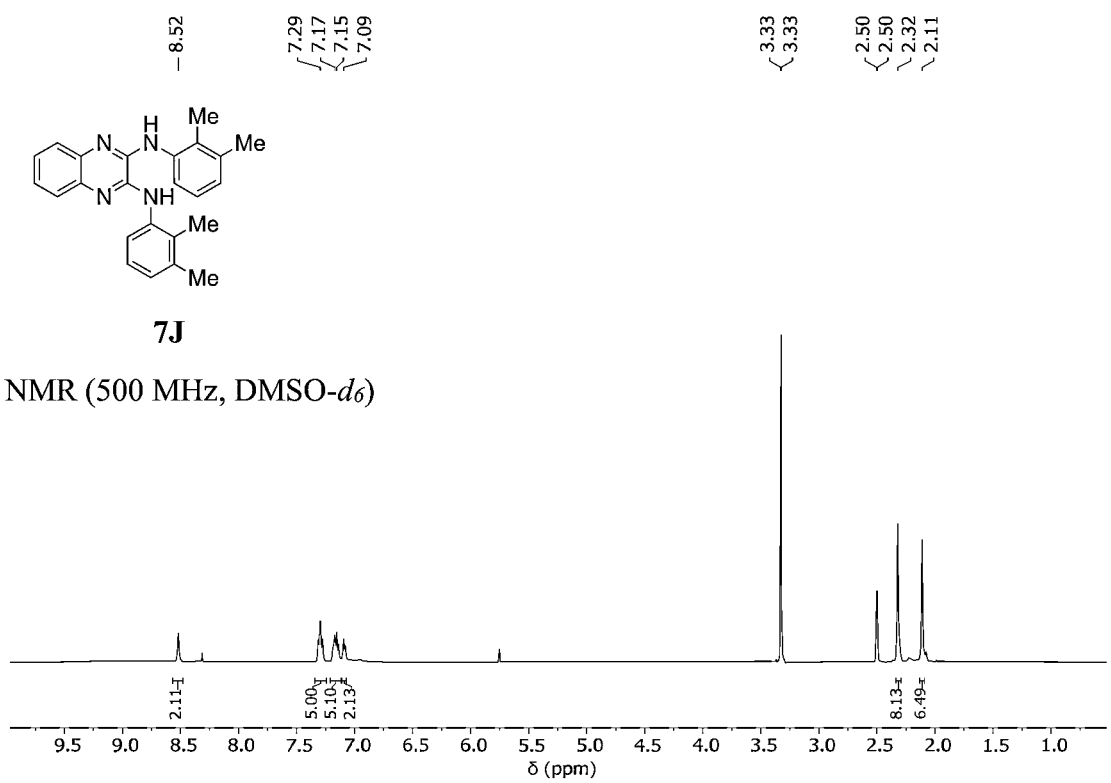
FIG. 7 shows the $^1$H or $^{13}$C NMR spectrum of the indicated compound.
Figure 8:
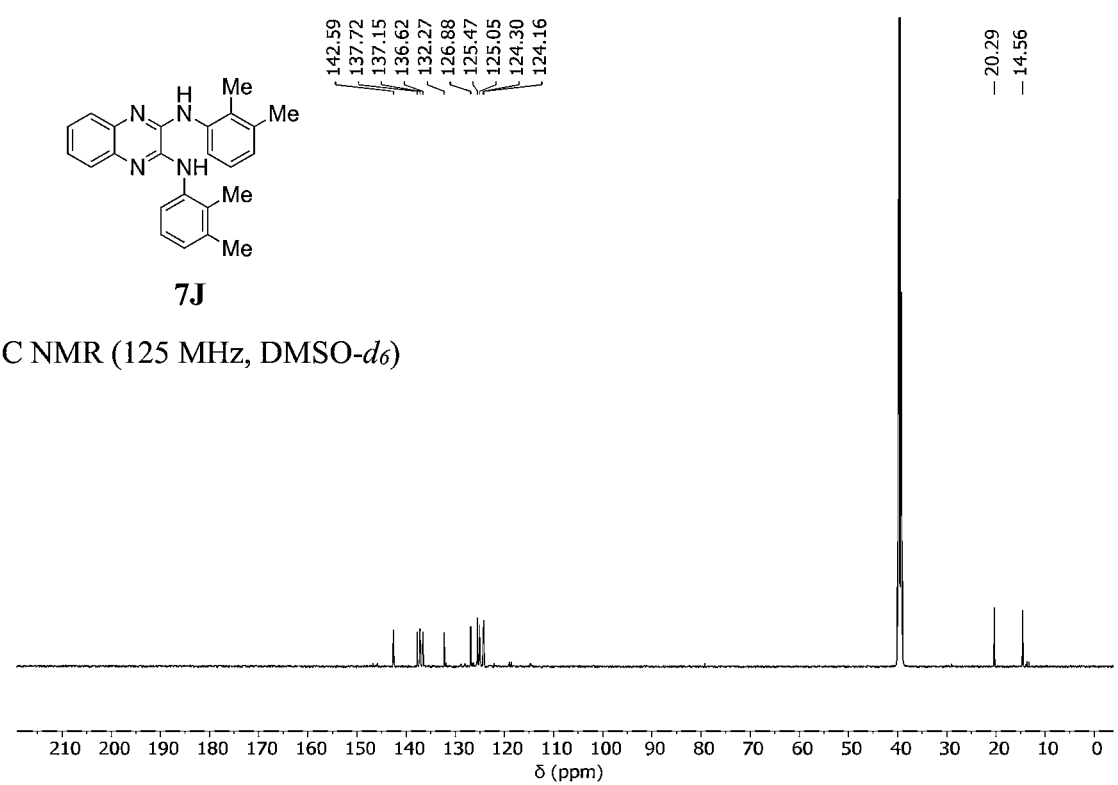
FIG. 8 shows the $^1$H or $^{13}$C NMR spectrum of the indicated compound.
Figure 9:
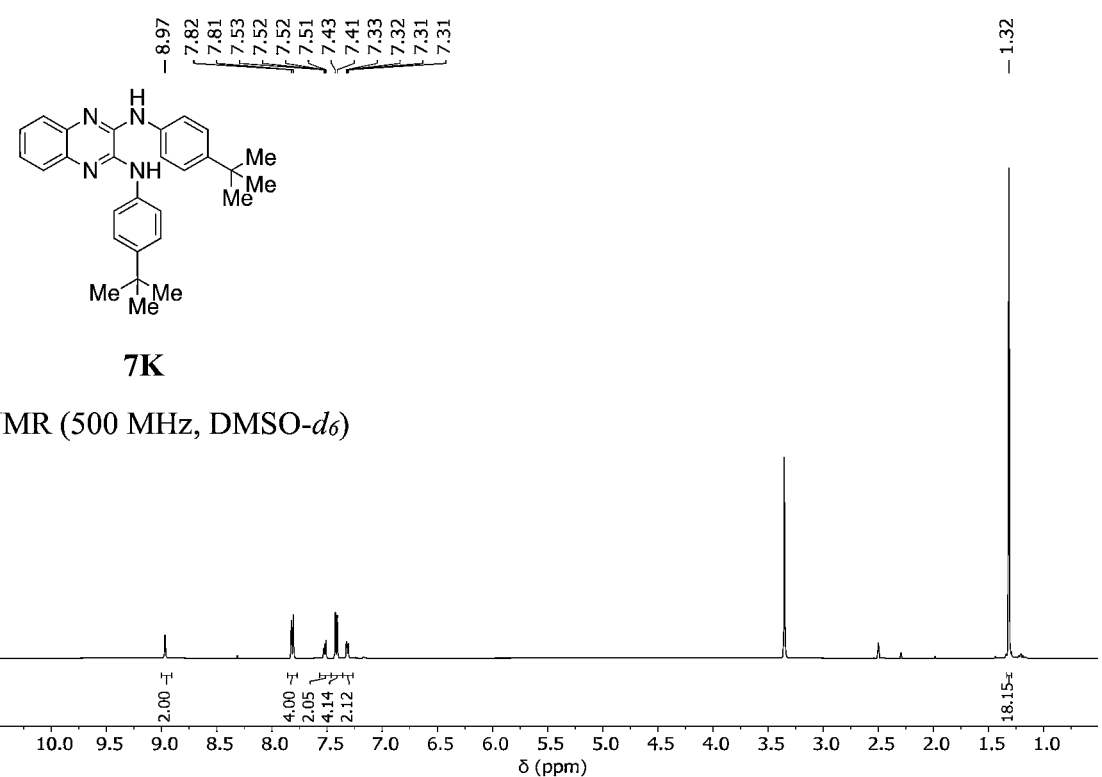
FIG. 9 shows the $^1$H or $^{13}$C NMR spectrum of the indicated compound.
Figure 10:
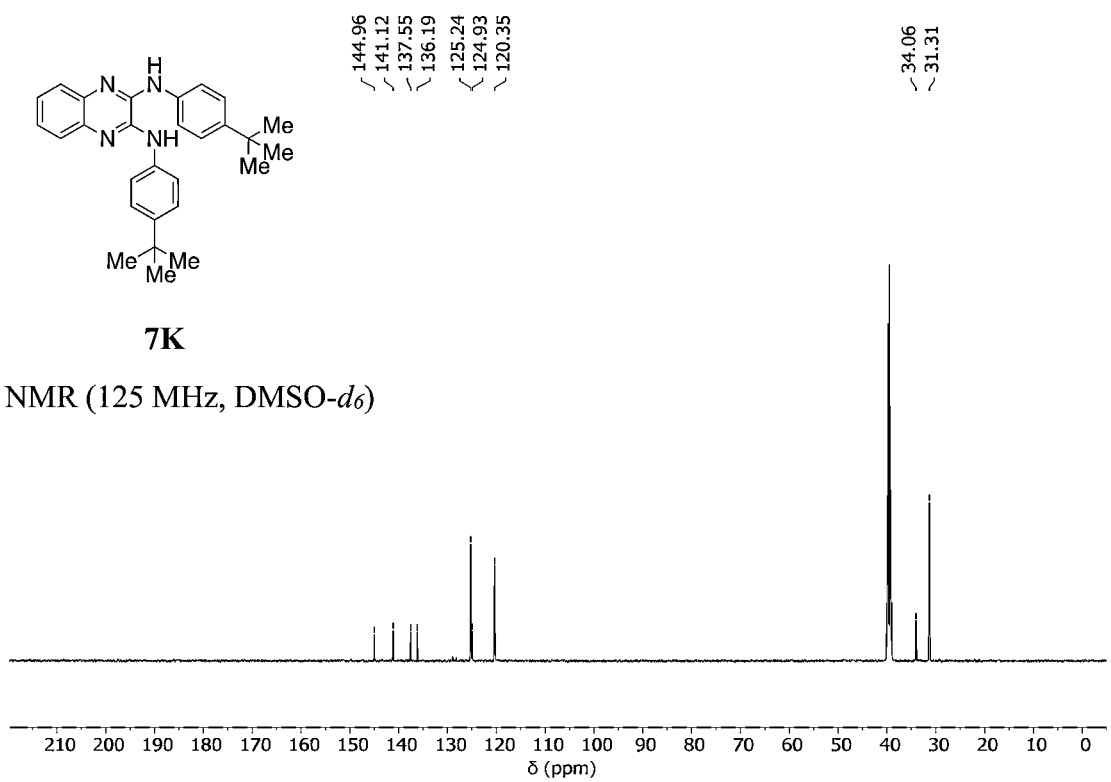
FIG. 10 shows the $^1$H or $^{13}$C NMR spectrum of the indicated compound.
Figure 12C:
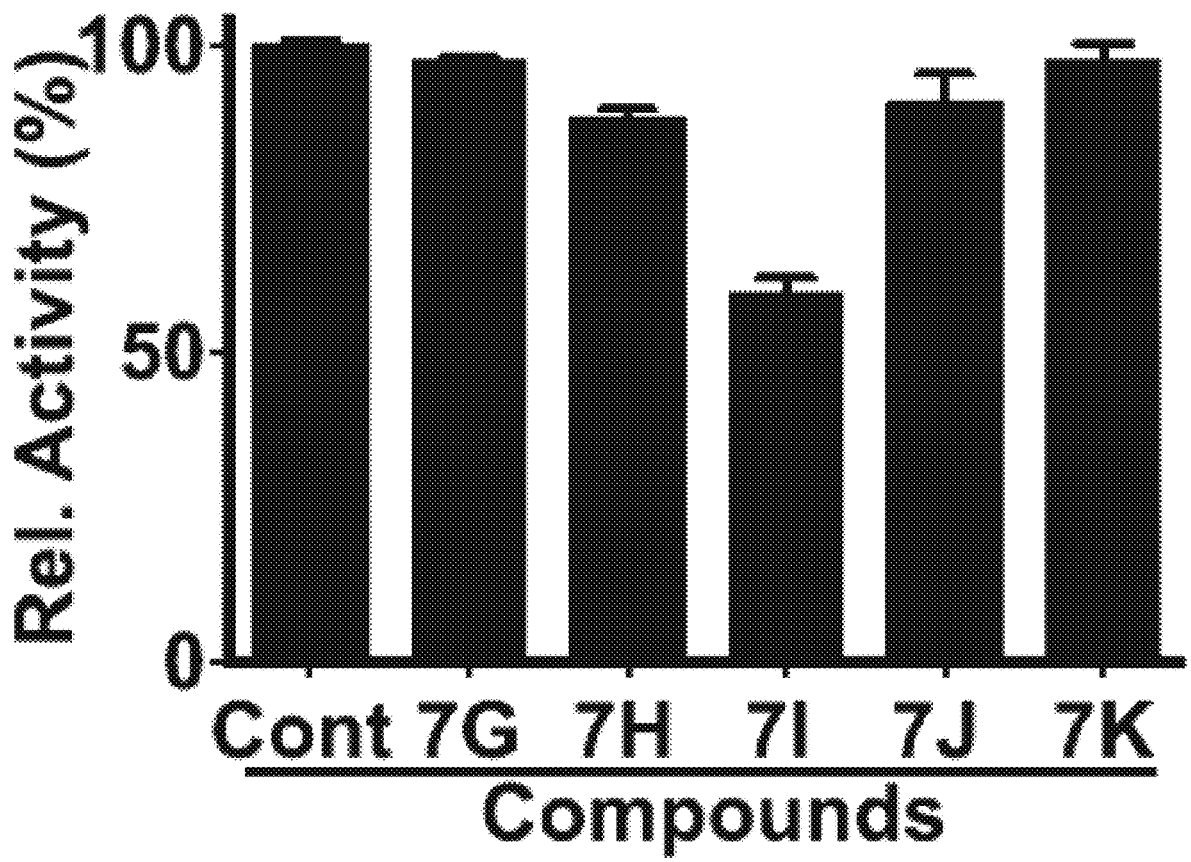

7I inhibits survivin dimerization. As this series of survivin inhibitors are designed to exert their action through interaction with the dimeric interface and disruption of survivin dimerization, we next assessed their activity in inhibiting survivin dimerization using a mammalian two hybrid assay by fusing one survivin molecule to the GAL4-DNA-binding domain and another to the VP16 activation domain. Dimerization of survivin activates the expression of Secreted Embryonic Alkaline Phosphatase (SEAP) reporter gene, which can be monitored. As shown in FIG. 12C, 7I significantly decreased the SEAP reporter expression, while the other compounds did not reduce reporter expression, consistent with their cytotoxicity against C4-2 and PC-3 cells. Thus, 7I was chosen for further study.

Figure 12D:
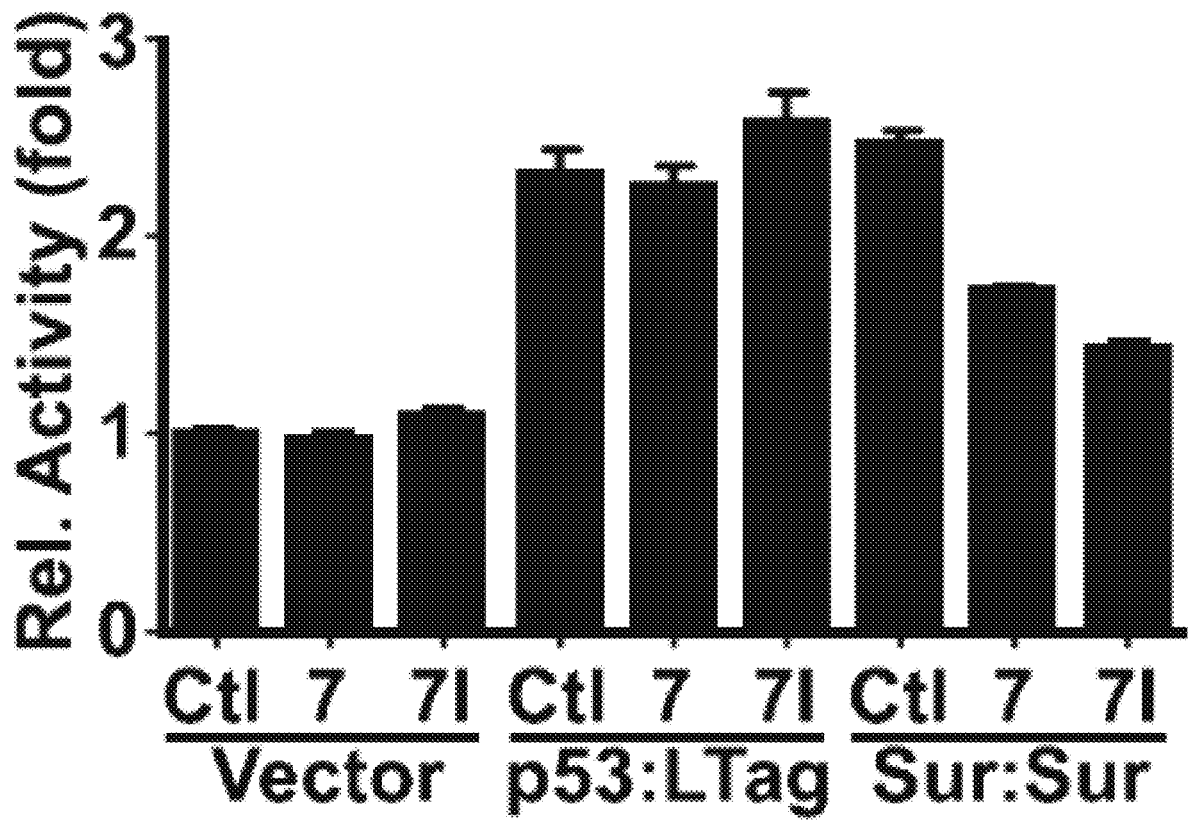

To ensure that the 7I inhibition of survivin dimerization in the above two hybrid assay is specific to survivin and to eliminate any potential non-specific effect, we tested the effect of 7I on the dimerization of p53 with the large T antigen using the same assay and by including the vector control. As shown in FIG. 12D, both 7I and the parental compound LQZ-7 significantly inhibited survivin dimerization. However, they both had no effect on p53-large T antigen dimerization or the basal reporter expression from vector alone, suggesting that the 7I inhibition of survivin dimerization may be specific. Furthermore, 7I is significantly more effective than LQZ-7 in inhibiting survivin dimerization, consistent with the difference in their IC50. These findings also suggest that 7I may inhibit cell survival via inhibiting survivin dimerization.

Figure 13A:
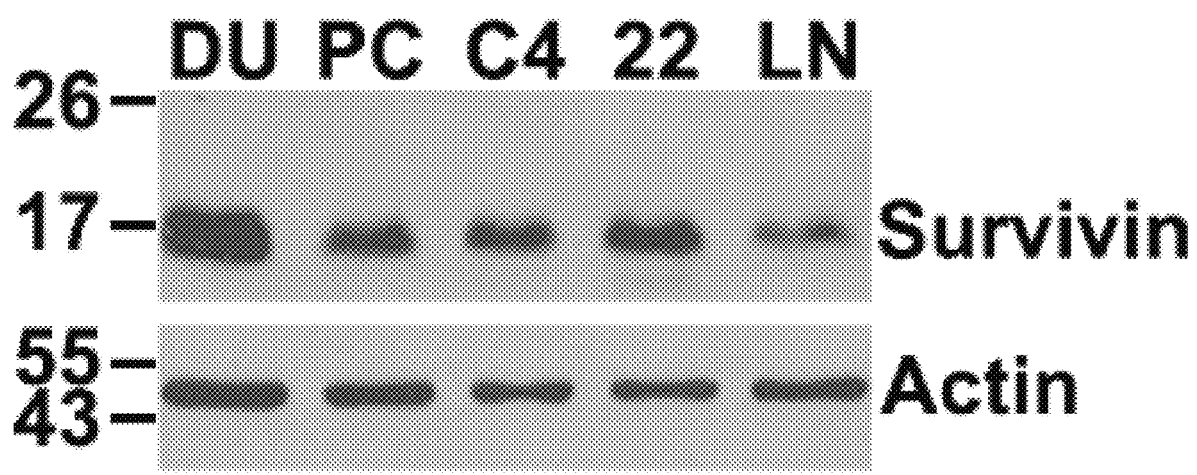
FIGS. 13A-13F show survivin level correlates with 7I IC50, survivin overexpression decreases cellular sensitivity to 7I and selectivity of 7I.
Figure 13A:
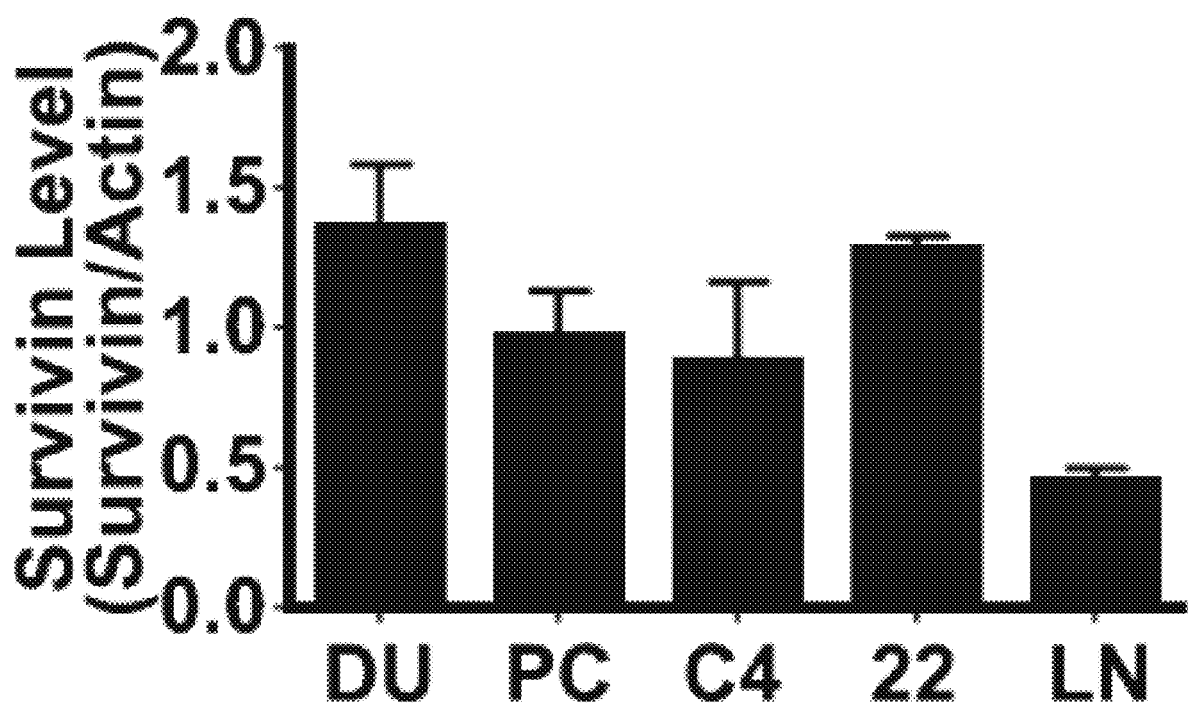
Figure 13B:
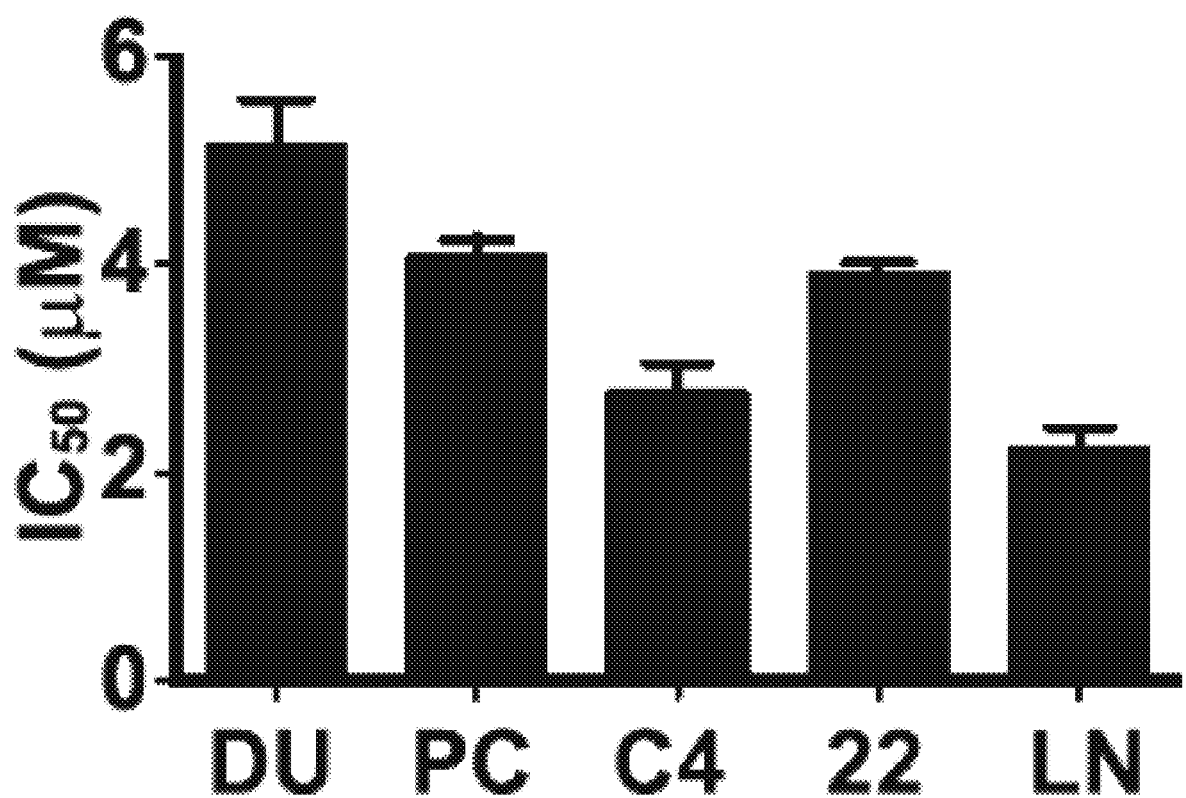
Figure 13C:
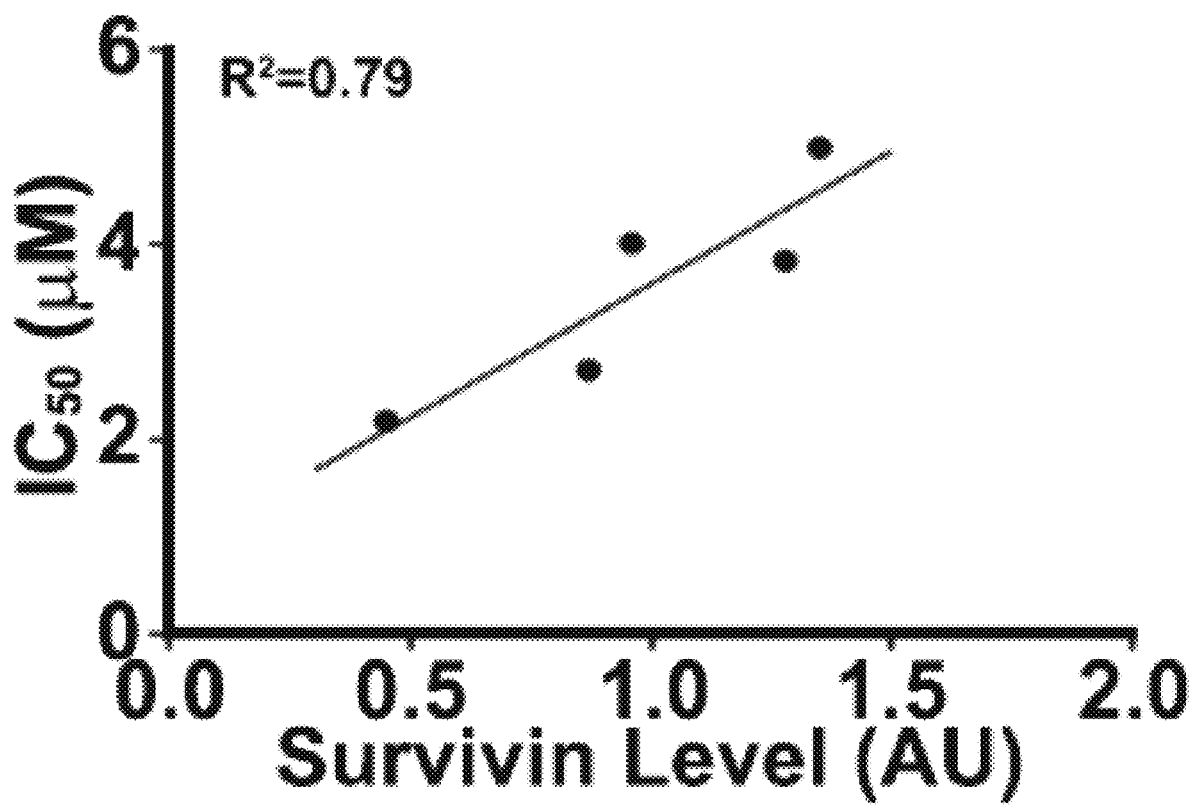

Survivin level correlates with 7I IC50. To determine if 7I inhibits cell survival via inhibiting survivin, we next performed an association analysis of survivin expression with 7I IC50 in five prostate cancer cell lines. FIG. 13A shows the relative survivin level in 5 prostate cancer cell lines assessed using Western blot analyses. FIG. 13B shows the IC50 of 7I in these cell lines. Association analysis showed that the IC50 of 7I strongly correlates with the survivin expression level with a correlation coefficient $R^2=0.9$ (FIG. 13C). This finding suggests that the cancer cells with higher level of survivin expression is more resistant to 7I. Thus, 7I likely exerts its cytotoxicity via survivin.

Figure 13D:
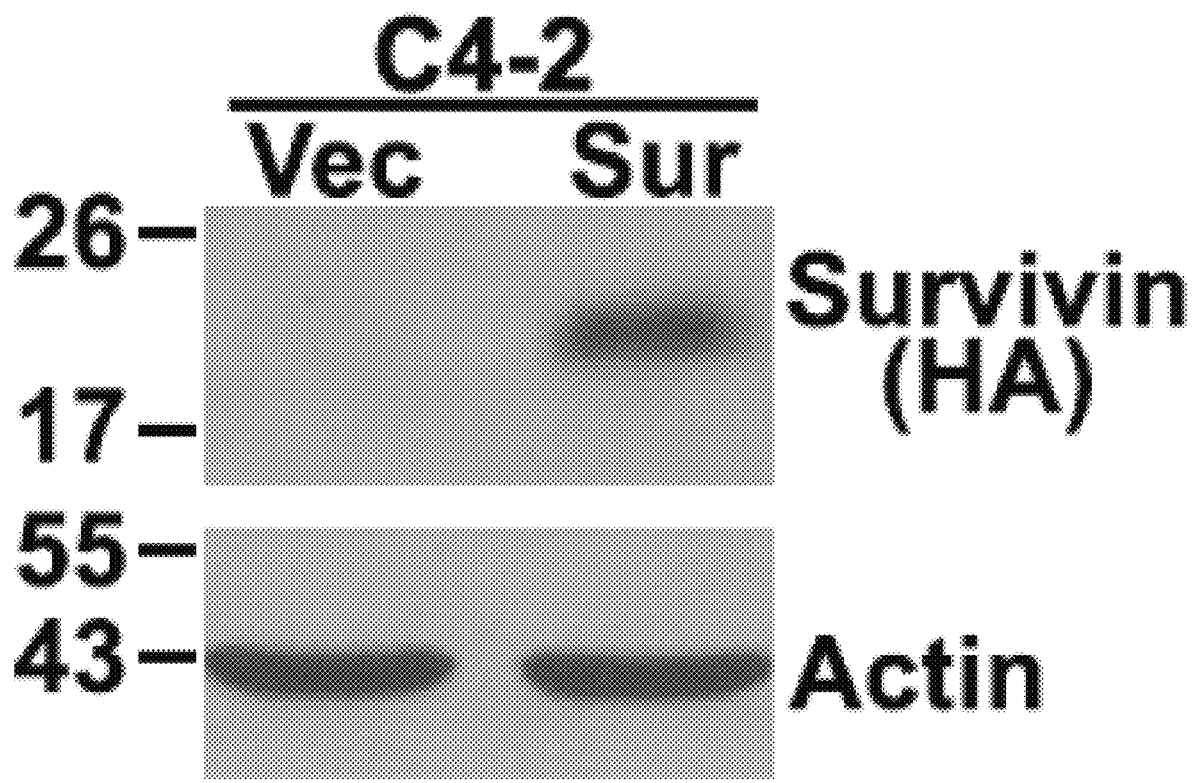
Figure 13E:
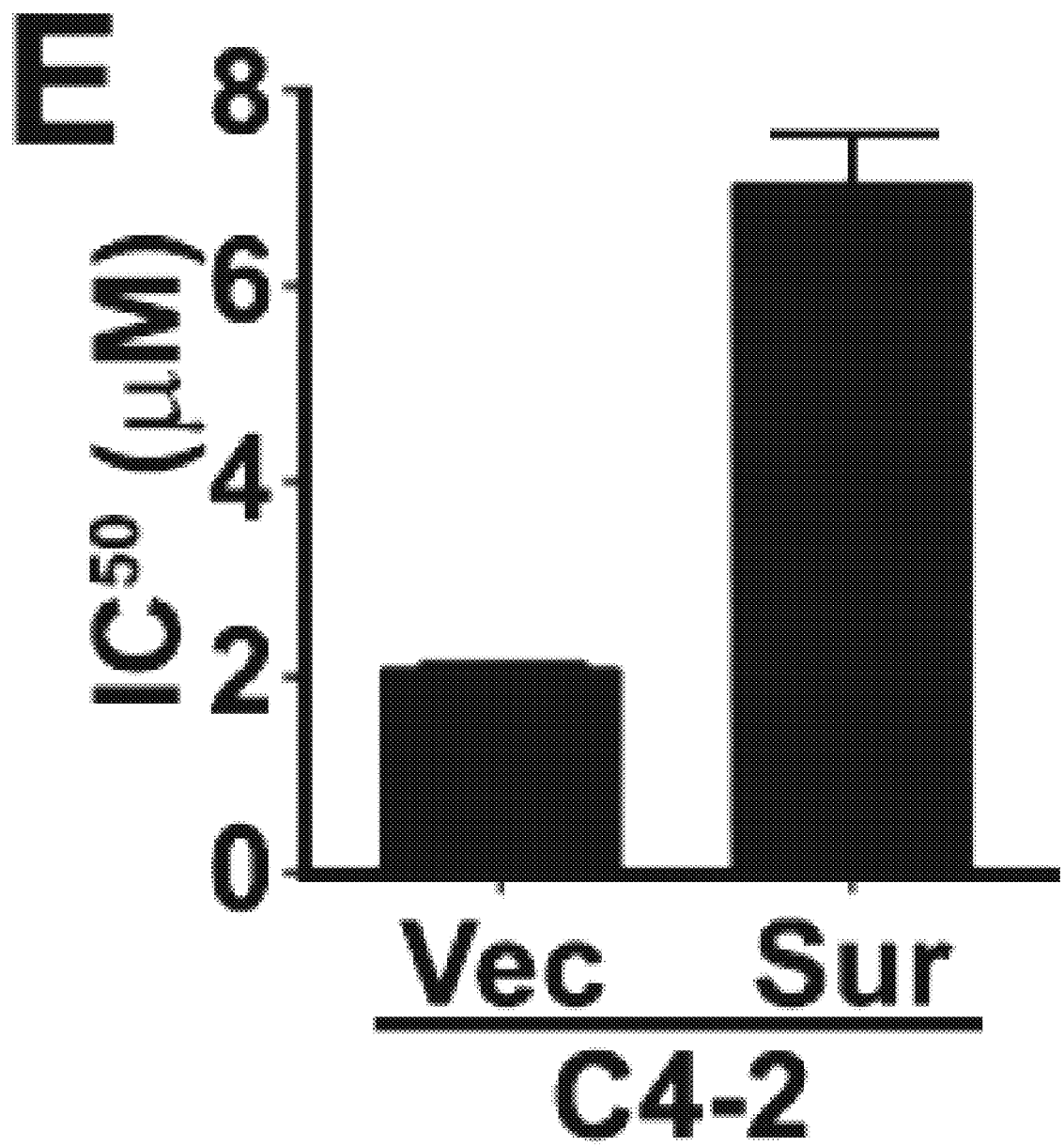

Survivin overexpression decreases cellular sensitivity to 7I. To corroborate above findings and to further investigate 7I inhibition of cancer cell survival via survivin, we generated a stable C4-2 clone with overexpression of HA-tagged survivin (FIG. 13D) and tested the effect of survivin overexpression on 7I cytotoxicity. As shown in FIG. 13E, survivin over-expression significantly increased cellular resistance to 7I with an IC50 of ~7 µM compared with ~2 µM in vector-transfect control clone. Thus, 7I likely works via inhibiting survivin.

Figure 13F:
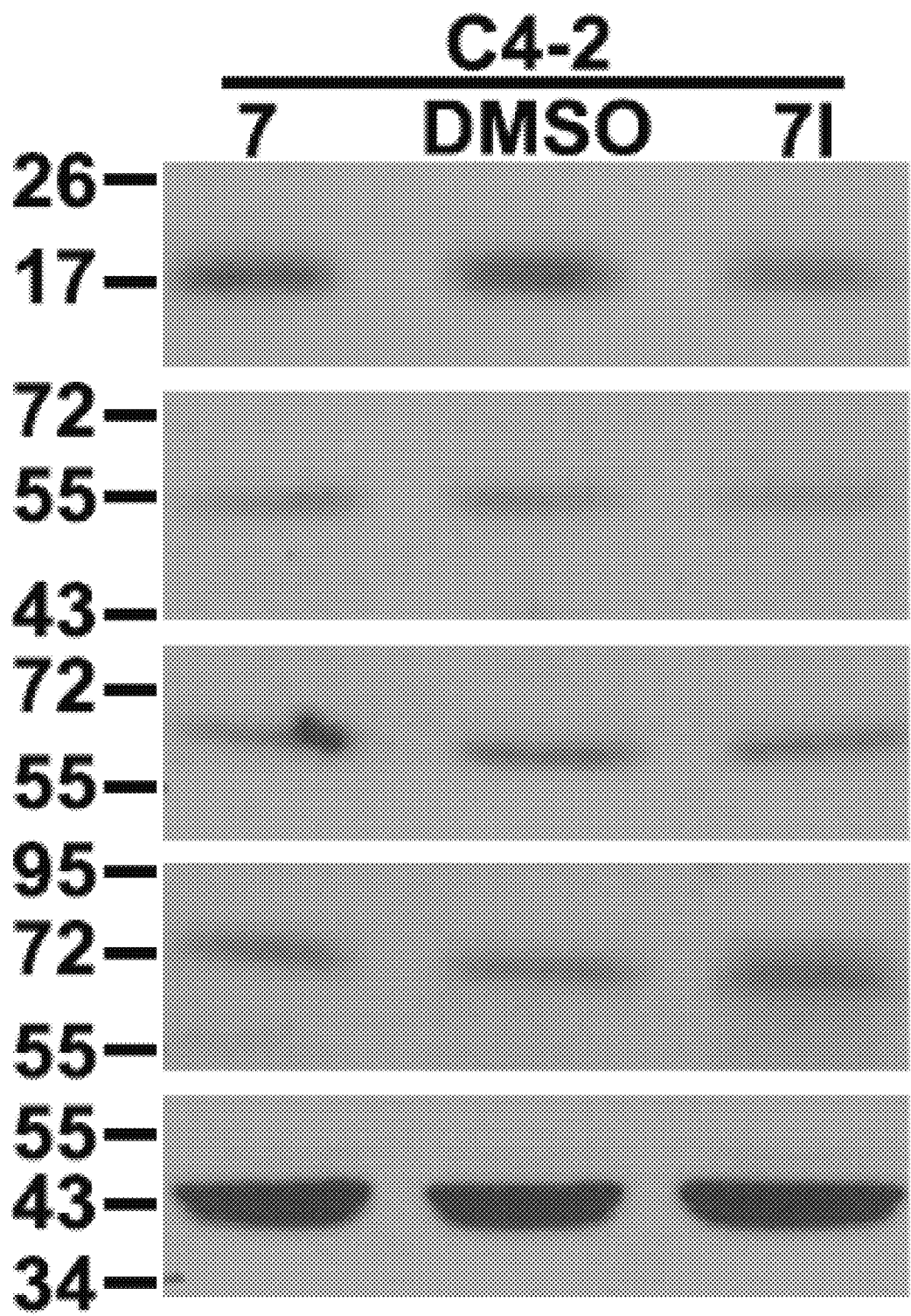
Figure 13F:
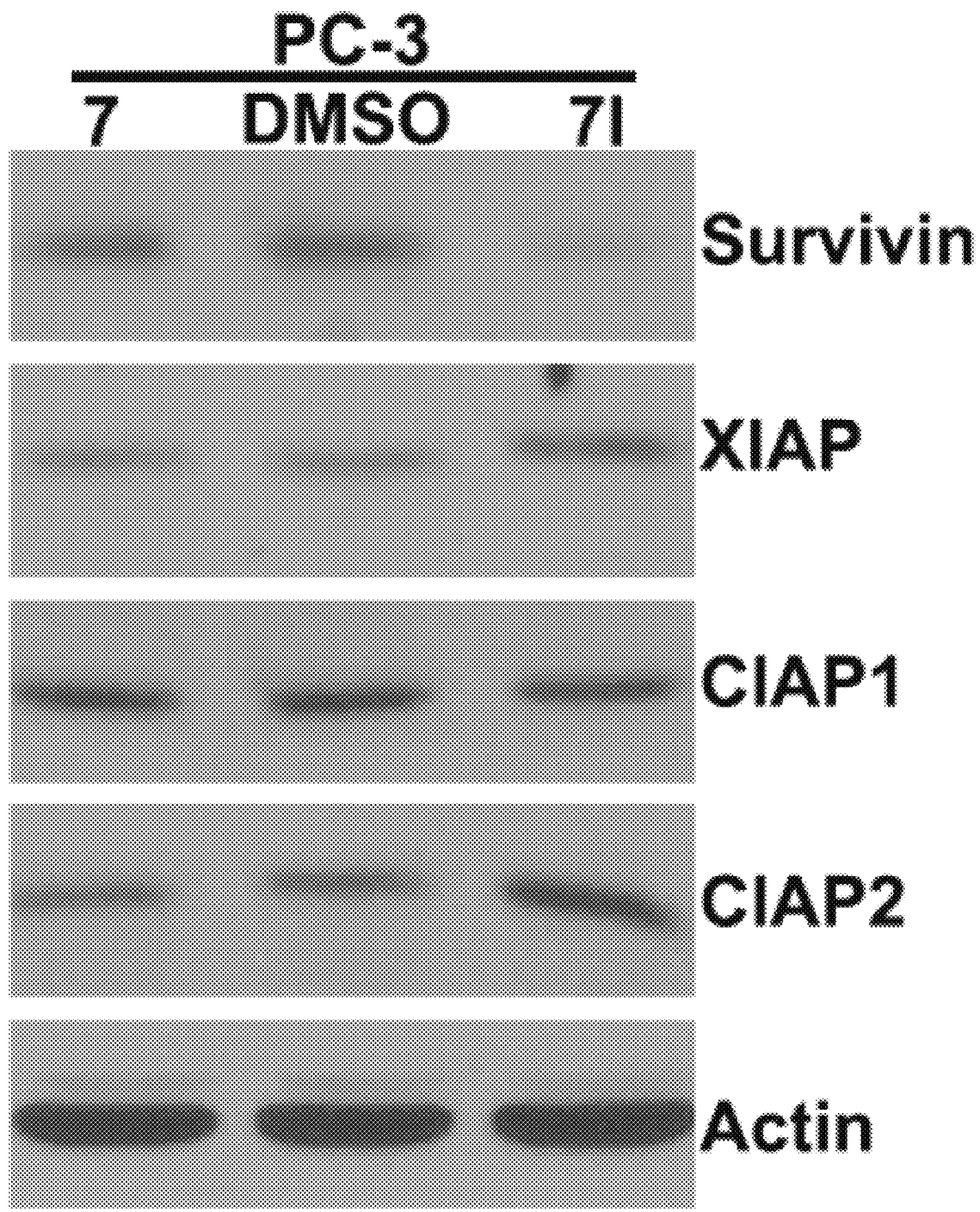
Figure 14A:
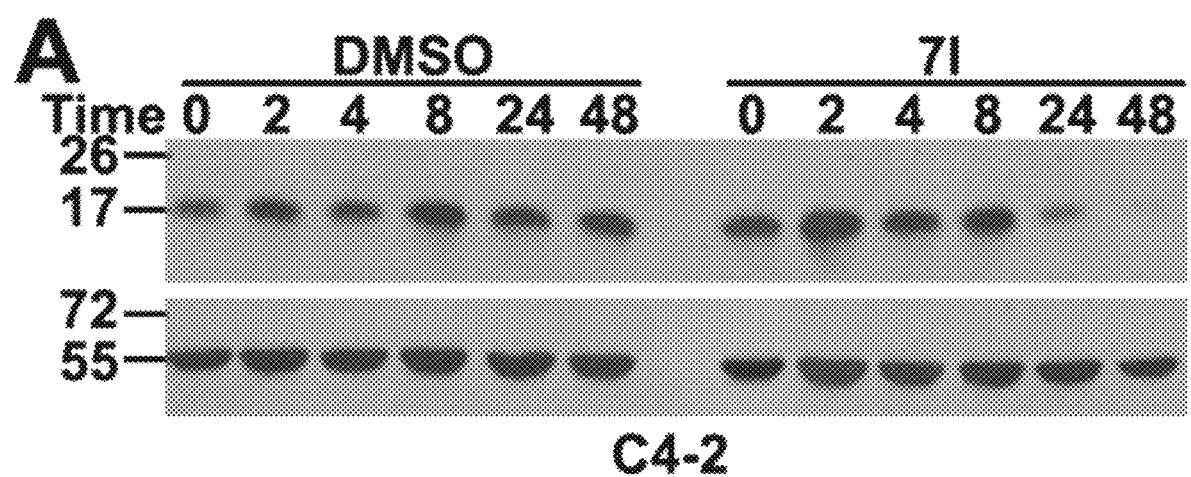
FIGS. 14A-14D show that 7I induces survivin degradation in a proteasome-dependent manner.
Figure 14A:
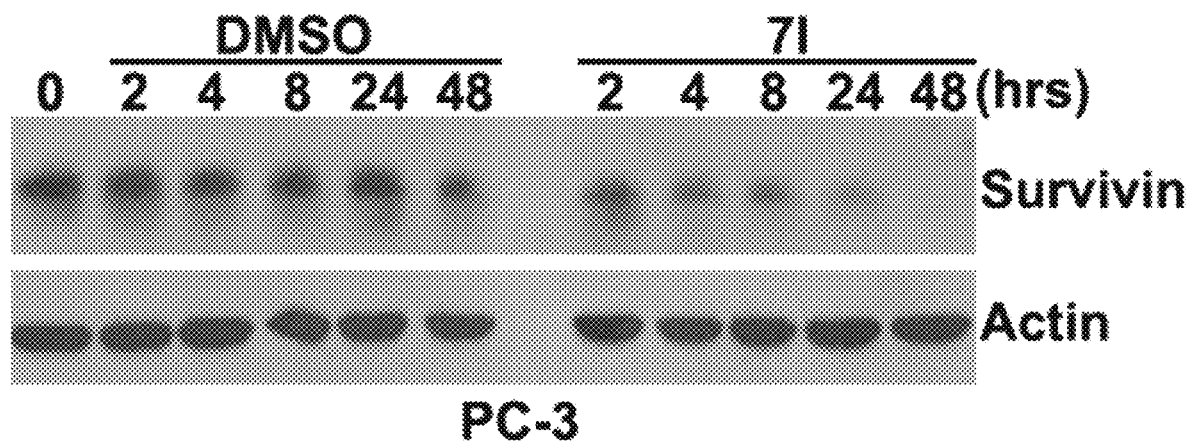
Figure 14B:
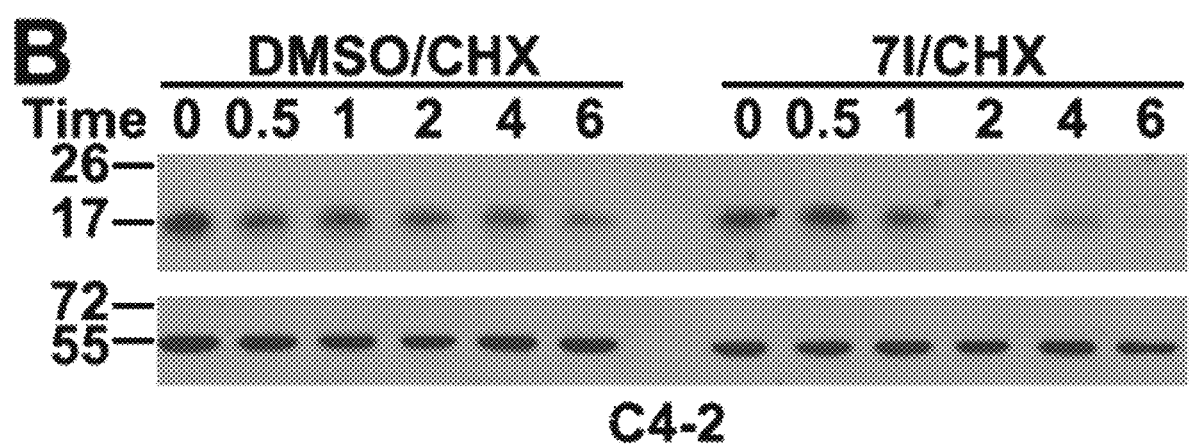
Figure 14B:
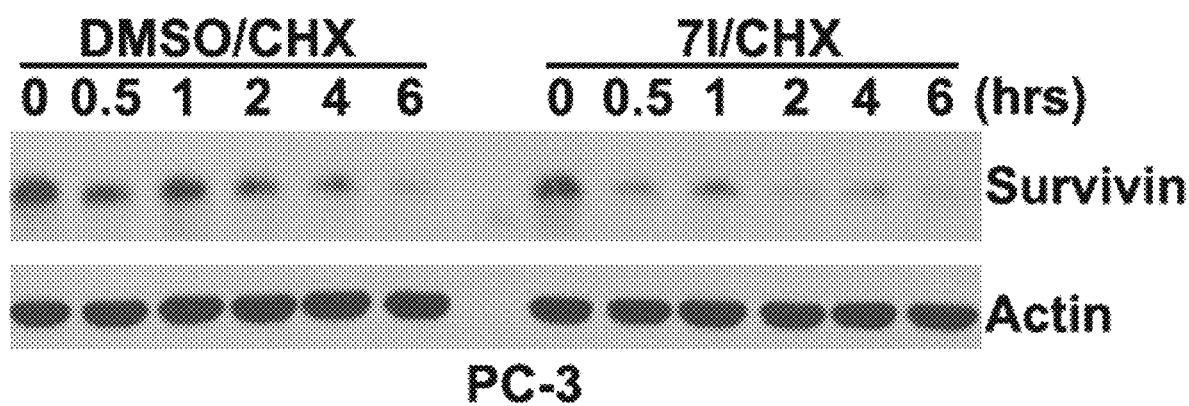
Figure 14C:
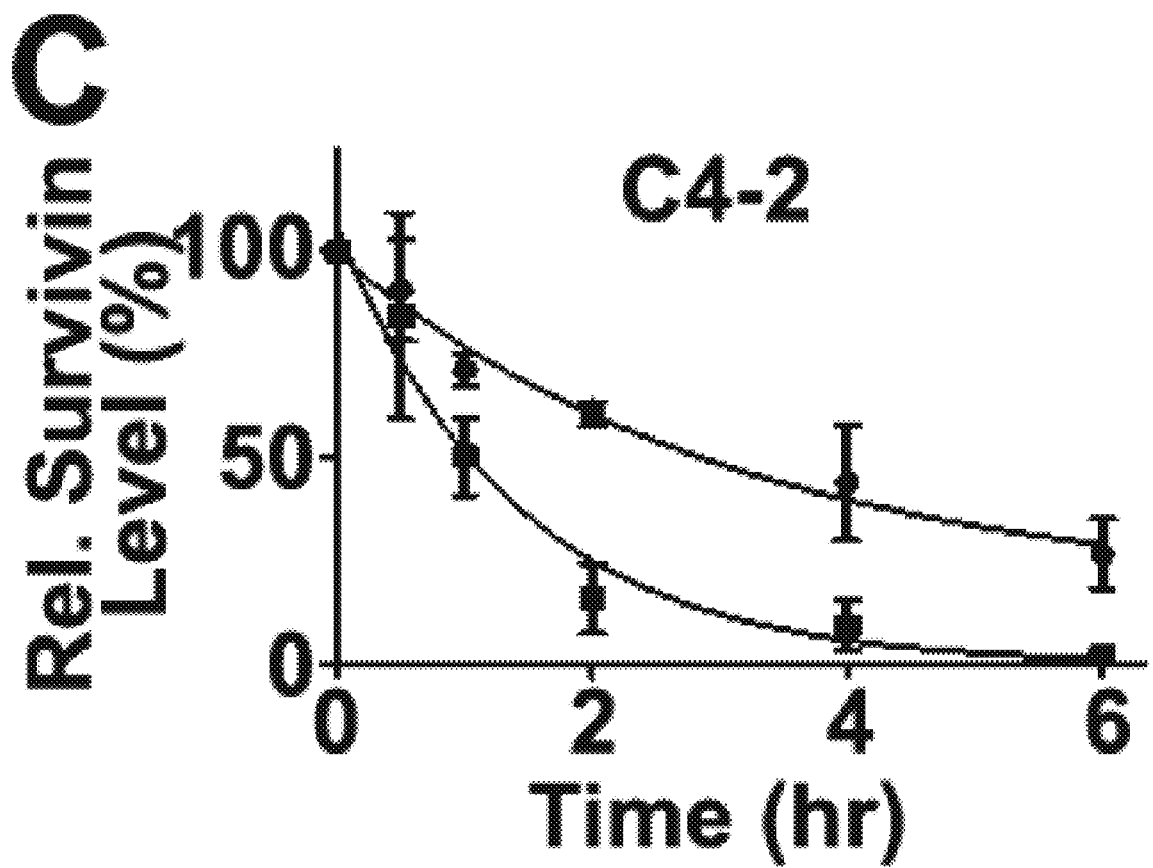
Figure 14C:
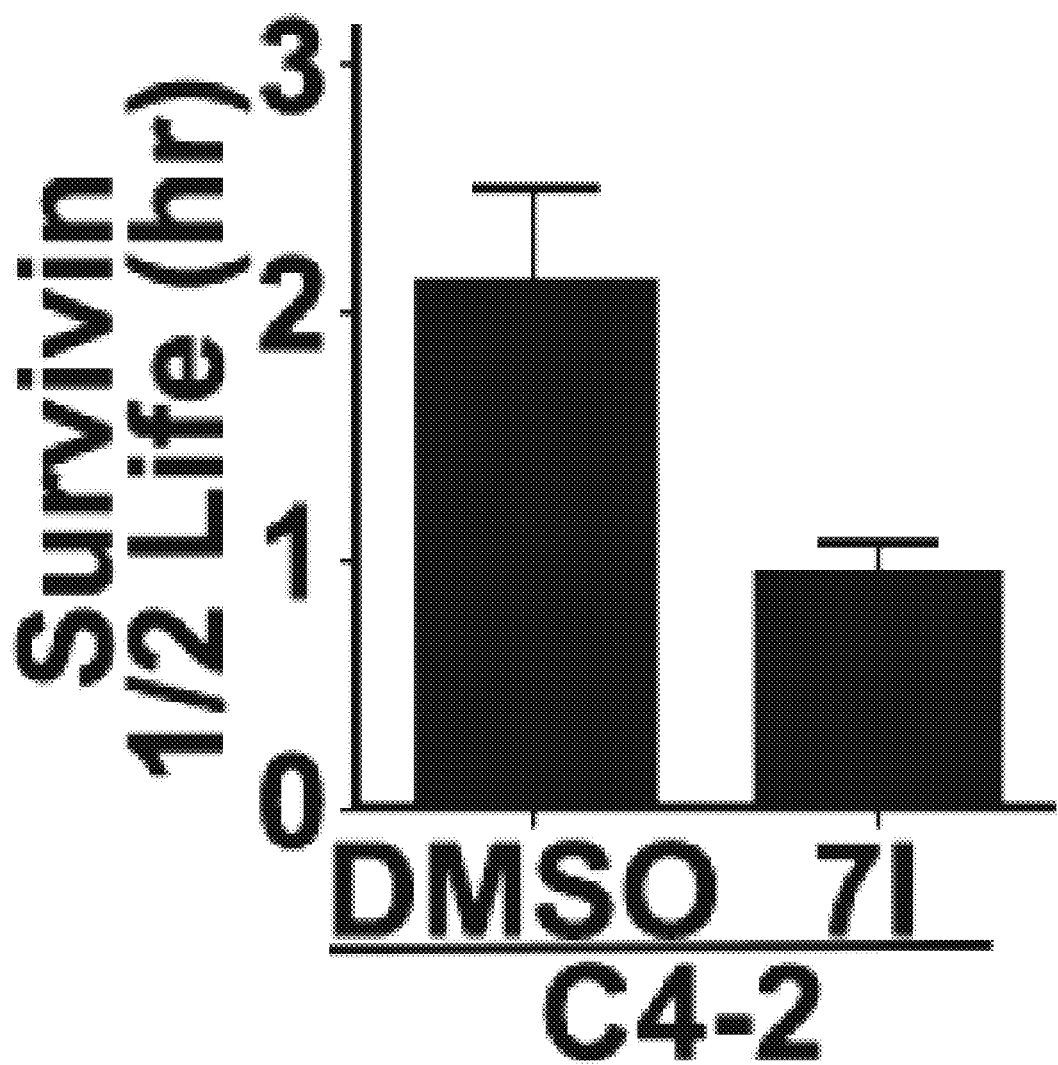
Figure 14C:
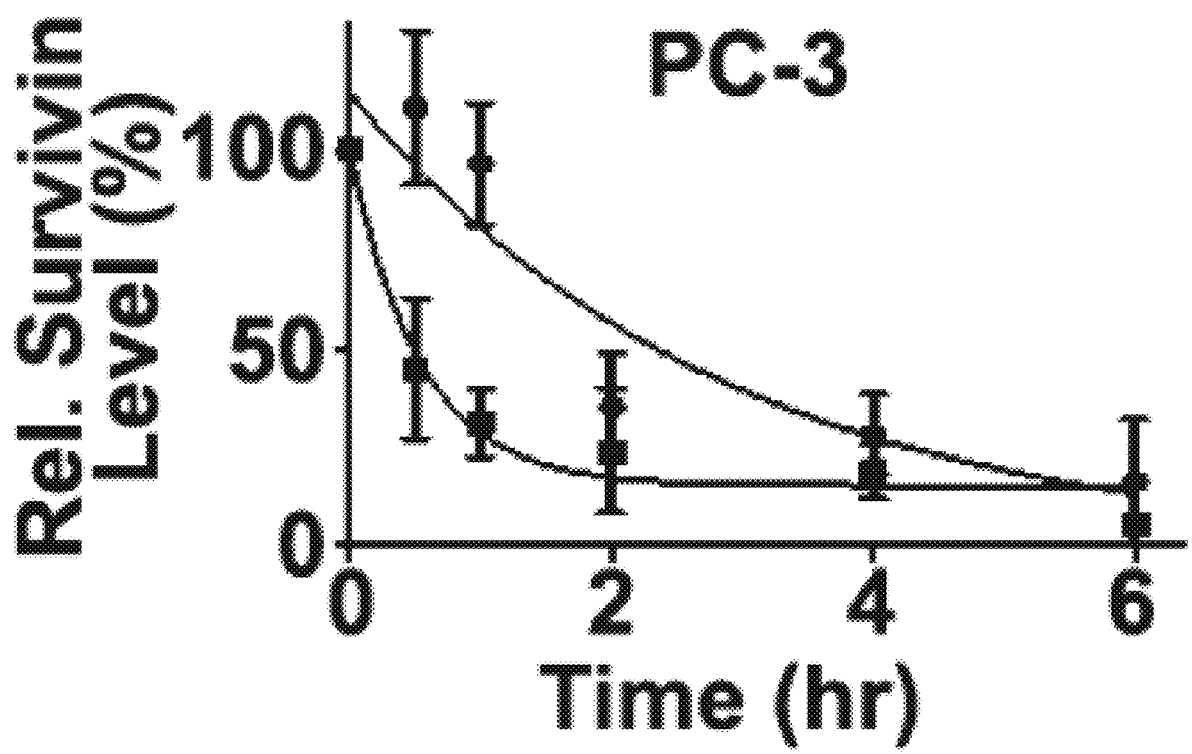
Figure 14C:
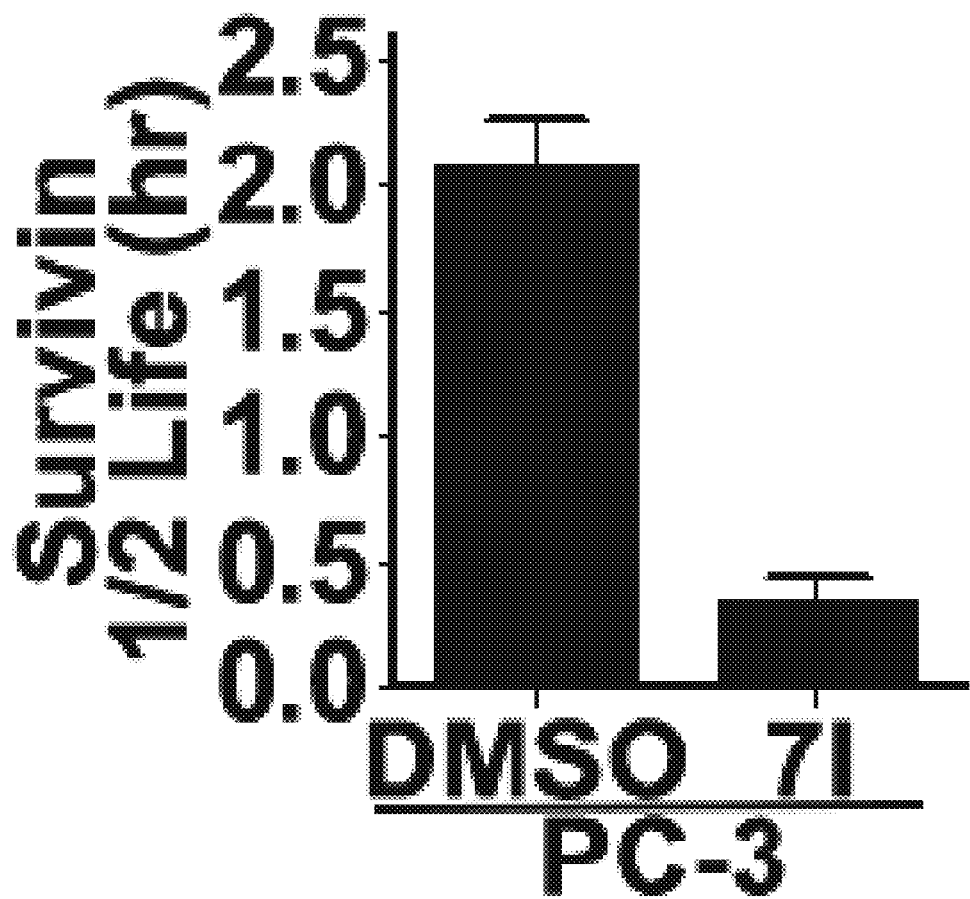

Selectivity of 7I. As discussed above, survivin belong to an IAP family of proteins. To ensure 7I is selective to survivin, we tested its effect on other members of the IAP family by taking advantage of its induction of target loss. For this purpose, we performed Western blot analysis to determine the expression level of other IAPs including XIAP, CIAP1, and CIAP2 in addition to survivin following 7I treatment of C4-2 and PC-3 cells. As shown in FIG. 13F, 7I treatment reduced the expression of survivin. However, it had no effect on the expression of XIAP, CIAP1, and CIAP2. Thus, 7I may be selective to its intended target survivin. 7I induces survivin degradation in a proteasome-dependent manner. Previously, it has been shown that the parent compound LQZ-7 induces survivin degradation via proteasome-dependent manner by inhibiting survivin dimerization. Because 7I inhibited survivin dimerization as shown above, we hypothesized that 7I will also induce survivin degradation. To test this hypothesis, we examined survivin expression level in C4-2 and PC-3 cells following 7I treatments. As shown in FIG. 14A, 7I treatments induced time-dependent survivin loss in both cell lines. We next performed a cycloheximide-chase experiment following 7I treatment to determine the half-life of survivin. As shown in FIG. 14B-C, the half-life of survivin was reduced from 2.2 and 2.3 hrs to 50 and 25 minutes in C4-2 and PC-3 cells, respectively, after 7I treatments. Thus, 7I induces survivin degradation in both cell lines.

Figure 3:
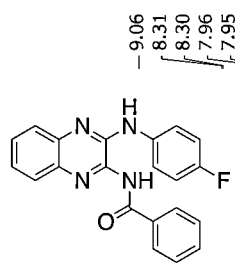
FIG. 3 shows the $^1$H or $^{13}$C NMR spectrum of the indicated compound.
Figure 3:
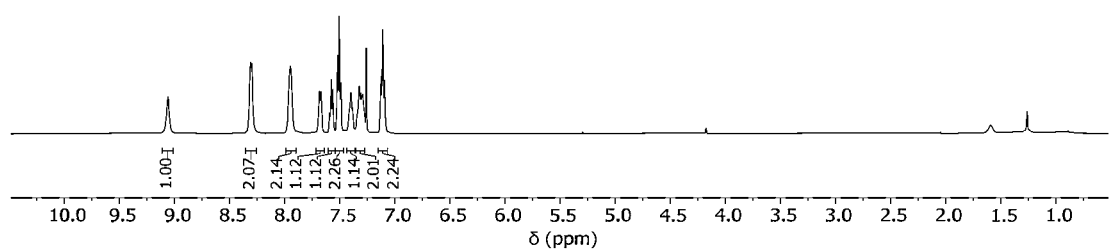
Figure 4:
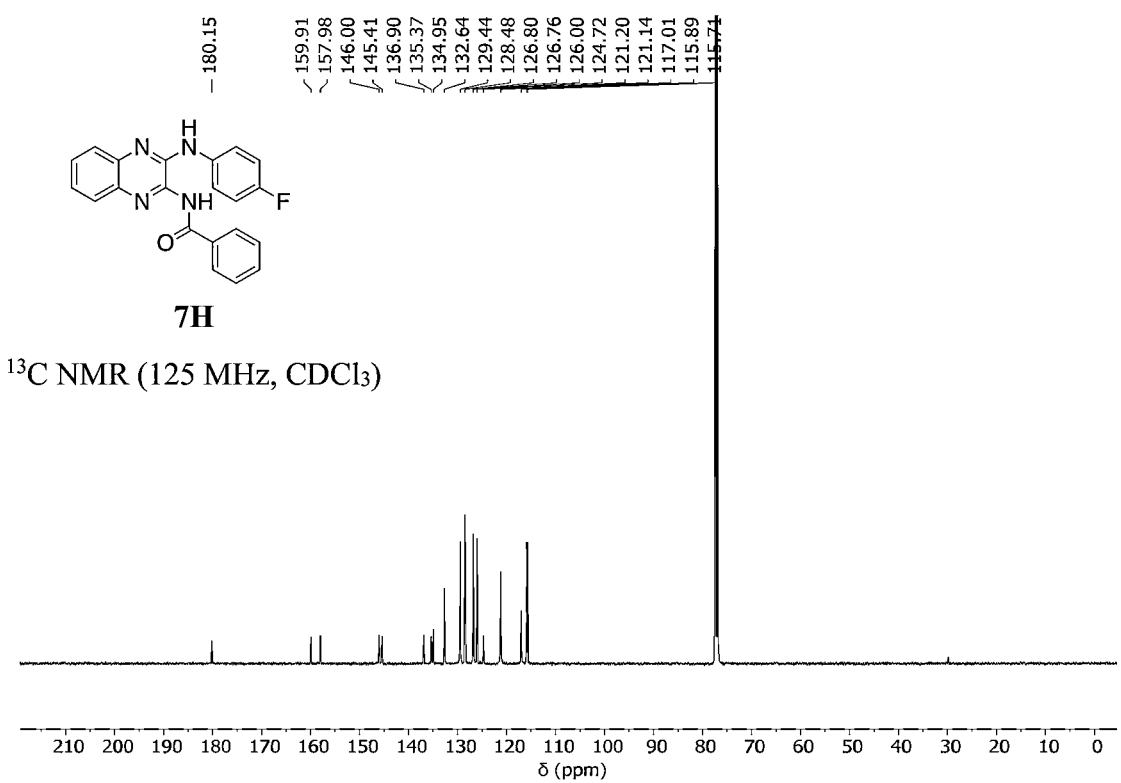
FIG. 4 shows the $^1$H or $^{13}$C NMR spectrum of the indicated compound.
Figure 5:
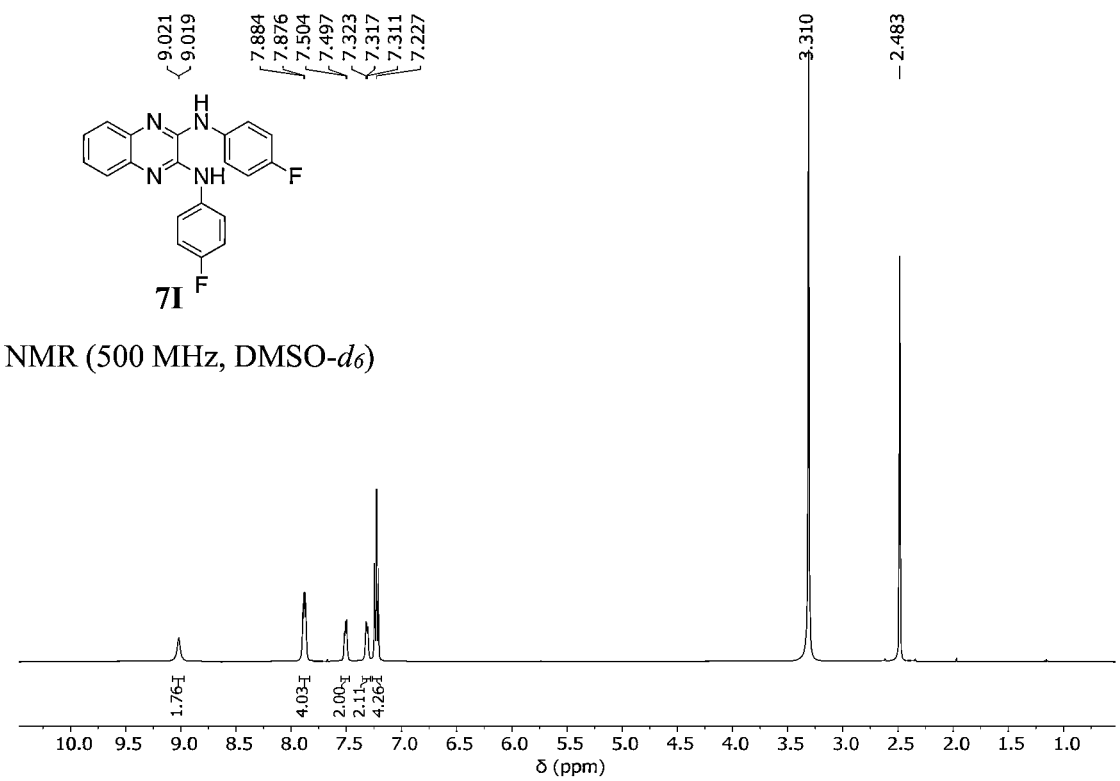
FIG. 5 shows the $^1$H or $^{13}$C NMR spectrum of the indicated compound.
Figure 6:
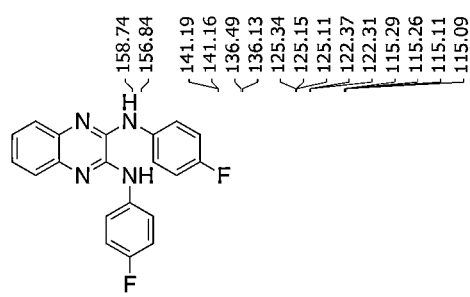
FIG. 6 shows the $^1$H or $^{13}$C NMR spectrum of the indicated compound.
Figure 6:
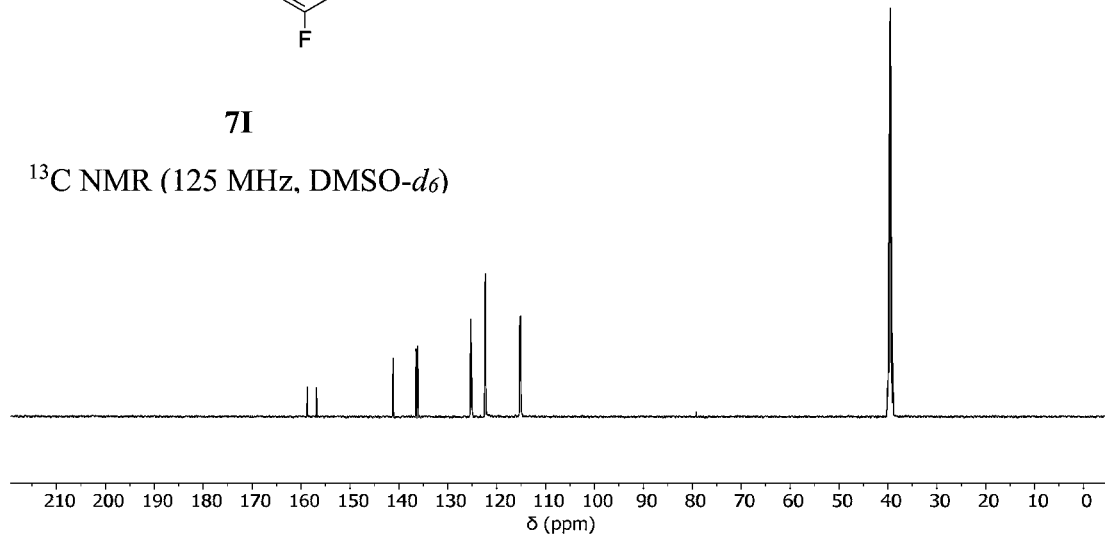
Figure 14D:
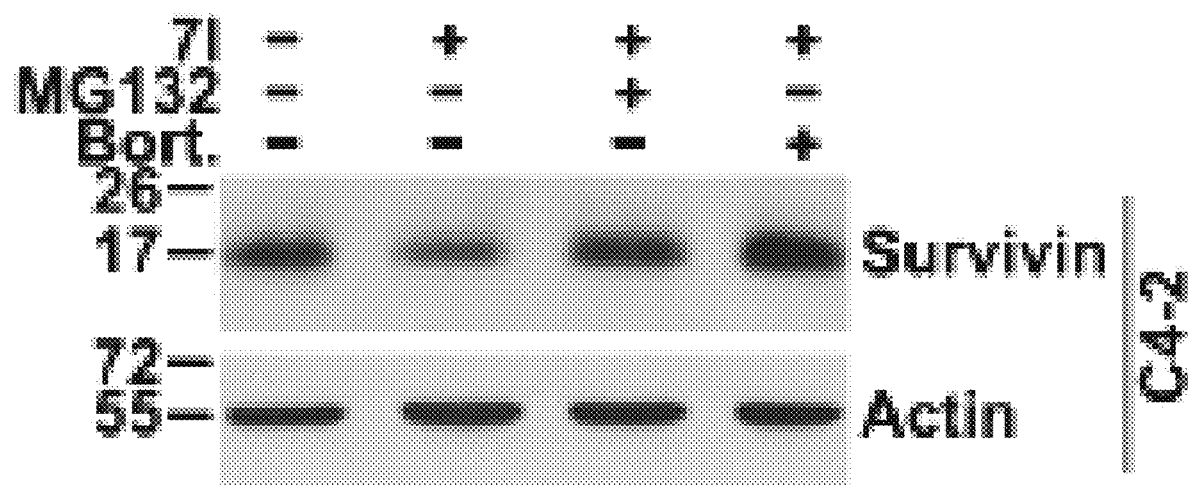
Figure 14D:
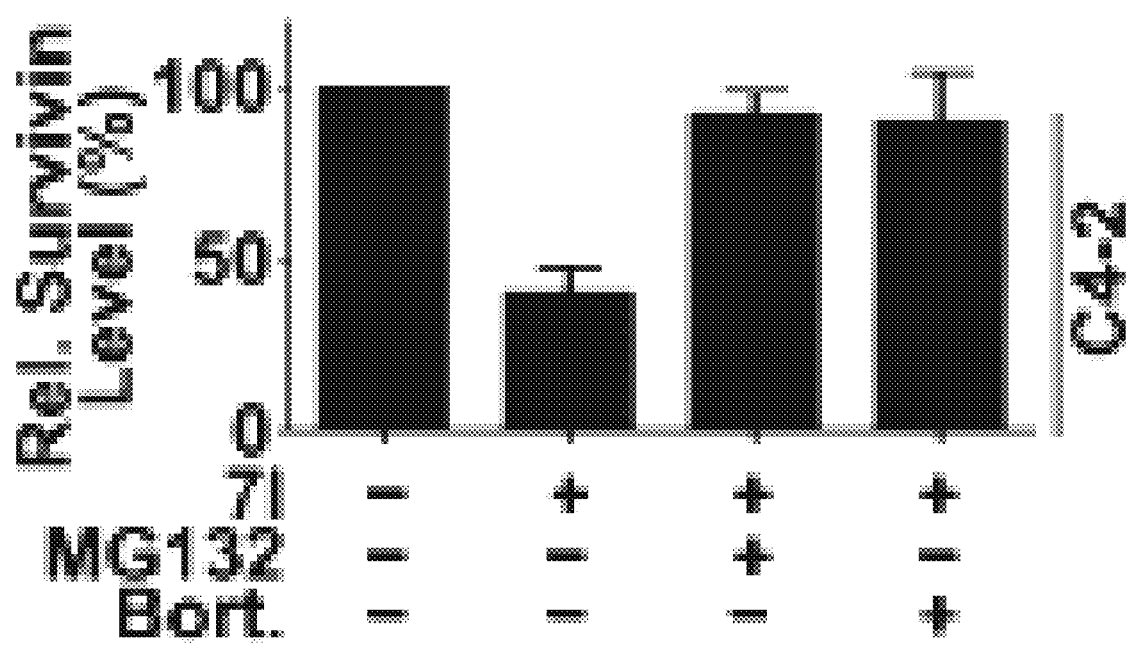
Figure 14D:
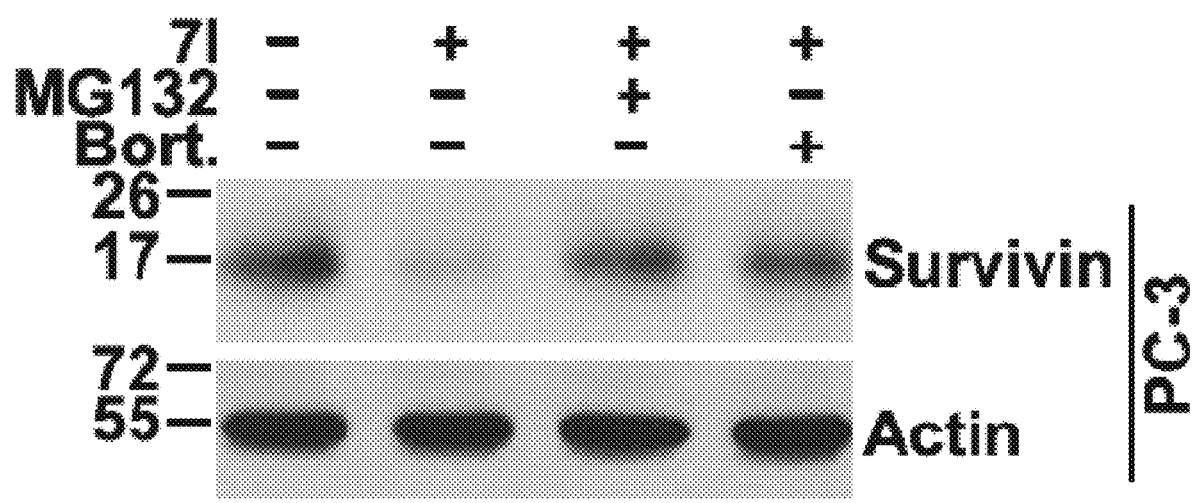
Figure 14D:
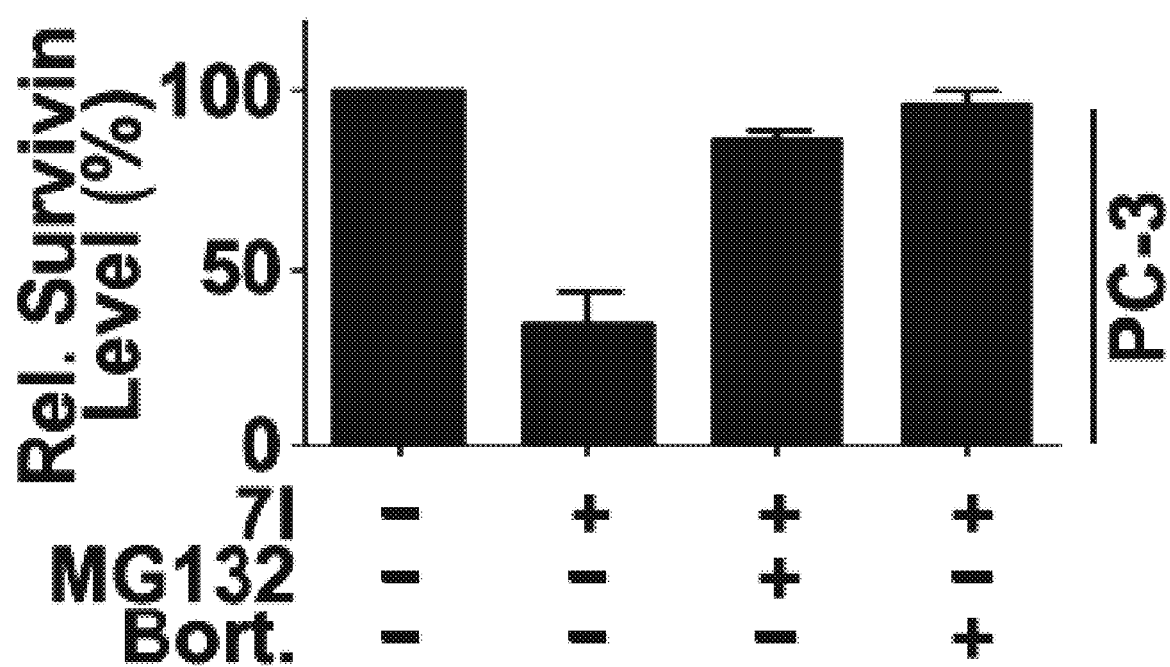
Figure 15A:
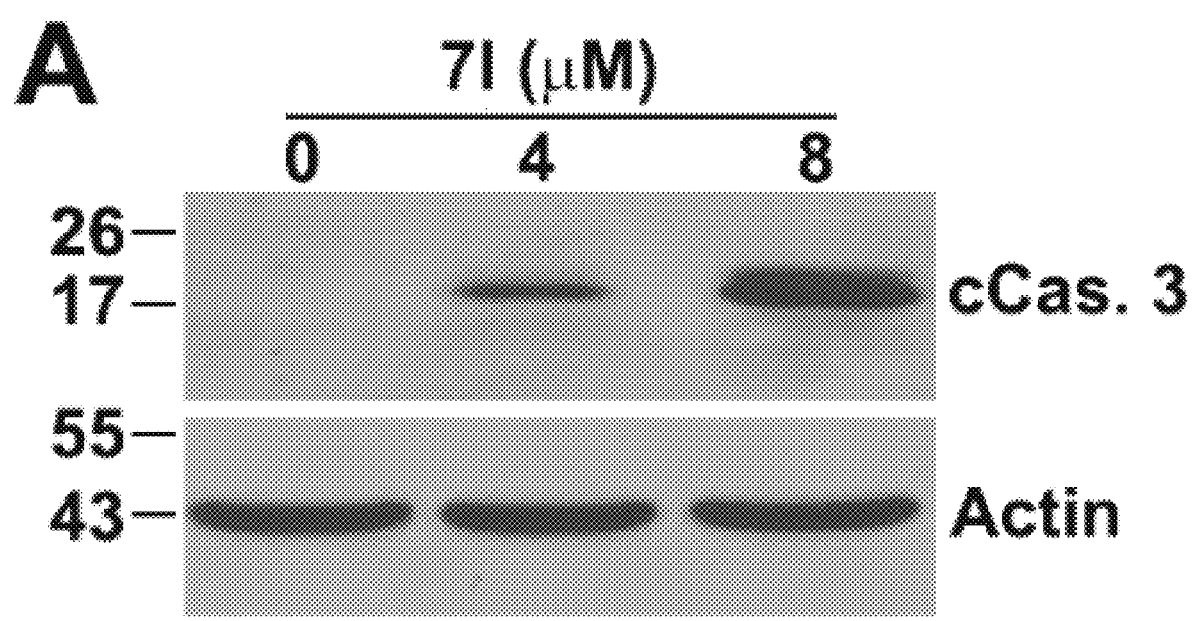
FIGS. 15A-15C show that 7I induces apoptosis.
Figure 15A:
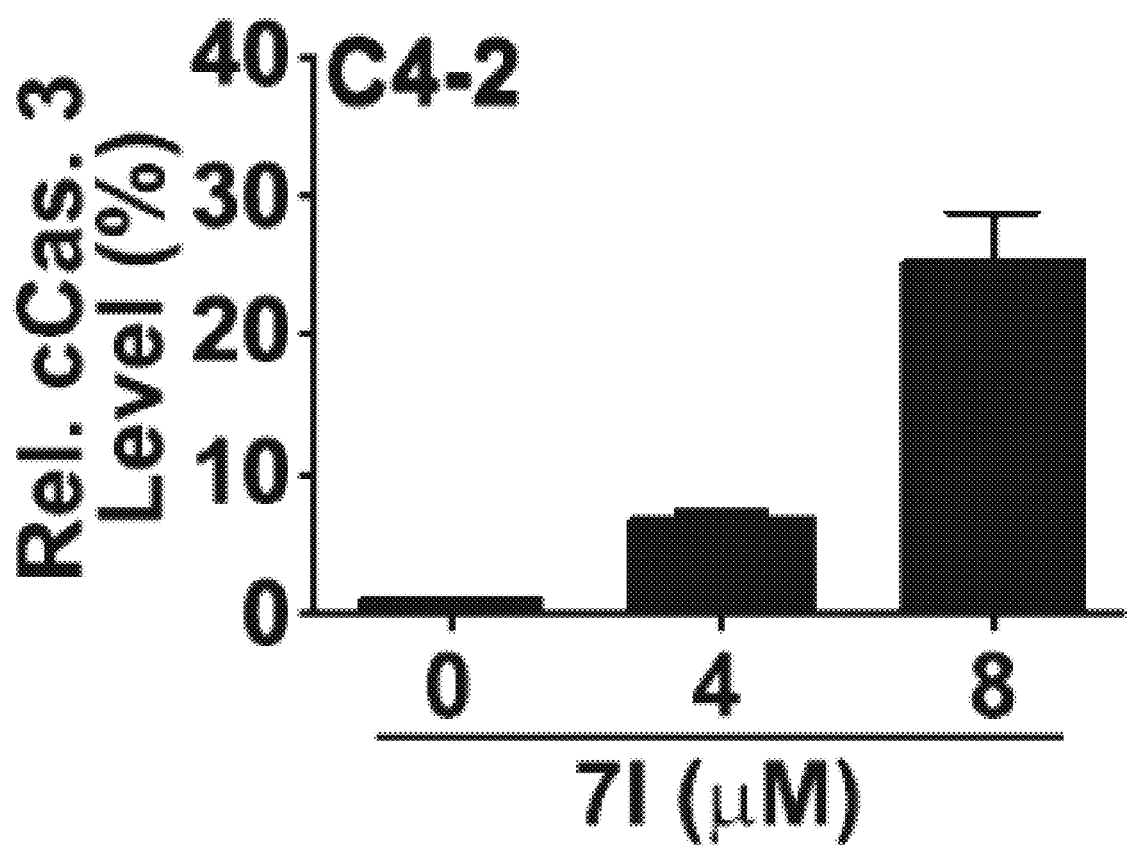
Figure 15B:
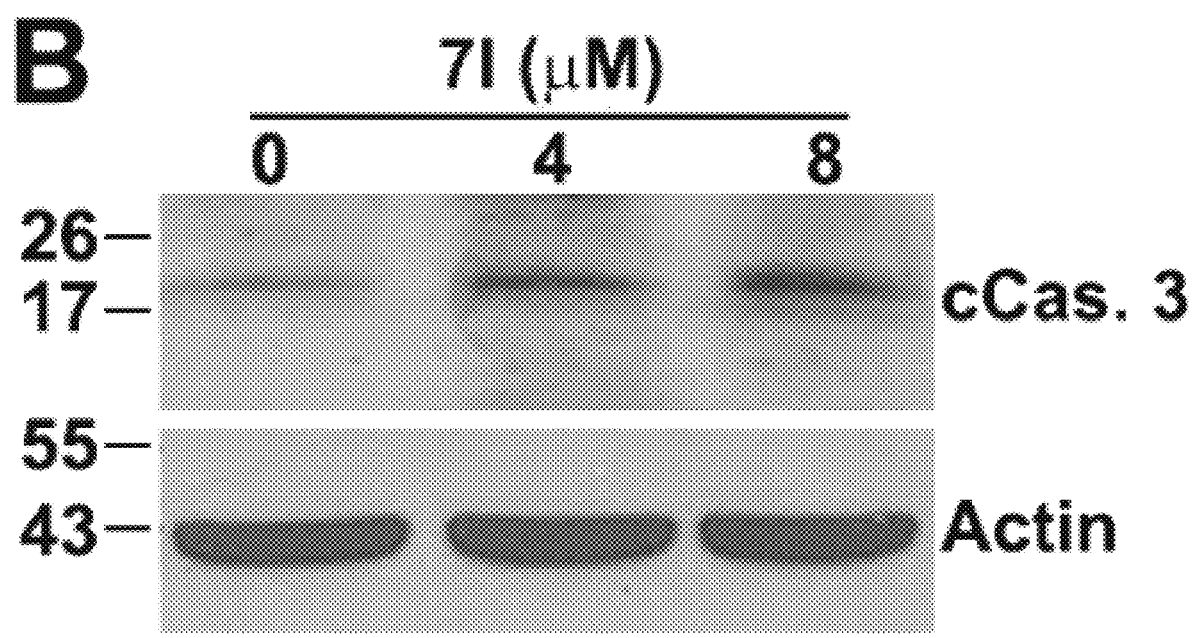
Figure 15B:
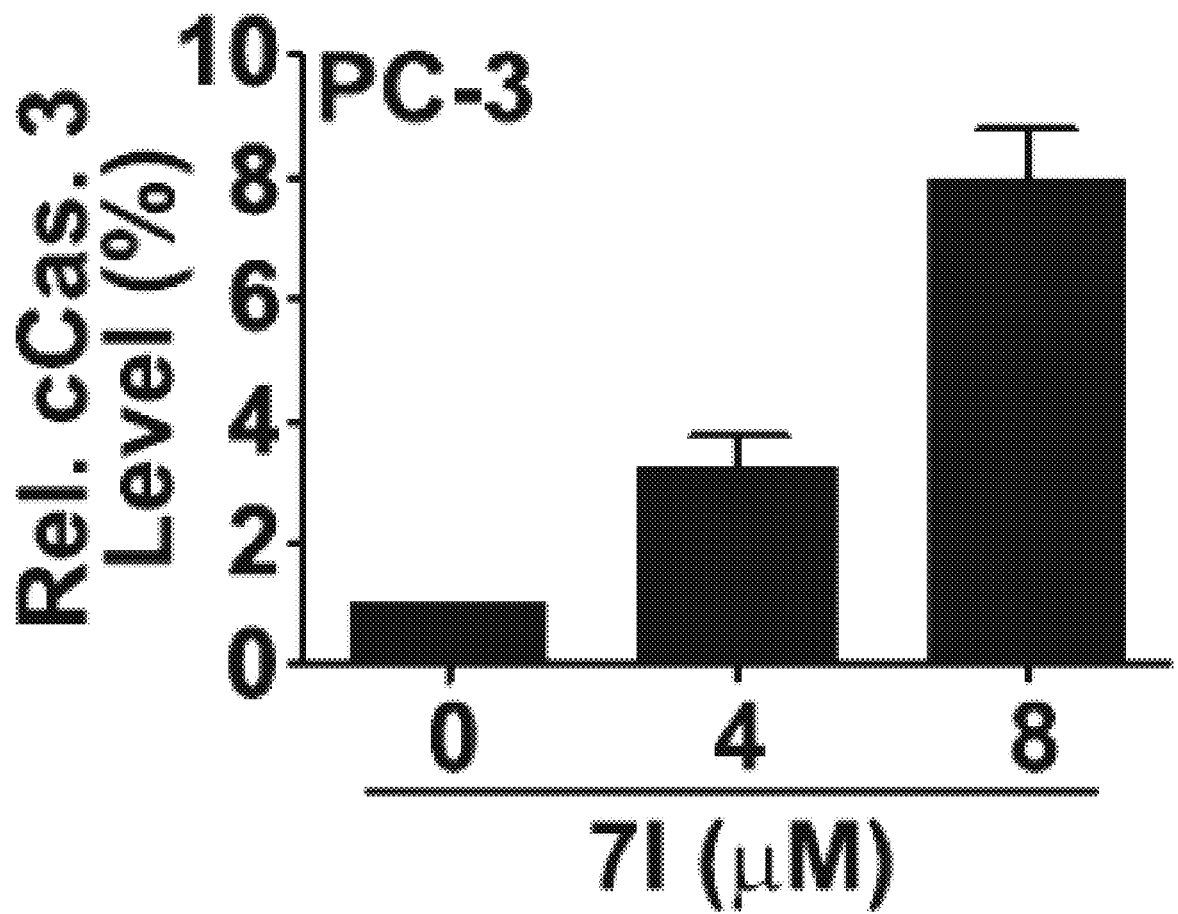
Figure 15C:
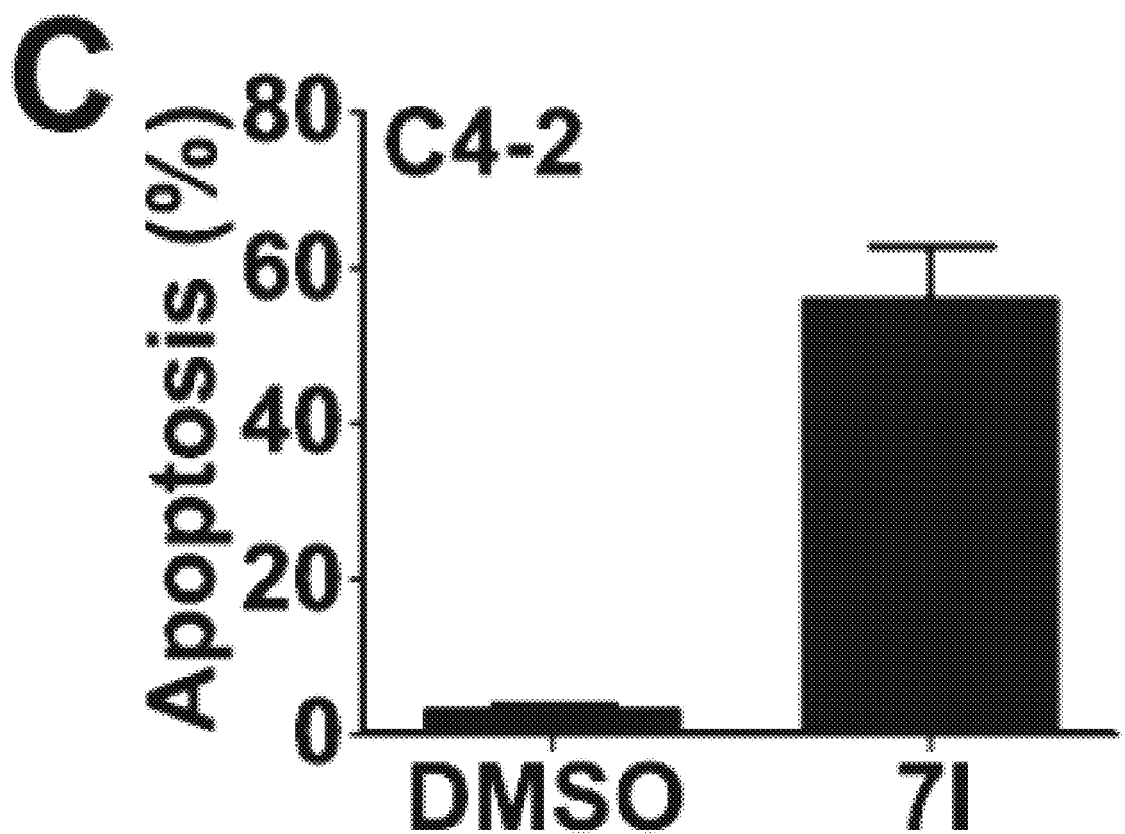
Figure 15C:
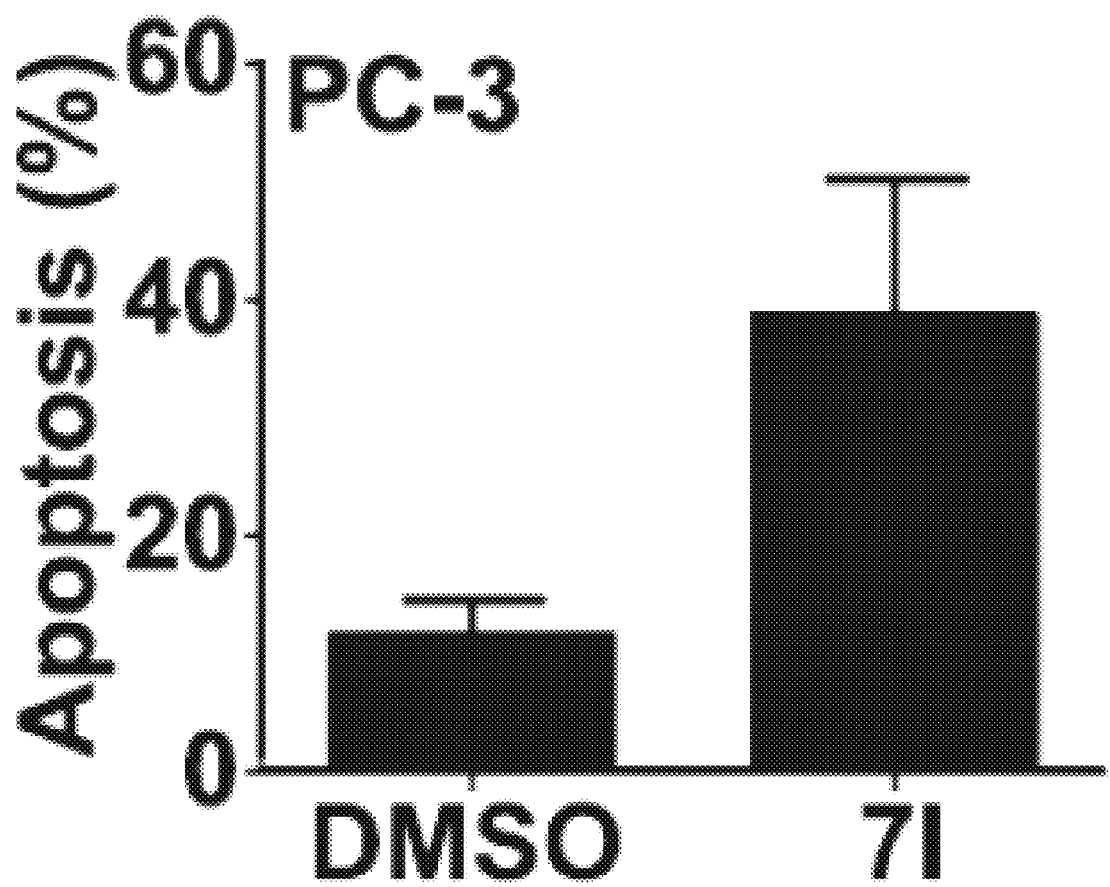
Figure 16A:
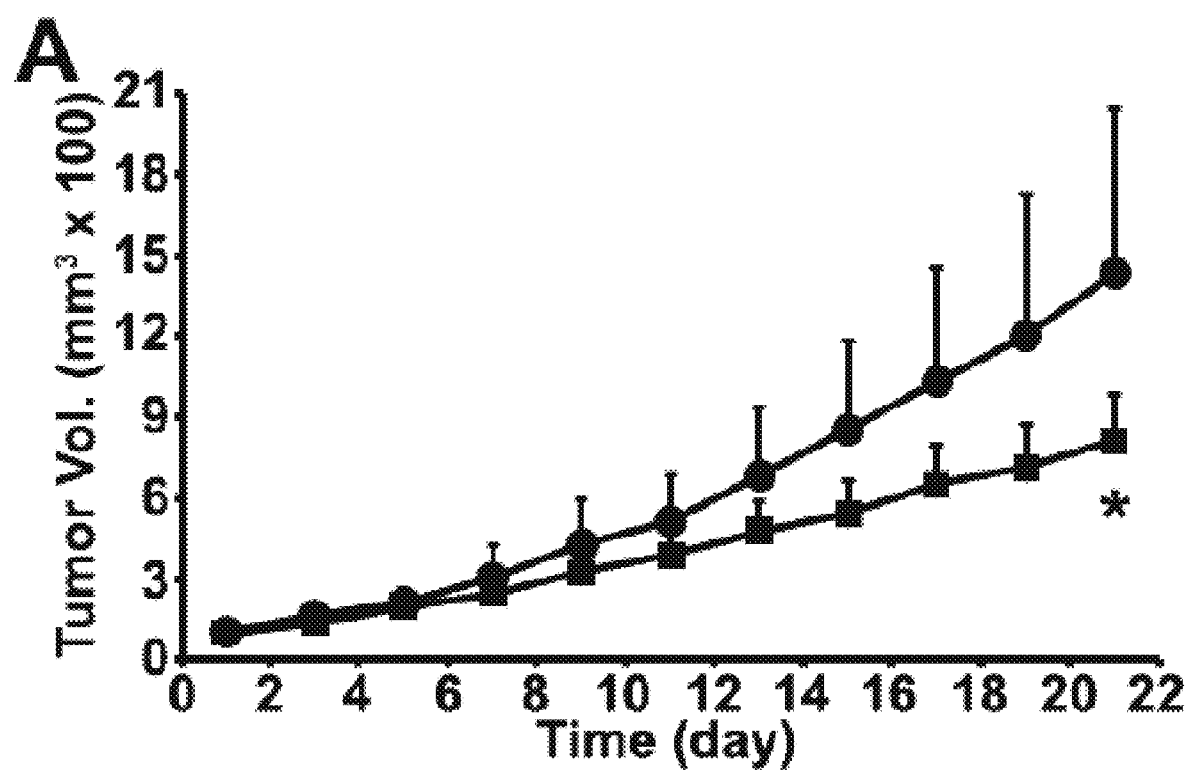
FIGS. 16A-16G show that 7I inhibits growth of PC-3 xenograft tumors by inhibiting surviving.
Figure 16B:
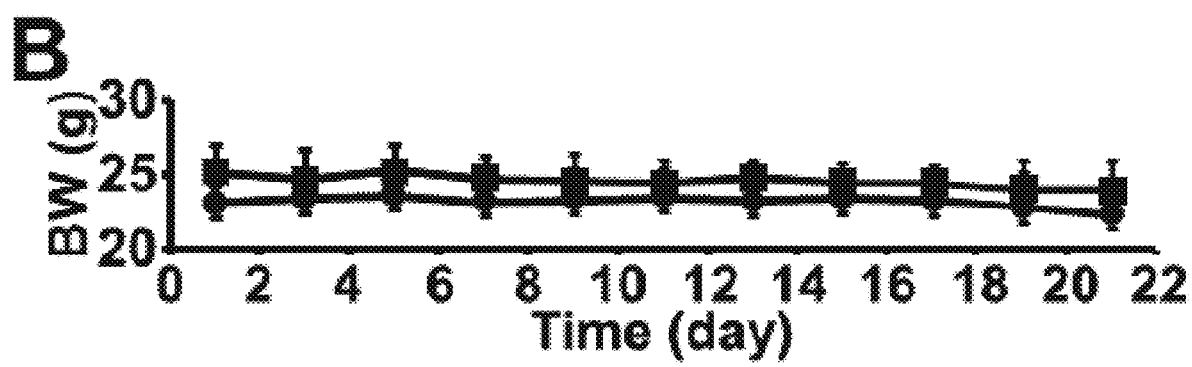
Figure 16C:
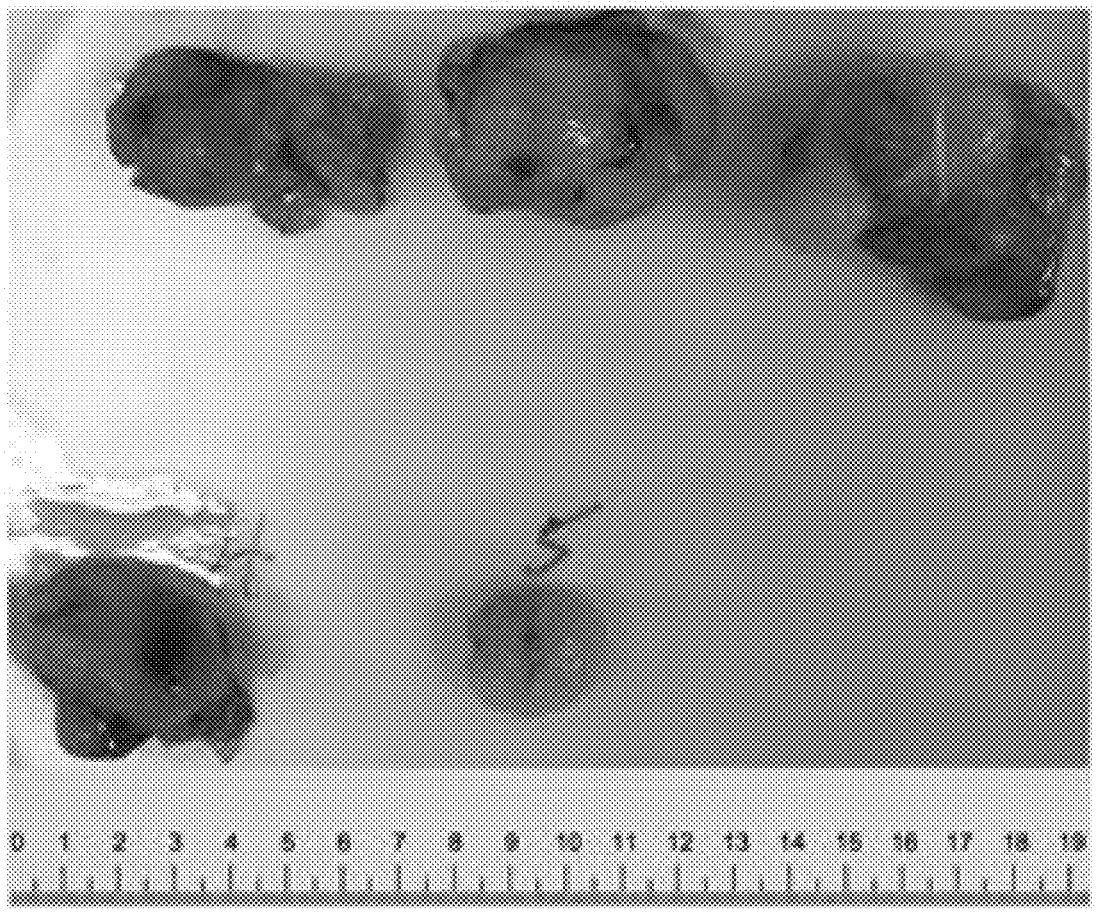
Figure 16C:
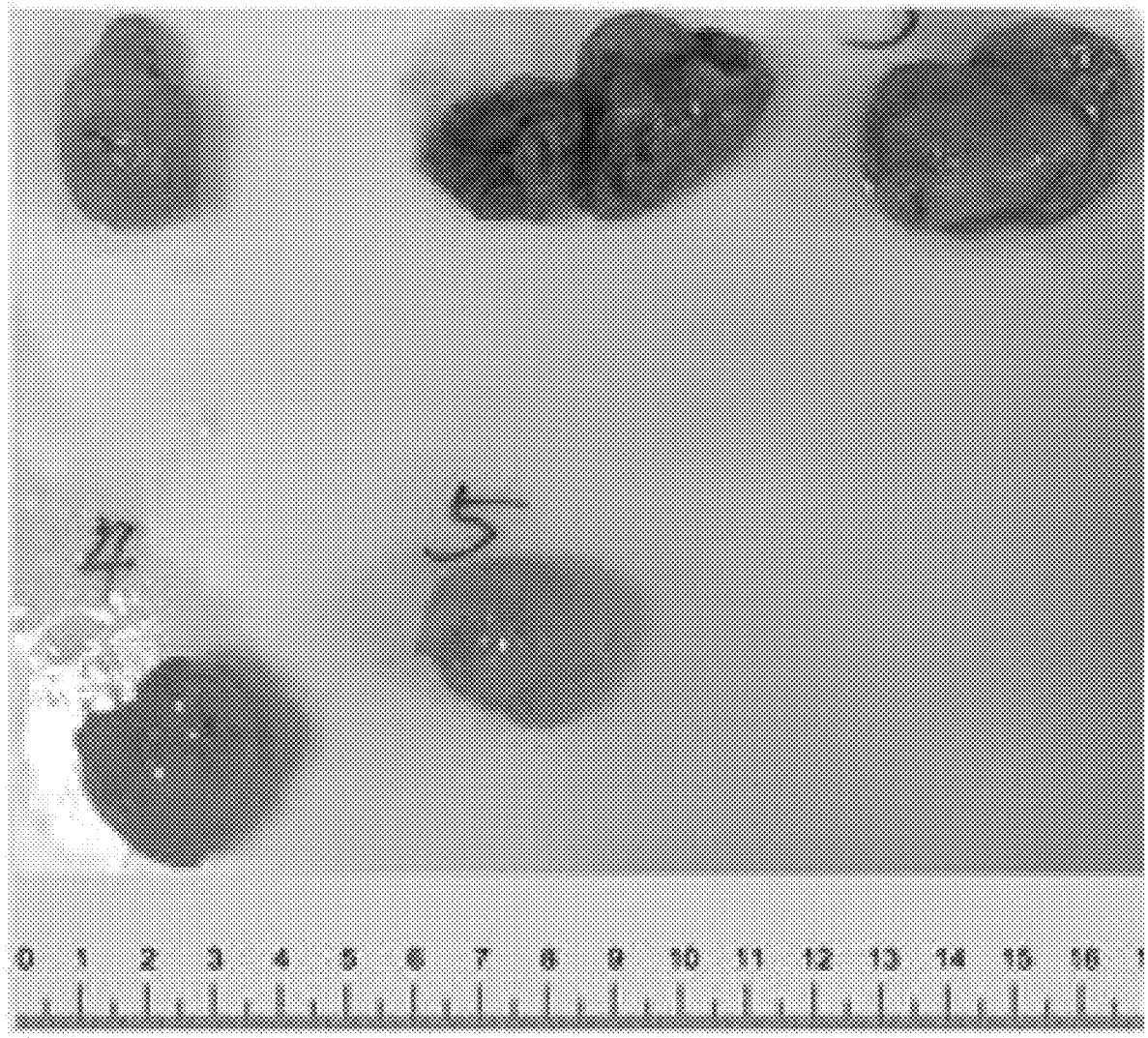
Figure 16D:
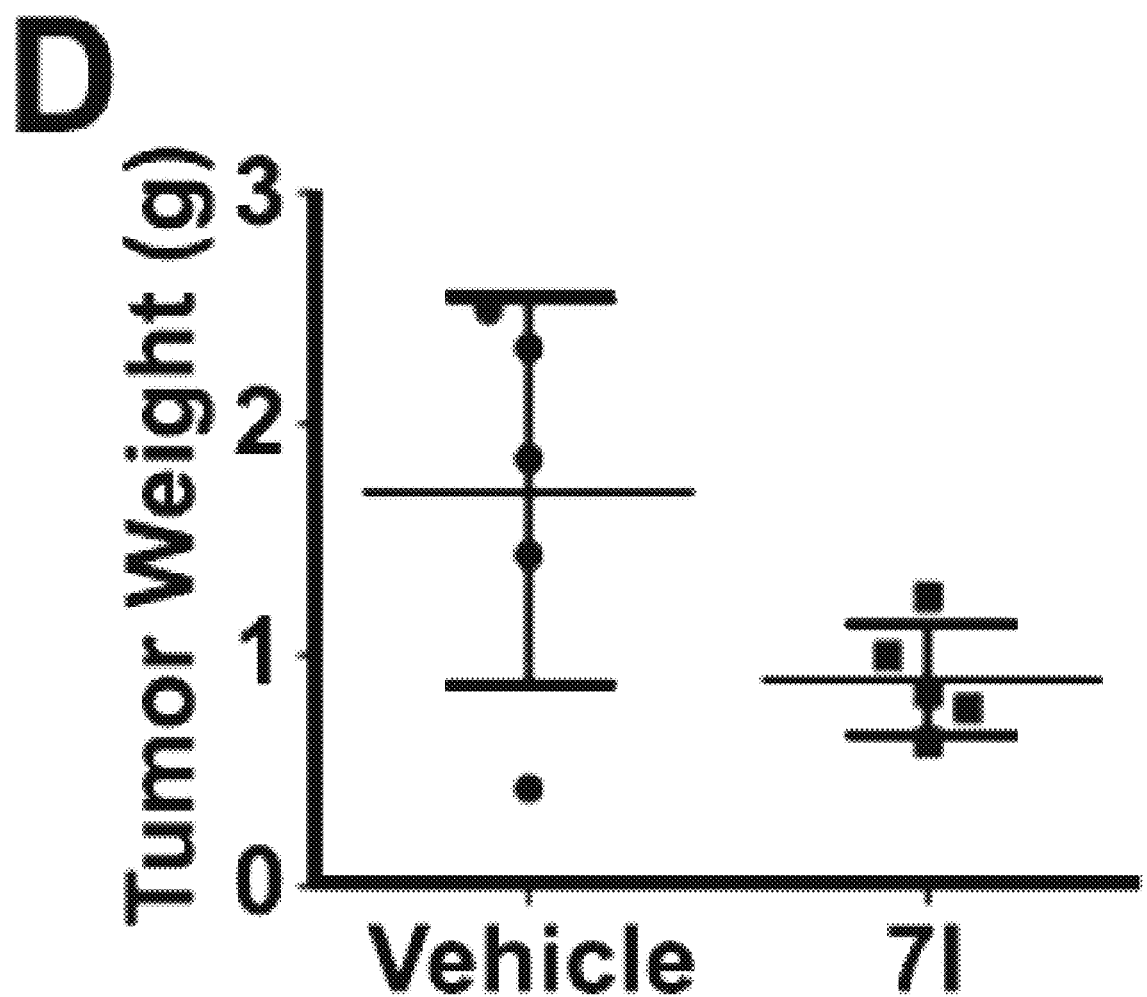
Figure 33:
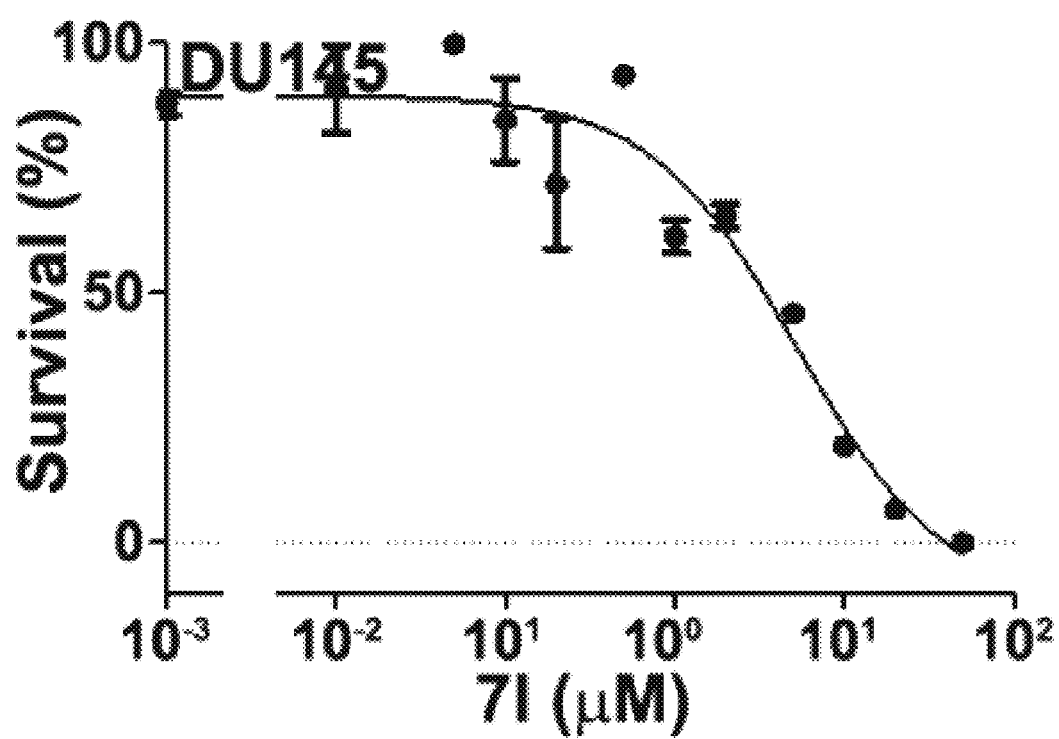
FIG. 33 shows a dose-response effect of 7I on survival of different human prostate cancer cells as determined using methylene blue assay.
Figure 33:
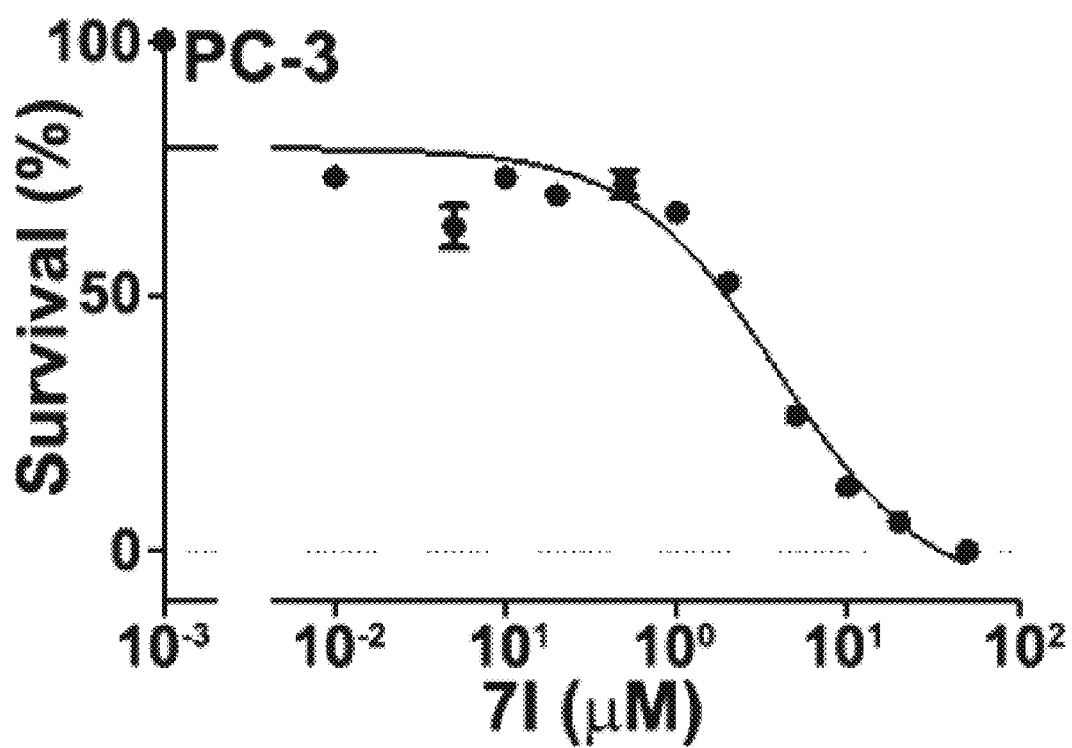
Figure 33:
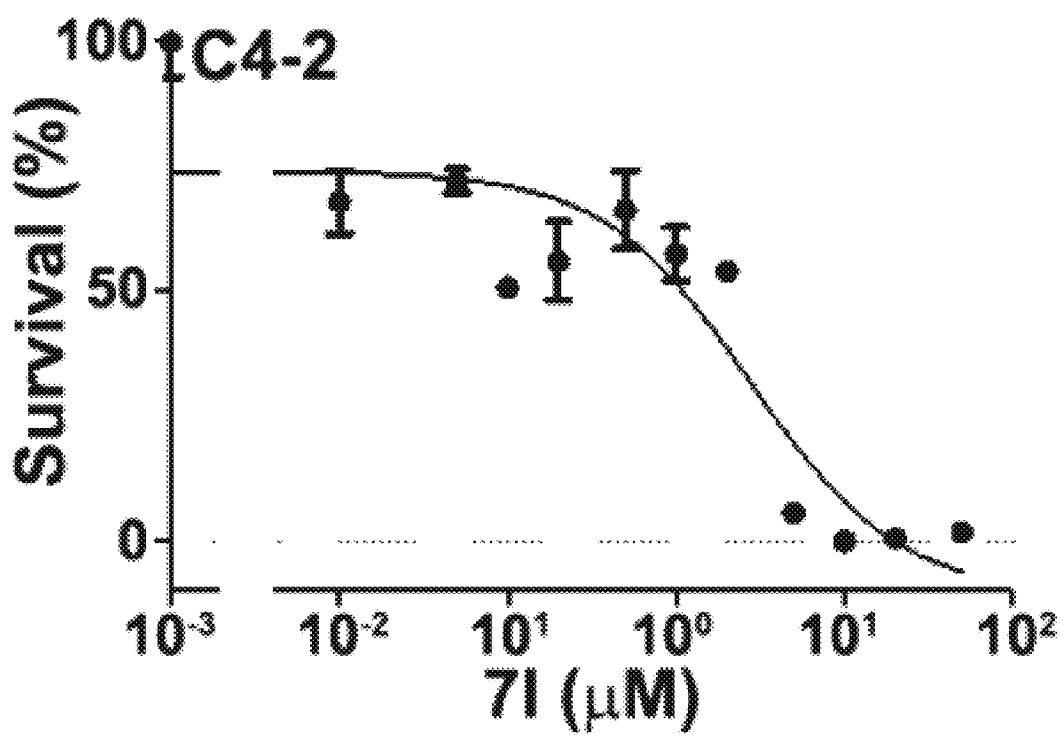
Figure 33:
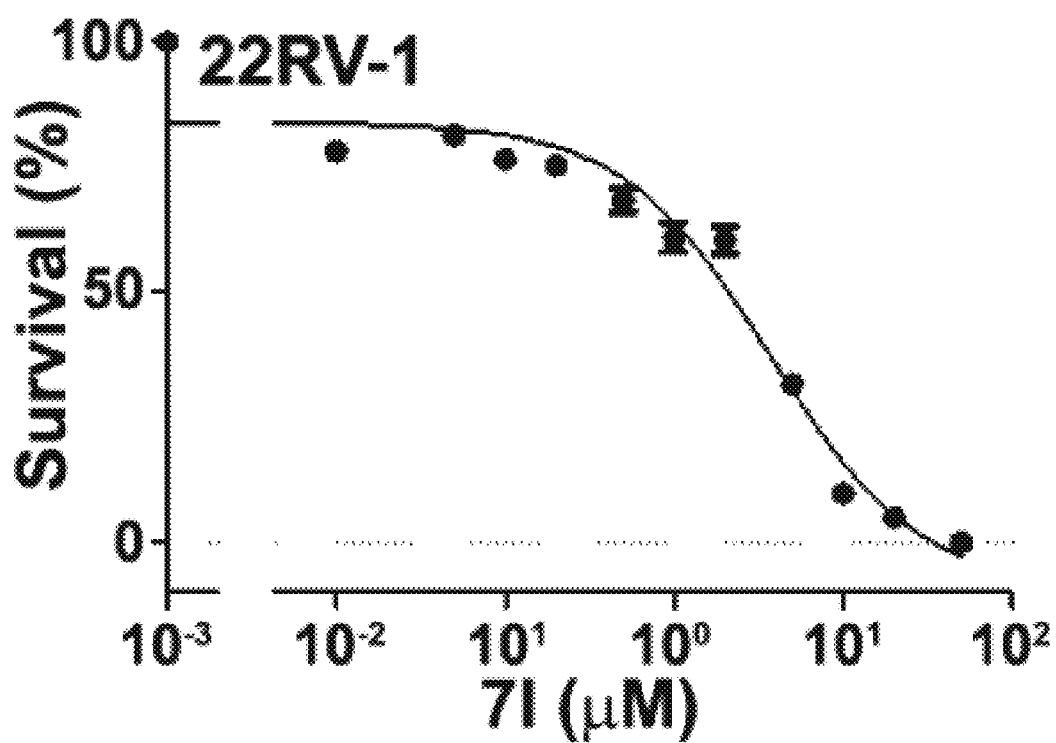
Figure 33:
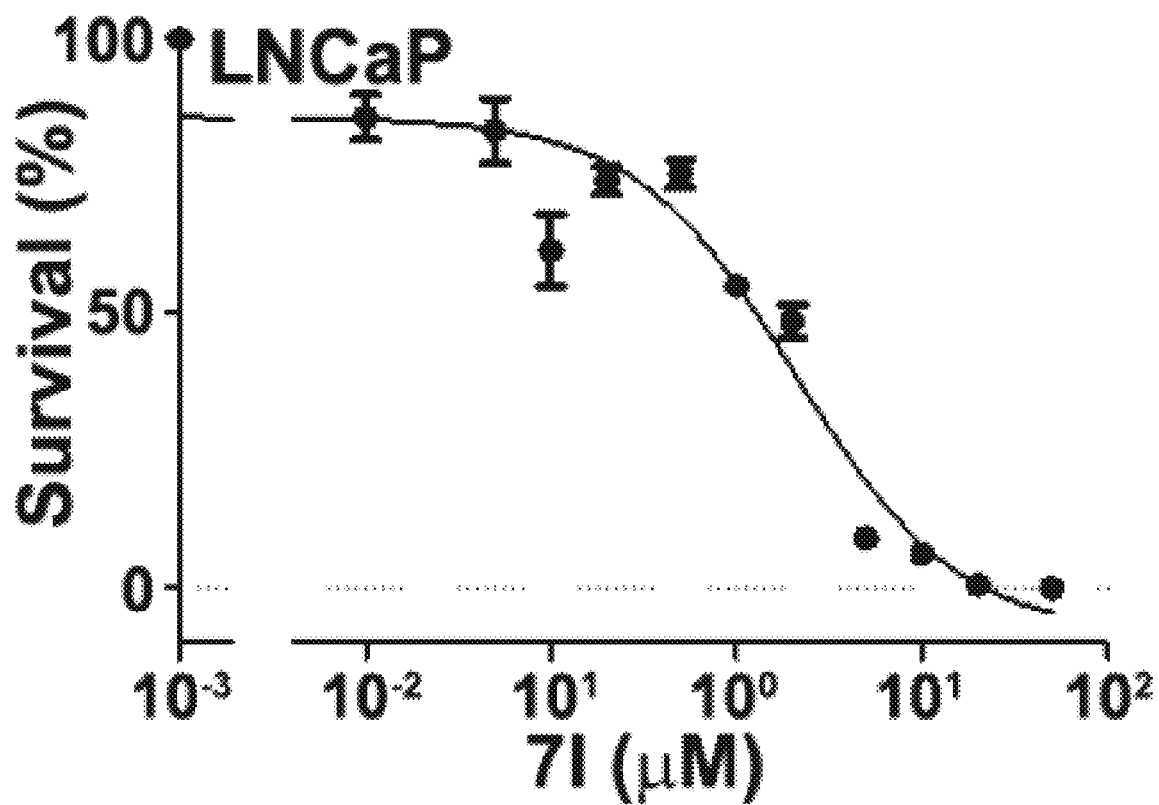
Figure 34:
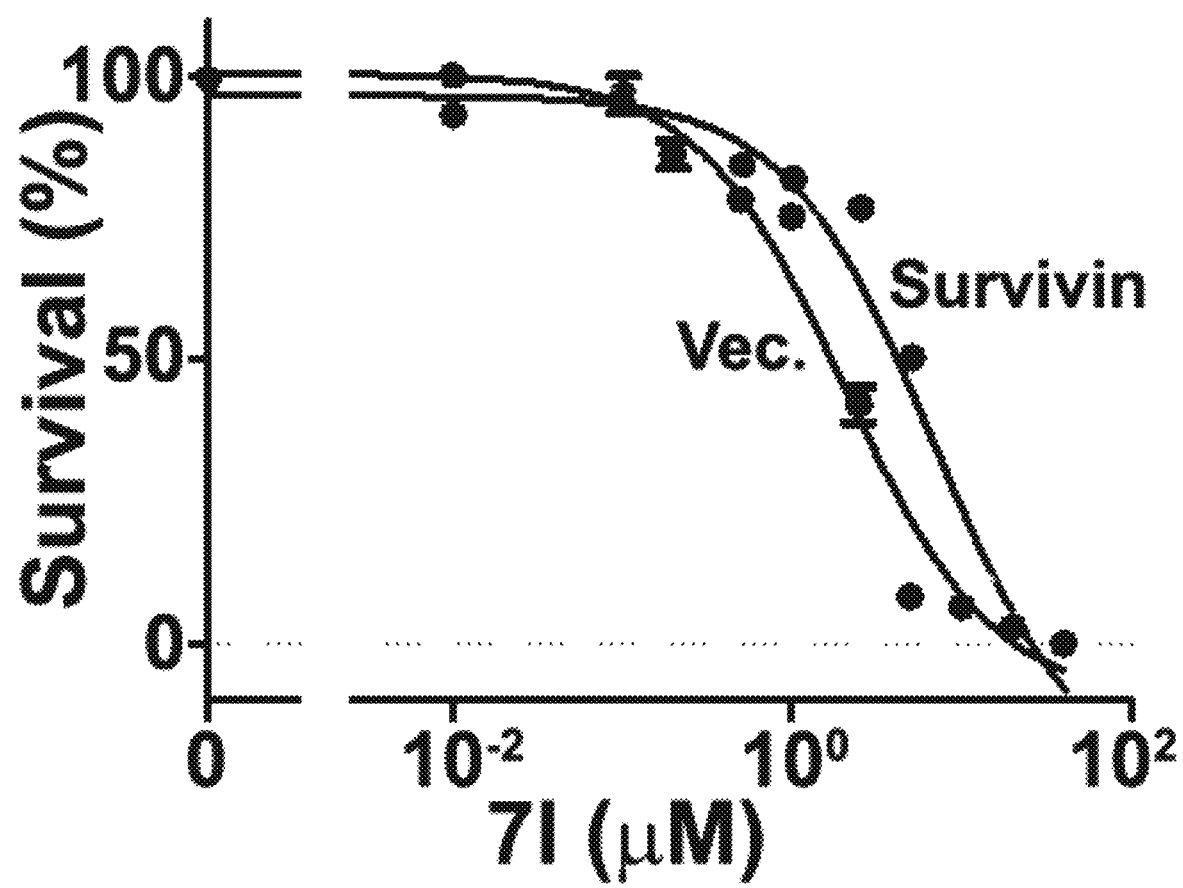
FIG. 34 shows a dose-response effect of 7I on survival of stable C4-2 cells over expressing surviving or transfected with vector (Vec) control as determined using methylene blue assay.
Figure 35:
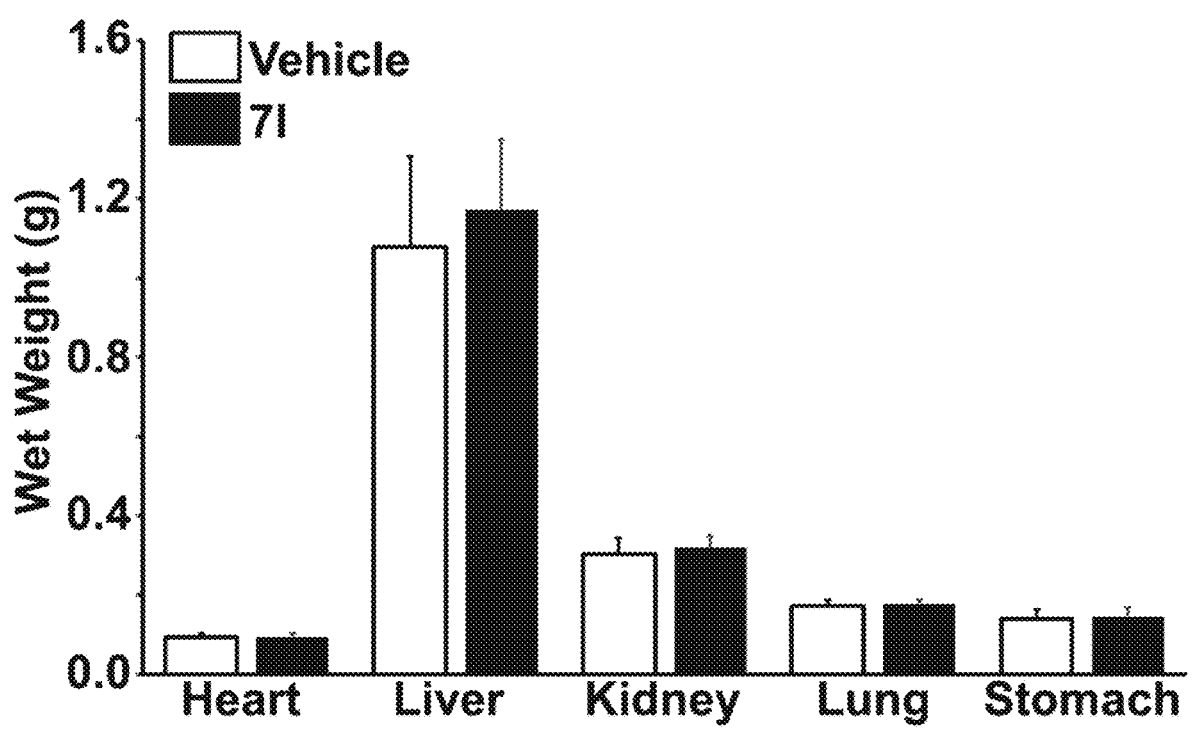
FIG. 35 shows the mean net weight of major organs in mice treated with control vehicle or 7I.

To determine if 7I-induced survivin degradation occurs in proteasome, we performed a rescue experiment by pre-treating cells using proteasome inhibitors MG132 and bortezomib for 1 hr prior to 7I treatment. As shown in FIG. 14D, both MG132 and bortezomib significantly reversed 7I-induced survivin loss. Thus, 7I likely induces survivin degradation via proteasome. 7I induces apoptosis. It has been shown previously that depleting survivin or inhibiting survivin using dominant negative forms of survivin cause spontaneous apoptosis in cancer cells (ref) and that the parent compound LQZ-7 also induces apoptosis. We next tested if 7I would induce apoptosis by inhibiting survivin. For this purpose, we first performed Western blot analysis of cleaved caspase 3 in C4-2 and PC-3 cells following 7I treatments. As shown in FIG. 15A-B, 7I induced cleavage of caspase 3 in a dose dependent manner in both cell lines. We also performed annexin V staining of C4-2 and PC-3 cells as another indicator of apoptosis following 7I treatments. As shown in FIG. 15C, 3 µM 7I induced ~48% and ~39% apoptosis in C4-2 and PC-3 cells, respectively. 7I inhibits growth of PC-3 xenograft tumors by inhibiting survivin. We next determined if 7I is active in suppressing tumor growth in vivo using a PC-3 xenograft model. As shown in FIG. 16A, 7I treatment at 100 mg/kg significantly suppressed tumor growth without any remarkable adverse effect on the mice as indicated by lacking changes in body weight (FIG. 17B) and in wet weight of major organs at the end of the study (FIG. 33). The xenograft tumors in the 7I-treatment group trended to be smaller and pale in color than the control group (FIG. 16C-D). Thus, 7I may be effective in inhibiting tumor growth with little toxicity.

Figure 16E:
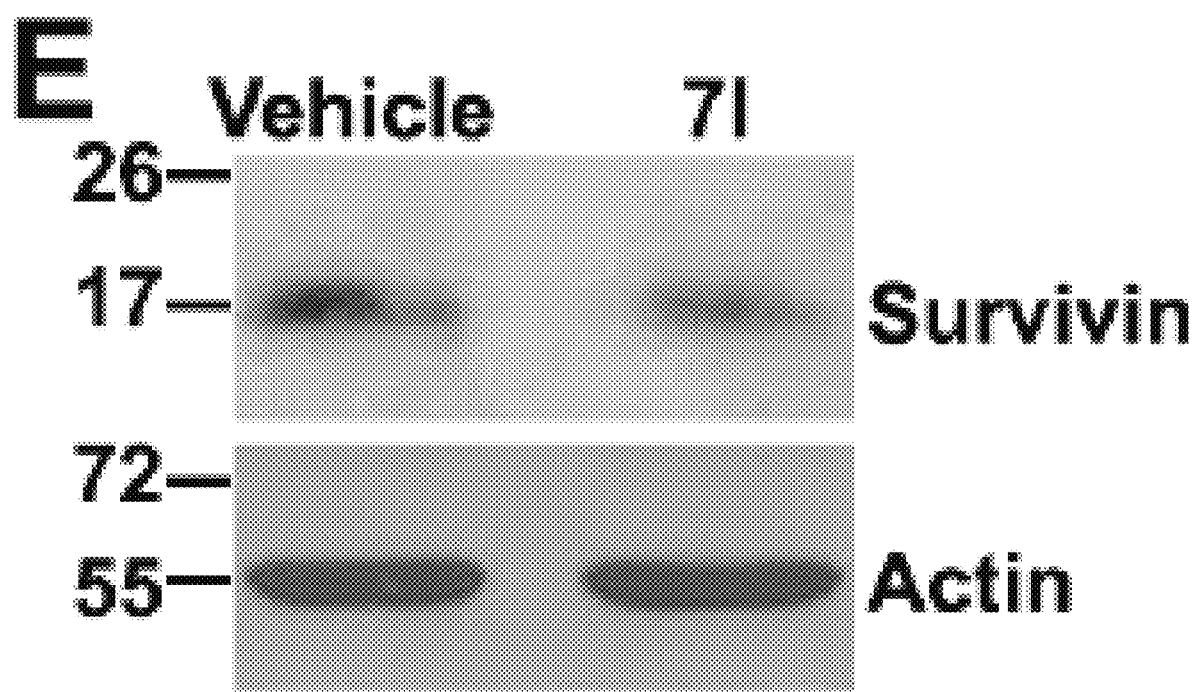
Figure 16F:
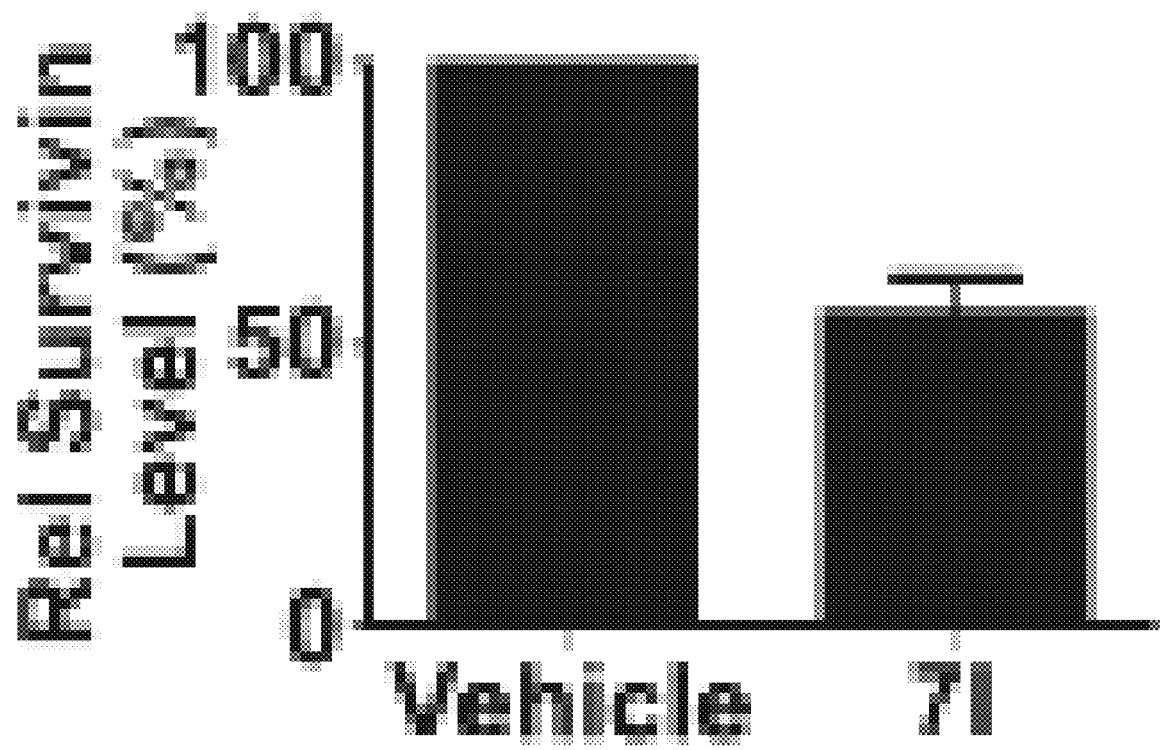
Figure 16G:
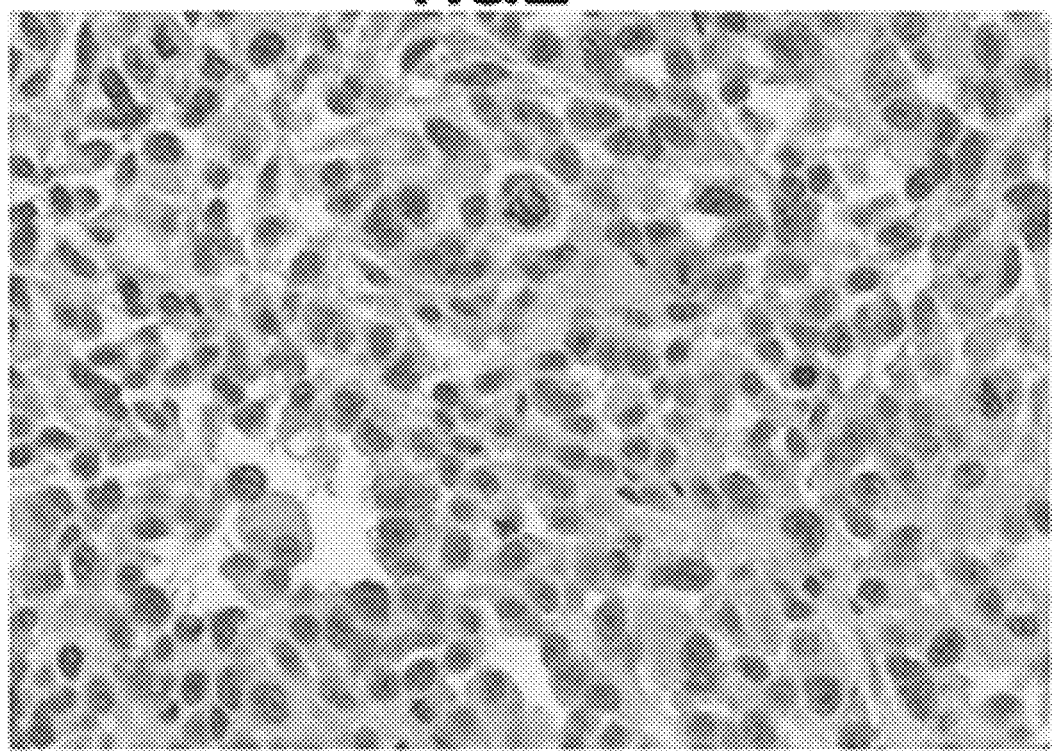
Figure 16G:
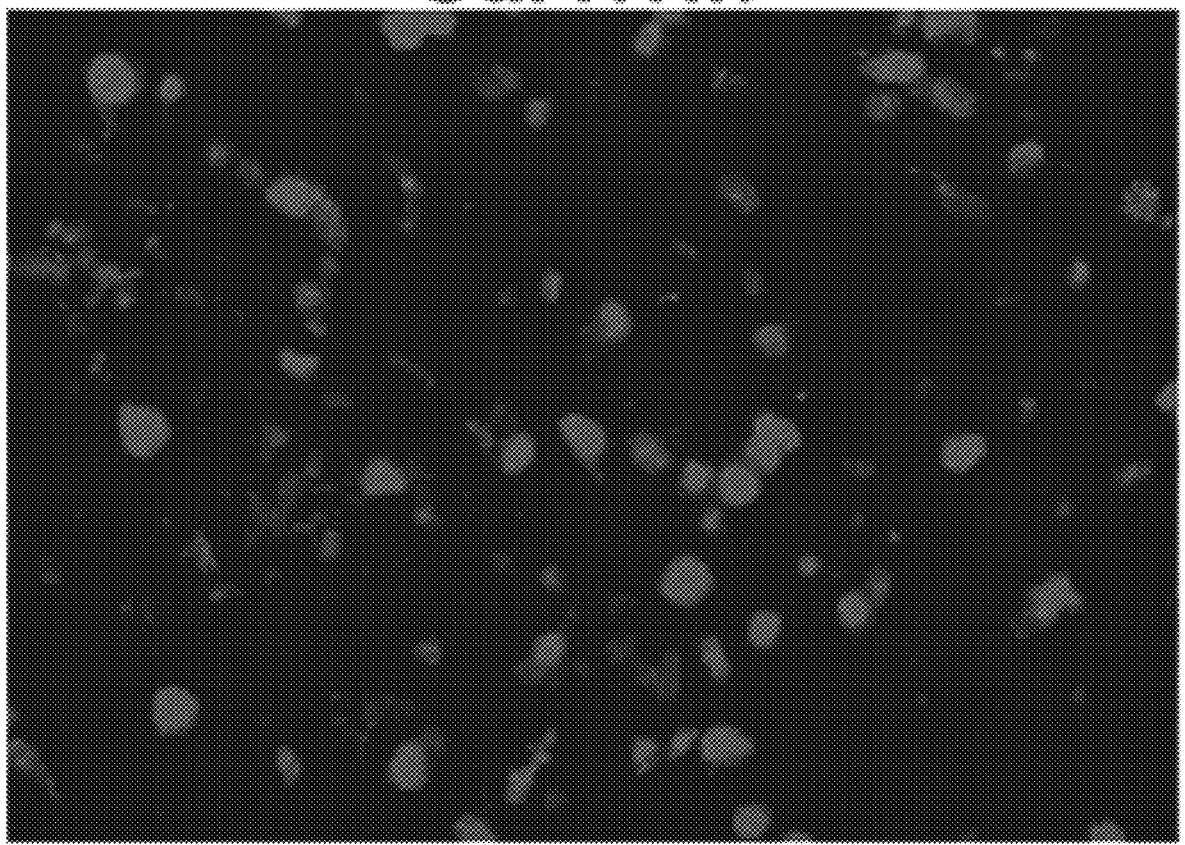
Figure 16G:
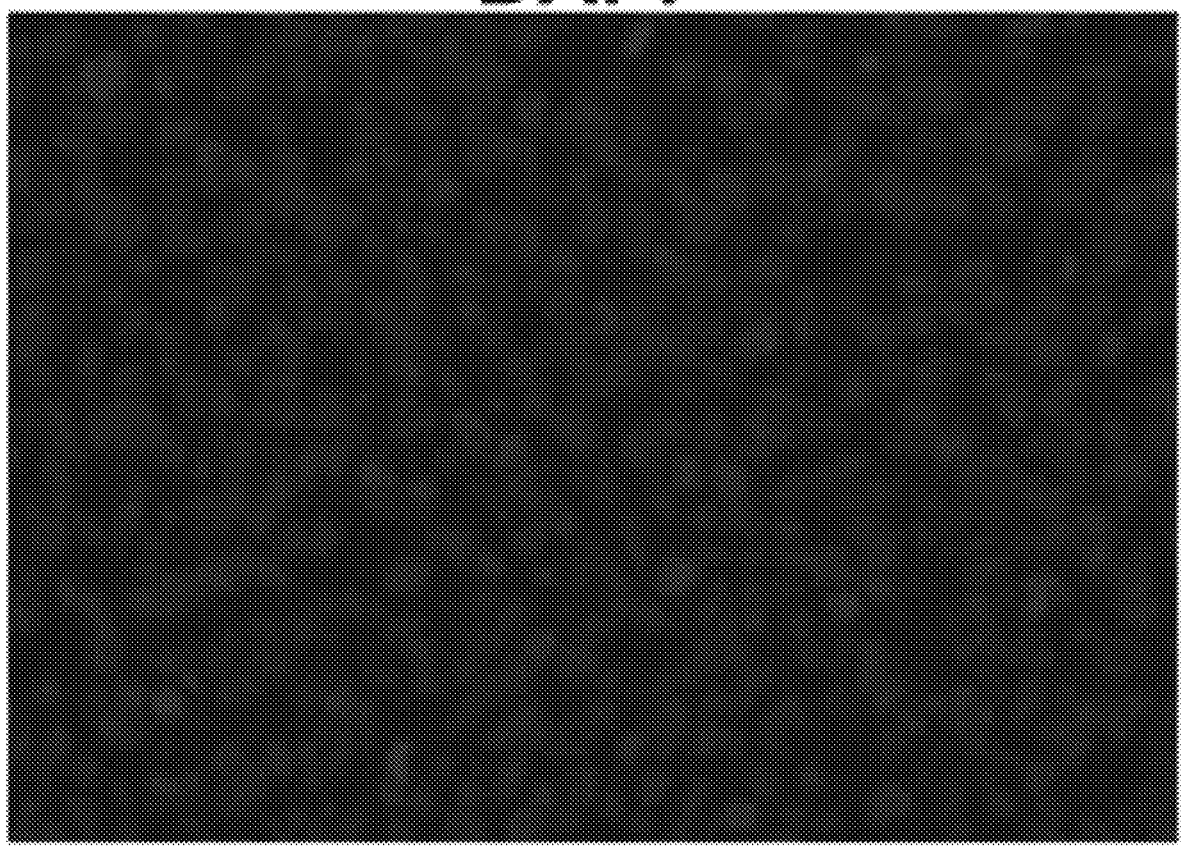
Figure 16G:
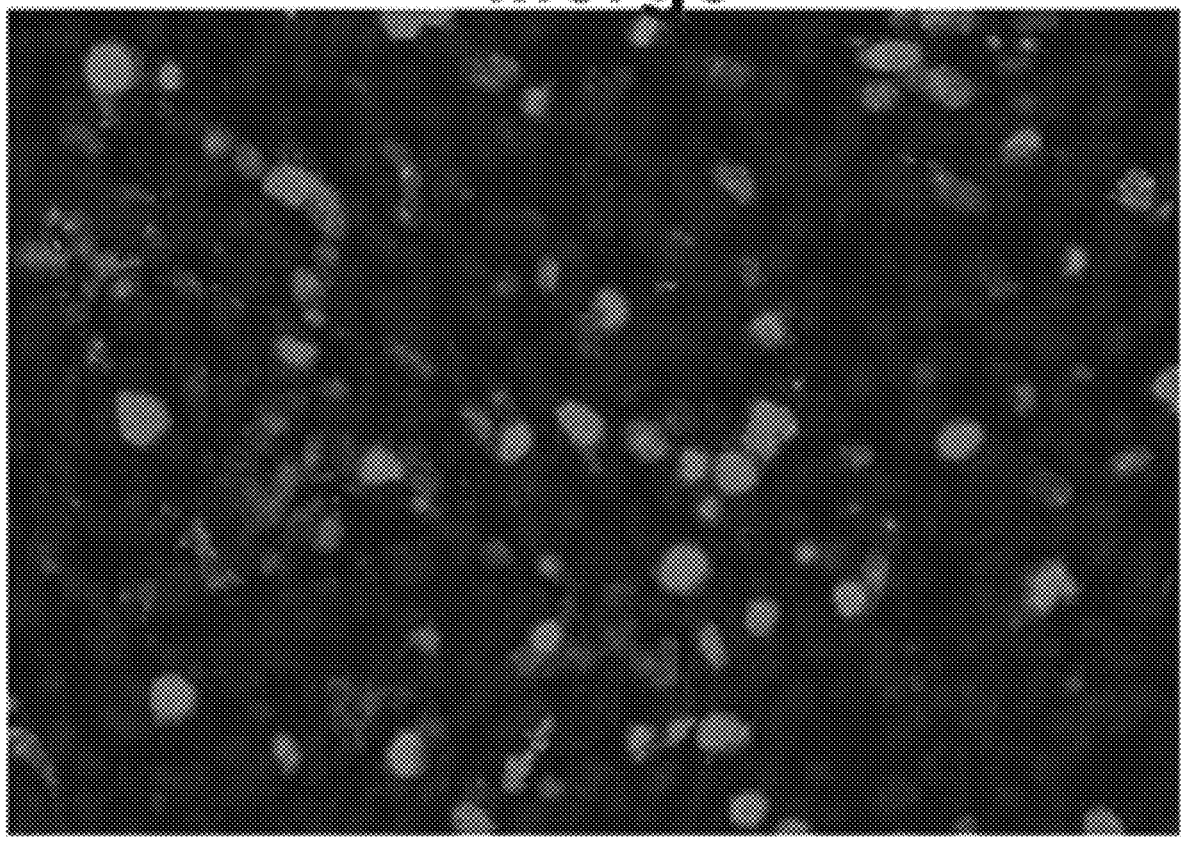
Figure 16G:
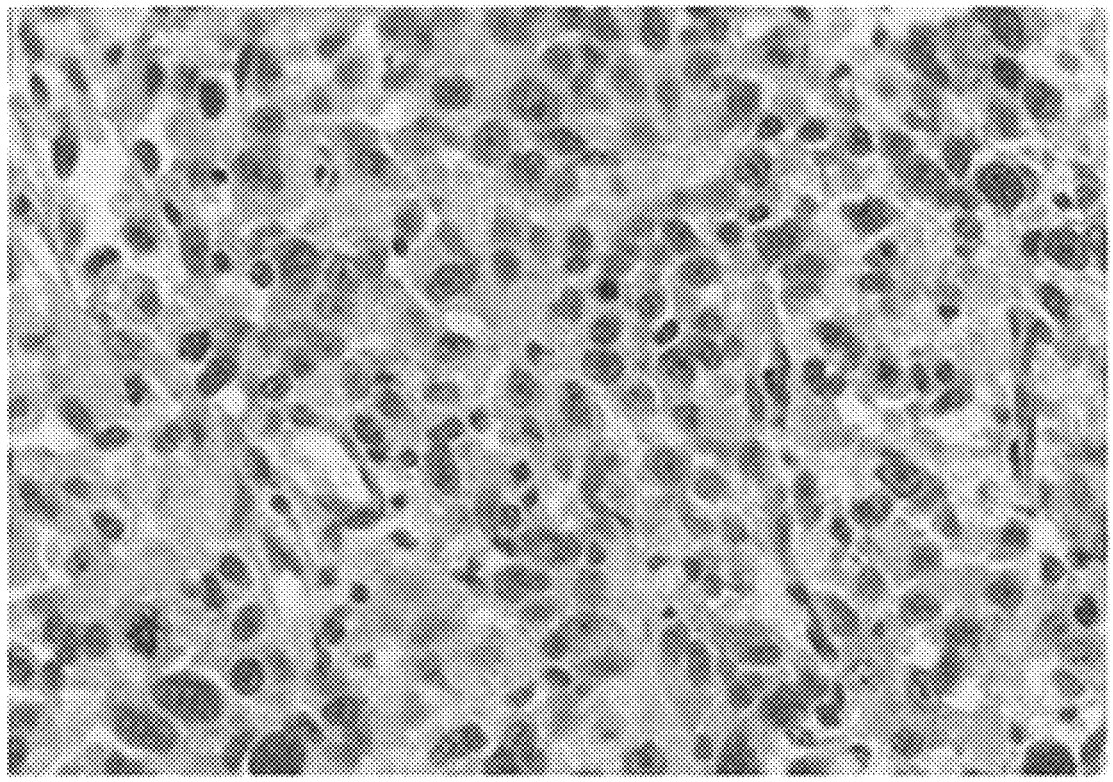
Figure 16G:
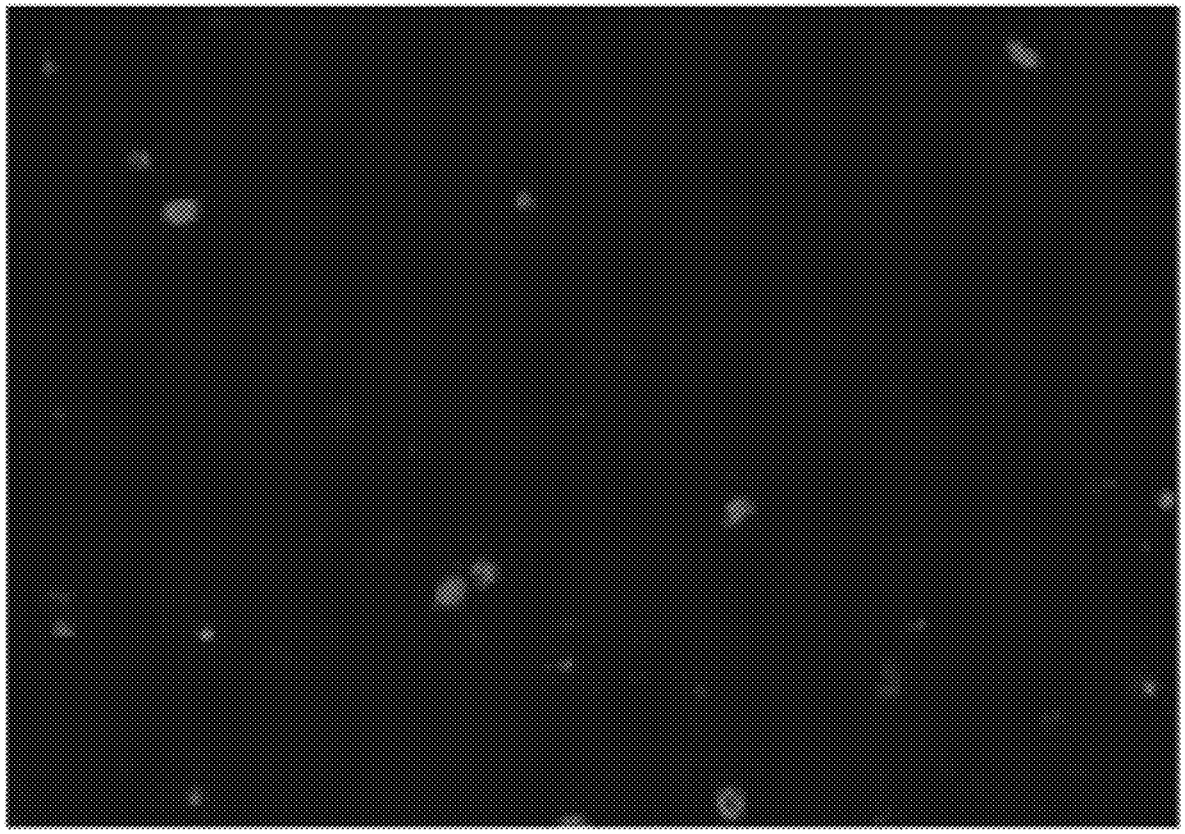
Figure 16G:
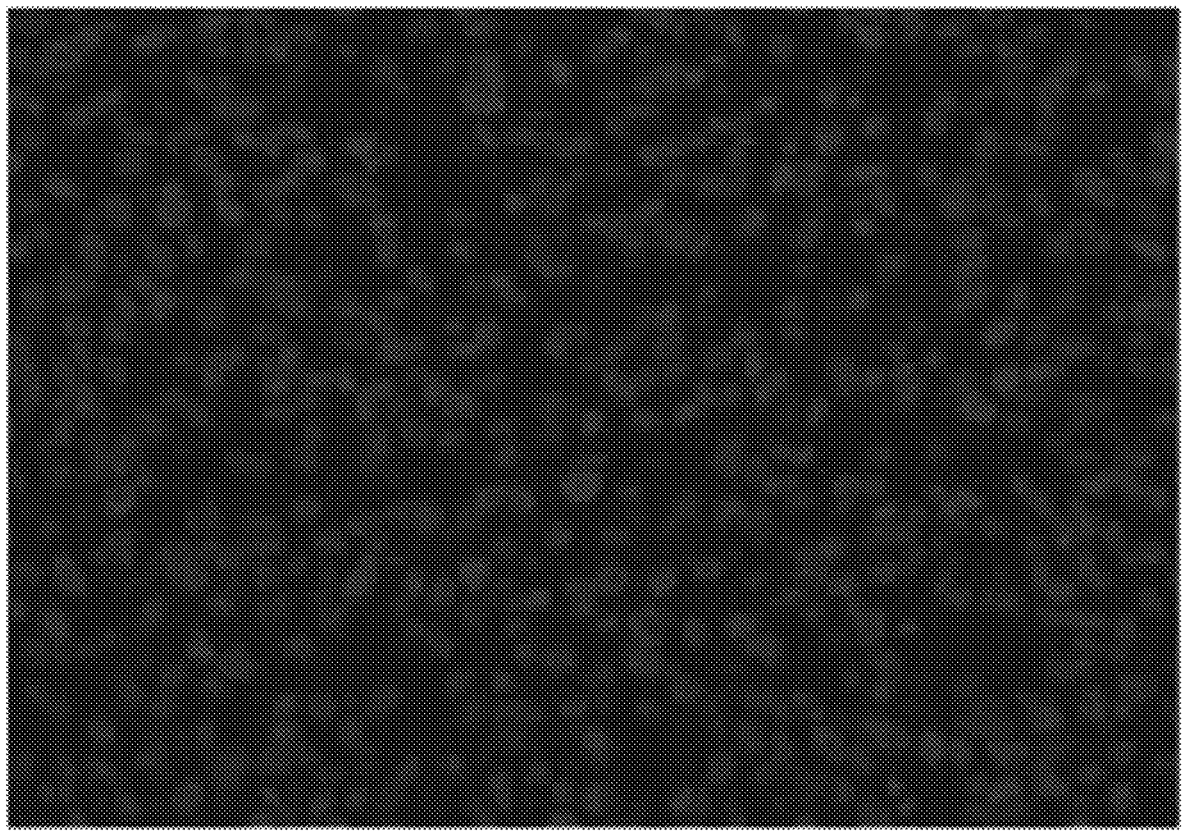
Figure 16G:
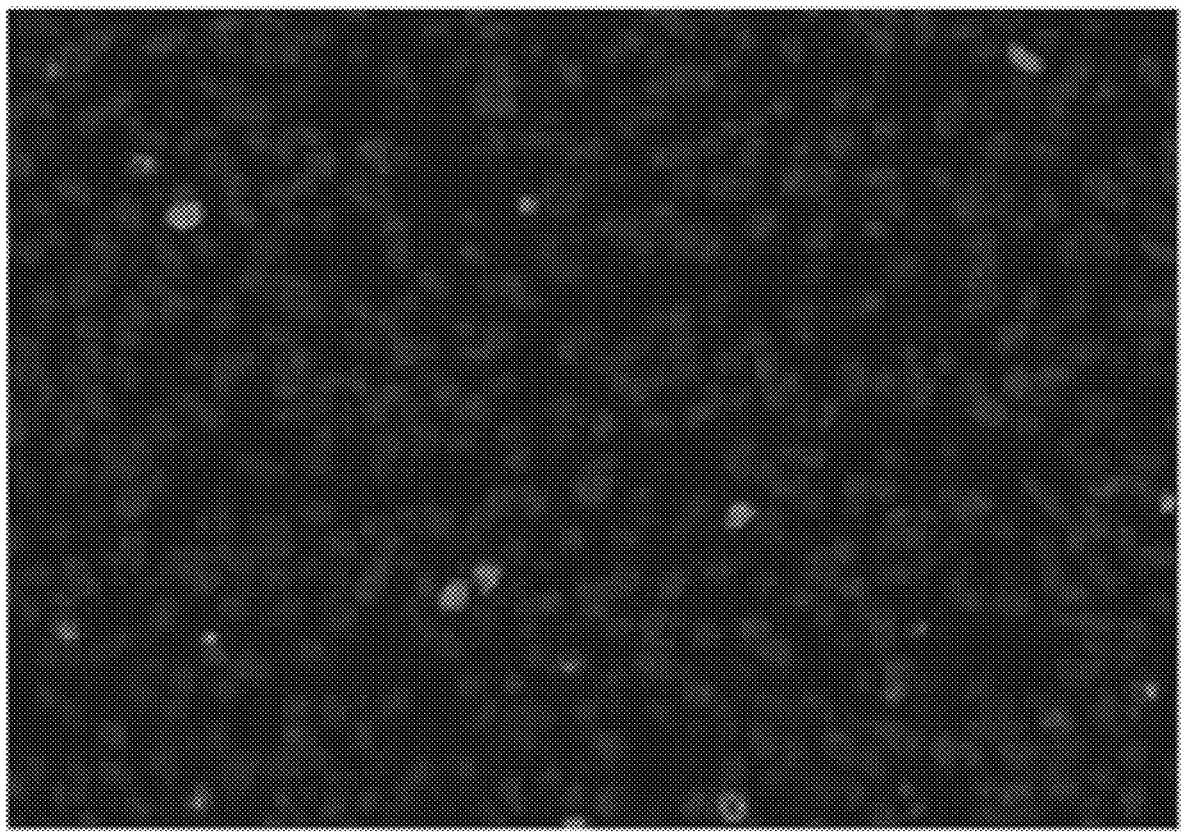

We finally examined if 7I inhibits the in-vivo survivin target in the treatment group by performing a Western blot and immunofluorescence staining analysis of xenograft tumors. As shown in FIG. 16E-G, survivin expression was drastically reduced in the xenograft tumors of the treatment group compared with that of the control group. These findings suggest that 7I inhibits xenograft tumor growth possibly by inhibiting survivin dimerization and inducing surviving degradation.

In this study, we synthesized five analogues of LQZ-7 to investigate the possibility of eliminating the labile hydrazone and replacing the furazanopyrazine with an anilin ring, resulting in an analogue, 7I, which is more active than the parent compound LQZ-7 and soluble in corn oil. 7I is also selective to survivin and induces apoptosis and survivin degradation in a proteasome-dependent manner. As a result, 7I inhibits cancer cell survival and suppresses xenograft tumor growth.

Of the 5 newly synthesized analogues, only 7I shows better activity in inducing survivin loss and inhibiting cancer cell survival compared with the parent compound LQZ-7. We presented several lines of evidence that strongly support the conclusion that 7I selectively inhibits survivin by inducing survivin loss, leading to inhibition of cancer cell survival and induction of apoptosis. These findings also confirm our previous observation on LQZ-7 in inducing survivin degradation by potential binding to the dimerization interface of survivin.

The discovery of the original hit compound, LQZ-7, and the next iterative generation analogue, LQZ-7-3 with enhanced cytotoxicity were characterized. Next, a different compound with a more locked backbone, LQZ-7F, is examined. It was hypothesized that an optimized LQZ-7F inhibitor would have the greatest cytotoxicity in prostate cancer cells. The data in this section, identify a new lead compound, LQZ-7F-1, that has enhanced cellular cytotoxicity and promotes survivin degradation at substantially lower concentrations. The survivin loss resulting from LQZ-7F-1 treatment is also via a proteasome dependent mechanism. LQZ-7F-1 increases cellular apoptosis of prostate cancer cells as measured by flow cytometry and cleaved caspase 3 protein level increases. The positive cellular data resulting from the use of this compound warrants future exploration in a in vivo xenograft efficacy study.

Discovery of LQZ-7F. After the discovery of the original primary hit, LQZ-7, several analogues were generated and tested by similar means as before. One such compound, LQZ-7F, displayed more potent inhibition of cancer and had a strong positive correlation between survivin expression and cytotoxicity in these cancer cell lines. More importantly, in an in vivo xenograft efficacy model, LQZ-7F treatment via i.p. injection significantly inhibited the growth of prostate tumors growth. The interesting feature of LQZ-7F is that it was the only compound identified in the screenings that had a locked back bone confirmation consisting of 2 five-member rings and two-six member rings. The others compounds all consisted of a five member ring and dihydropyrazine ring connected other functional groups by amine groups creating this more flexible compound. The uniqueness of the backbone and preclinical success of this compound made this compound an ideal candidate for additional screening for an optimized structural derivative.

Figure 17:
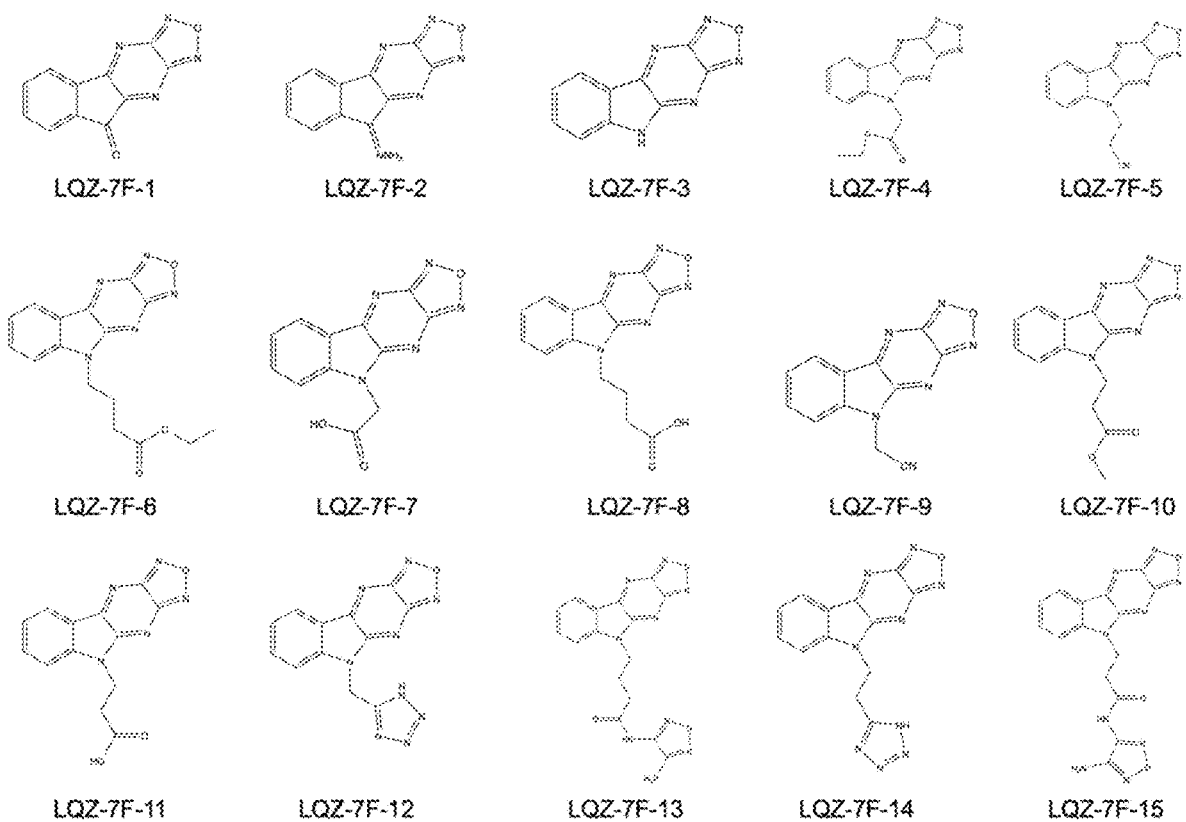
FIG. 17 shows chemical structures of LQZ-7F analogues with substitutions at cyclopentane group.

Generation of LQZ-7F Structural Analogues. The first generation of LQZ-F structural analogues were synthesized maintaining the 4 ring backbone of LQZ-7F that is critical for the stacking interactions with the dimerization core of survivin and changing the functional group attached to the cyclopentane ring. The idea behind additions of different functional groups at this position was to find an optimized functional group that strongly interacts with the survivin backbone. The functional group changes consisted of the addition of a simple carbonyl group to the cyclopentane to the addition of a complex n-amino-oxadiazolyl-butyramide group to the same position. The fifteen structural analogues of LQZ-7F are shown in FIG. 17.

Figure 18A:
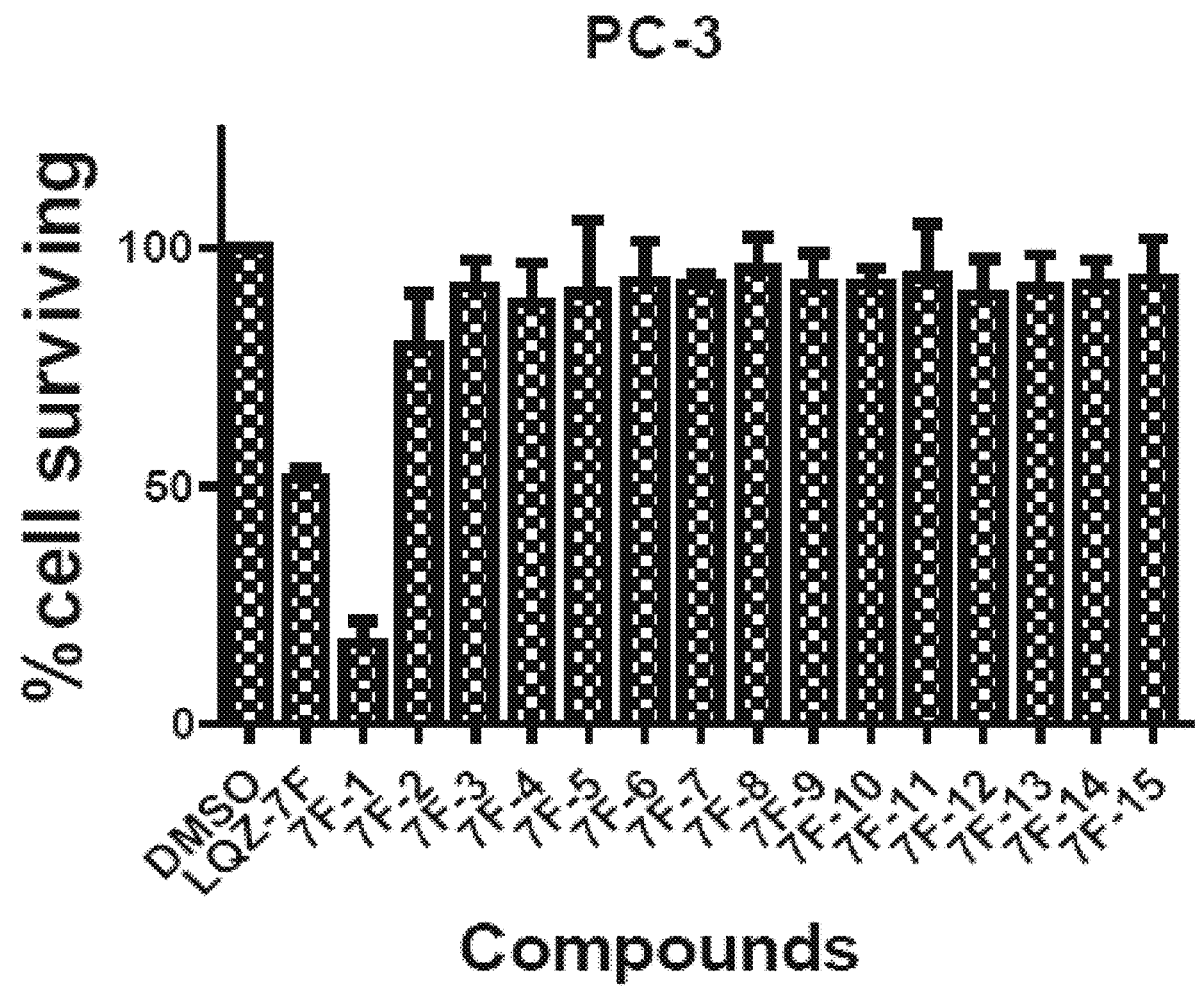
FIGS. 18A-18B show single concentration analysis of LQZ-7F and structural analogues. (A) PC-3 and (B) C4-2 cells were treated with 2.5 µM of each compound for 72 hours. The results indicate the percentage cells surviving after treatment. Only LQZ-7F-1 had a greater amount of cell killing as compared to parental LQZ-7F. Each data point was performed in triplicate. **=p-value<0.001. n=3 independent experiments. Error bars equal standard deviation.
Figure 18B:
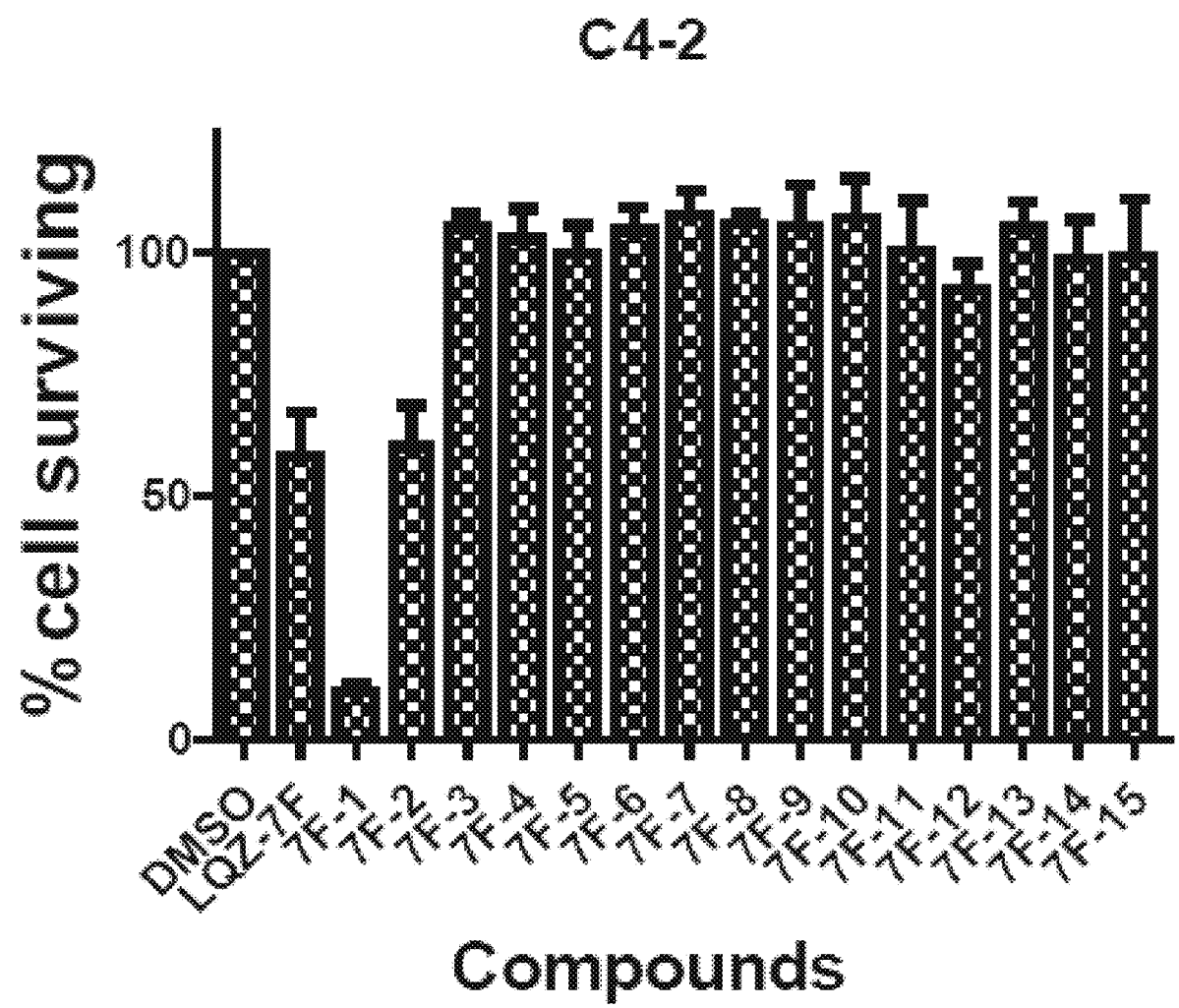

LQZ-7F Analogues Single Concentration Analysis. In order to determine if any of the LQZ-7F structural analogues had a greater ability to promote cancer cell killing than LQZ-7F, a single concentration analysis was first performed in PC-3 and C4-2 cells. For this series of experiments, cells were treated with 2.5 µM of each different compound for 72 hours. This concentration was specifically chosen as it represents the average IC50 value of LQZ-7F in prostate cancer cells. The results from the single concentration methylene blues are shown in FIG. 18.

As excepted, treatment of LQZ-7F at 2.5 µM inhibited both PC-3 and C4-2 roughly 50%. The only analogue that promoted cell killing to a greater extent than the parental compound was, LQZ-7F-1. This compound with the carbonyl substitution on the cyclopentane had less than 20% cells surviving in both cell lines after 72 hour treatment. The data in this section positioned LQZ-7F-1 for further in vitro testing to LQZ-7F-1 Cytotoxicity.

Figure 19A:
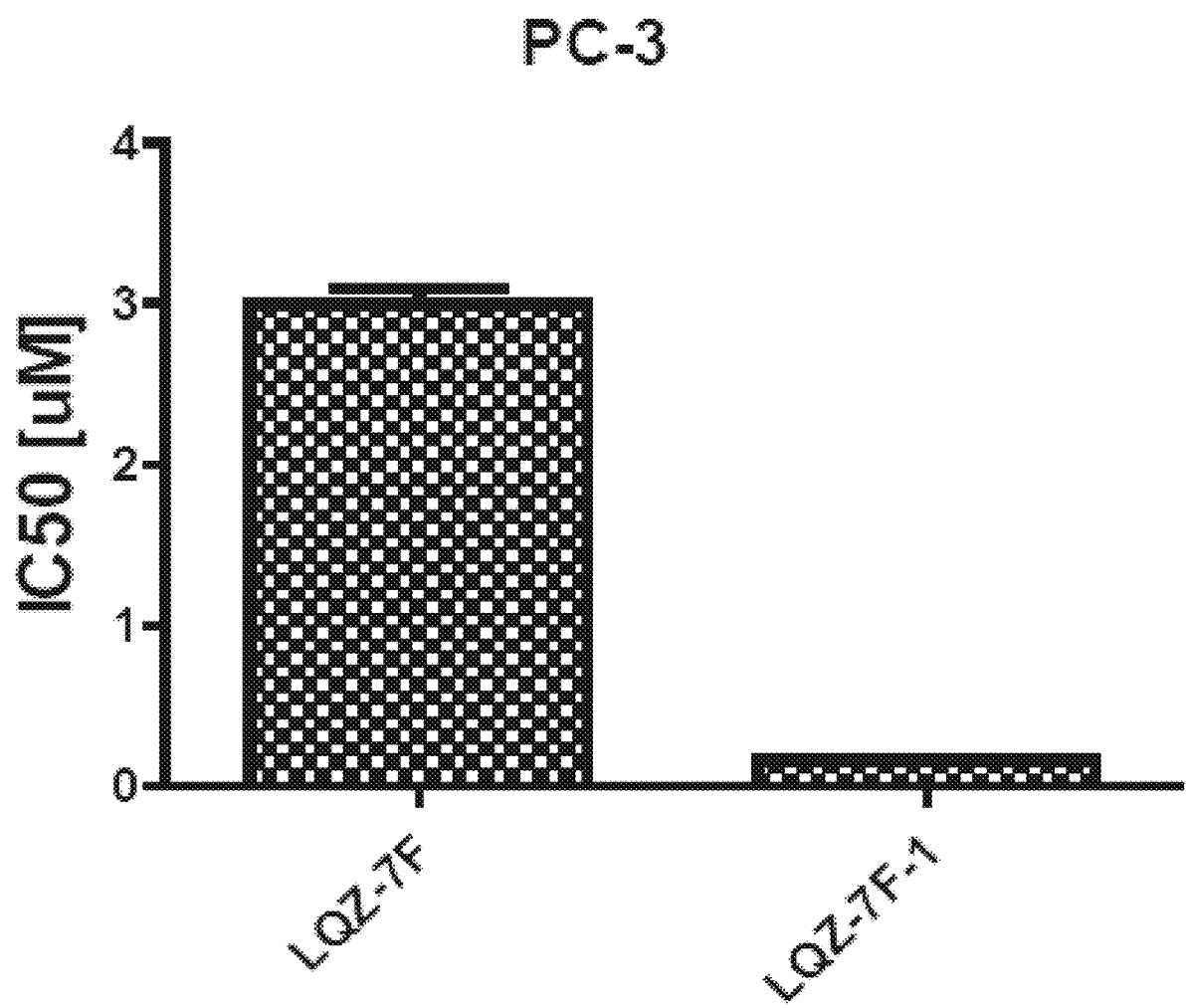
FIGS. 19A-19B show LQZ-7F-1 is more potent inhibitor than LQZ-7F in prostate cancer cells. LQZ-7F-1 has a significantly lower IC50 value in (A) PC-3 (158 nM) and (B) C4-2 (175 nM) cells than parental compound LQZ-7F. LQZ-7F-1 is the first sub micromolar inhibitor identified during screening. Each concentration was performed in triplicate. ***=p-value<0.001. n=3 independent experiments. Error bars equal standard deviation.
Figure 19B:
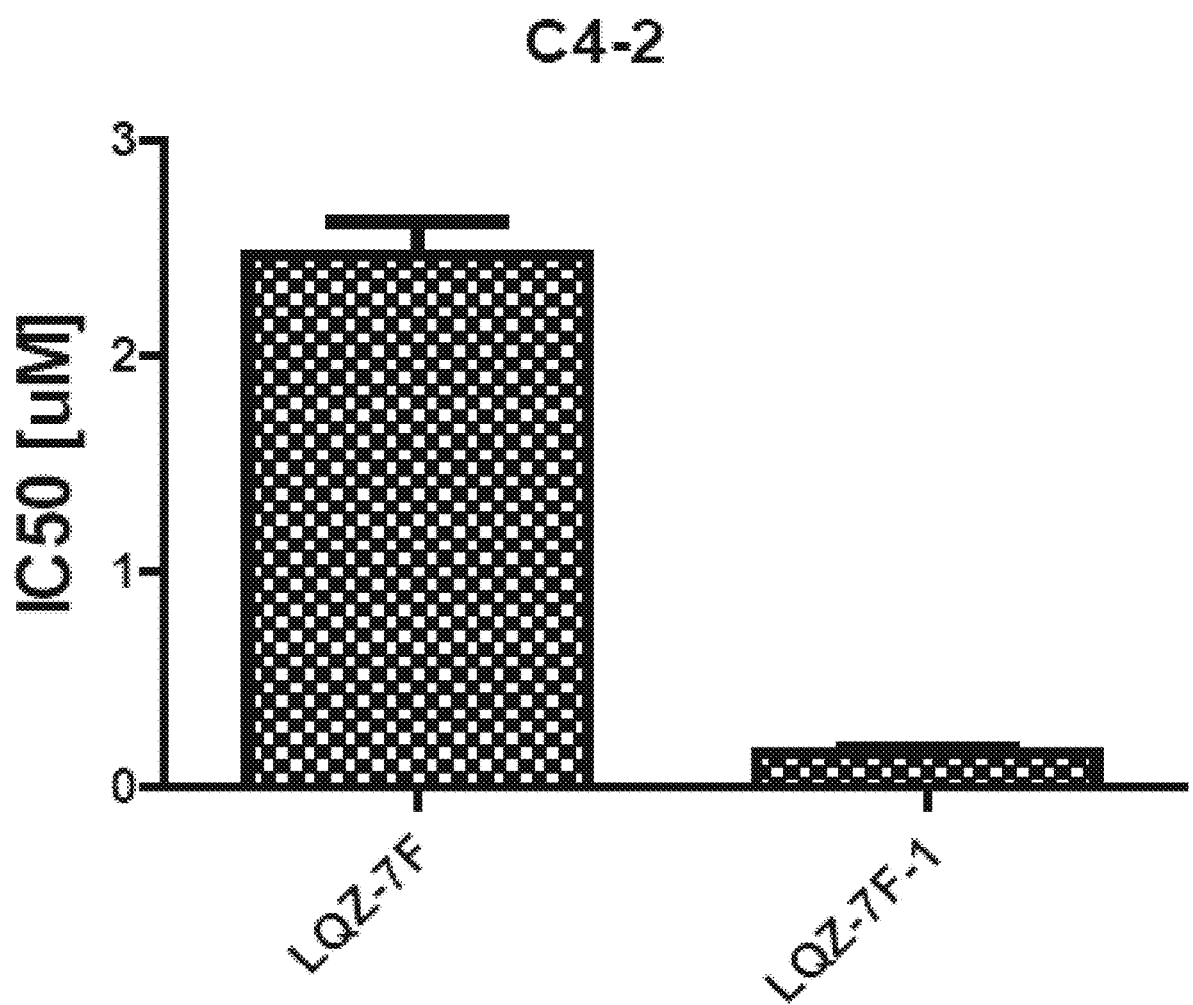

The results of the single concentration analysis indicated that LQZ-7F-1 is a more potent inhibitor than LQZ-7F. To clearly define the IC50 values of LQZ-7F in prostate cancer cells and additional methylene blue experiment was performed. PC-3 and C4-2 were tested with LQZ-7F-1 over a concentration range of 1 nM to 20 µM. As shown in FIG. 19, LQZ-7F-1 had a significantly lower IC50 value than LQZ-7F-1 with IC50 values of 158 nM and 170 nM in PC-3 and C4-2 respectively. In fact, LQZ-7F-1 represents the first survivin inhibitor identified in the screening process to show a submicromolar IC50 in cancer cells in vitro.

Figure 20:
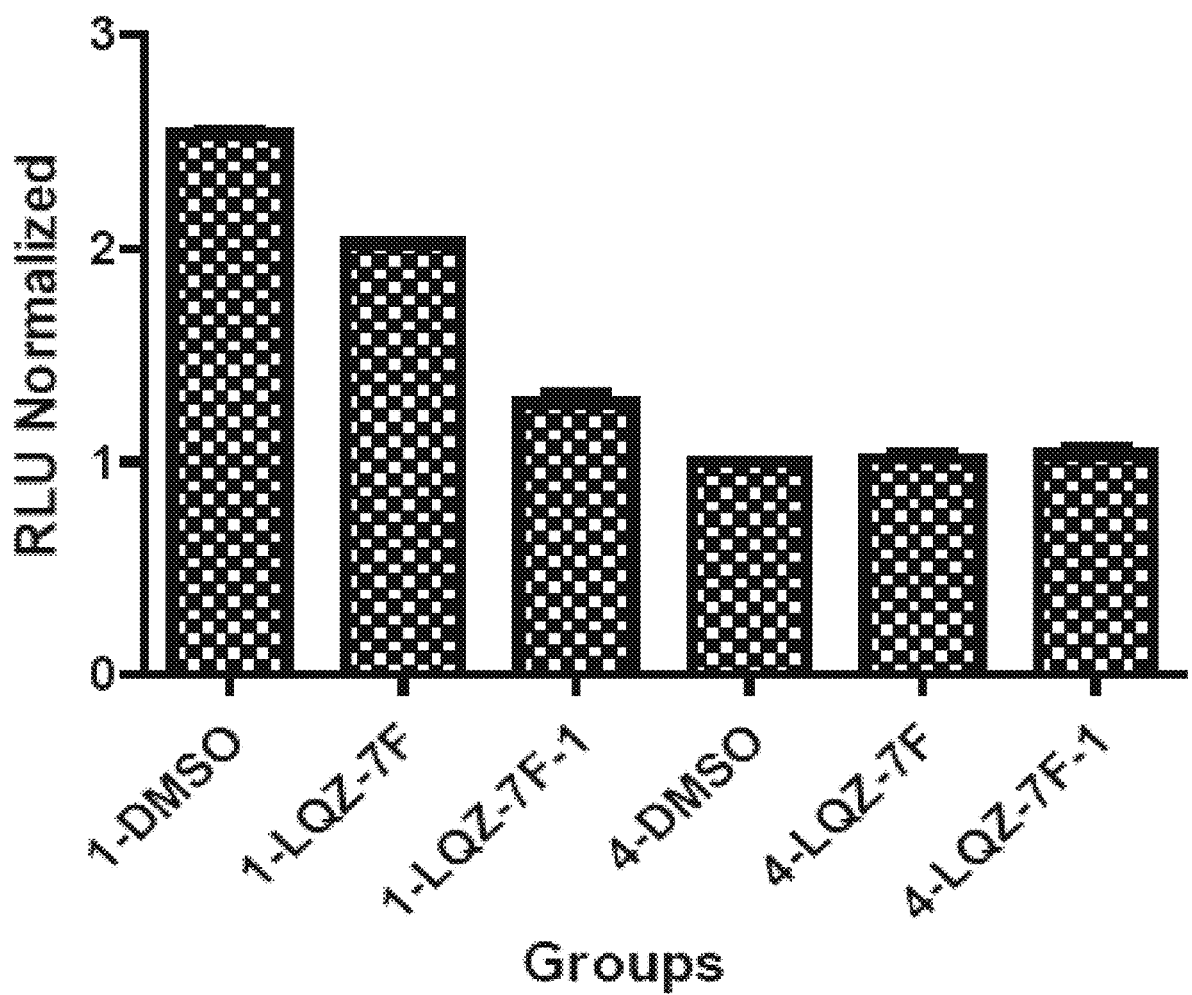
FIG. 20. shows LQZ-7F-1 decreases survivin dimerization greater than LQZ-7F in a mammalian two hybrid assay. LQZ-7F-1 had a significantly lower normalized RLU value than LQZ-7F, indicating a decrease in survivin dimerization in the assay. Each compound was utilized at a concentration of 1 µM. Each transfection was performed in triplicate. ***=p-value<0.001. n=3 independent experiments. Error bars equal standard deviation.

Mammalian Two Hybrid LQZ-7F1. After confirming the increase in potency by dose response curves, the next step was to establish that LQZ-7F-1 also exerts its function through disruption of survivin dimerization as expected. Similarly to the previous section, a mammalian two hybrid assay was performed to compare the dimerization inhibition by LQZ-7F and LQZ-7F-1 where group 1 represents the cloned survivin plasmids and group 4 are empty vectors controls for measuring basal RLU (SEAP) levels in the media. Treatment with LQZ-7F and LQZ-7F-1 both significantly reduced survivin dimerization in this assay (FIG. 20). However, LQZ-7F-1 decreased SEAP reporter gene production in survivin containing plasmid group to a greater extent than LQZ-7F. Importantly, neither compound interfered with the empty vector controls relative light values. The data in this section indicates LQZ-7F-1 is not only a more potent inhibitor in terms of cell killing but also interfering with the intended target survivin's dimerization.

Figure 21:
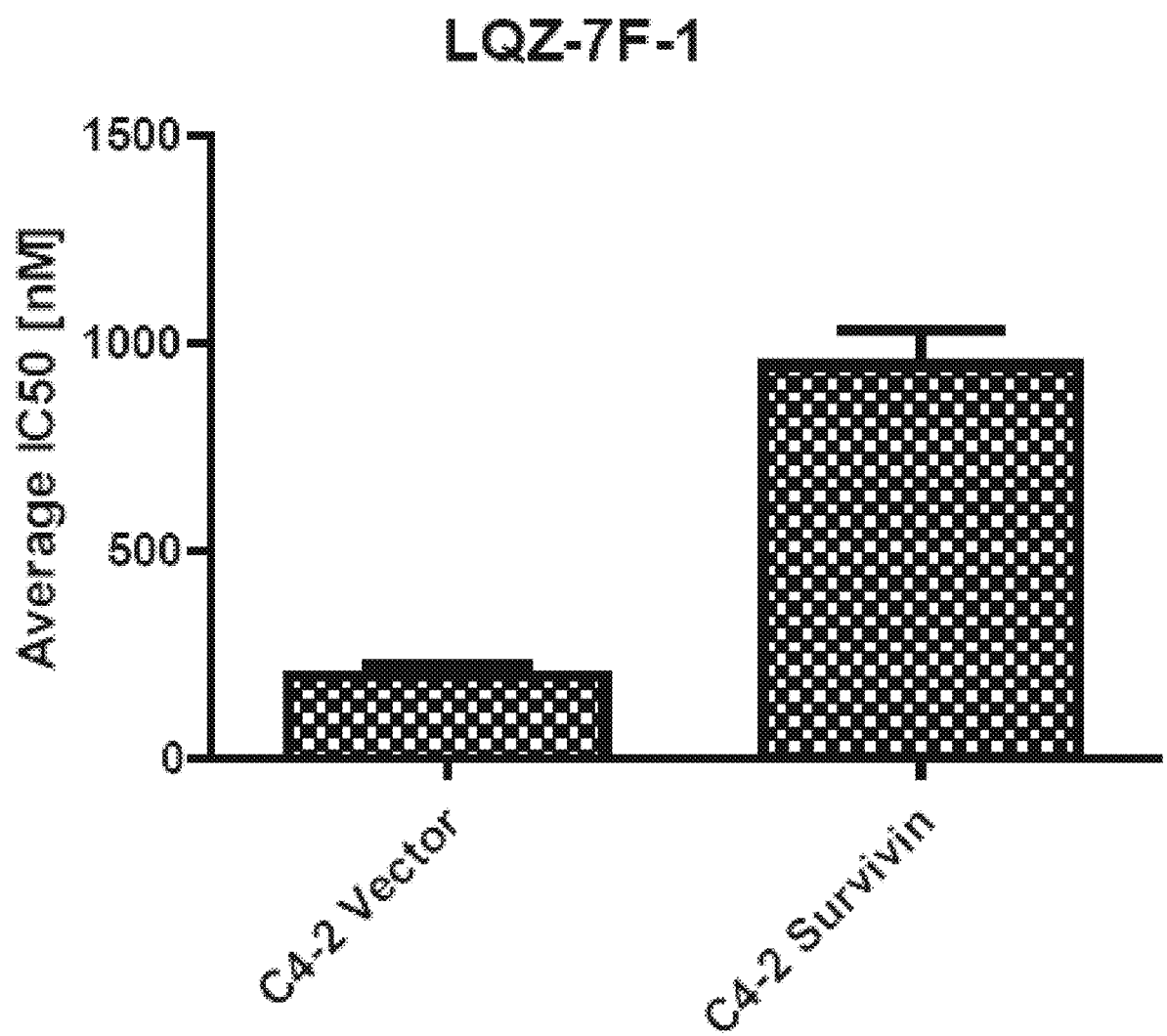
FIG. 21 shows survivin overexpression decreases sensitivity to LQZ-7F-1. LQZ-7F-1 has a significantly higher IC50 value in survivin stable overexpression cells. As the intended target of LQZ-7F-1, one would expect increasing survivin levels would require more compound to overcome this increase. ***=p-value<0.001. n=3 independent experiments. Error bars equal standard deviation.

LQZ-7F-1 Cytotoxicity in Survivin Overexpression Cells. To determine if survivin overexpressing cells have a decreased sensitivity to LQZ-7F-1, C4-2 survivin stable overexpressing cells were once again used in a cell cytotoxicity assay. After 72 hour treatment, the C4-2 vector cells had an IC50 of roughly 200 nM, while C4-2 survivin cells had a significantly higher IC50 of 947 nM (FIG. 21). The data indicate that overexpression of survivin decreases sensitivity to LQZ-7F-1.

Figure 22:
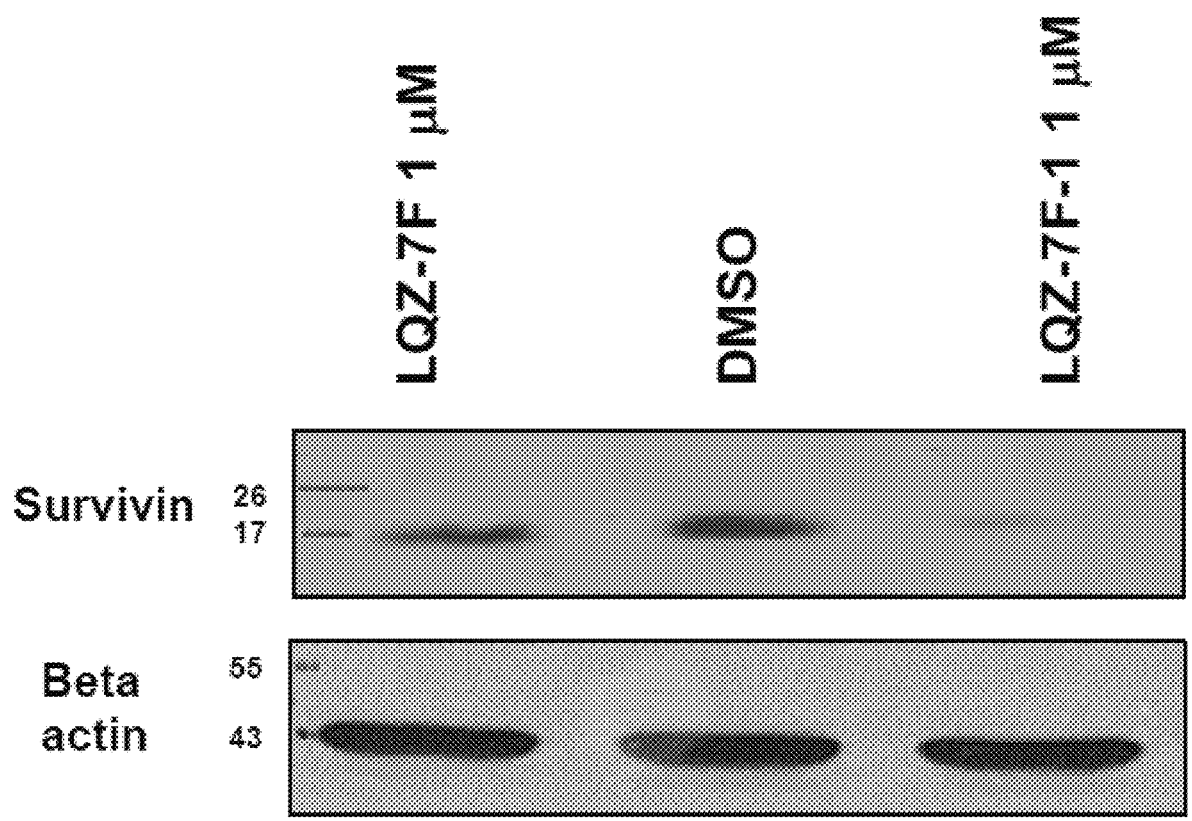
FIG. 22 shows LQZ-7F-1 decreases survivin protein level greater than LQZ-7F. LQZ-7F-1 decreases survivin level significantly as early as 8 hours. This decrease is greater than that seen by parental compound LQZ-7F. This experiment was performed in PC-3 cells. ***=p-value<0.001. n=3 independent experiments. Error bar equals standard deviation.
Figure 22:
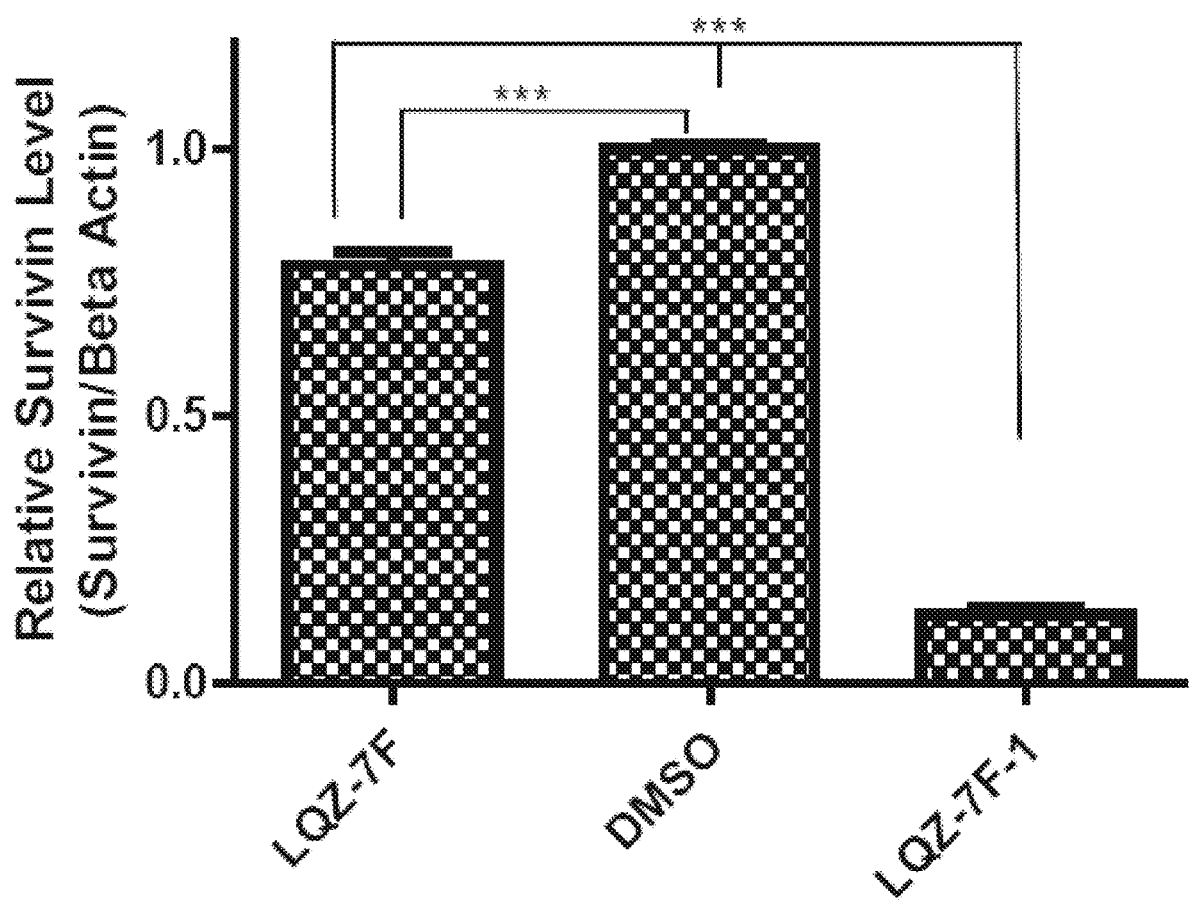
Figure 23:
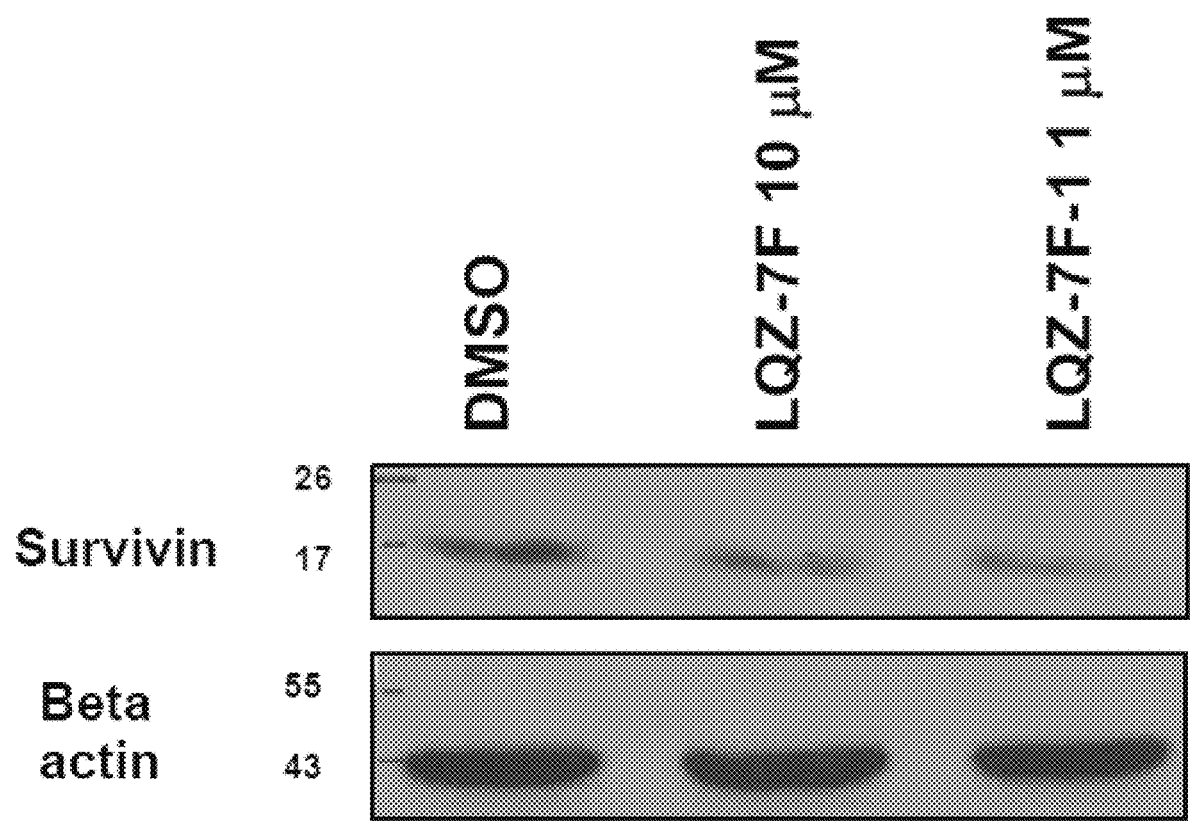
FIG. 23 shows LQZ-7F-1 decreases survivin protein level greater than previous generation inhibitor even at a significantly lower concentration. LQZ-7F-1 treated at 1 µM decreases survivin level significantly more than LQZ-7F at 10 µM. This experiment was performed in C4-2 cells. ***=p-value<0.001. *=p-value<0.05. n=3 independent experiments. Error bar equals standard deviation.
Figure 23:
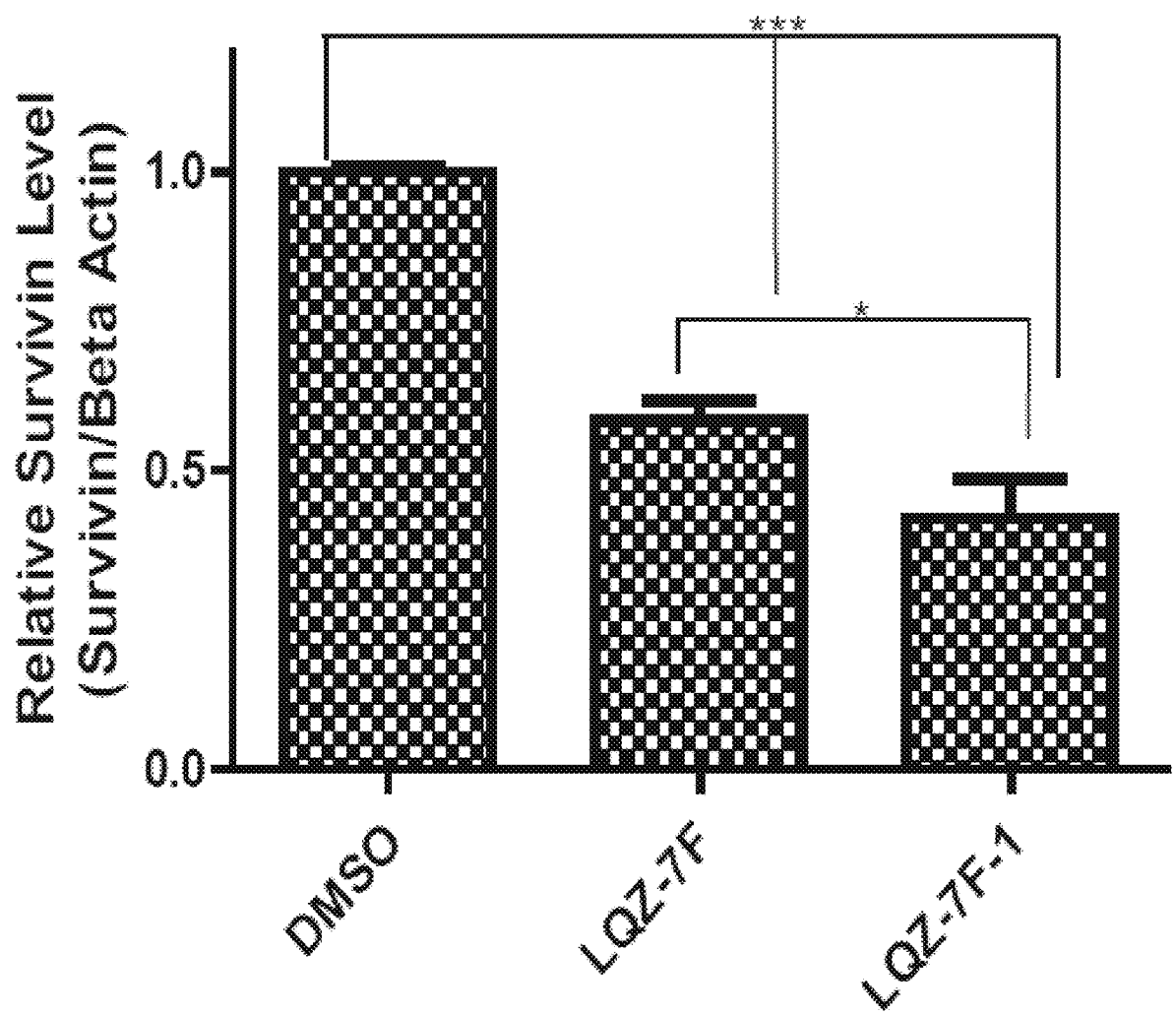

LQZ-7F1 Survivin Degradation. Previous sections have illustrated that this group of survivin inhibitors upon treatment result in prompt survivin loss and degradation in the cell via interference with survivin dimerization interface. To confirm that LQZ-7F-1 also reduces target protein survivin levels in prostate cancer cells, a series of western blot analyses were performed. In PC-3 cells, both LQZ-7F and LQZ-7F-1 were treated at 1 µM for only 8 hours. LQZ-7F-1 robustly decreased survivin levels even as early as 8 hours in these cells (FIG. 22). LQZ-7F-1 analogue also significantly decreases survivin levels greater than parental compound at this concentration and timepoint. In C4-2 cells, LQZ-7F was treated at 10 µM while LQZ-7F-1 concentration for treatment remained at 1 µM for 8 hours. As shown in FIG. 23, LQZ-7F-1 even at a lower concentration significantly decreased survivin protein level greater than does a higher concentration of LQZ-7F at an 8 hour timepoint. The data indicate LQZ-7F-1 is not only a more inhibitor but also causes survivin loss faster than the progenitor compound, LQZ-7F.

Figure 24A:
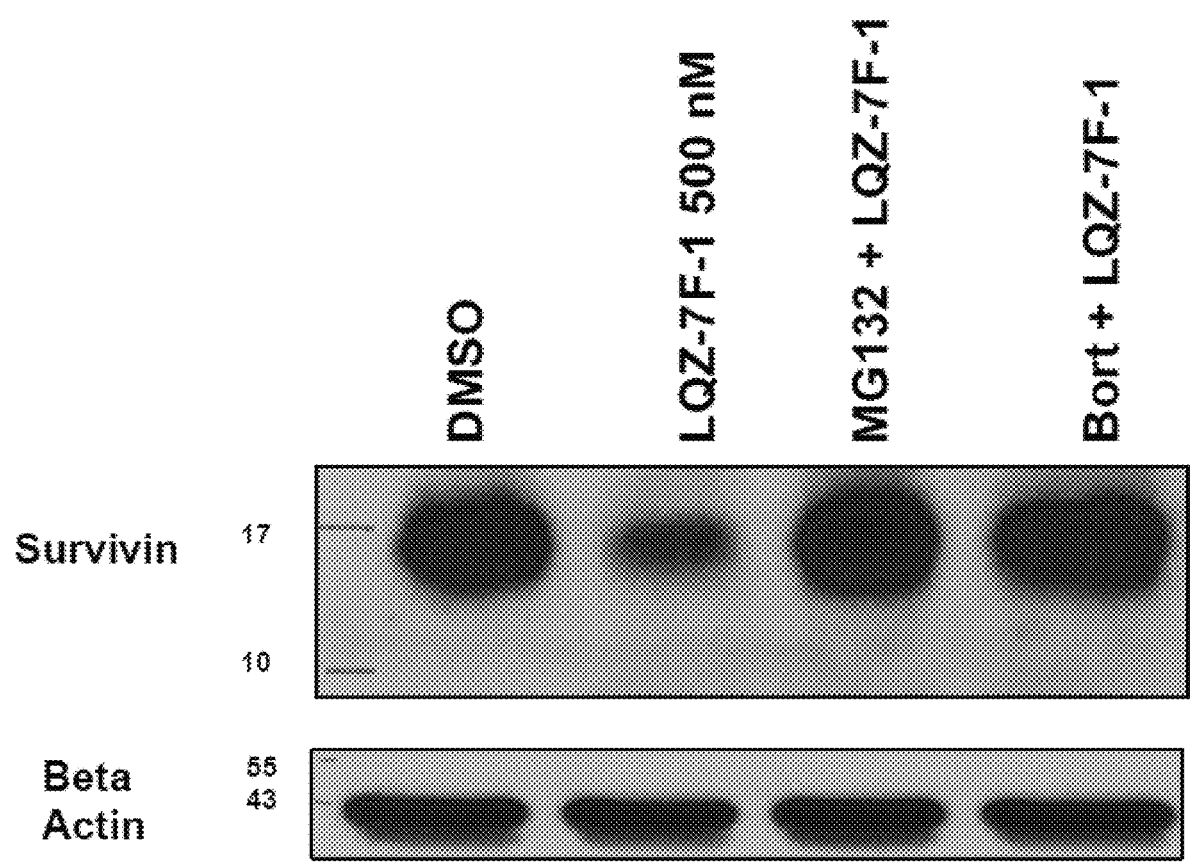
FIGS. 24A-24B show pretreatment with proteasome inhibitors rescues LQZ-7F-1 induced survivin degradation. Survivin loss caused by 24 hour treatment with LQZ-7F-1 was able to be rescued by blocking proteasome activity via pretreatment with two different inhibitors 7 µmol/L MG132, or 70 nmol/L bortezomib for 2 hours in (A) PC-3 and (B) C4-2 cells. Survivin level was nearly completely rescued to DMSO control level. ***=p-value<0.001. n=3 independent experiments. Error bar equals standard deviation.
Figure 24A:
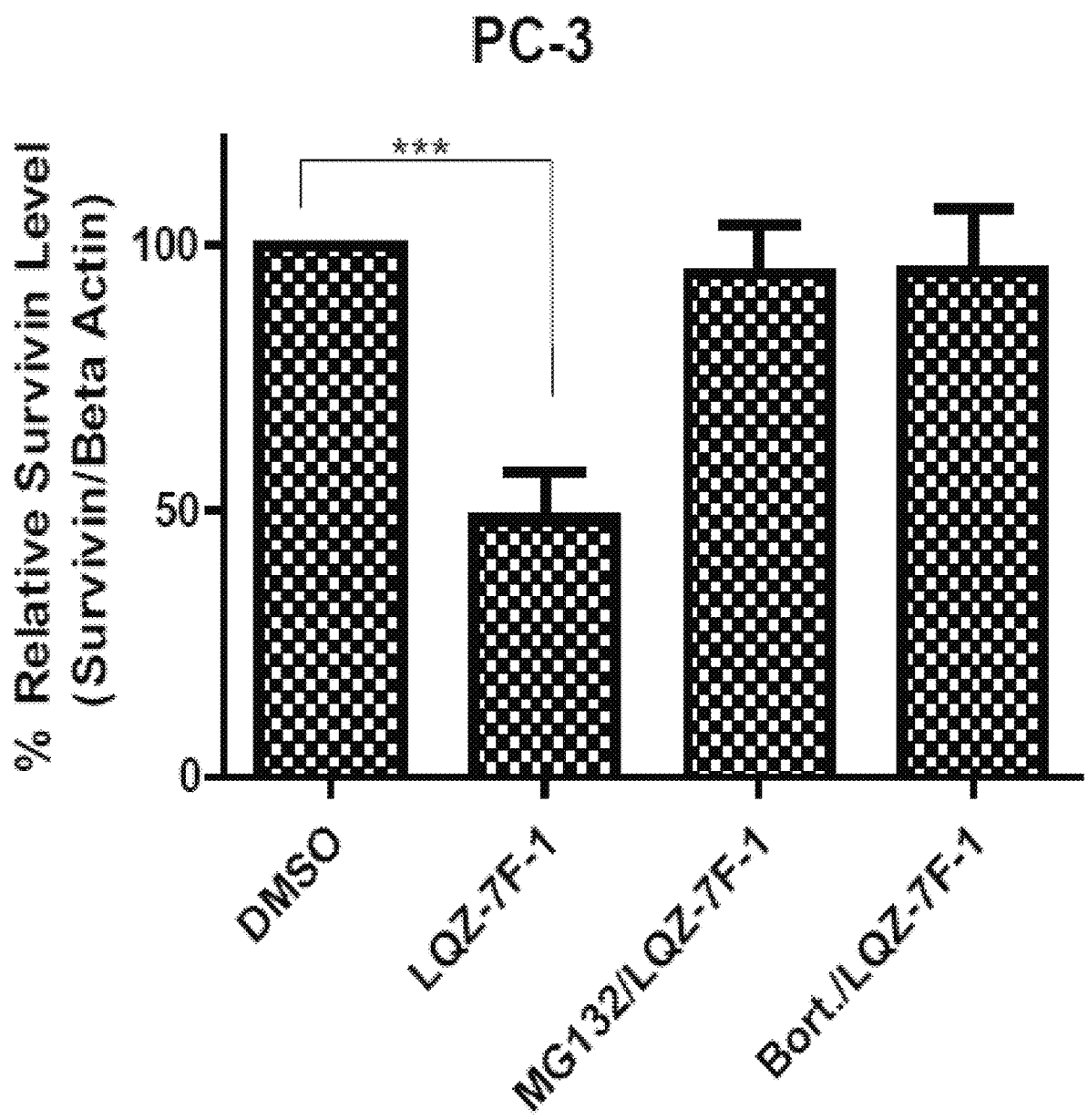
Figure 24B:
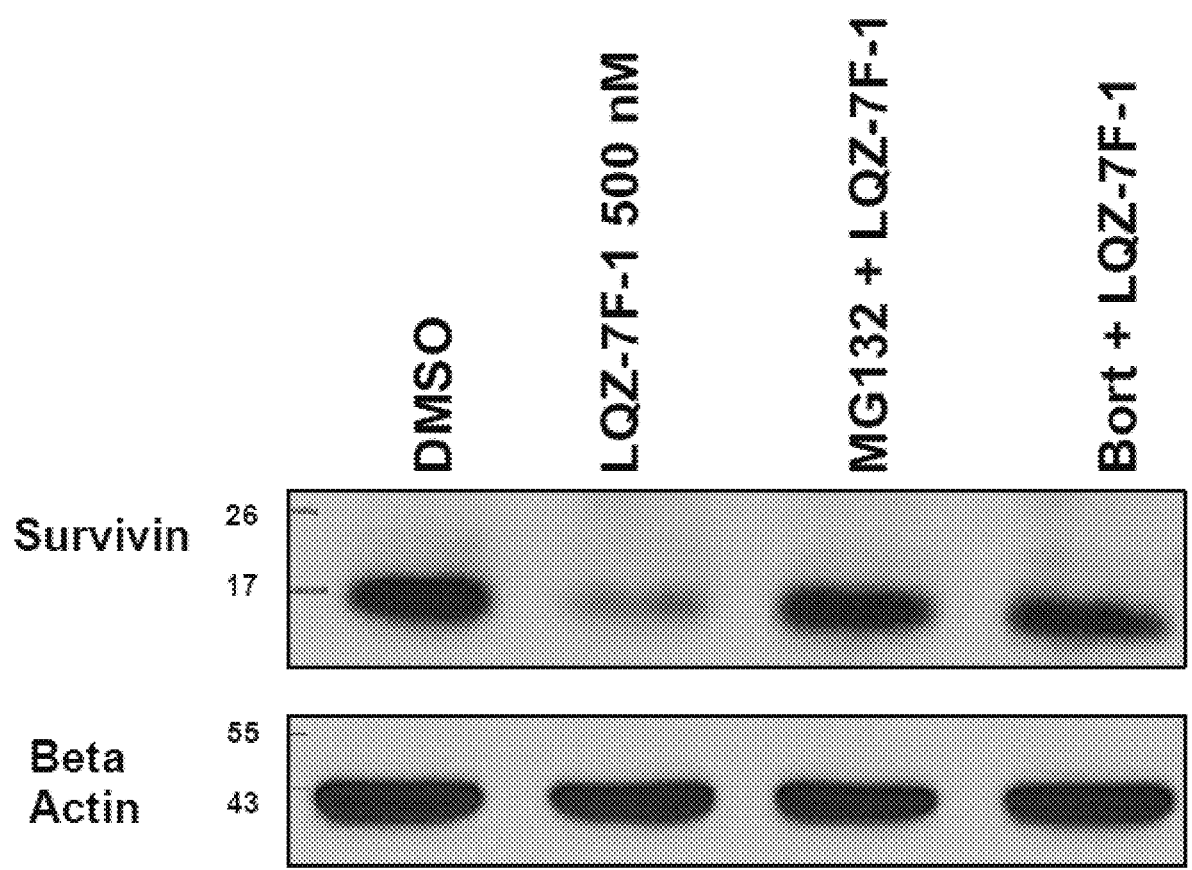
Figure 24B:
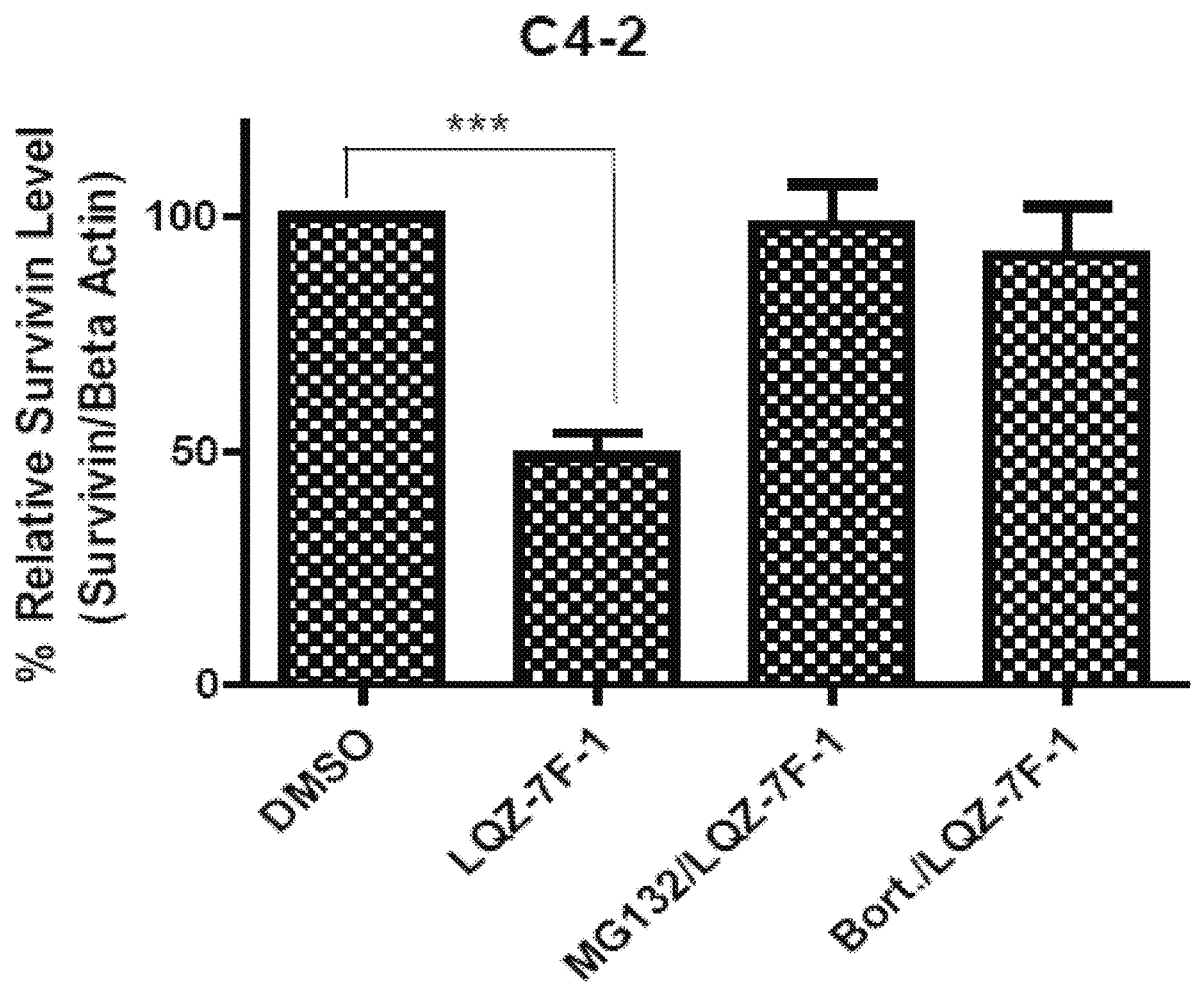

LQZ-7F-1 and Proteasome Inhibitors Experiment. To determine if LQZ-7F-1 also promotes survivin degradation via proteasome, PC-3 and C4-2 cells were pretreated with two different proteasome inhibitors MG132 and bortezomib for two hours before treatment with the compound. As expected LQZ-7F-1 at 500 nM reduced survivin level significantly as compared to DMSO control (FIGS. 24A and 24B). Interestingly, pretreatment with the proteasome inhibitors rescued the survivin level to a similar level as seen in the DMSO treatment group. Thus, it appears LQZ-7F-1 treatment also promotes survivin degradation via the proteasome.

Figure 25A:
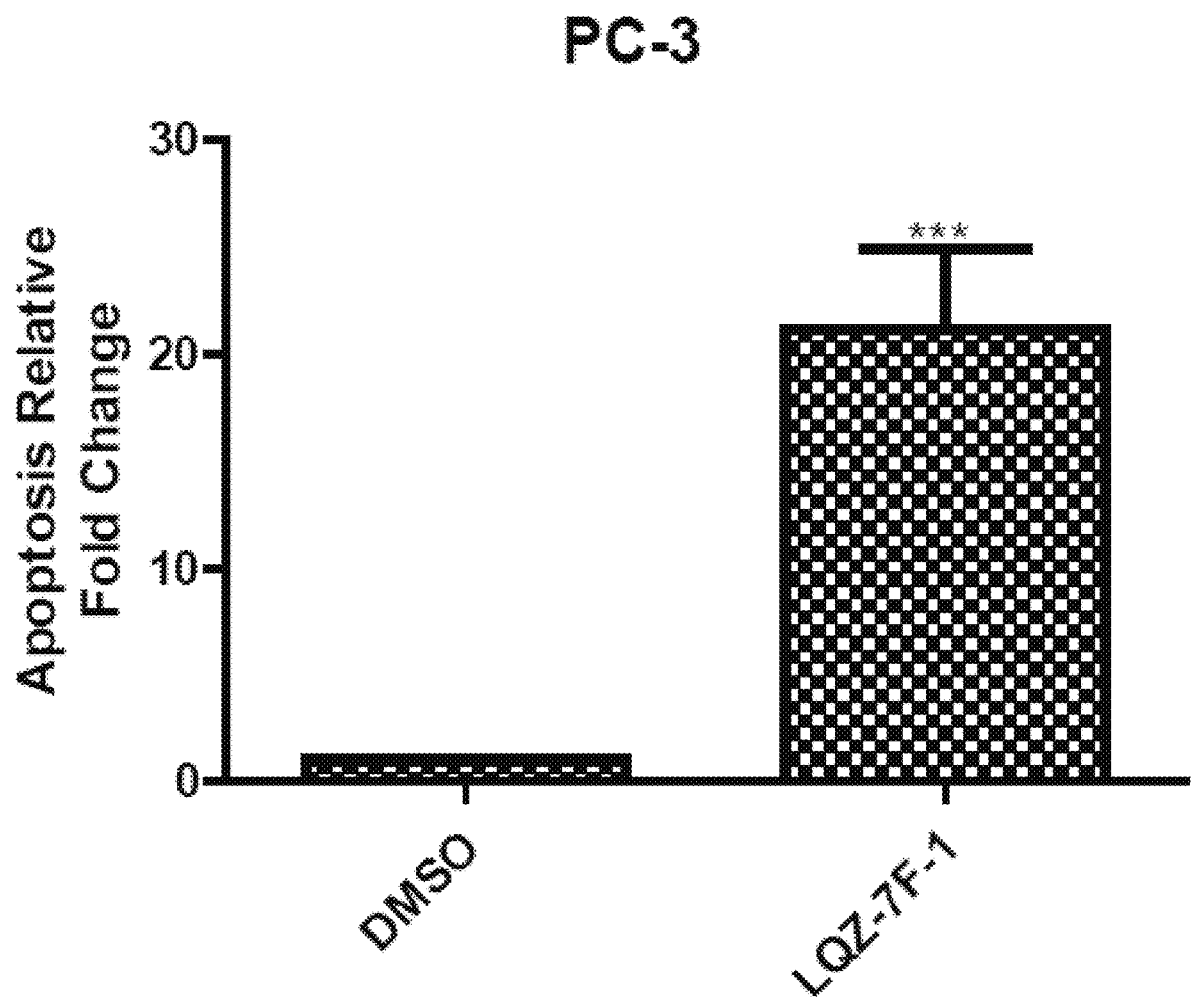
FIGS. 25A-25B show LQZ-7F-1 treatment causes increased apoptosis in prostate cancer cells. Survivin loss caused by treatment with LQZ-7F-1 causes increased levels of apoptosis (A) PC-3 and (B) C4-2 cells as evidenced by increased Annexin V staining Flow Cytometry. ***=p-value<0.001. n=3 independent experiments. Error bar equals standard deviation.
Figure 25B:
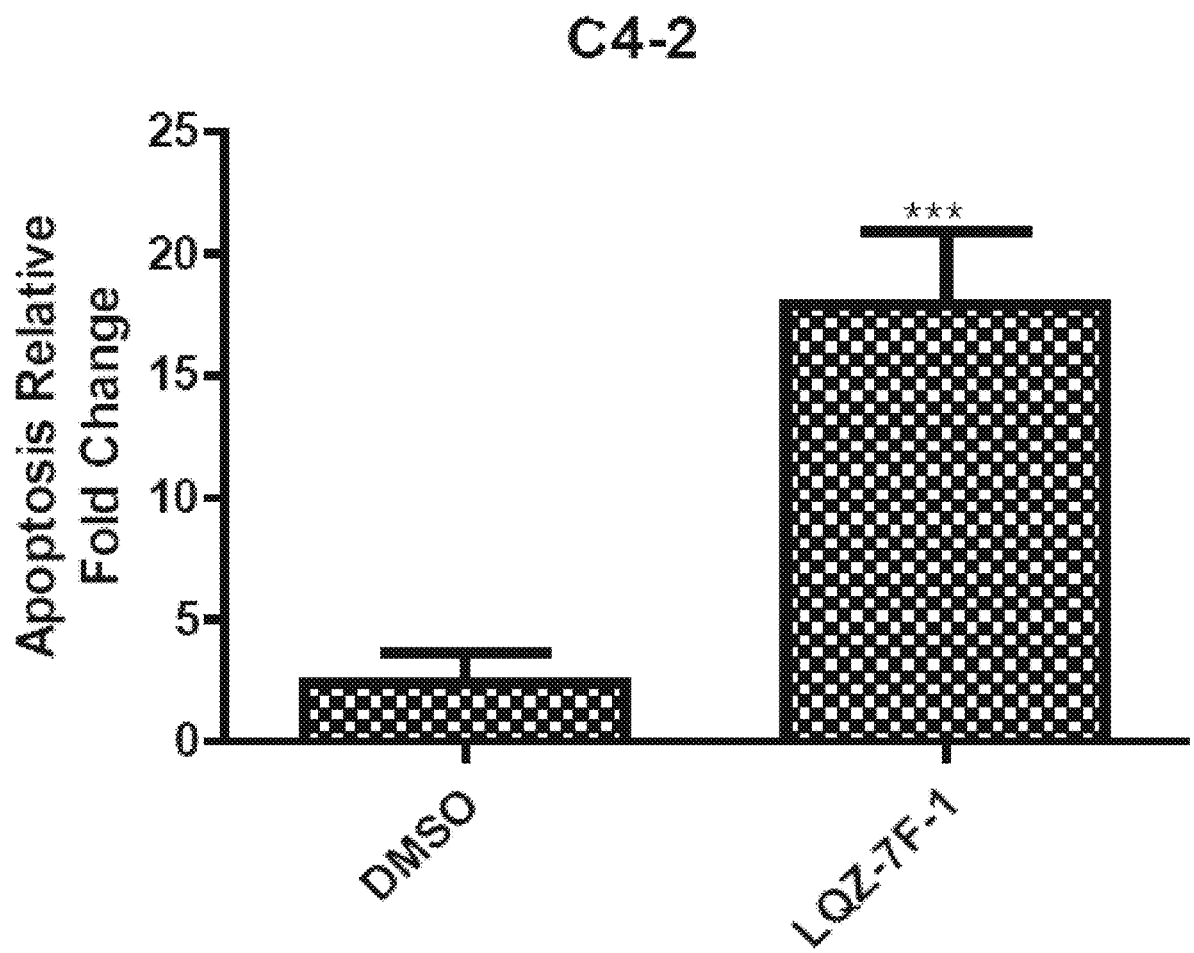
Figure 26A:
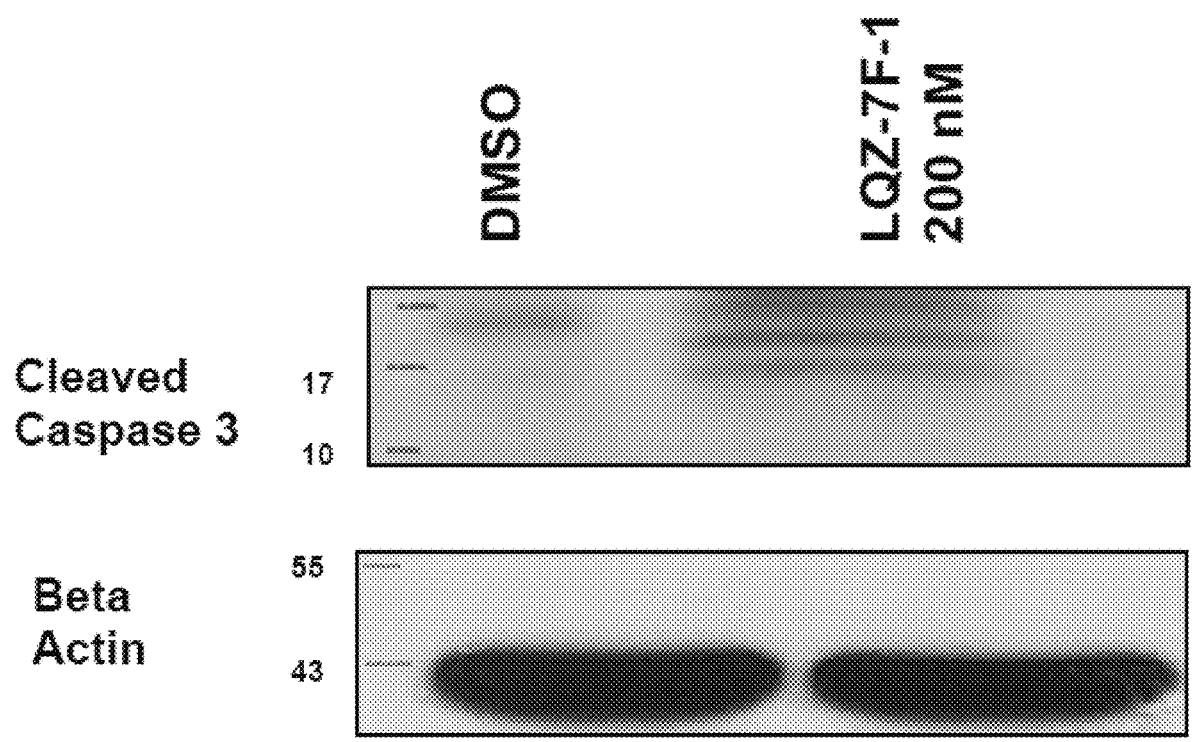
FIGS. 26A-26B show LQZ-7F-1 treatment causes increased cleaved caspase 3 in prostate cancer cells. Treatment with LQZ-7F-1 leads to an increase in cleaved caspase 3 levels as seen by western blot analysis in (A) PC-3 and (B) C4-2 cells. The increase in cleaved caspase 3 is confirmation of the Flow cytometry data indicating increased apoptosis after LQZ-7F-1 treatment. **=p-value<0.01. n=3 independent experiments. Error bar equals standard deviation.
Figure 26A:
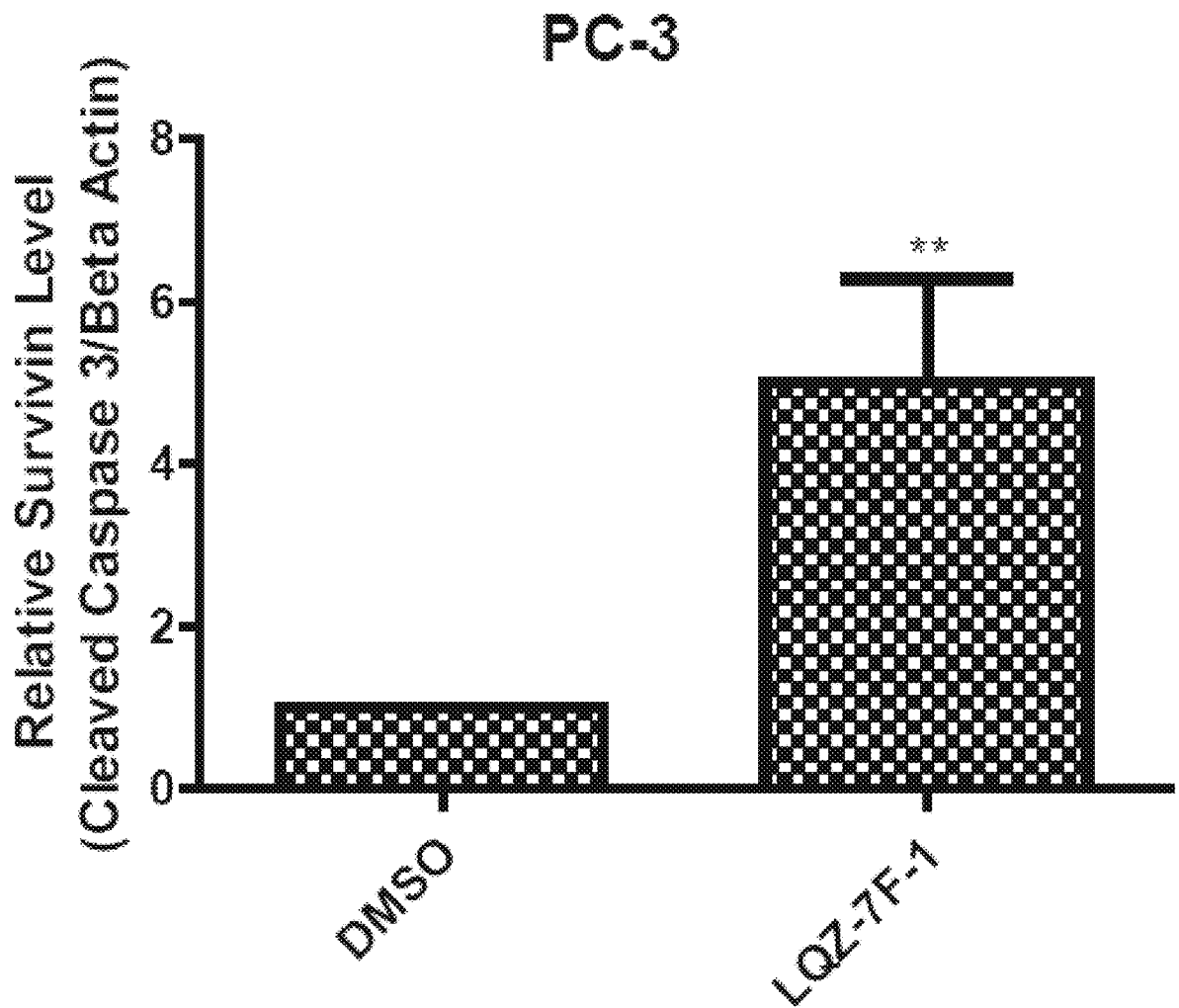
Figure 26B:
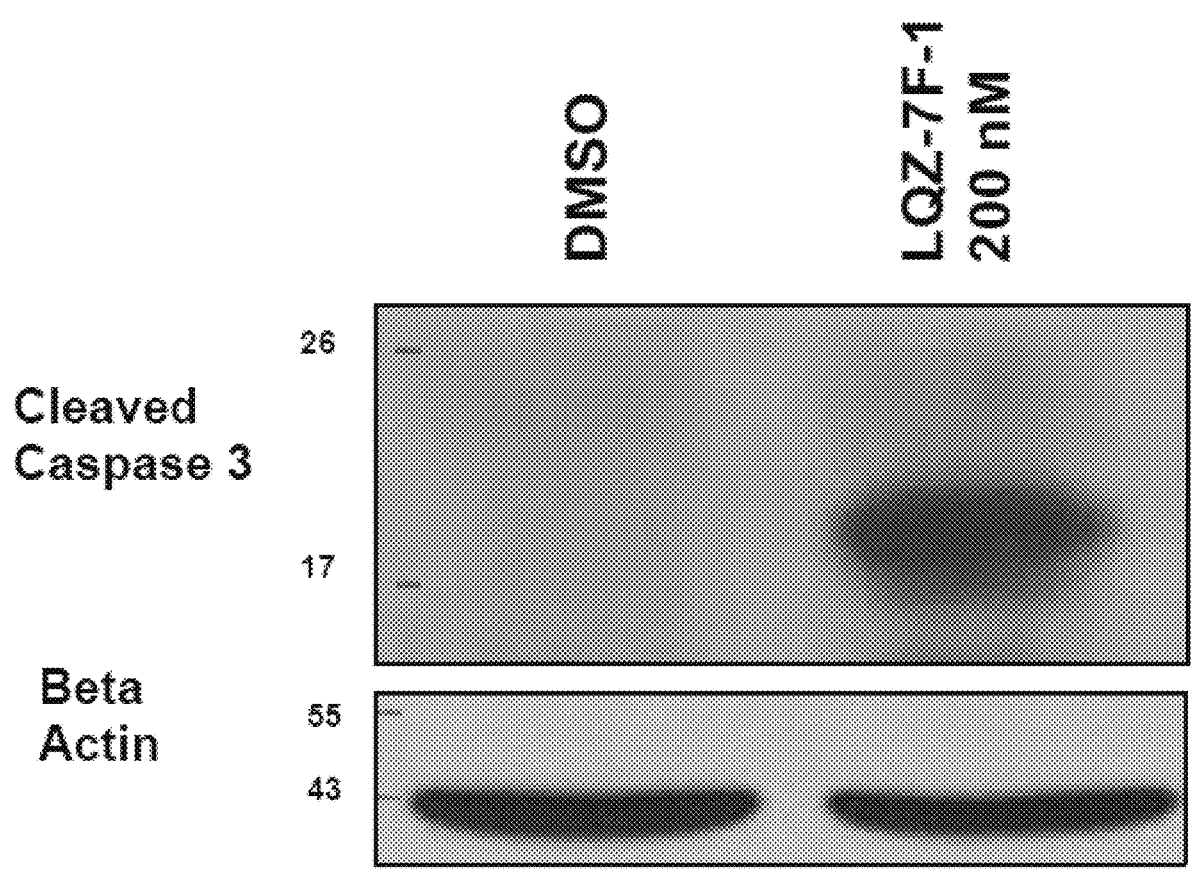
Figure 26B:
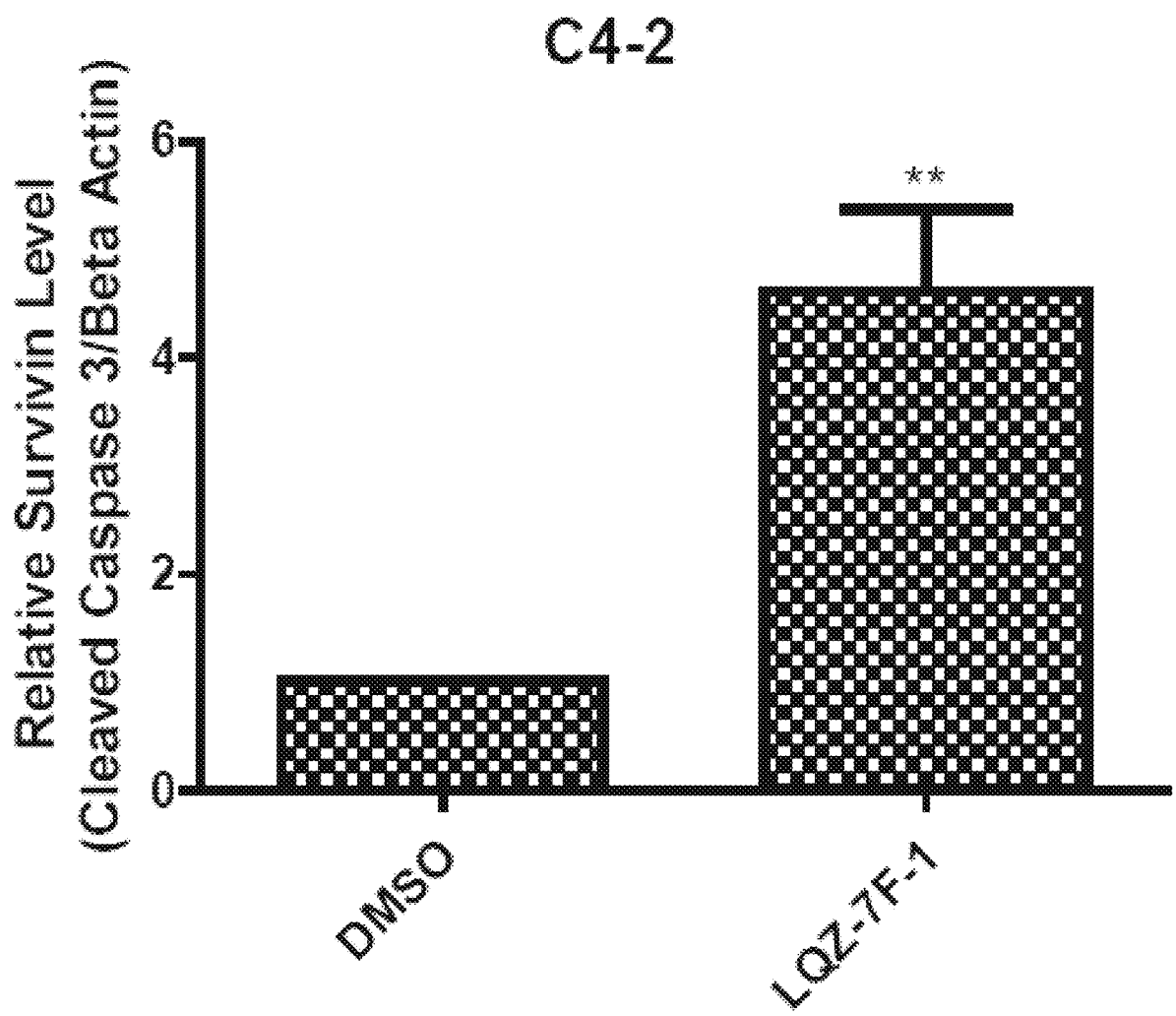

Apoptosis Studies. To determine if LQZ-7F-1 also induces apoptosis of cancer cells Flow Cytometry with Annexin V staining was performed in coordination with the Flow Cytometry Core. Treatment with 200 nM LQZ-7F-1 generated 21.15 and 17.91 relative fold apoptosis increase in PC-3 and C4-2 cells respectively (FIGS. 25A and 25B). In order to validate the apoptosis data from the annexin v staining, western blotting analysis was performed utilizing an apoptosis marker, cleaved caspase 3, which is activated and protein levels increase during the apoptosis cascade. As shown in FIGS. 26A and 26B, treatment with LQZ-7F-1 also caused an increase in cleaved caspase 3 levels in both PC-3 and C4-2 cells. Overall this section provides evidence that LQZ-7F-1 also promotes cancer cell death after survivin degradation by spontaneous apoptosis.

Figure 27A:
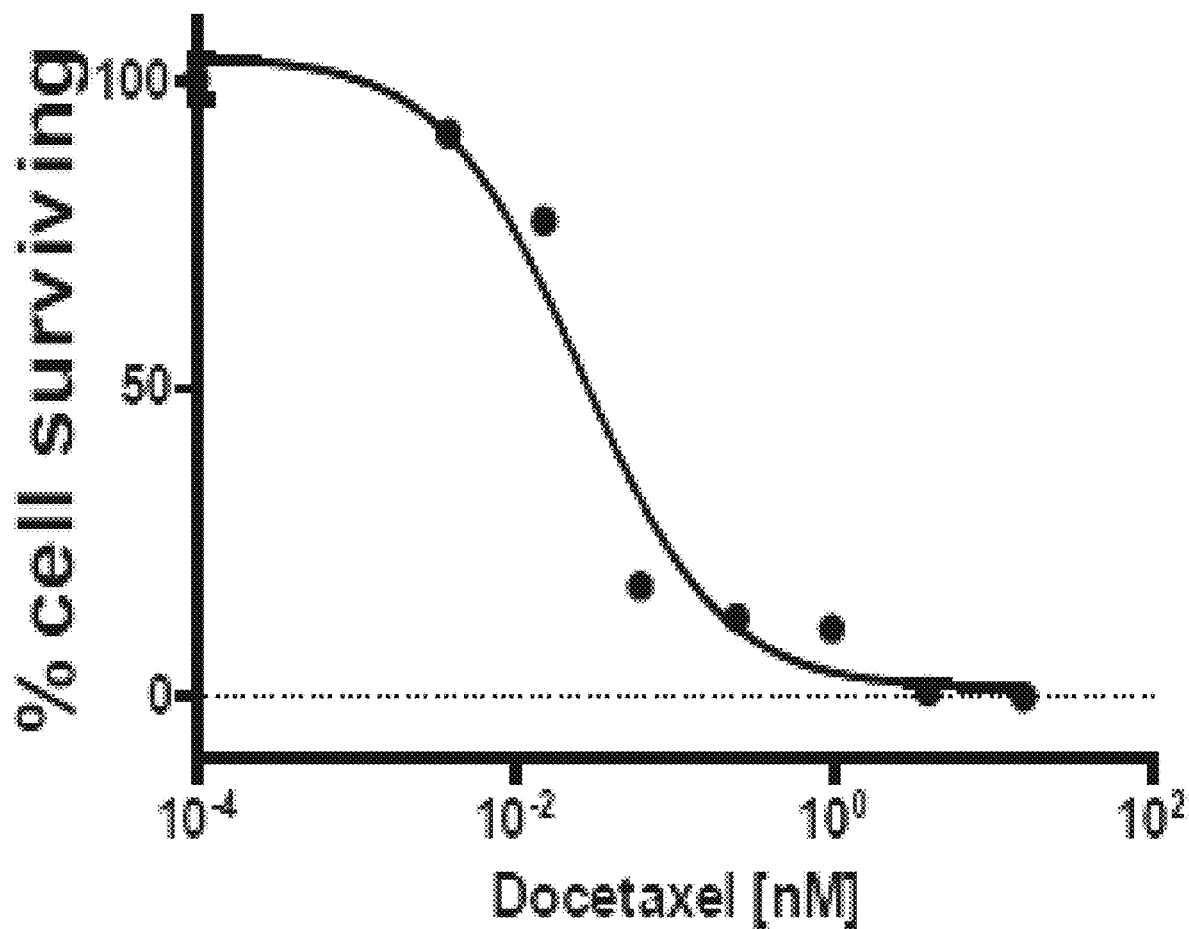
Figure 27A:
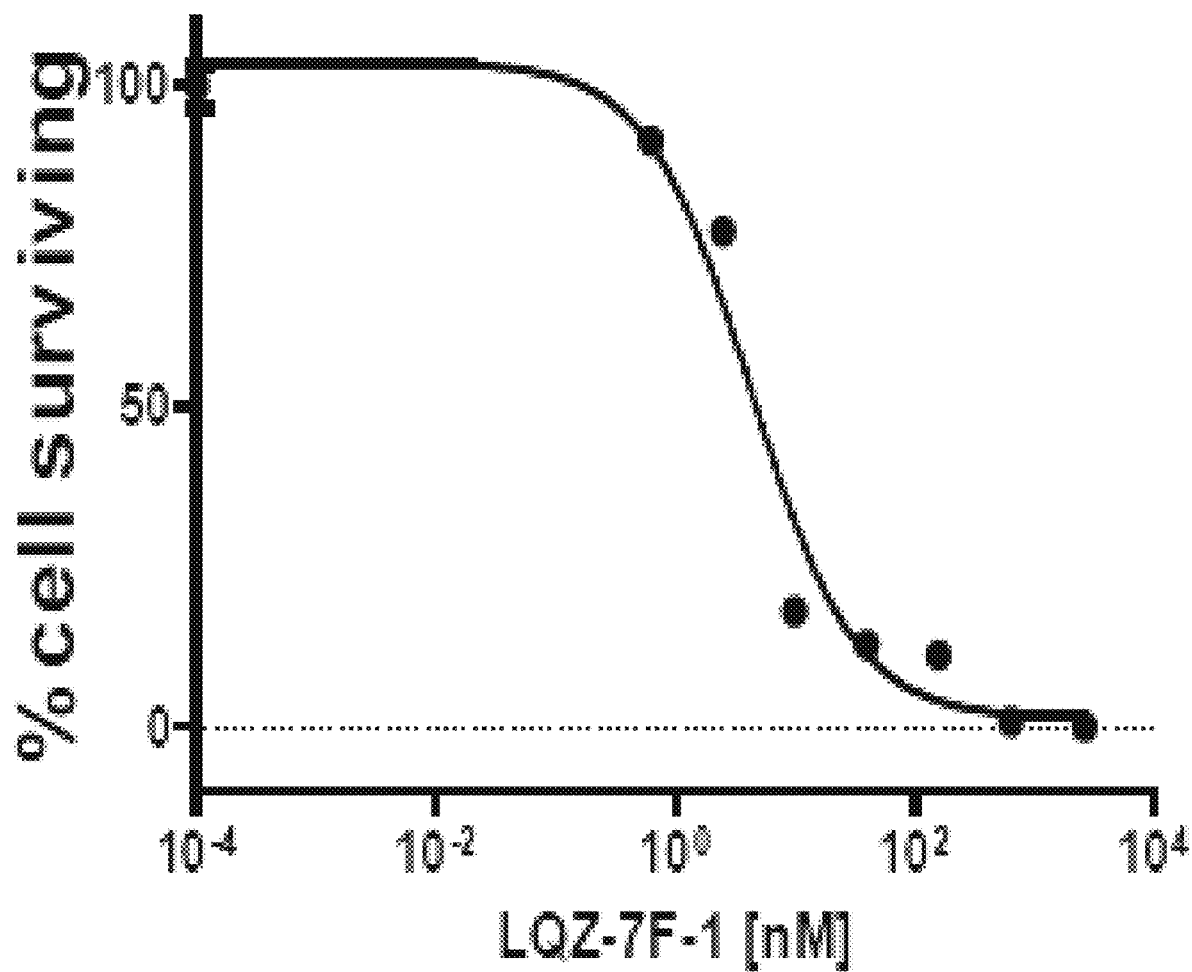
Figure 27A:
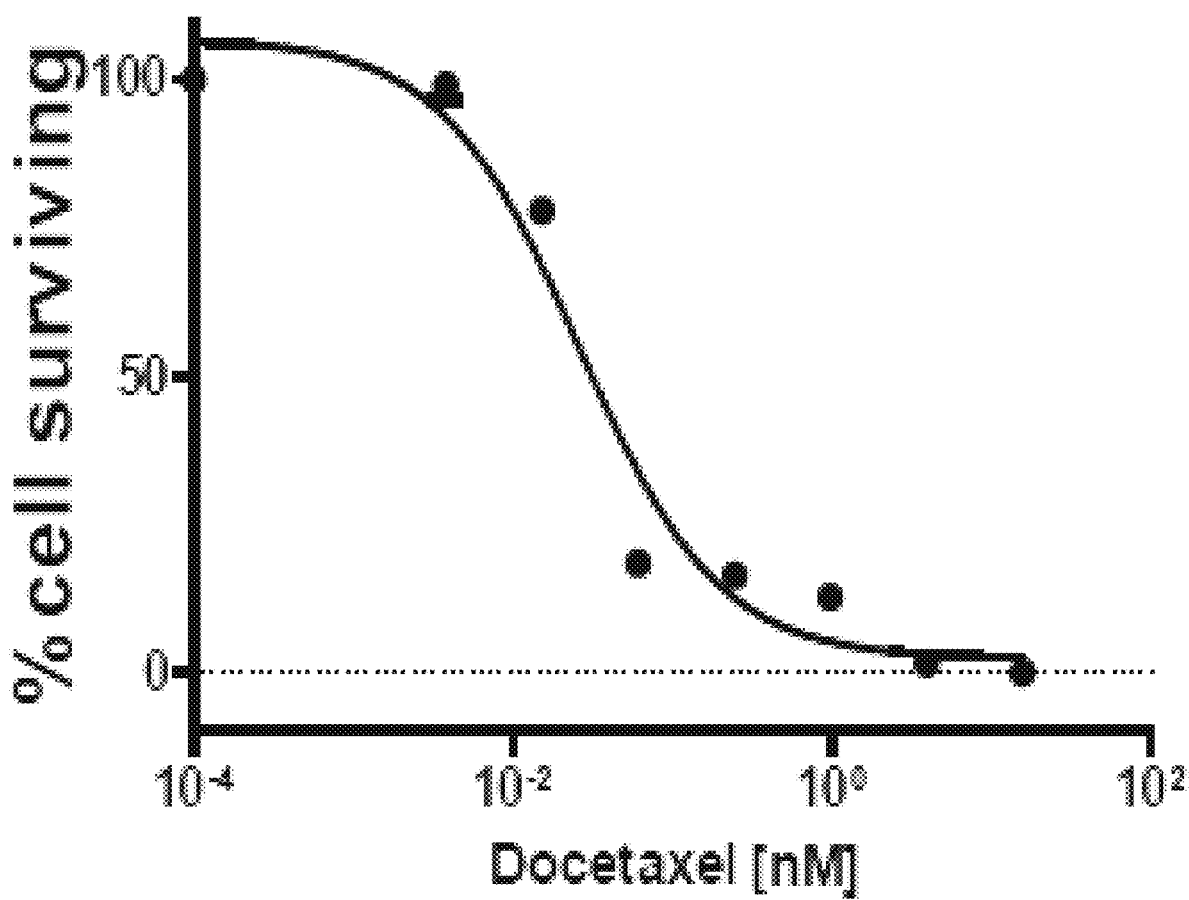
Figure 27A:
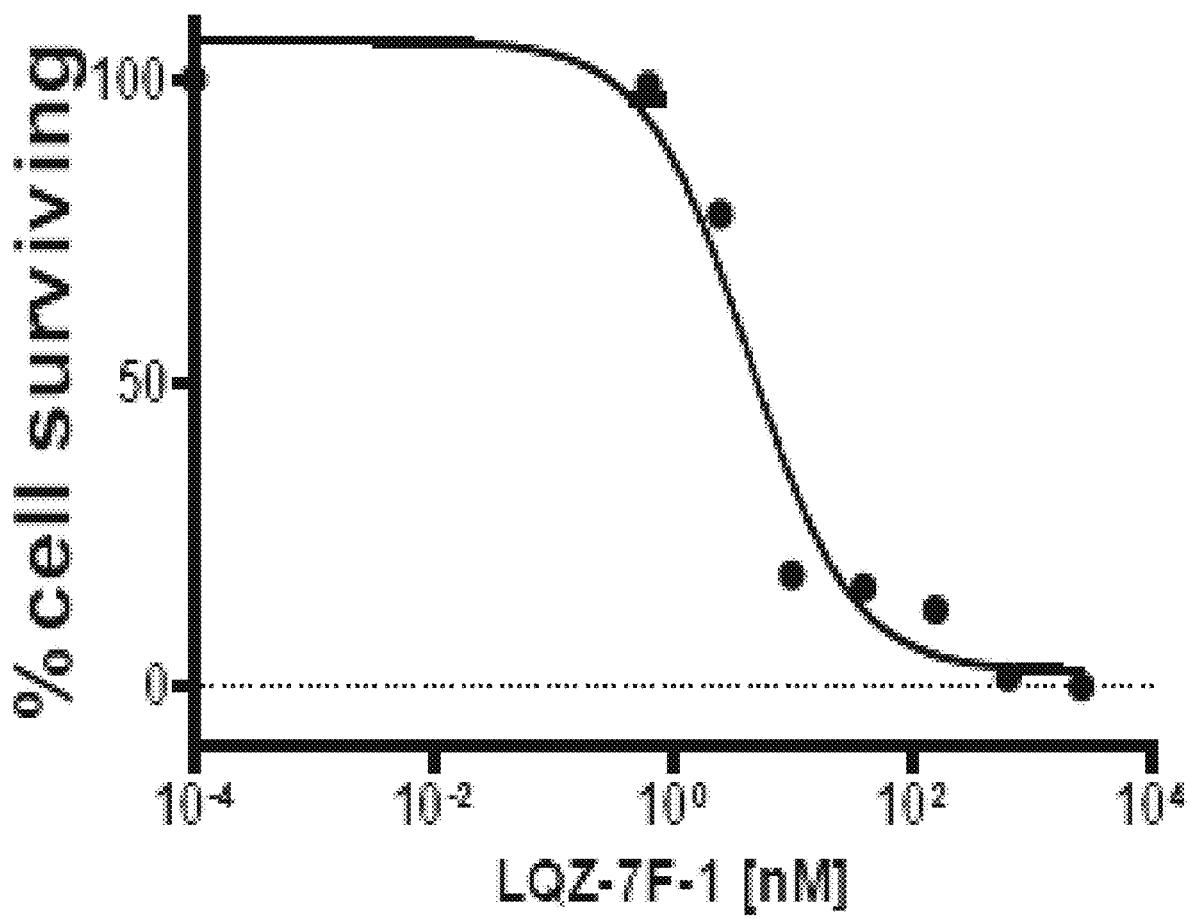
Figure 27A:
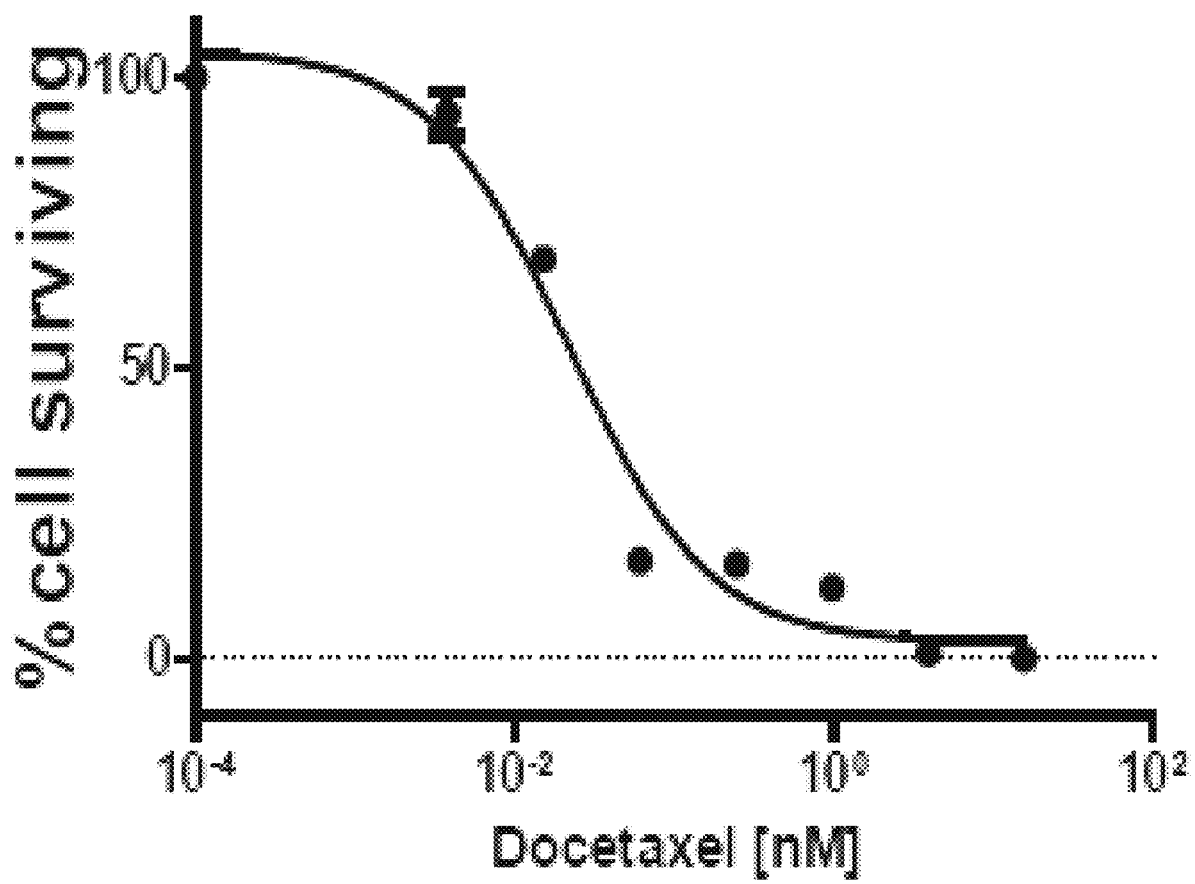
Figure 27A:
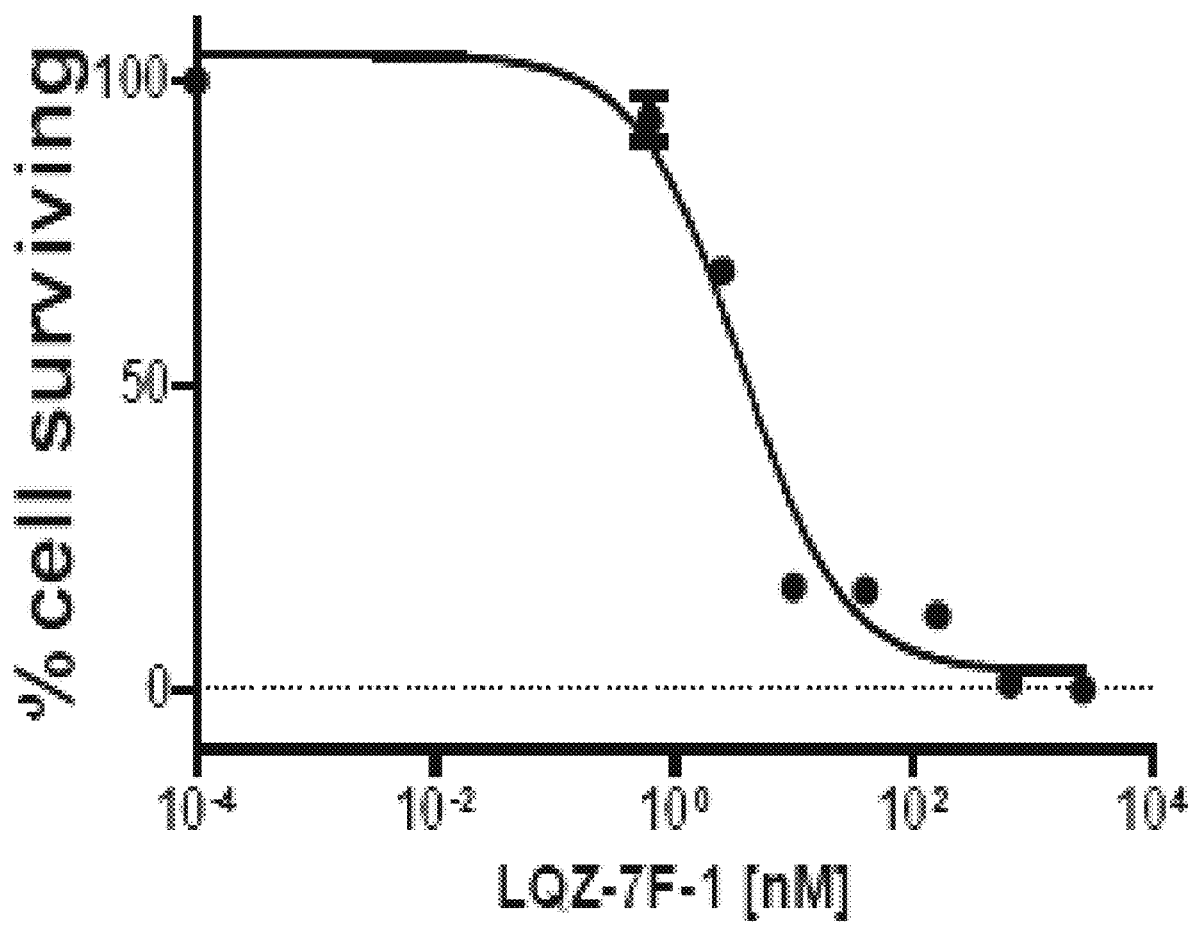
Figure 27A:
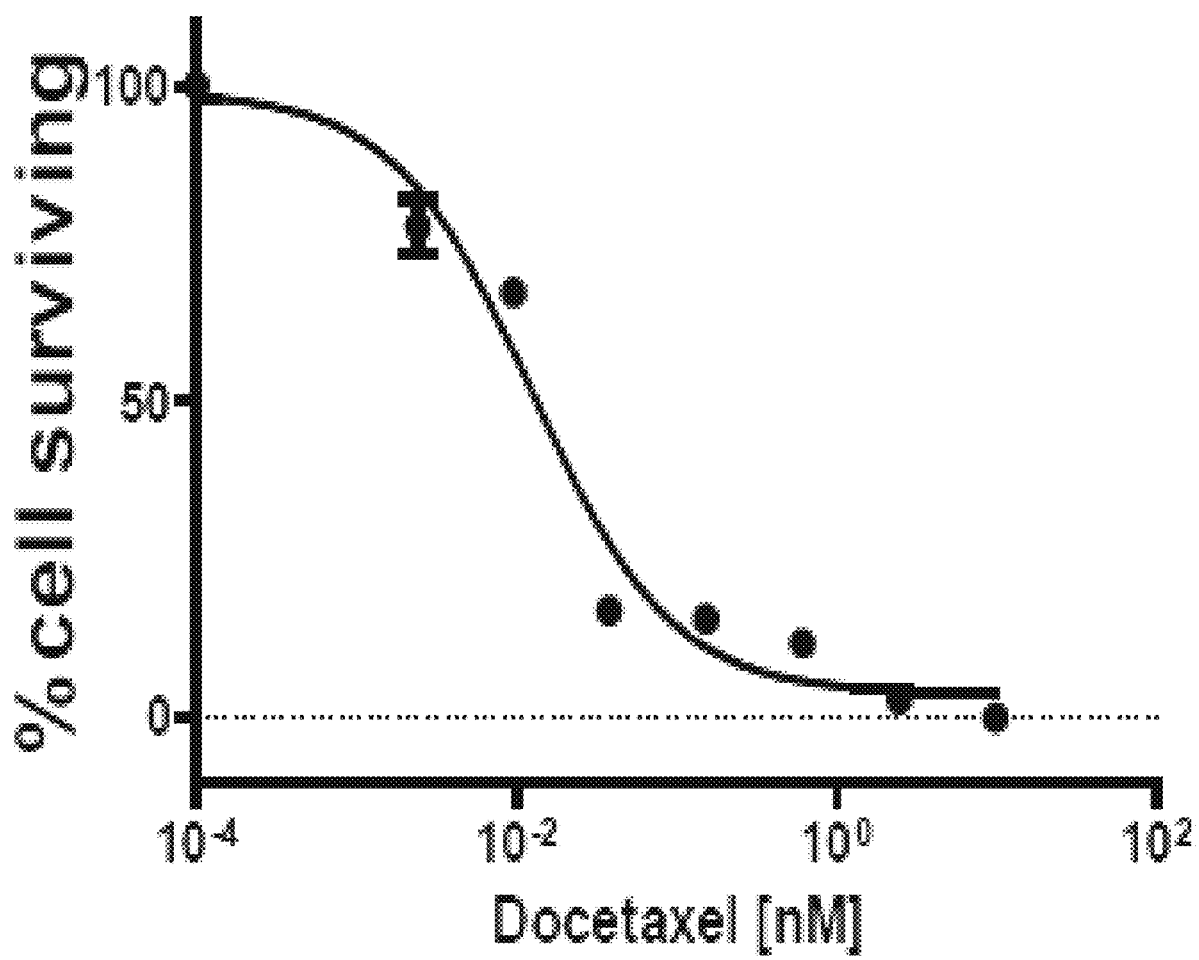
Figure 27A:
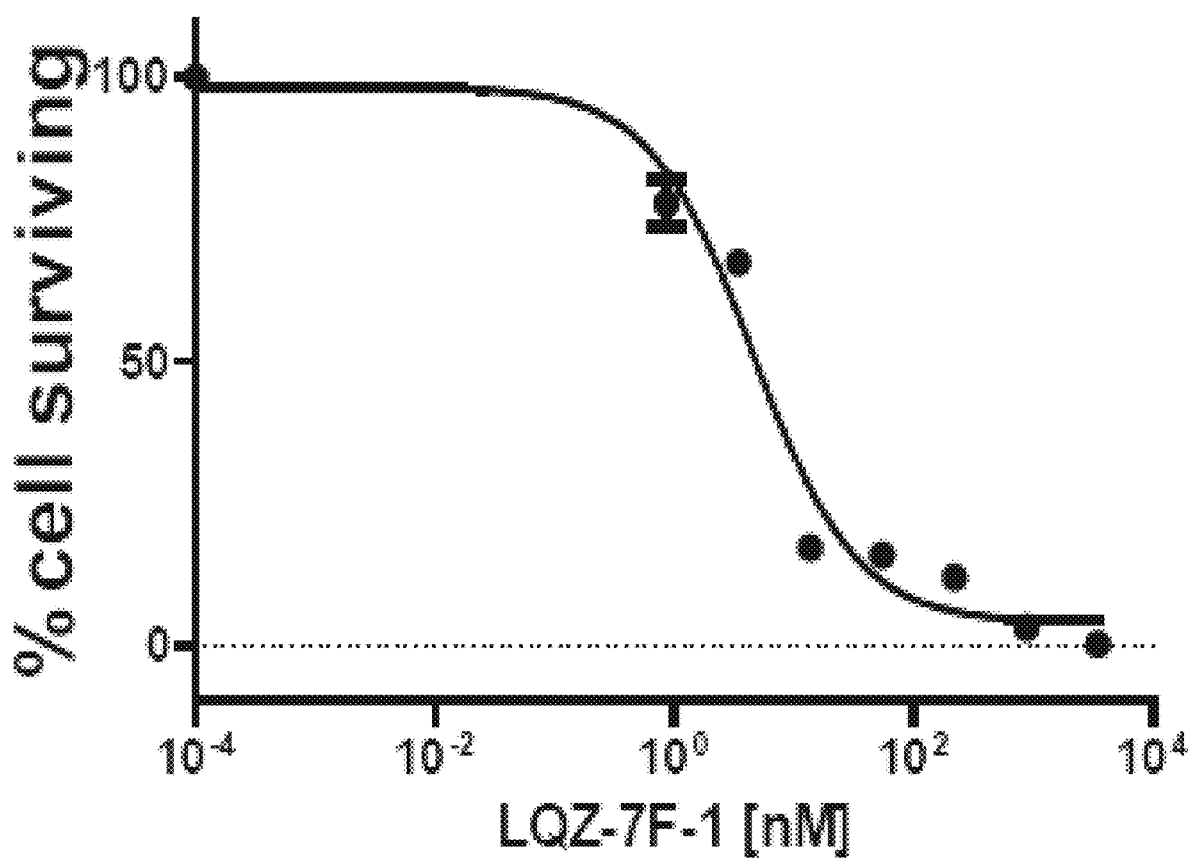
Figure 27A:
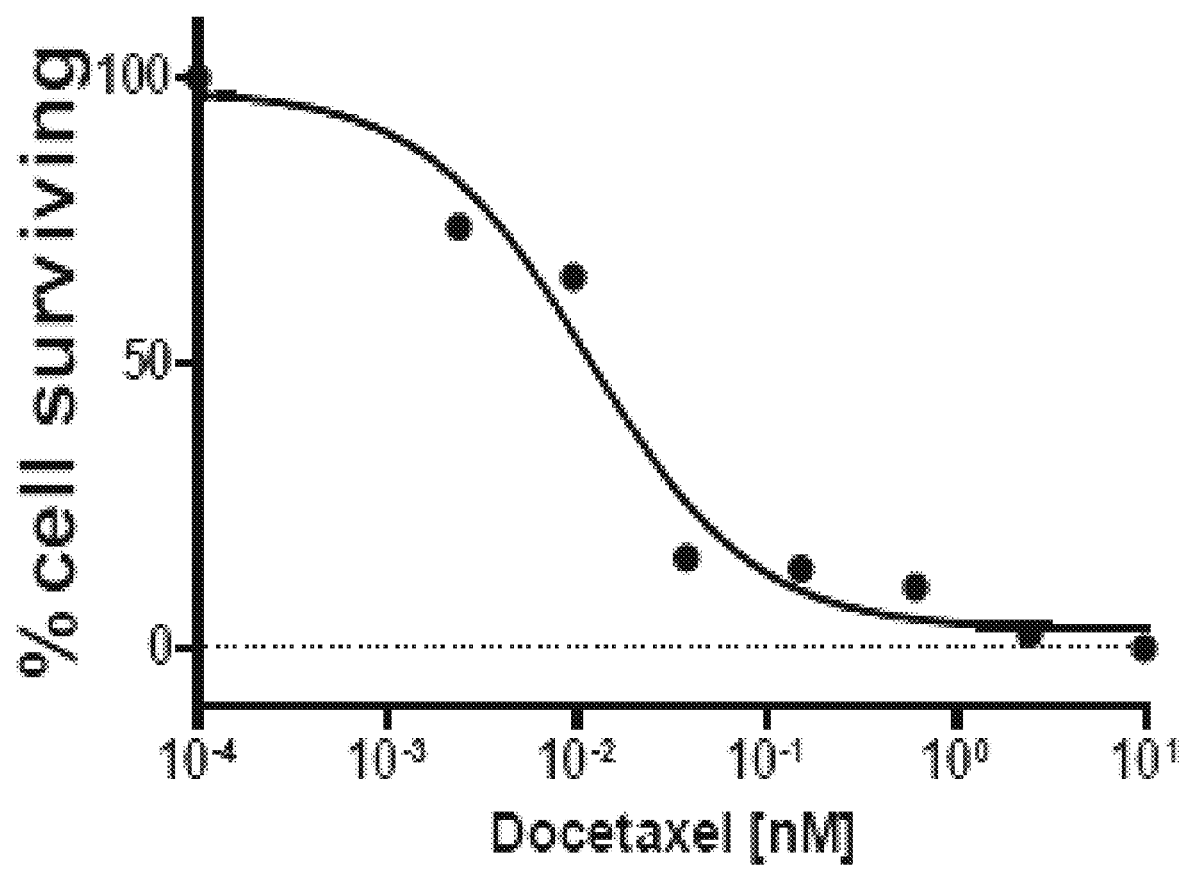
Figure 27A:
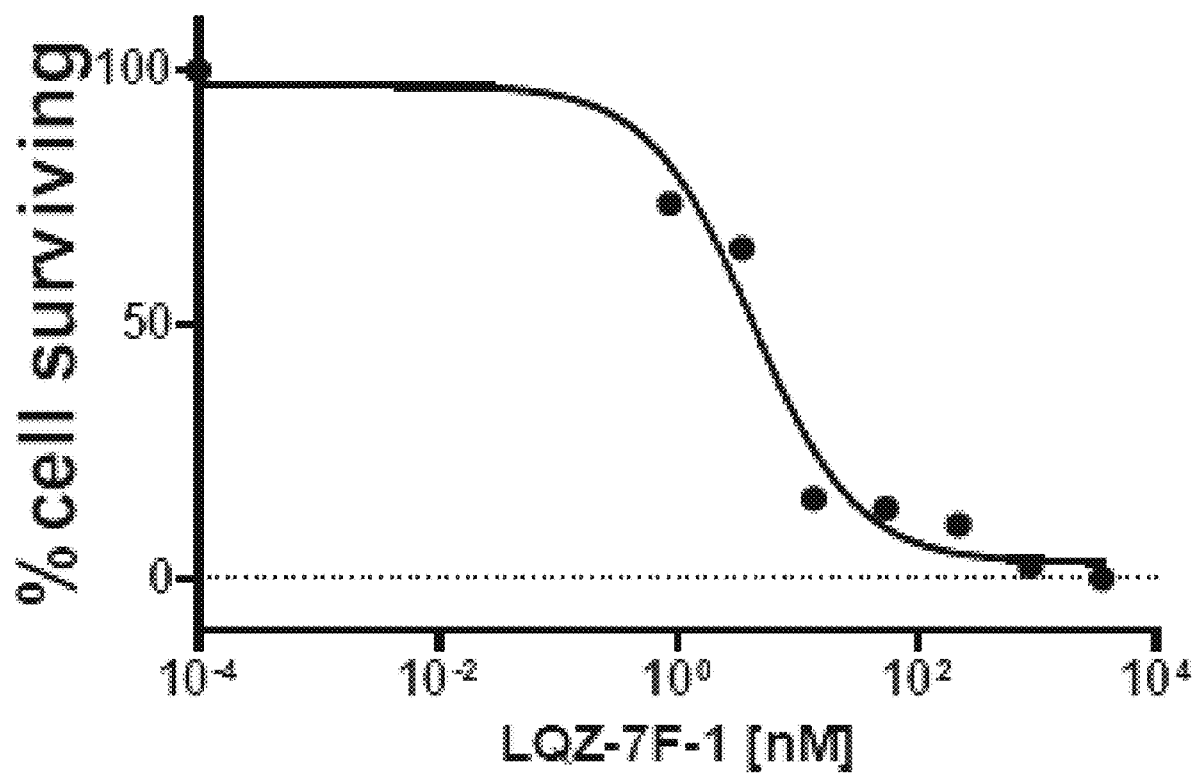
Figure 27A:
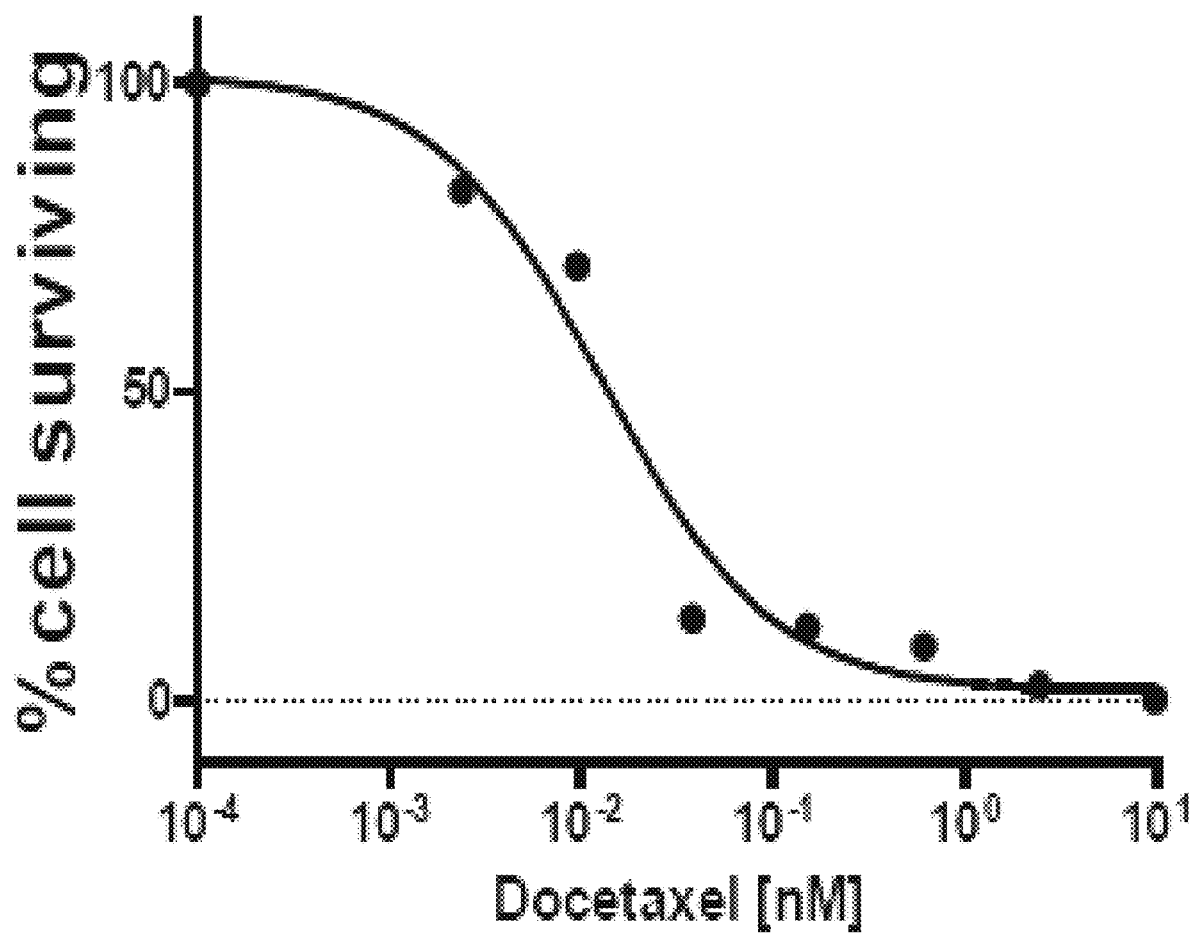
Figure 27A:
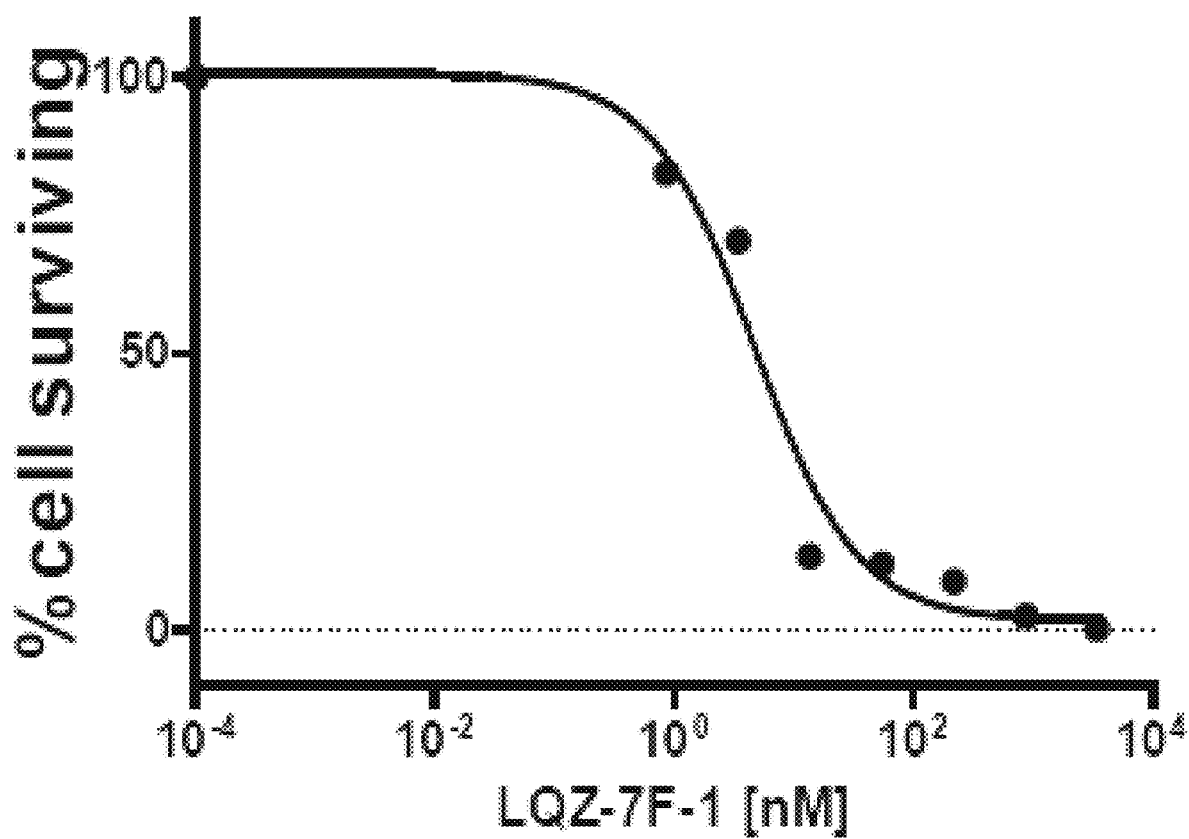
Figure 27B:
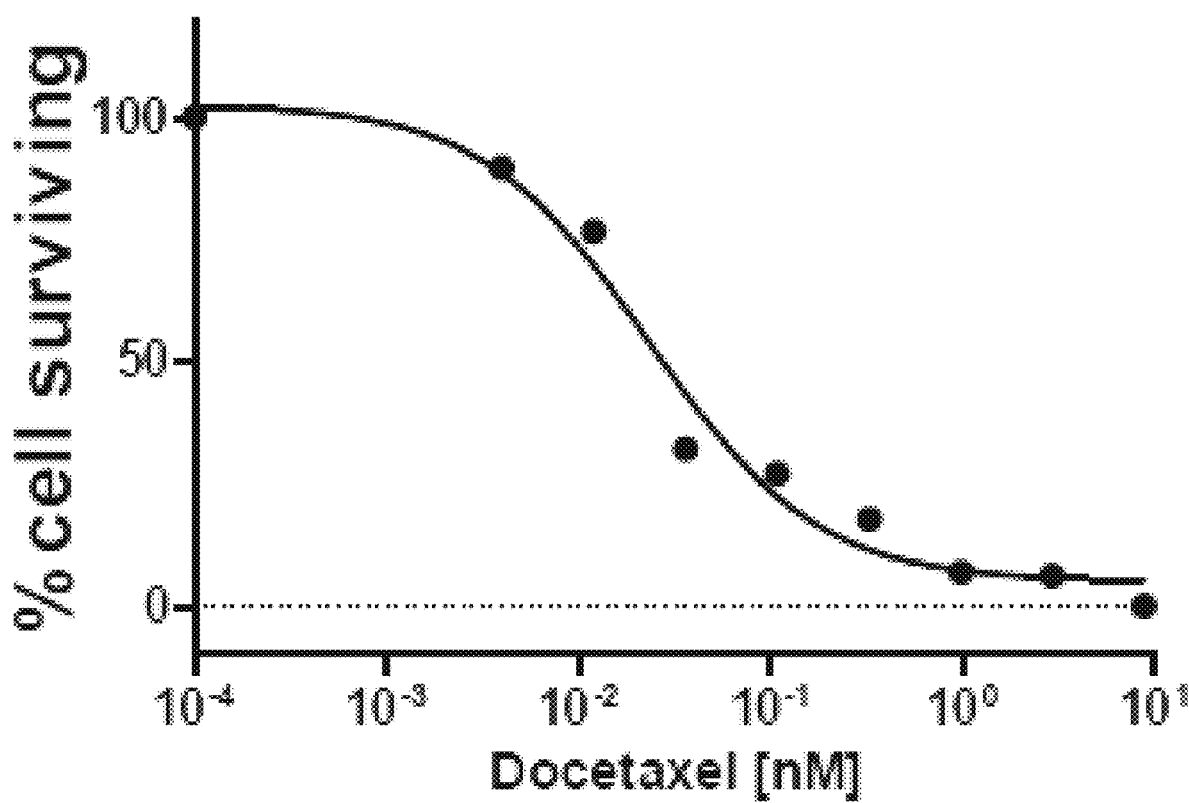
Figure 27B:
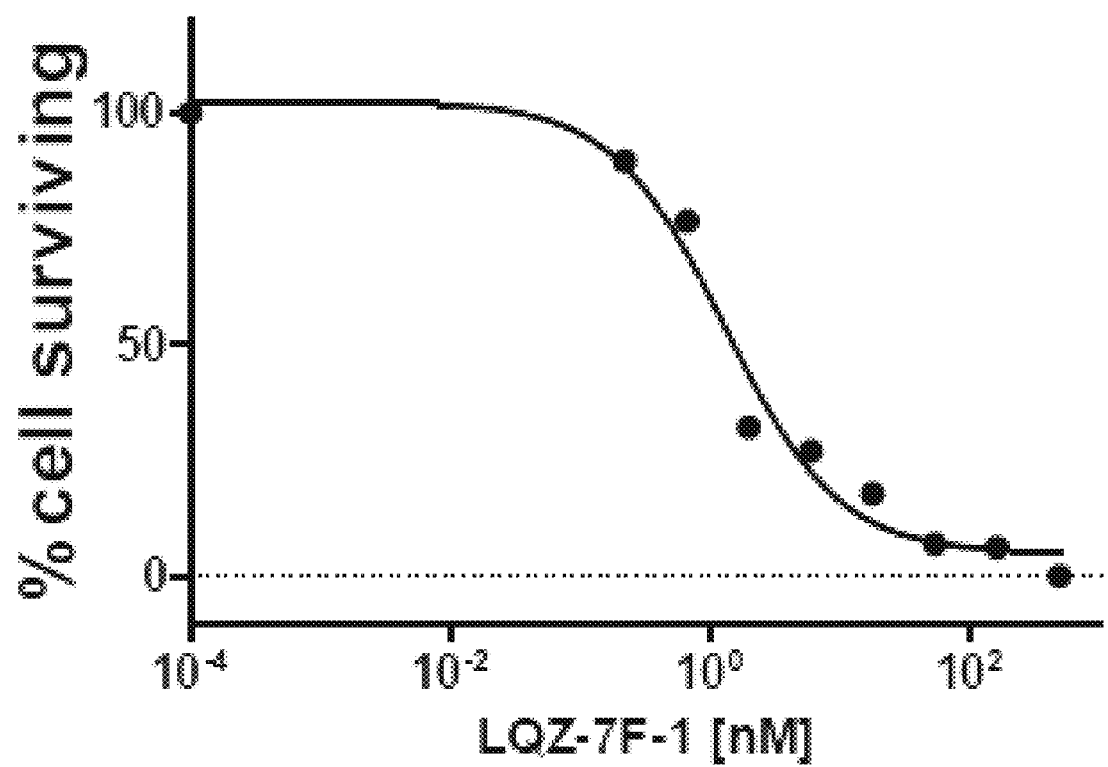
Figure 27B:
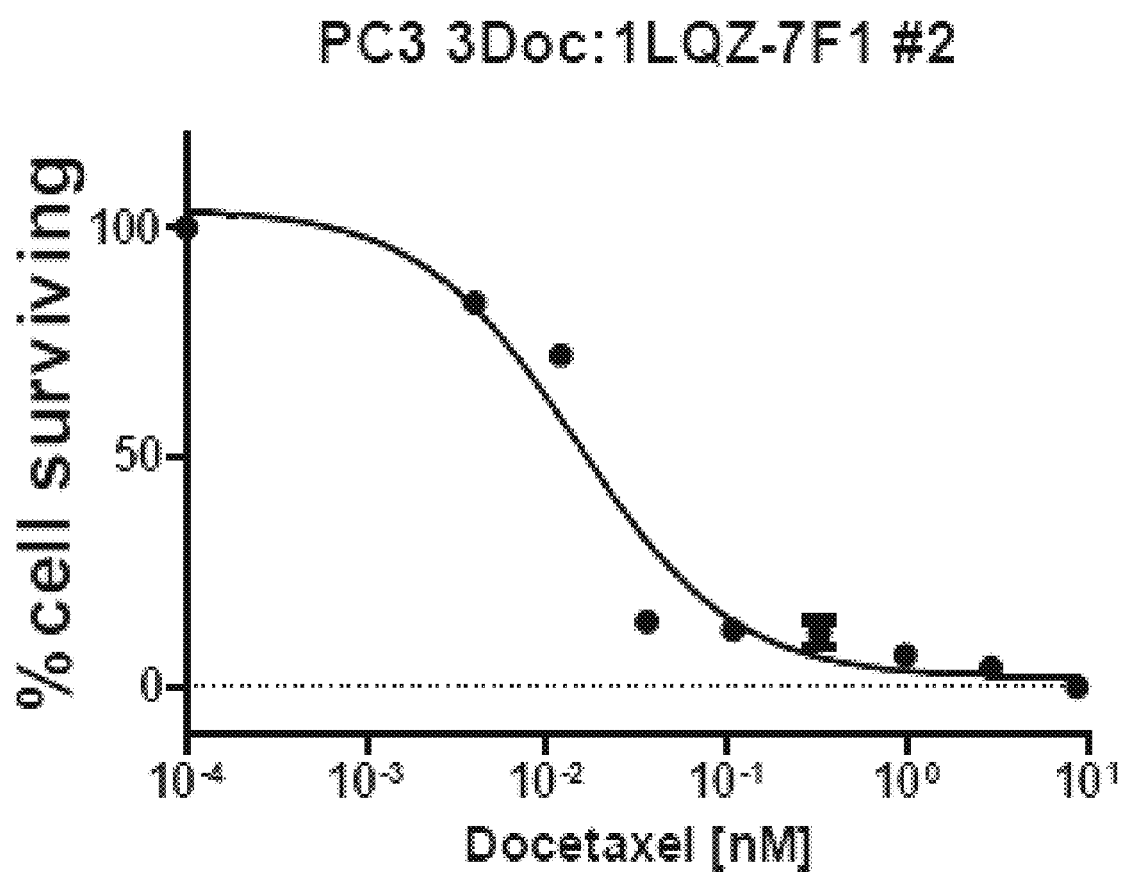
Figure 27B:
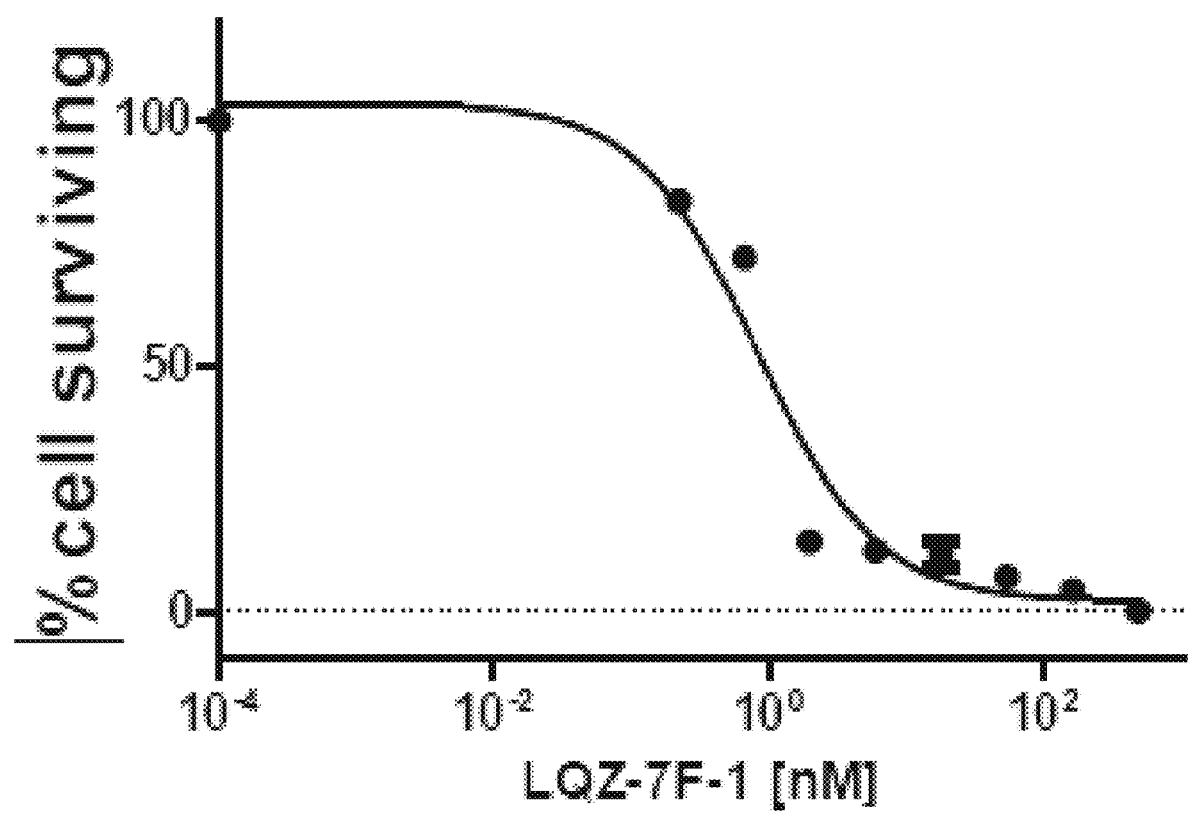
Figure 27B:
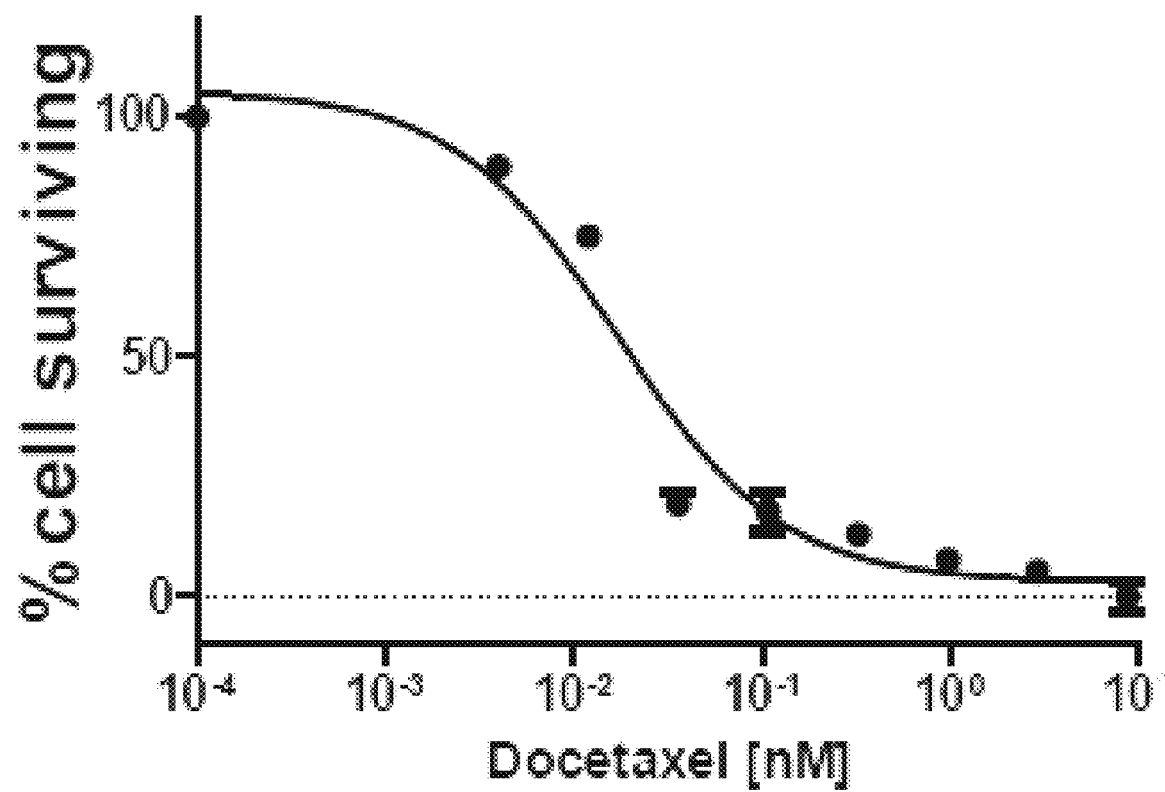
Figure 27B:
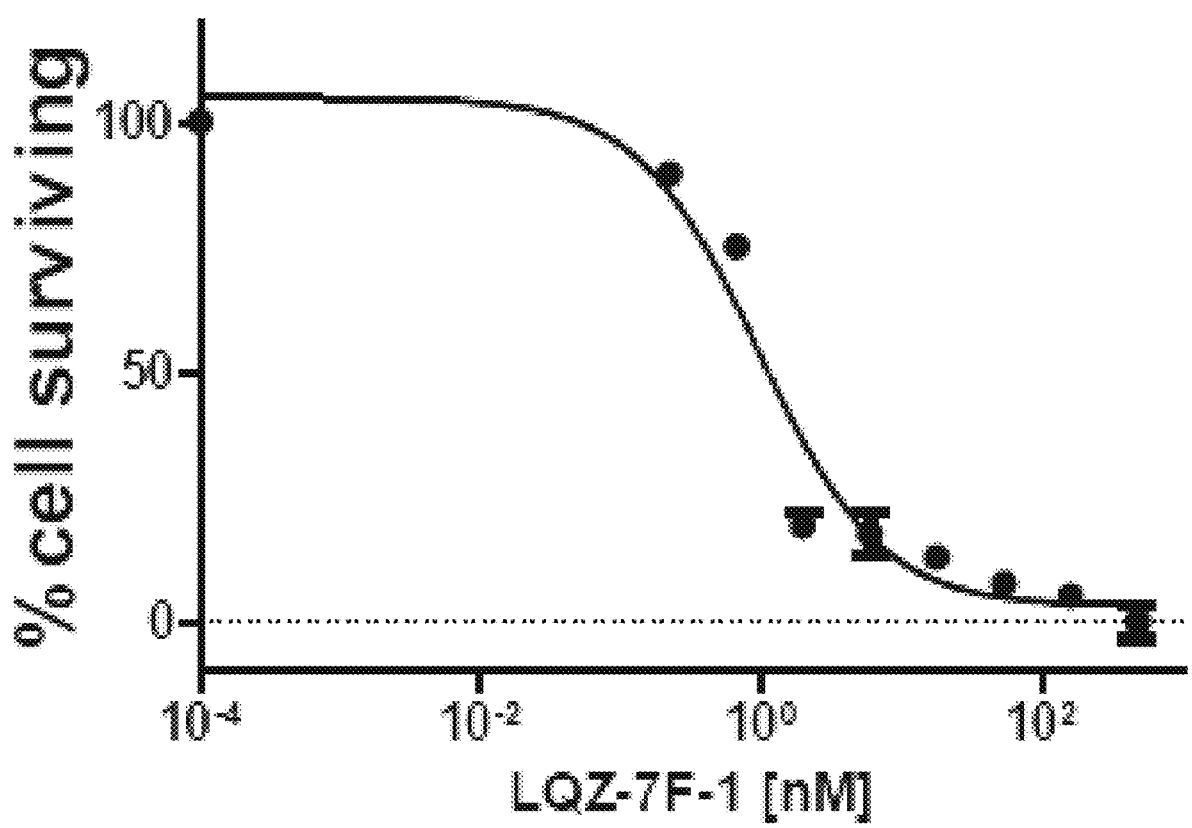
Figure 27B:
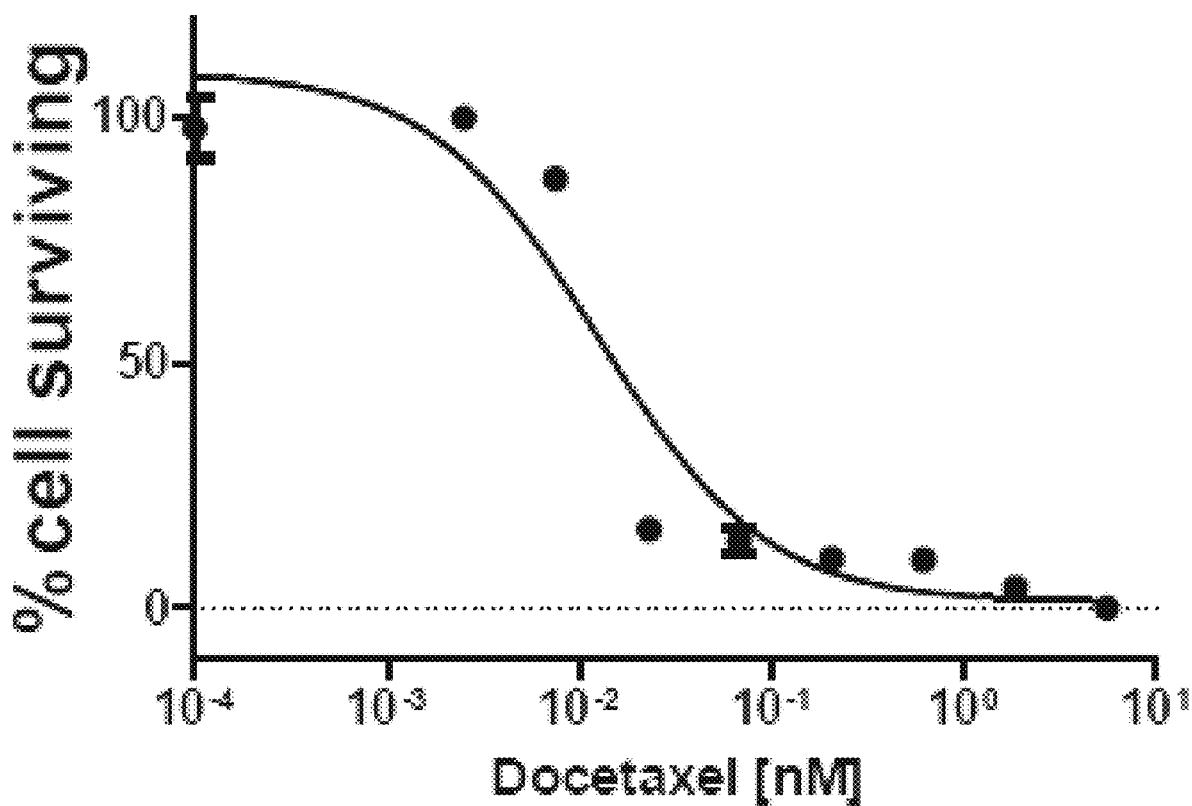
Figure 27B:
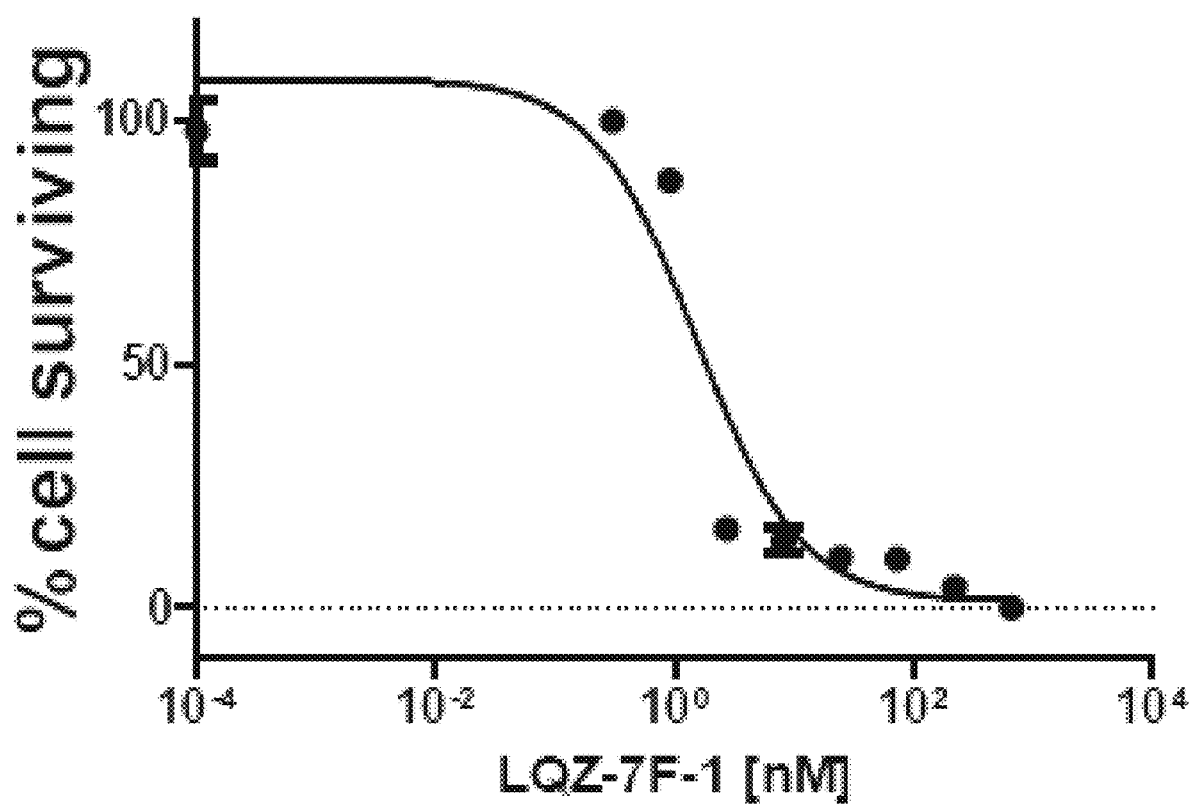
Figure 27B:
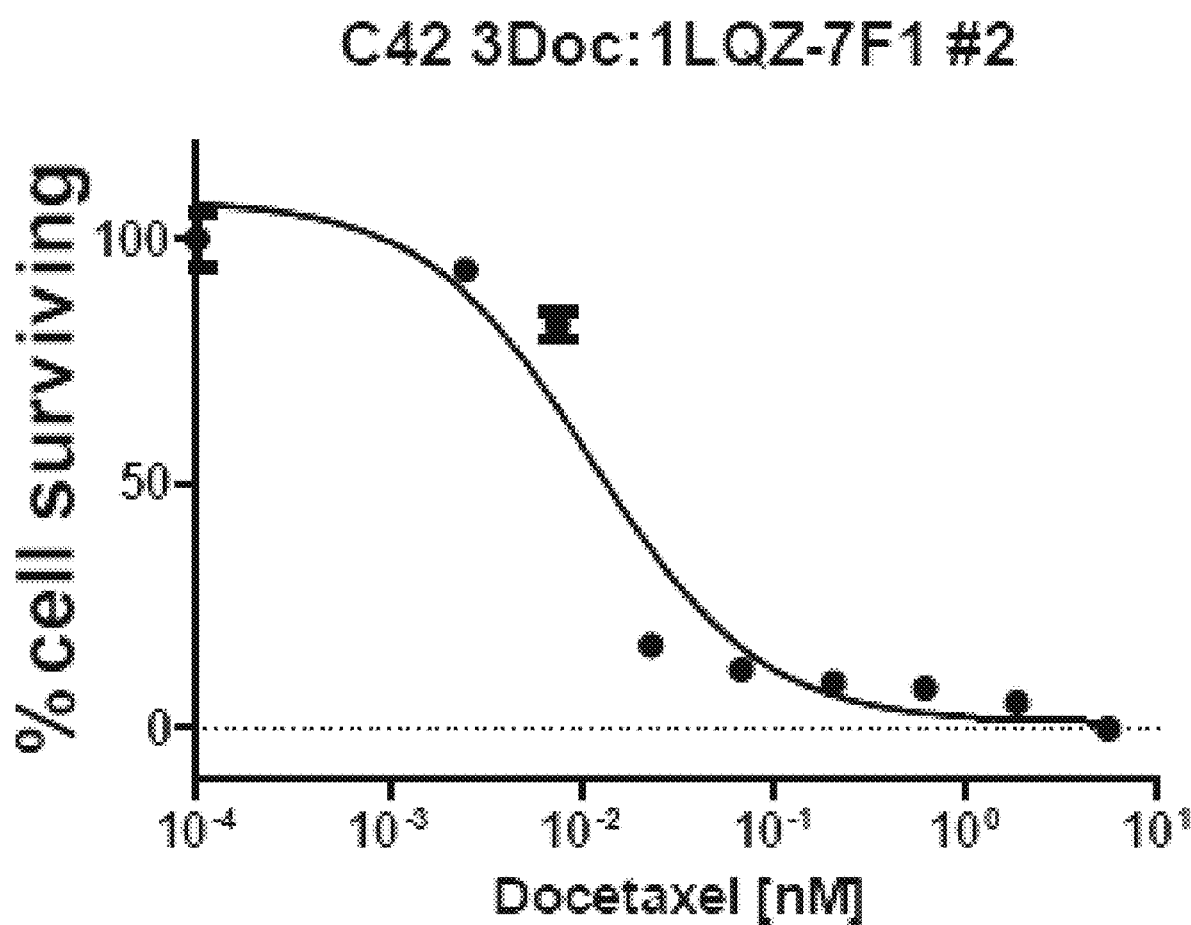
Figure 27B:
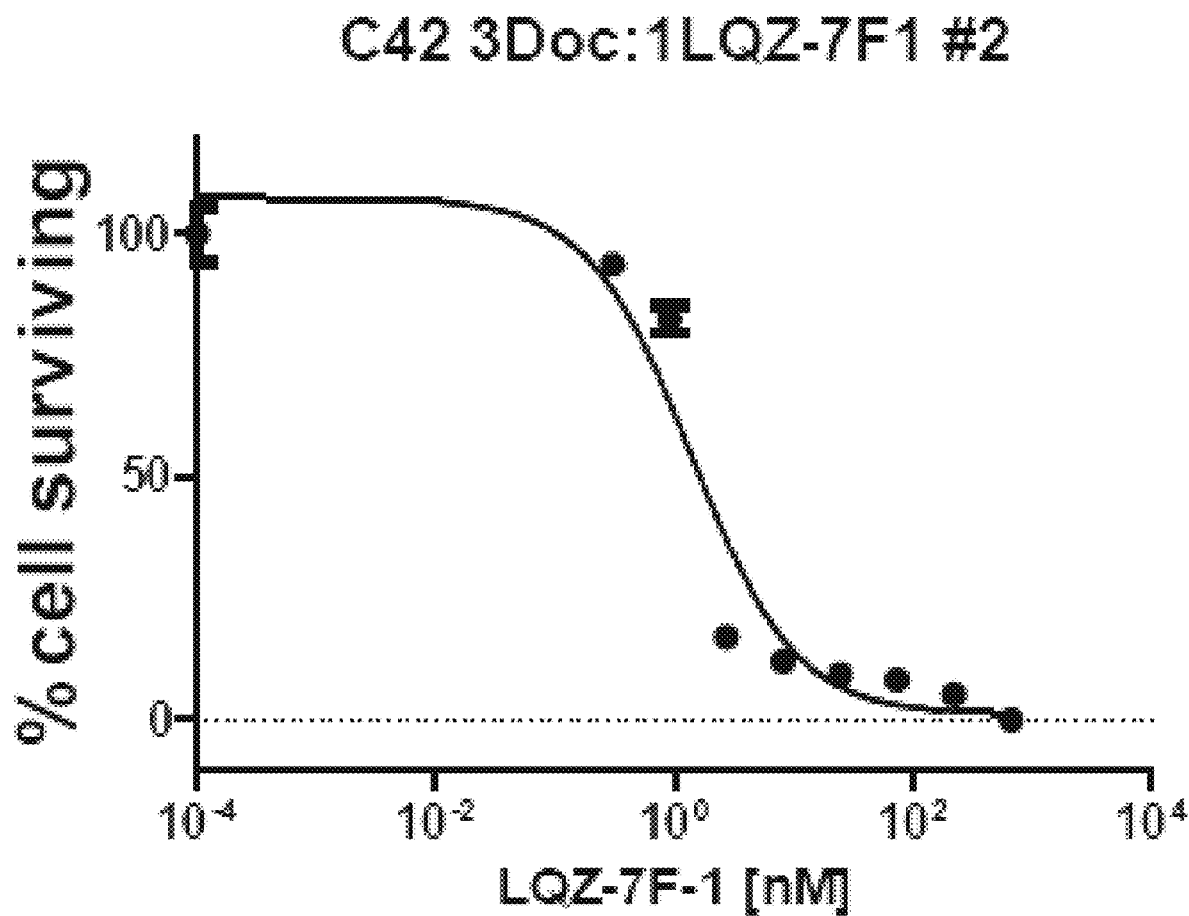
Figure 27B:
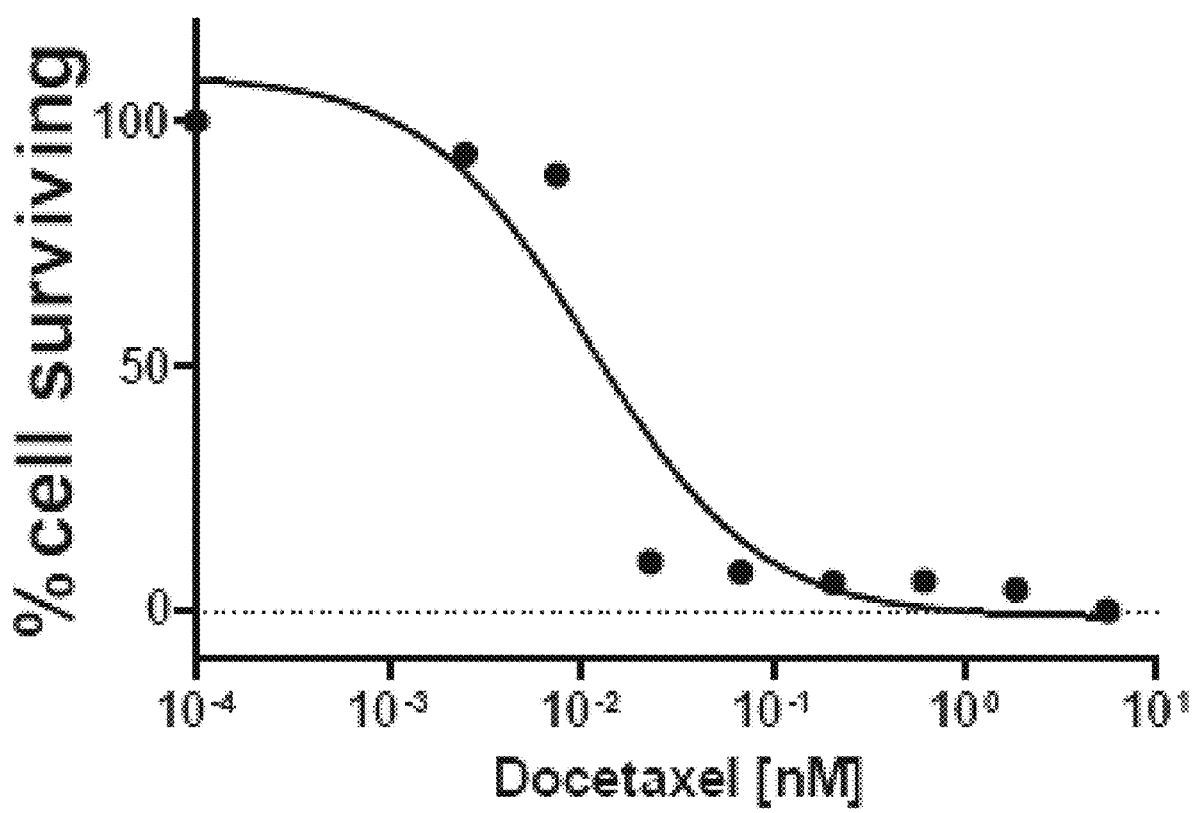
Figure 27B:
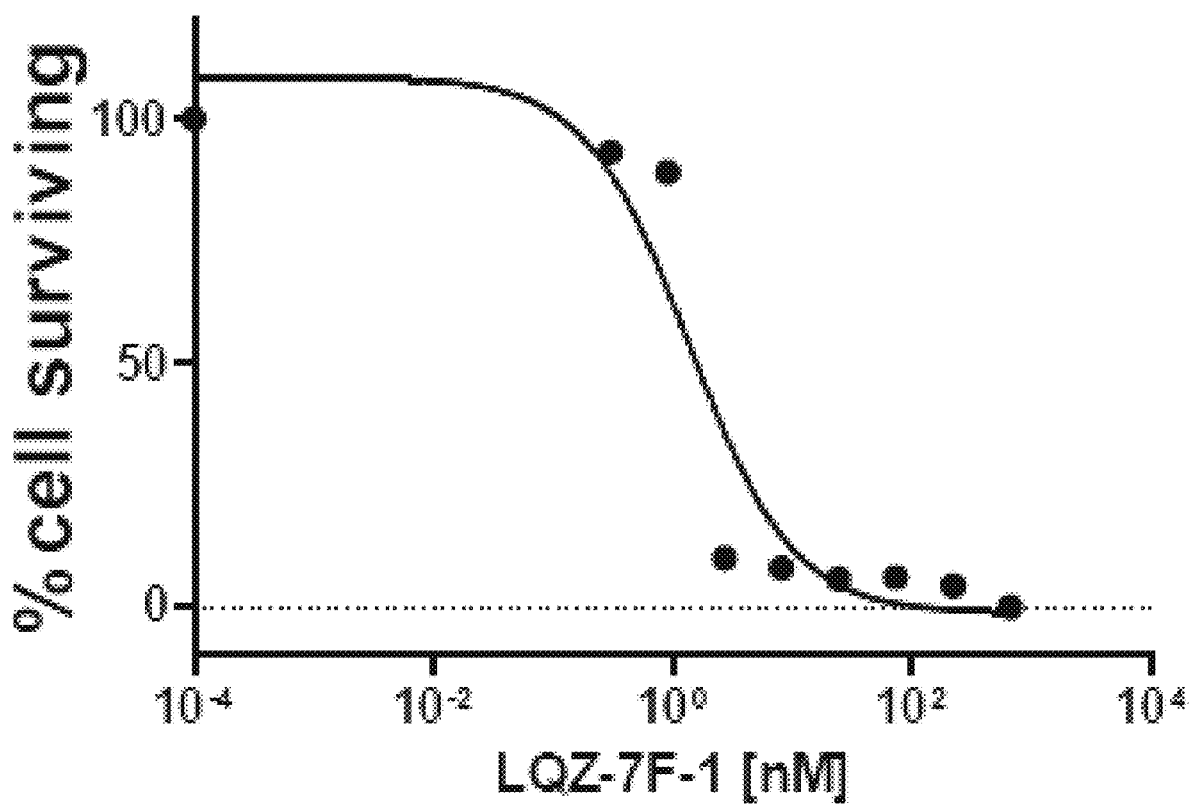
Figure 27C:
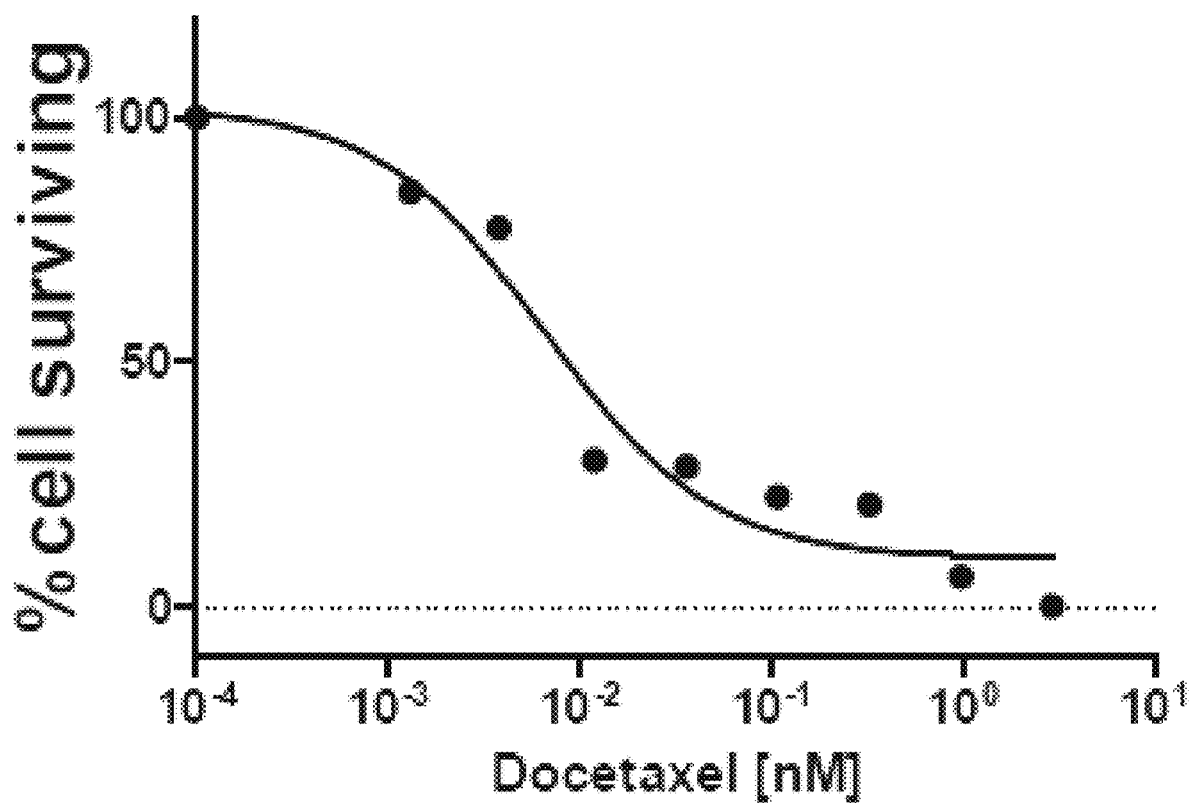
Figure 27C:
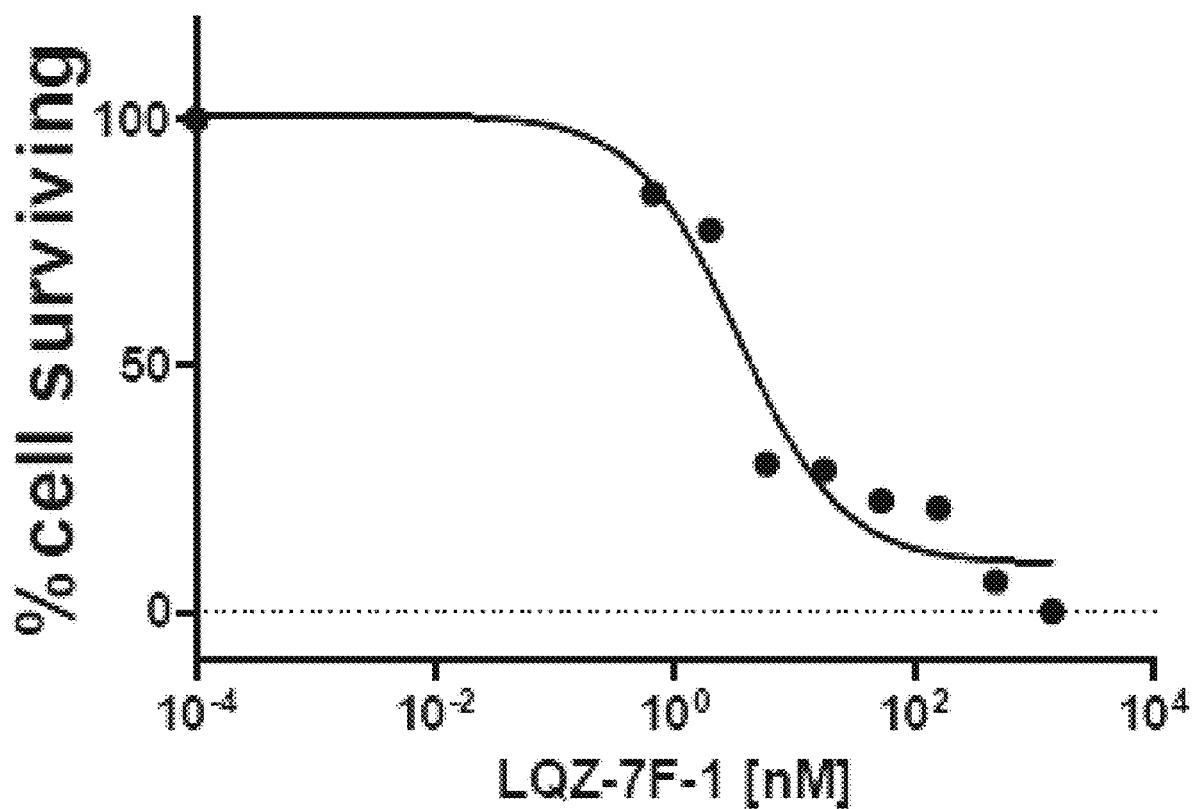
Figure 27C:
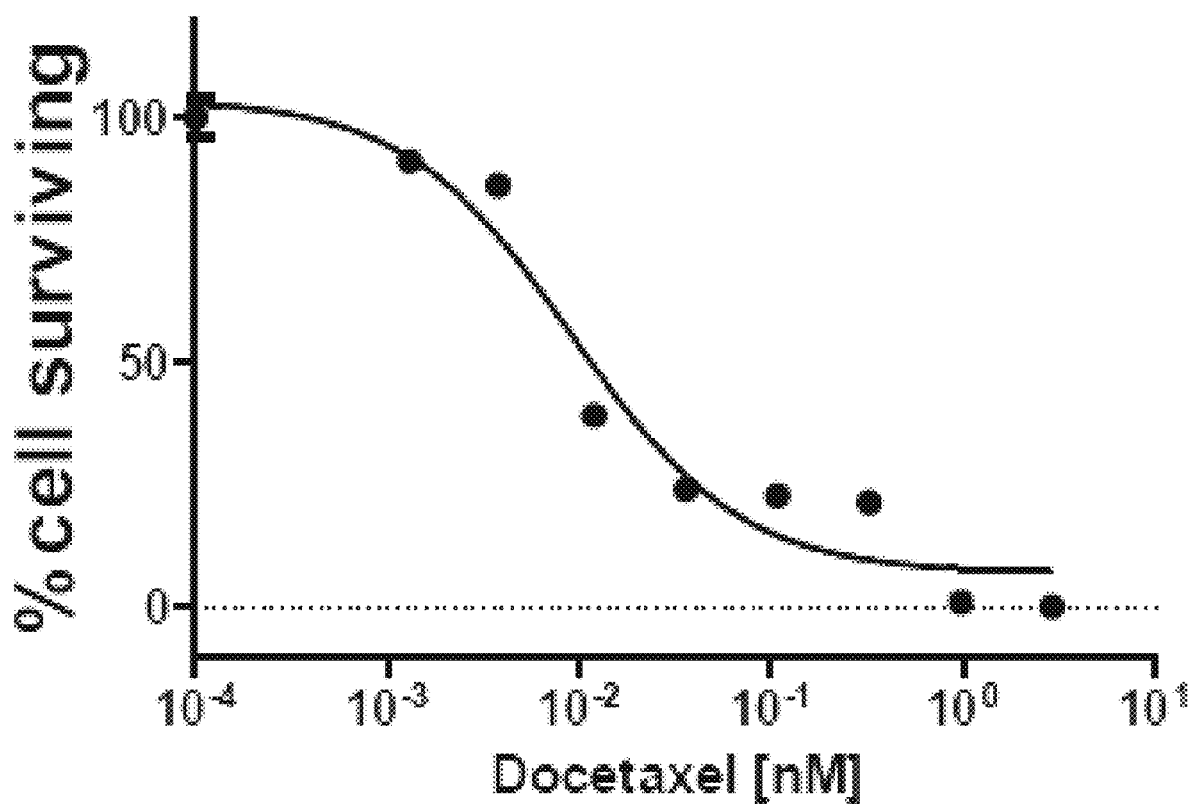
Figure 27C:
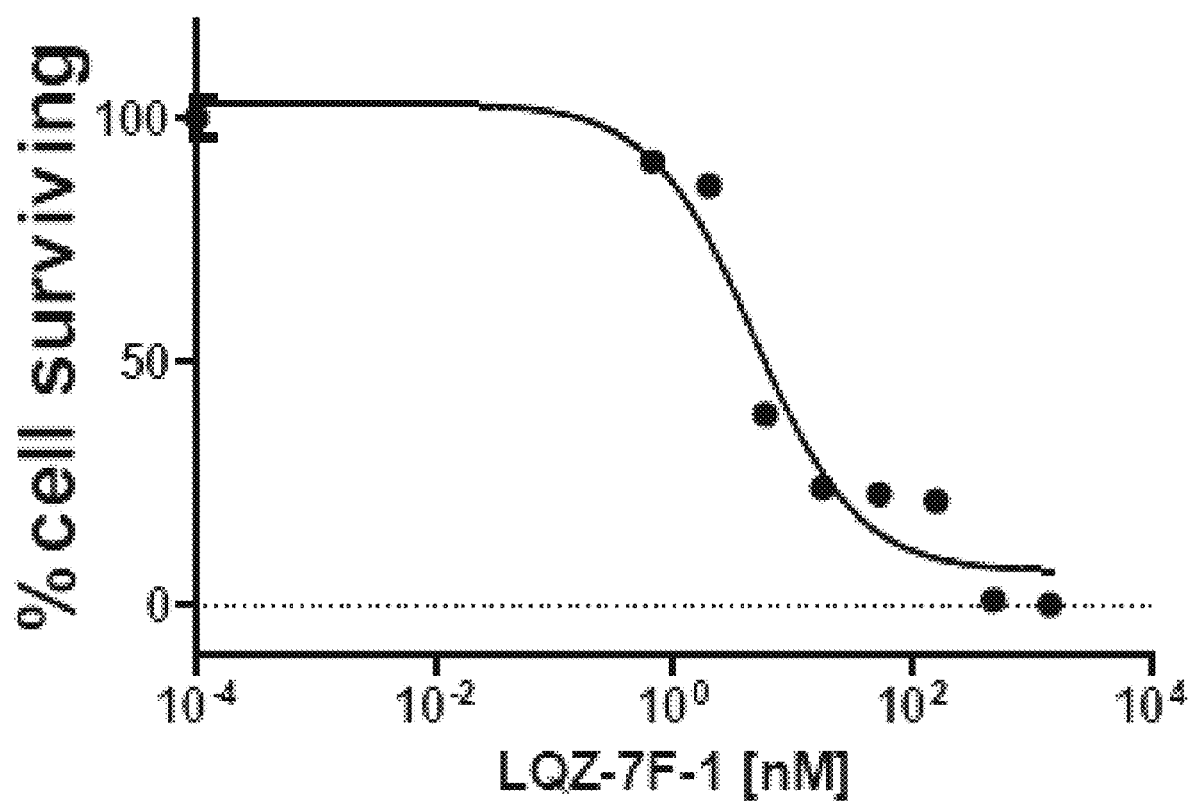
Figure 27C:
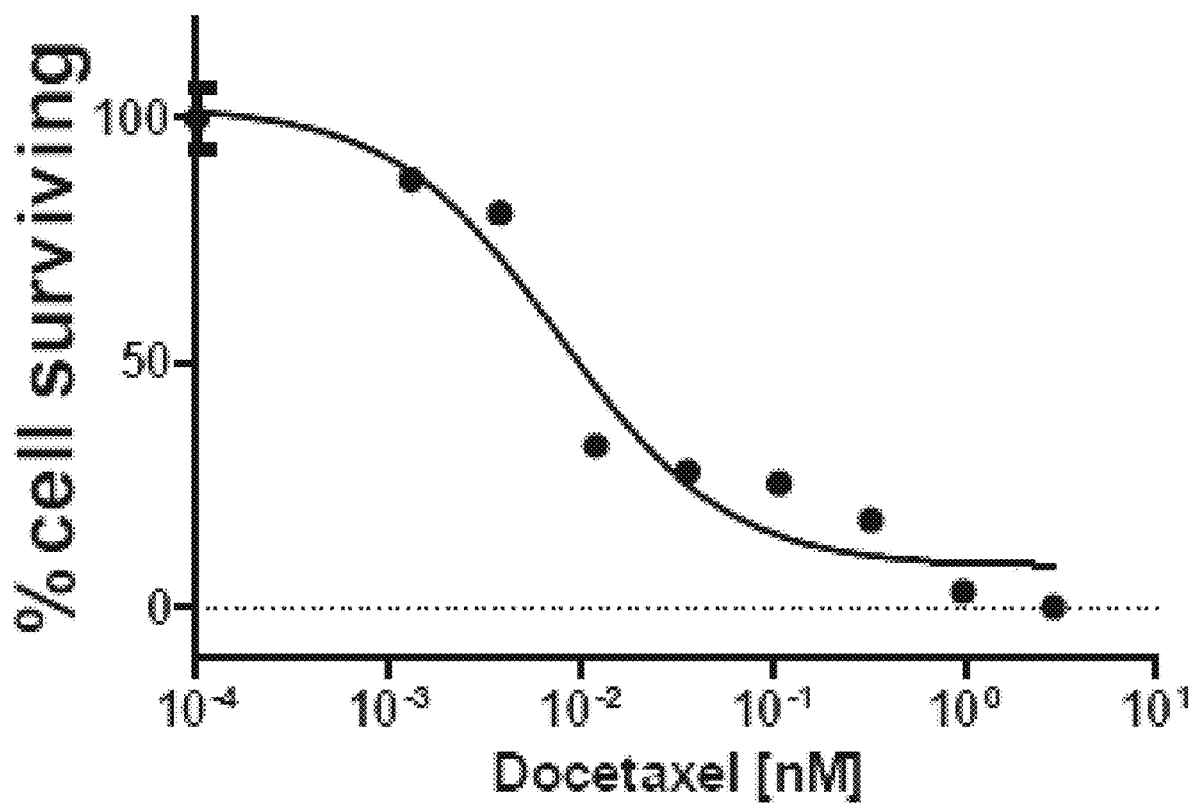
Figure 27C:
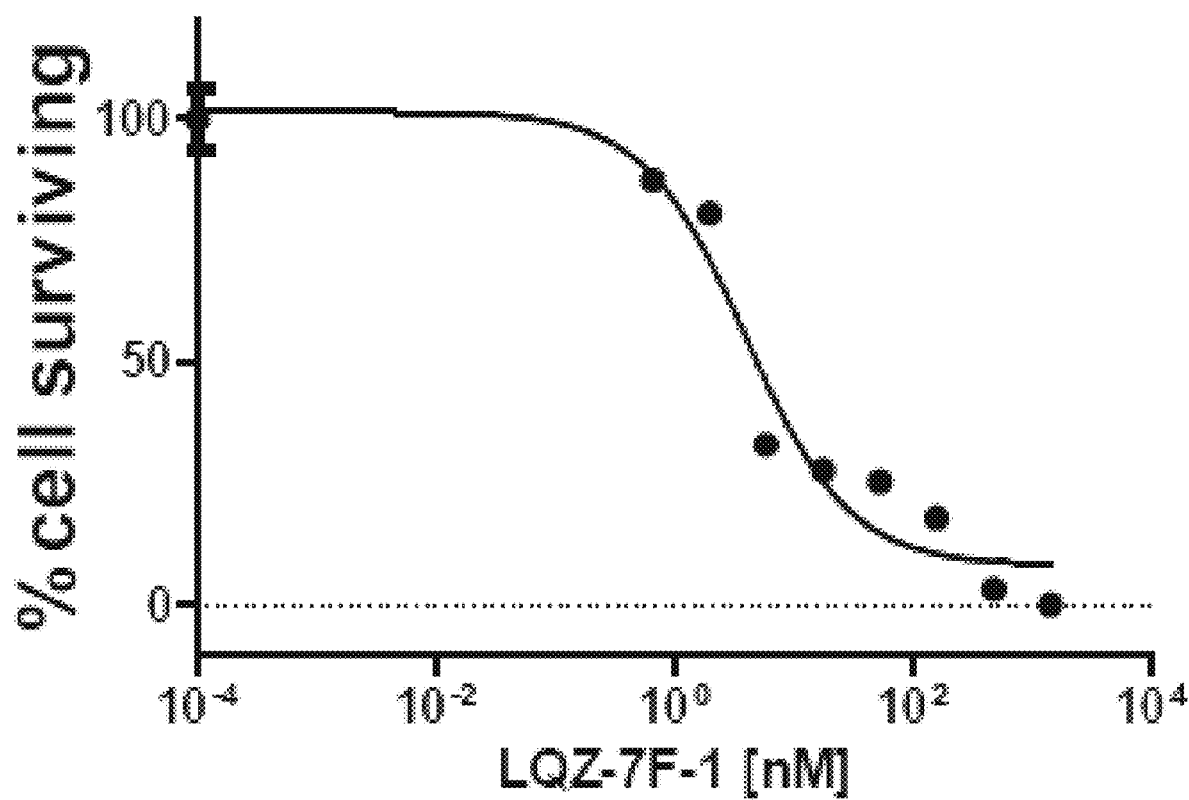
Figure 27C:
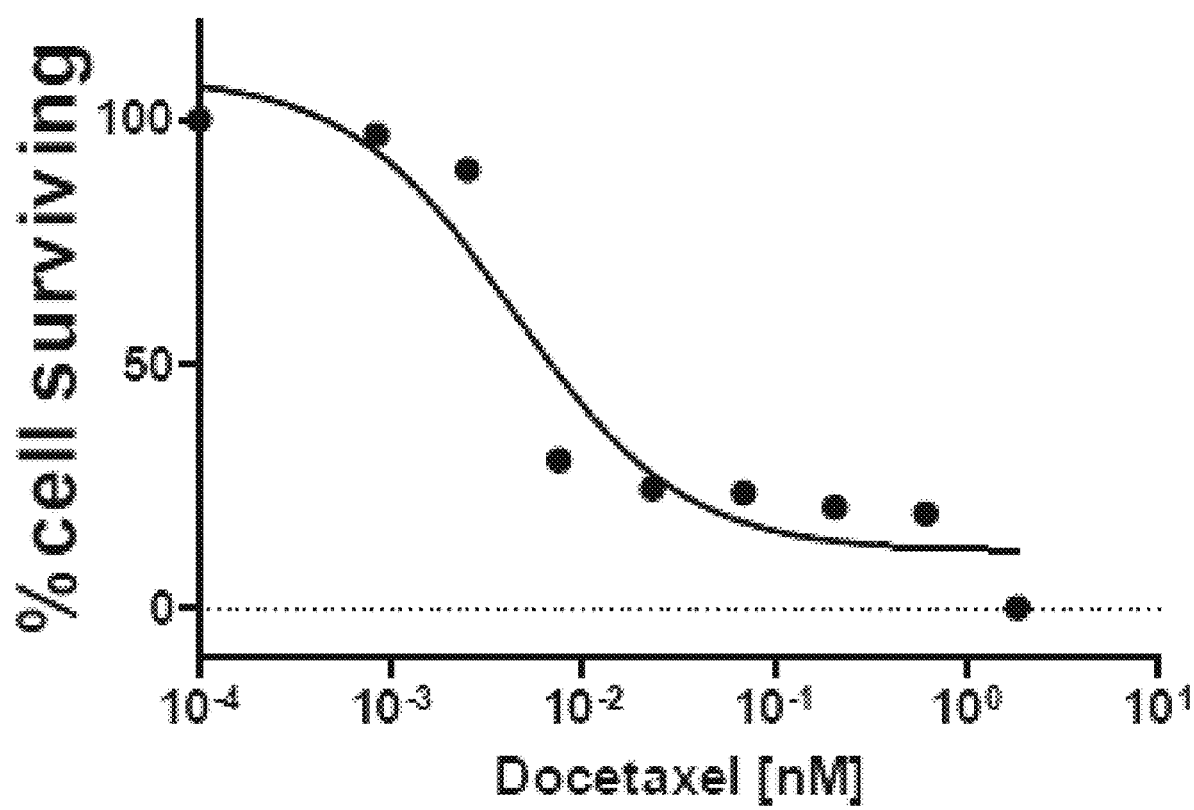
Figure 27C:
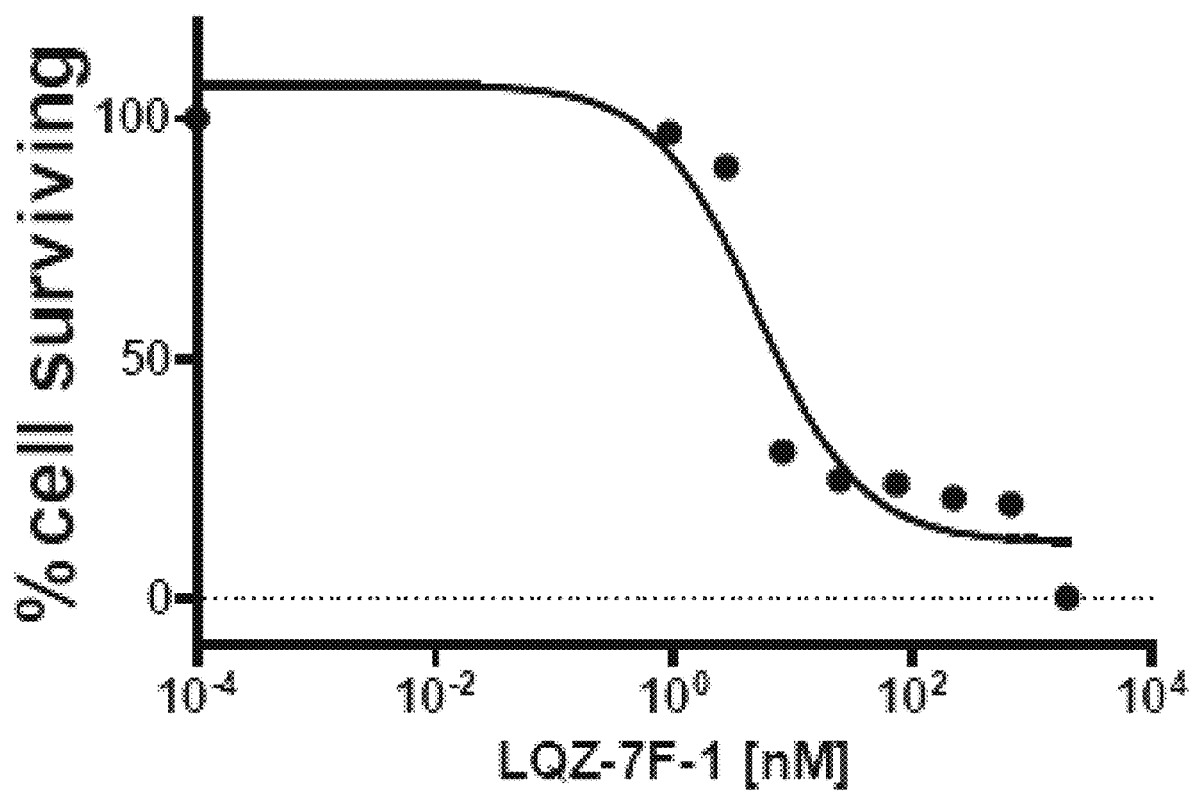
Figure 27C:
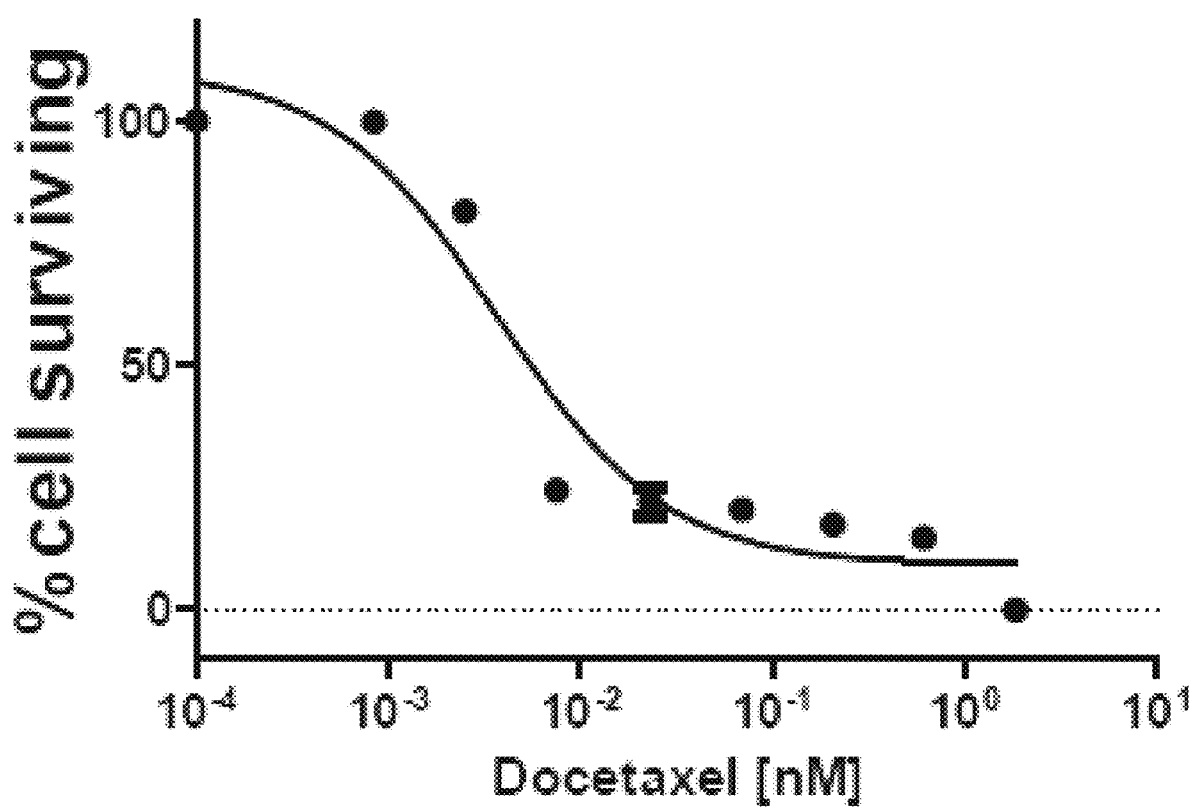
Figure 27C:
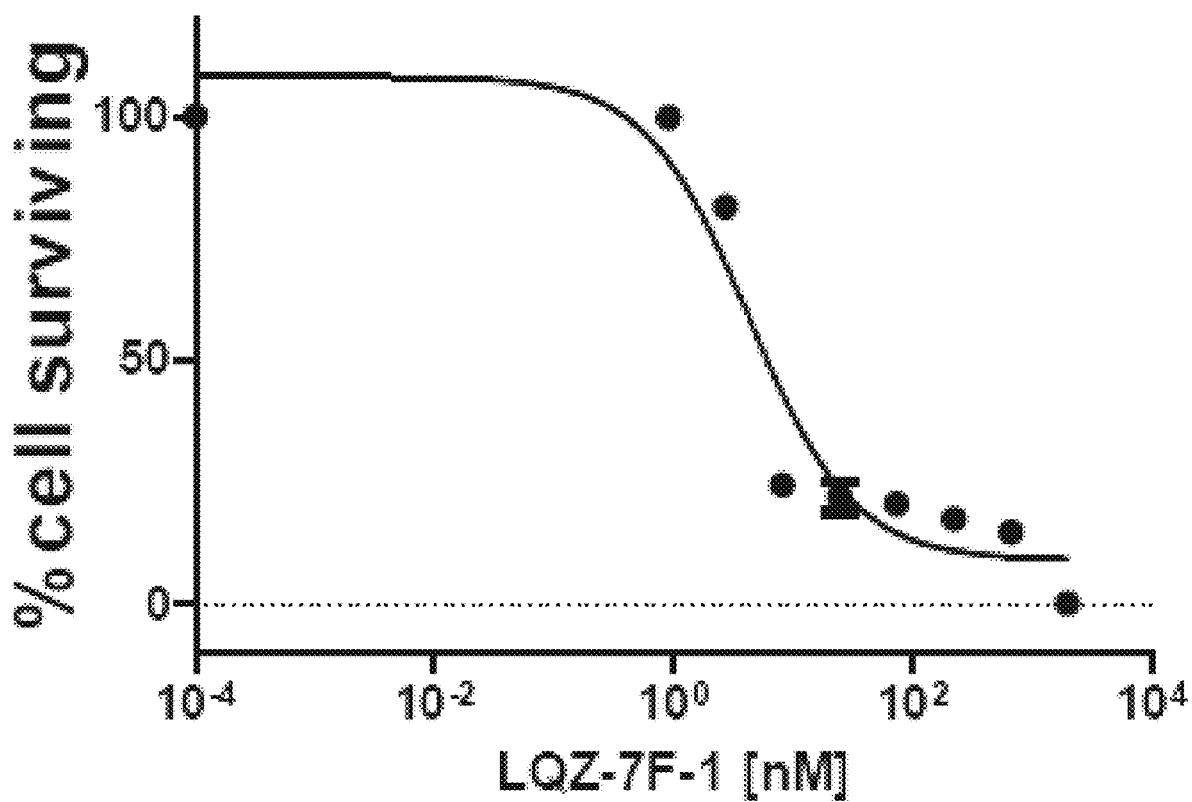
Figure 27C:
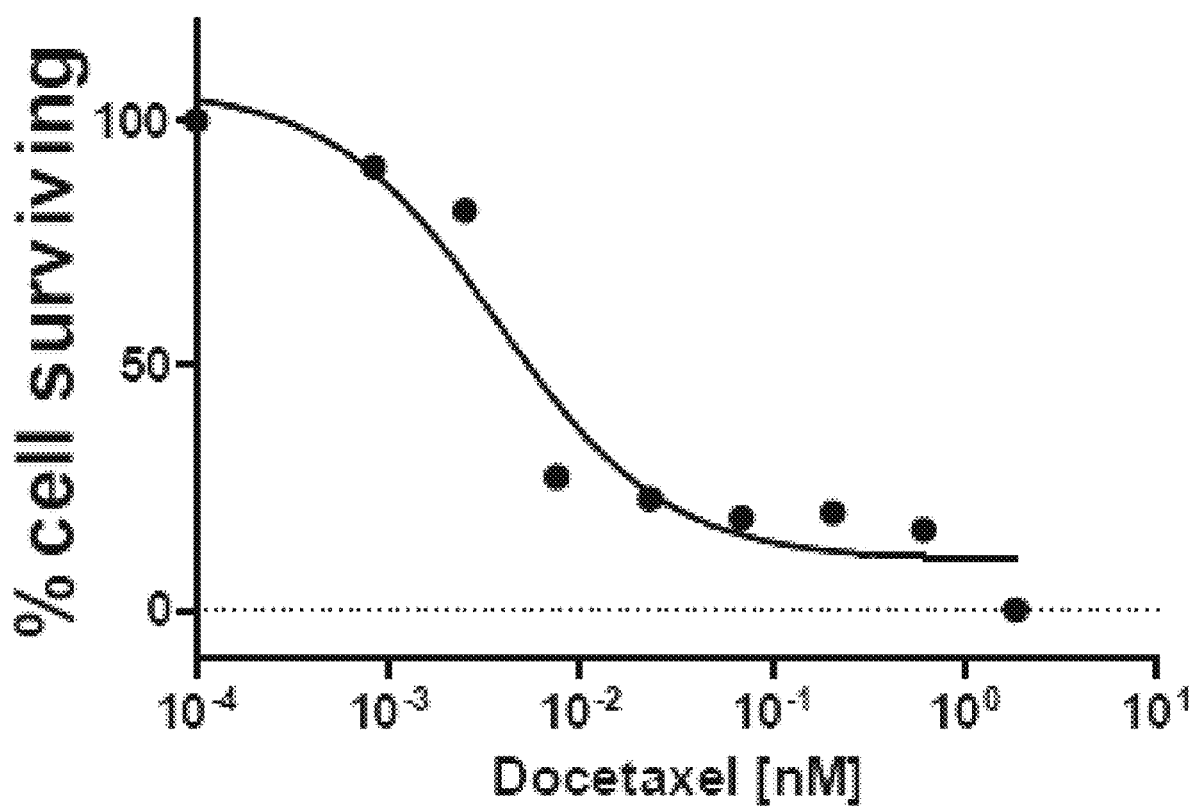
Figure 27C:
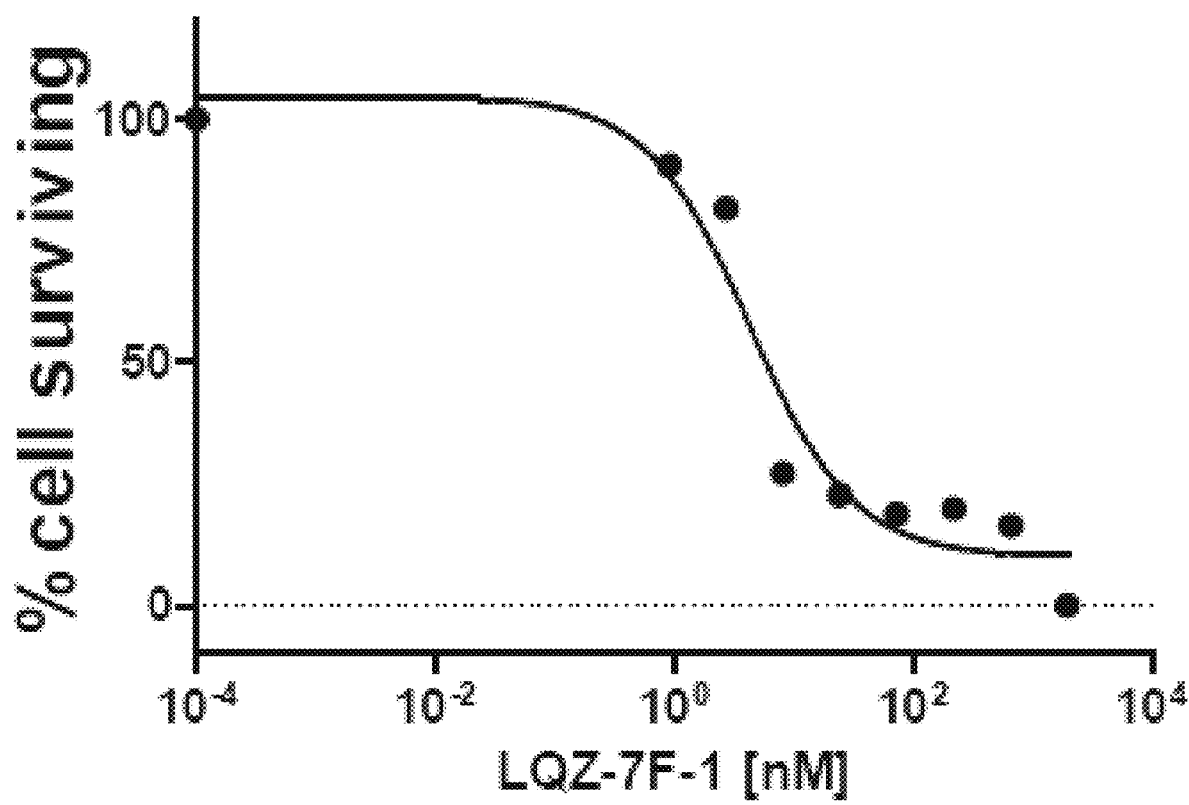
Figure 27D:
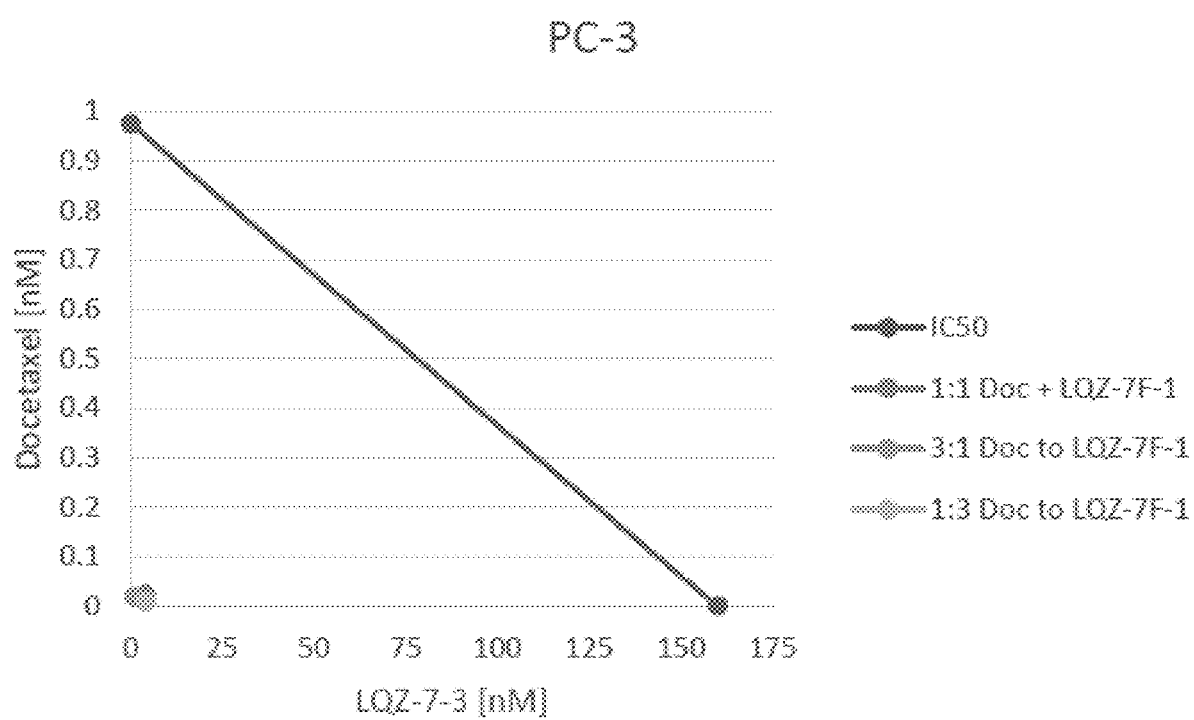
Figure 27E:
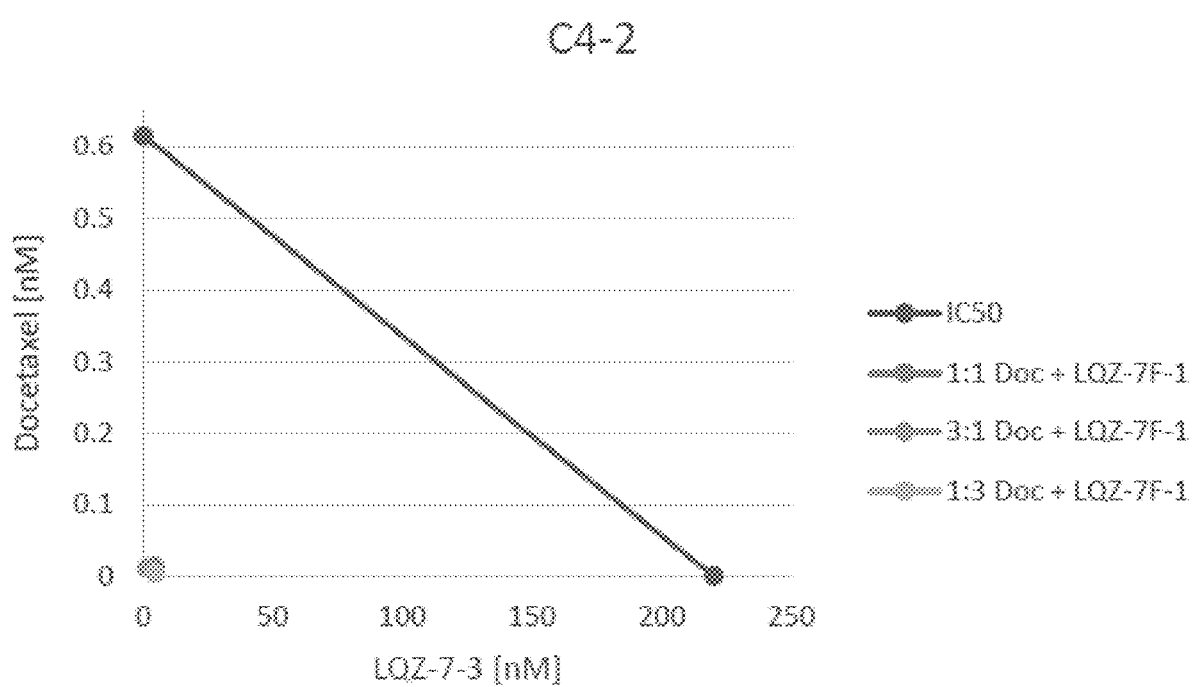

Combination Studies with Docetaxel. As a future in vivo efficacy study utilizing LQZ-7F-1 alone and in combination with docetaxel is likely warranted due to the positive in vitro data, potential synergism between the two agents was first tested in cell-based assays. For the cell-based assays the CI-isobol method was once again used to generate a combination index (CI) estimated from the known IC50 data of single drug treatments and then dose required to produce the same effect in combination treatments. The results utilizing this method for LQZ-7F-1 and docetaxel when given in a combination treatment at a 1:1 ratio of the IC50 to IC50 indicated strong synergism in both C4-2 and PC-3 cells with CI calculated well under 1 (FIG. 27). Additionally, using either agent in a 3:1 ratio also showed strong synergism in the tested cell lines. A 3:1 docetaxel to LQZ-7F-1 ratio displayed the lowest CI value in both PC-3 and C4-2 cells lines. The combination experiment results are detailed in the isobologram analysis (FIGS. 27D and E). This data provides support that a combination therapy between LQZ-7F-1 and docetaxel may be beneficial and synergize in prostate cancer in vivo models.

Figure 28:
FIG. 28 shows functional group analysis of analogue changes at the cyclopentane group position of LQZ-7F. LQZ-7F-1 has a carbonyl added to the cyclopentane had enhanced cytotoxicity in cell lines as well as improved performance in dimerization assay compared to other functional group changes at the same position.

LQZ-7F Structure Activity Relationship Analysis. The design and synthesis of the LQZ-7F structural analogues was performed to allow for information to be garnered from the effect of different functional group additions to one specific position of the backbone of LQZ-7F. Data from the single concentration analysis in three different cell lines was utilized to specifically compare the effect of additions of different moieties to the cyclopentane group in the LQZ-7F backbone. As shown in FIG. 28, there was clear evidence that the addition of a carbonyl functional group to the cyclopentane ring lead to a significantly more potent compound in terms of cell cytotoxicity and ability to inhibit dimerization in the two-hybrid assay than other analogues. No other moieties increased the performance of any of the other analogues in comparison to LQZ-7F. Almost all of the analogues performed significantly worse than LQZ-7F in this series of experiments. Overall, the carbonyl group addition to form a cyclopentanone in the LQZ-7F-1 backbone established a compound with significantly lower IC50 value and increased effect on target protein survivin.

Figure 29:
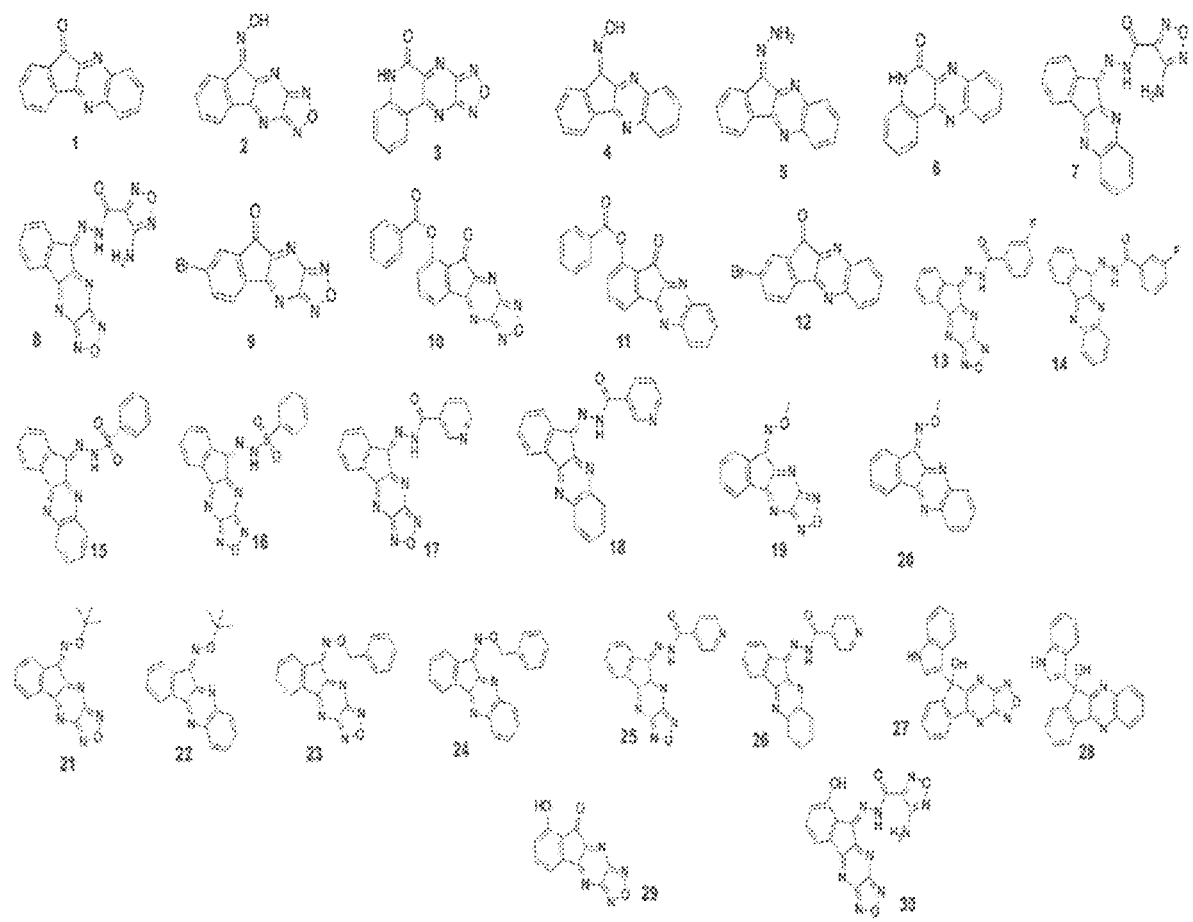
FIG. 29 shows chemical structures of LQZ-7F-1 analogues with substitutions at cyclopentane group, oxadiazine ring, or benzene ring of the parental compound's backbone.
Figure 30A:
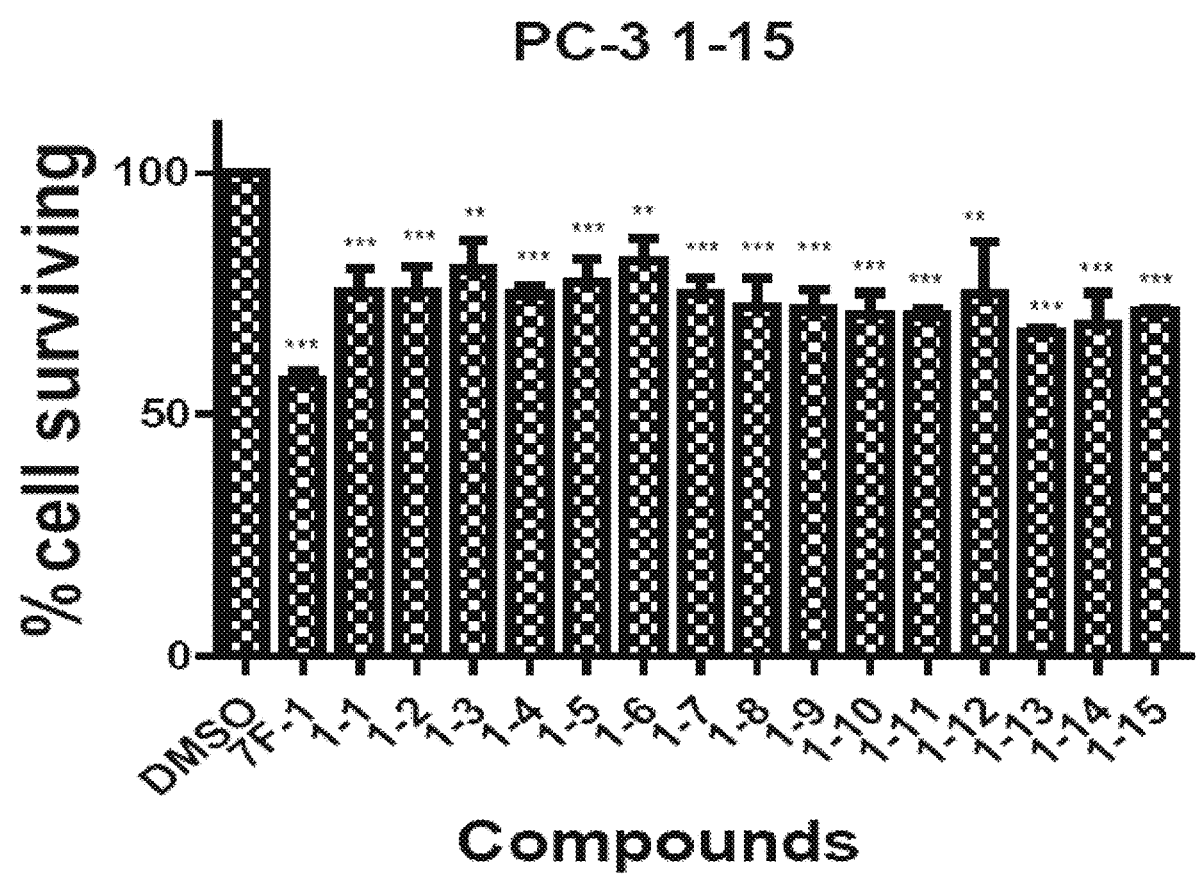
FIGS. 30A-30B show single concentration analysis of LQZ-7F-1 and structural analogues. (A) PC-3 and (B) C4-2 cells were treated with 150 nM of each compound for 72 hours. The results indicate the percentage cells surviving after treatment. No compound had greater amount of cell killing than parental LQZ-7F-1. Each concentration was tested in triplicate ***=p-value<0.001. n=3 independent experiments. Error bar equals standard deviation.
Figure 30A:
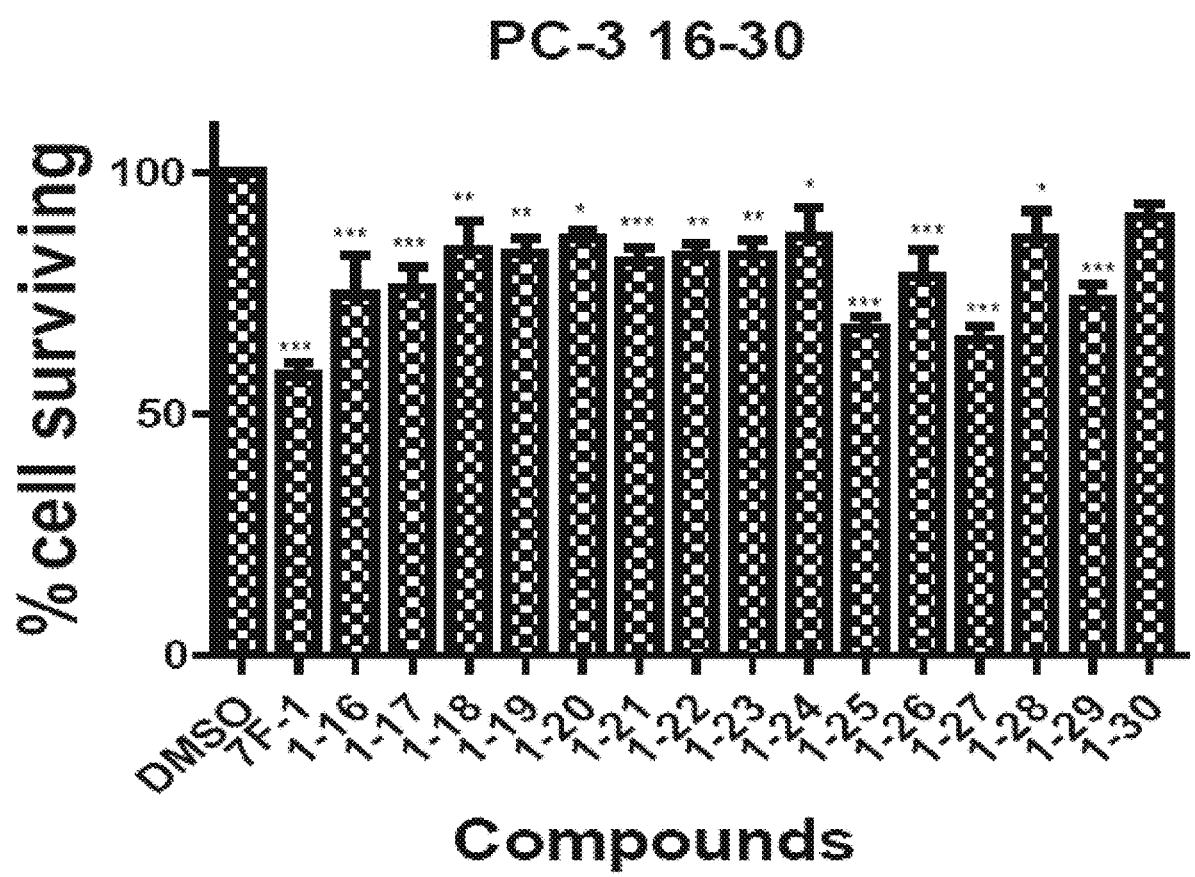
Figure 30B:
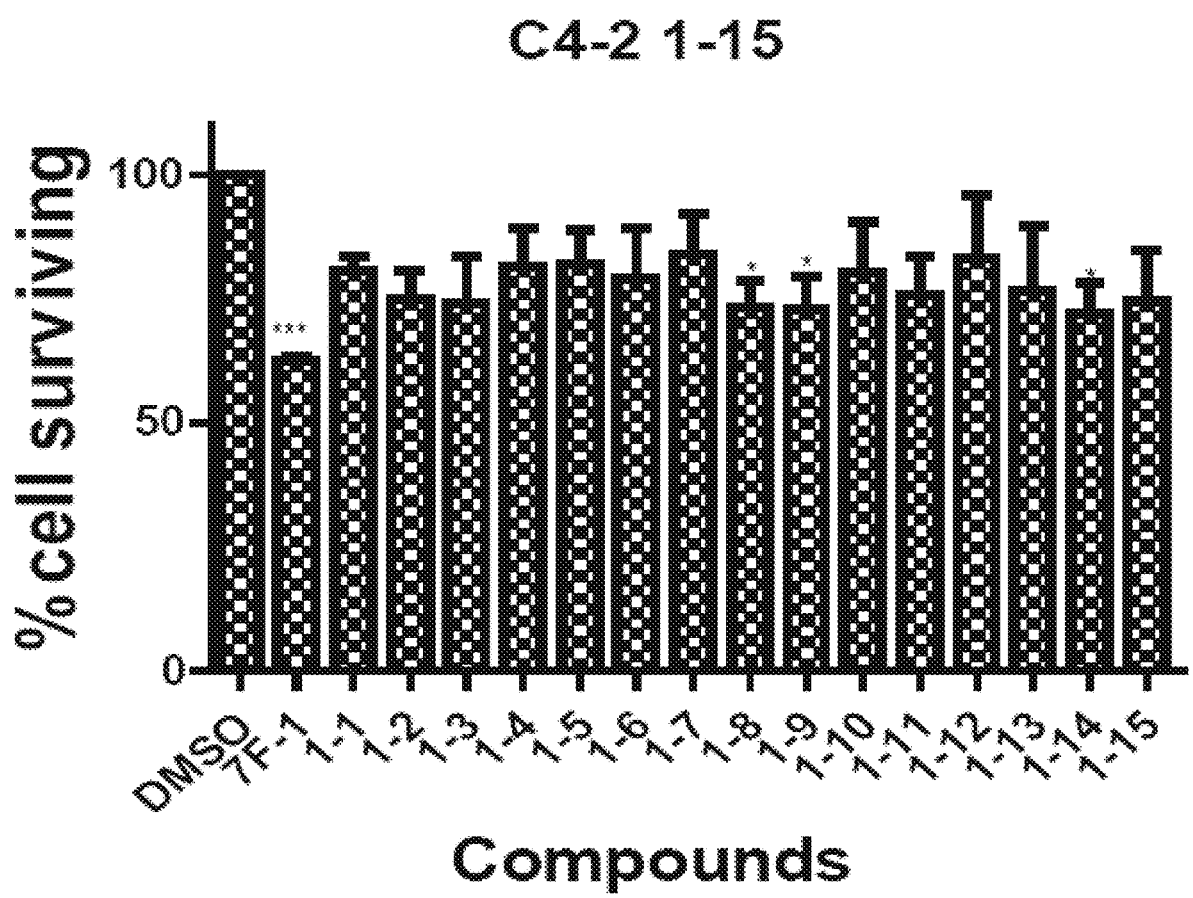
Figure 30B:
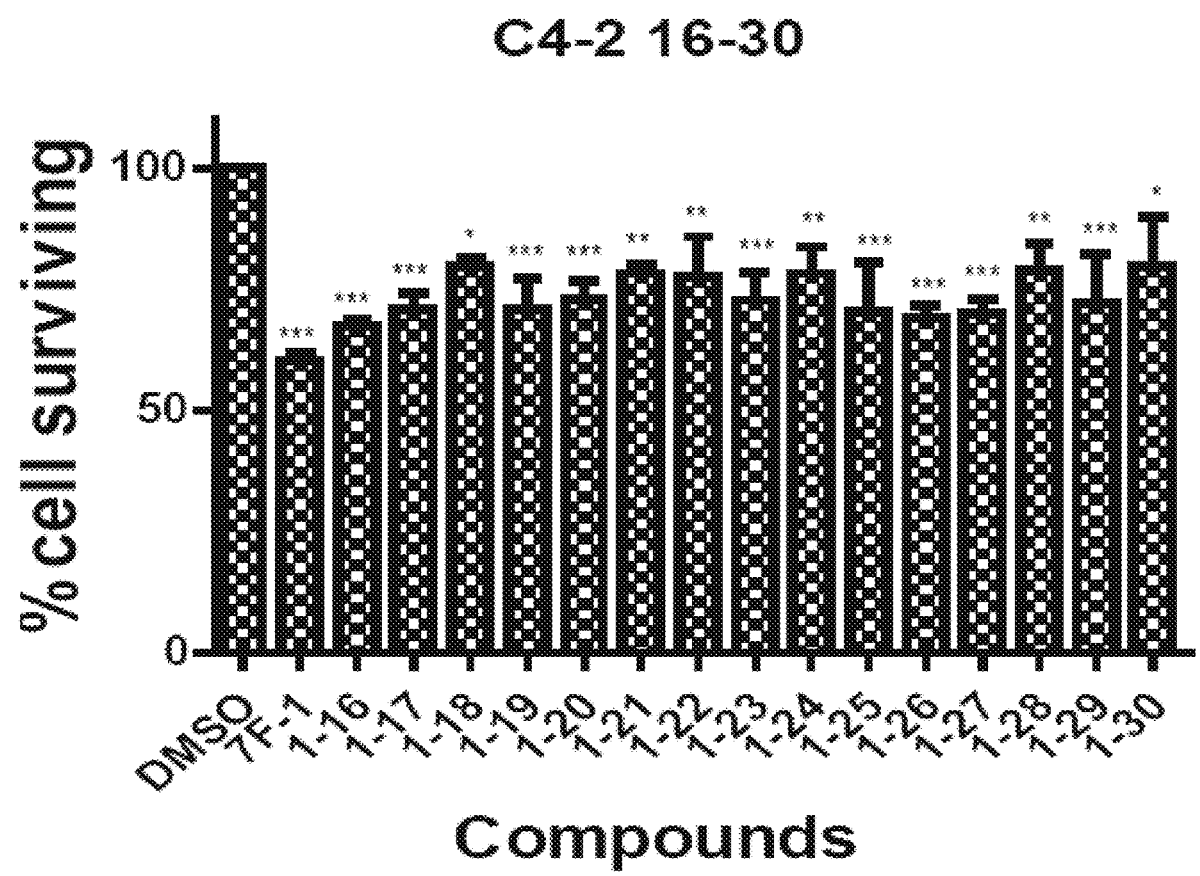

Generation of LQZ-7F-1 Structural Analogues. The next iterative generation of survivin inhibitors were structural analogues of LQZ-7F-1 and were synthesized with changes that can be grouped into three broad categories. The first group of analogues have additional functional group changes at the cyclopentane group. The second group involves changes to the oxadiazine ring in the backbone. The final group involves the addition of different functional groups to the benzene ring in the LQZ-7F-1 backbone. The idea behind this round of chemical synthesis of structural analogues was to garner further information on critical components of LQZ-7F-1 compound that are critical for its function. The thirty structural analogues of LQZ-7F-1 are shown in FIG. 29.

LQZ-7F-1 Analogues Single Concentration Analysis. In order to determine if any of the LQZ-7F-1 structural analogues had a greater ability to promote cancer cell killing than LQZ-7F-1, a single concentration analysis was first performed in PC-3 and C4-2 cells. For this series of experiments, cells were treated with 150 nM of each different compound for 72 hours. This concentration was specifically chosen as it represents roughly the average IC50 value of LQZ-7F-1 in prostate cancer cells. The results from the single concentration methylene blue assays are shown in FIG. 30. As excepted, treatment of LQZ-7F-1 at 150 µM inhibited both PC-3 and C4-2 roughly 50-60%. While many analogues displayed activity, none generated in this round of synthesis had a greater cell killing effect than LQZ-7F-1. The data in this section further positioned LQZ-7F-1 as the compound to use in future studies while also providing structure activity relationship insights in its backbone.

Figure 31:
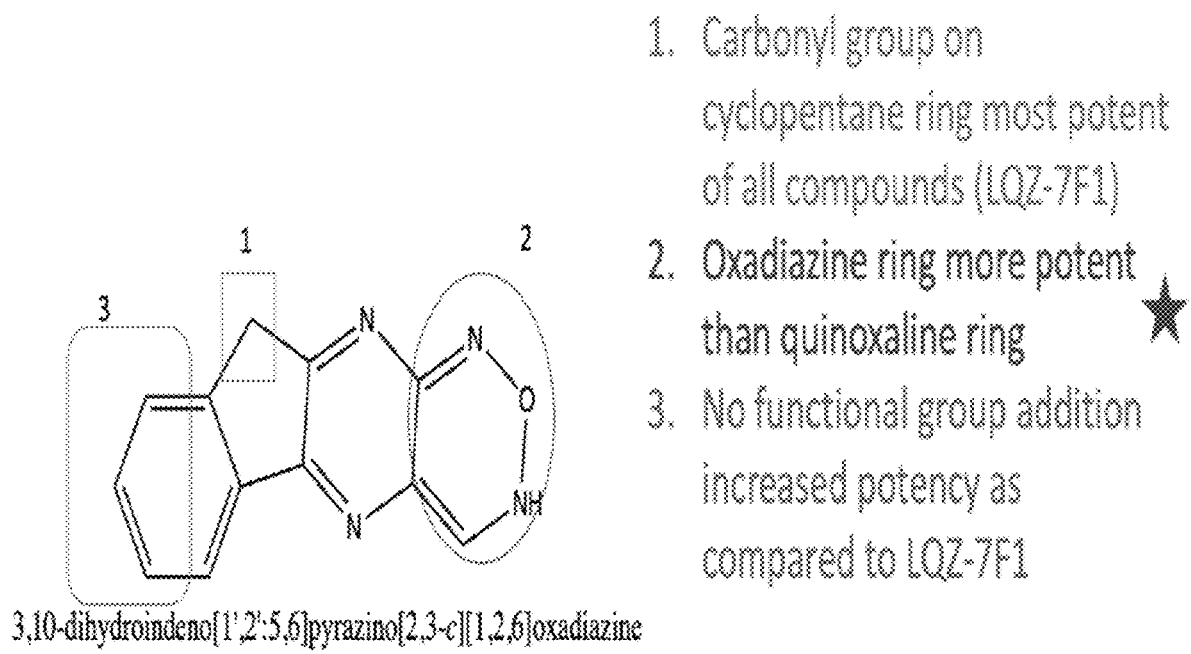
FIG. 31 shows major takeaways from structural analysis of LQZ-7F and LQZ-7F-1 rounds of analogue generation. (1) The carbonyl group addition to the cyclopentane group (LQZ-7F-1 compound) formed the most potent compound. (2) Compounds with the oxadiazine ring were more potent than compounds with quinoxaline ring at the same position. (3) No functional group addition to the benzene ring of the backbone increases potency in cell based assays.
Figure 32A:
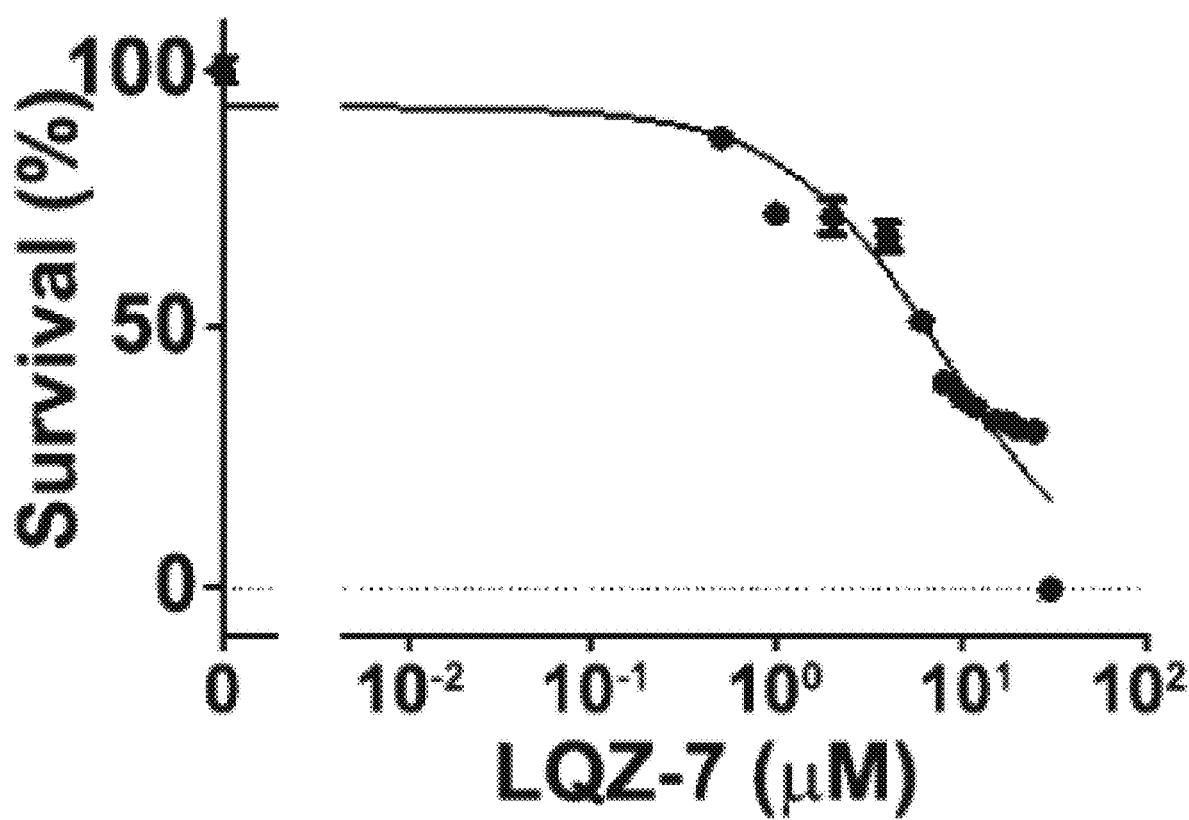
FIGS. 32A-32B show a dose-response effect of LQZ-7 and its analogues (7G, 7H, 7I, 7J, and 7K) on survival of human prostate cancer cell lines C4-2 (A) and PC-3 (B) as determined using methylene blue assay.
Figure 32A:
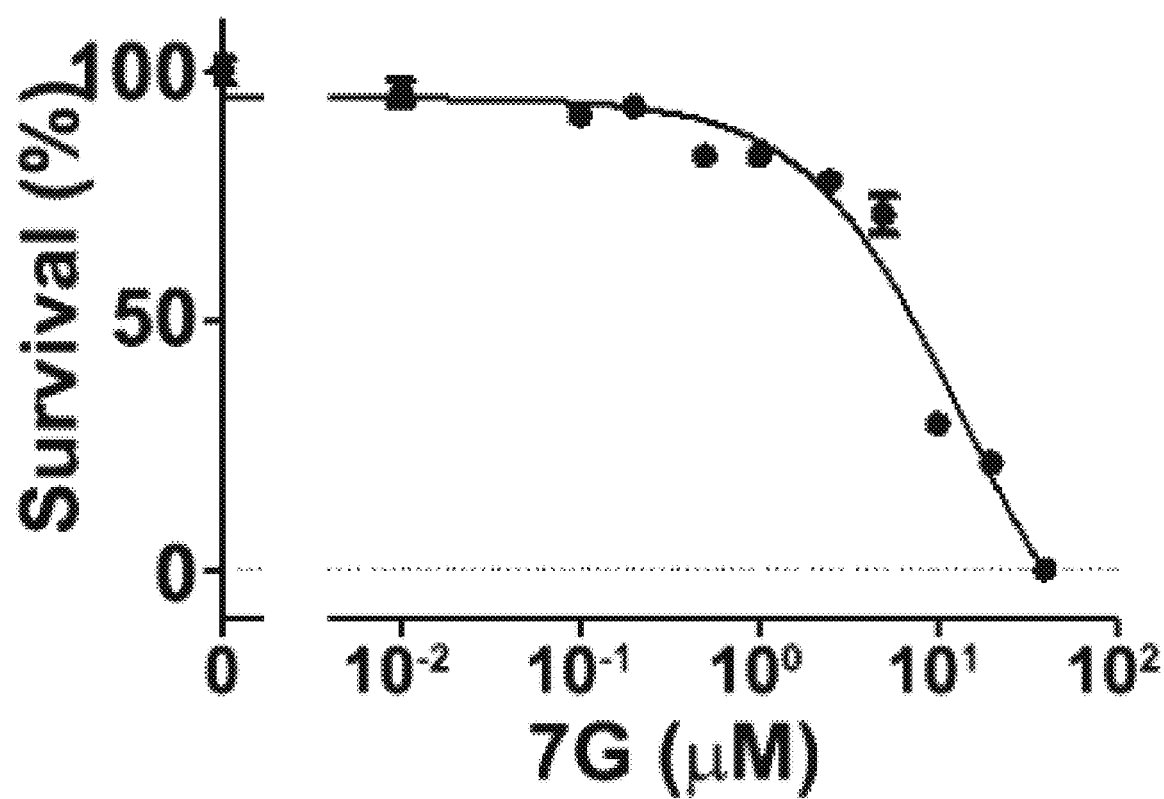
Figure 32A:
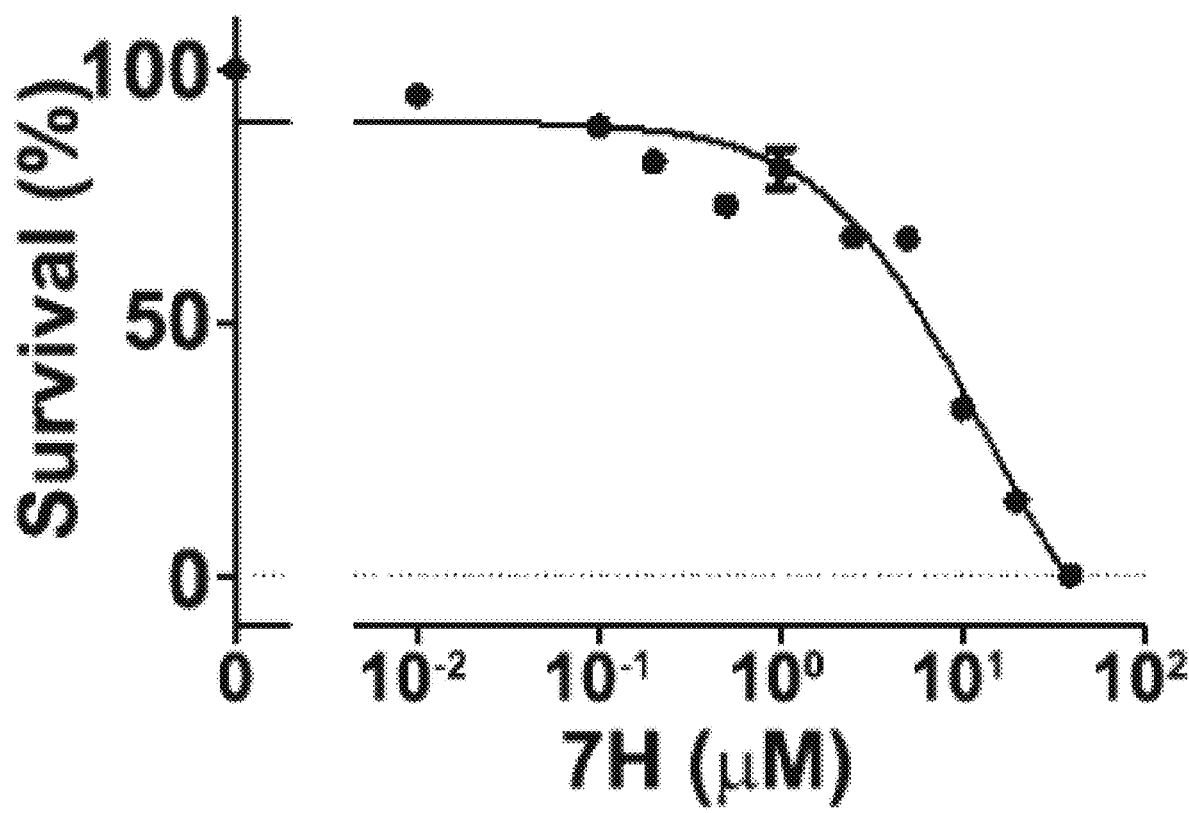
Figure 32A:
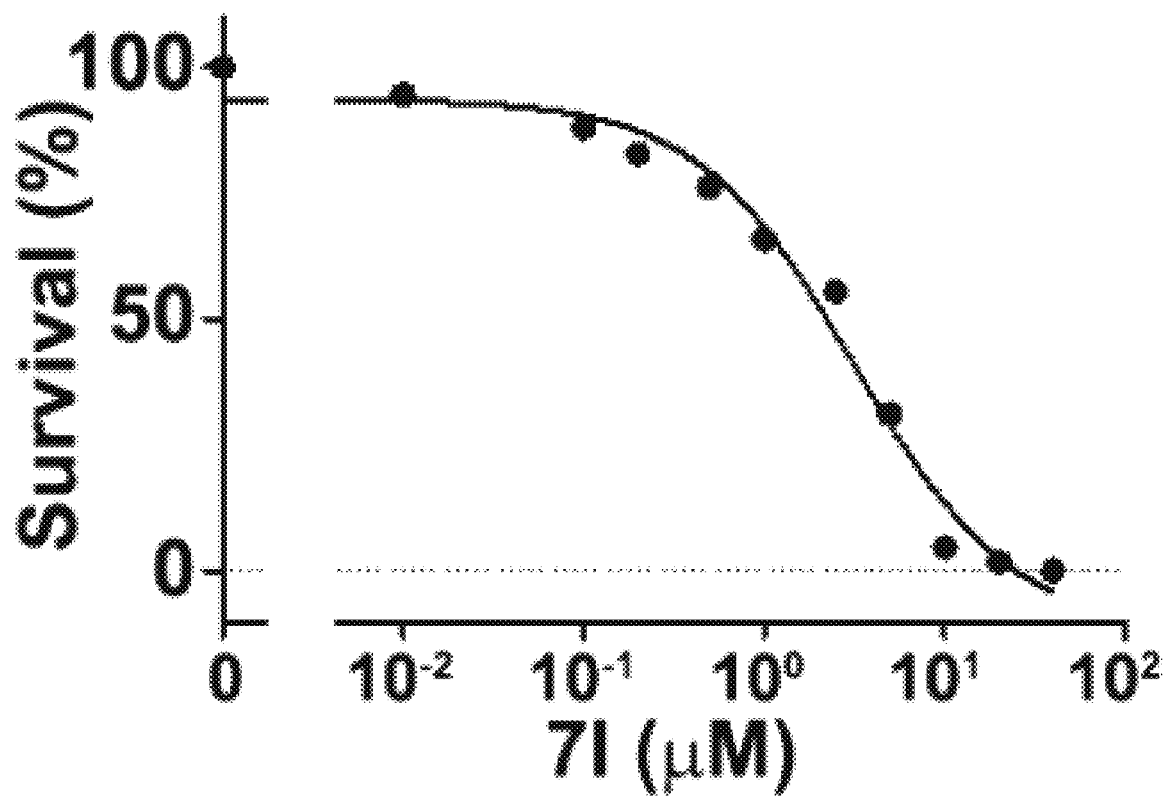
Figure 32A:
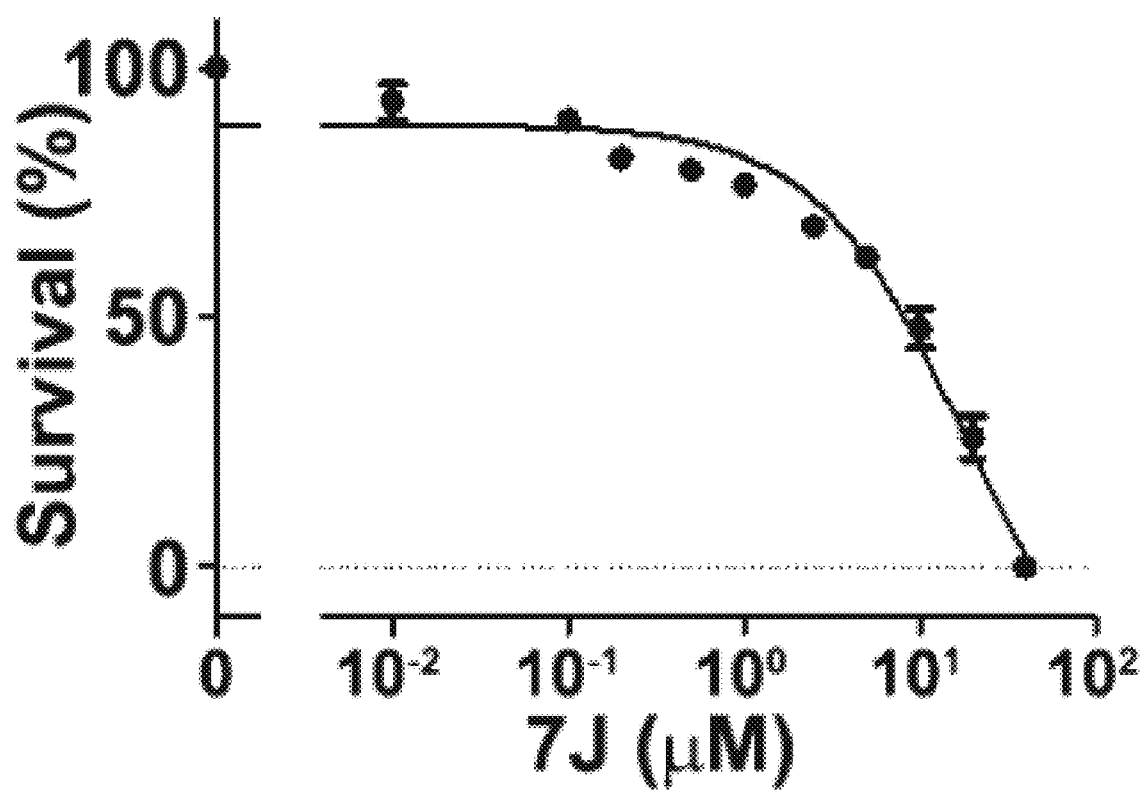
Figure 32A:
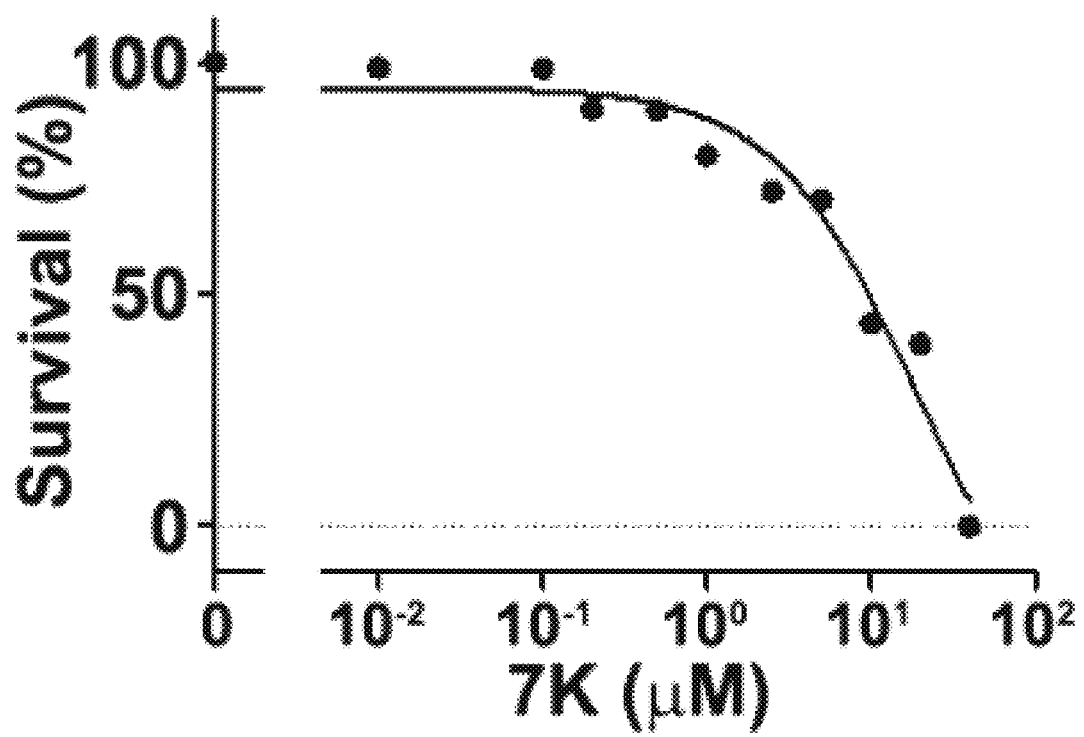
Figure 32B:
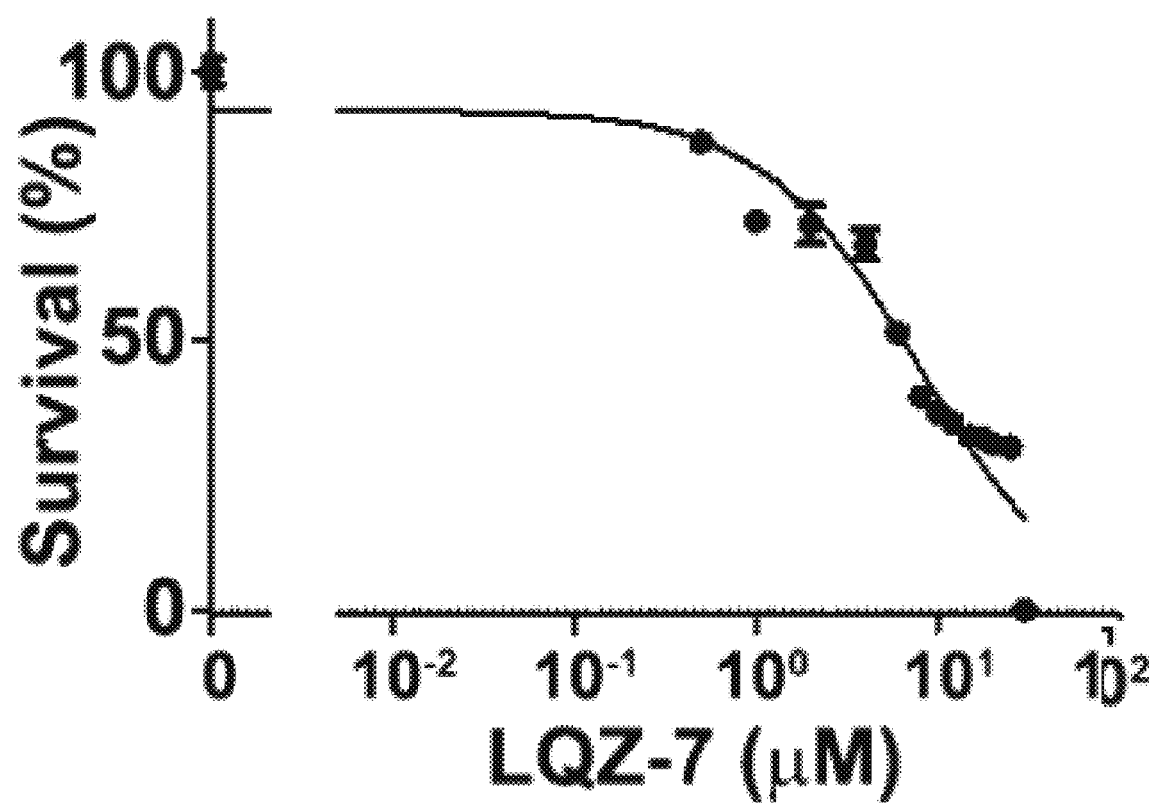
Figure 32B:
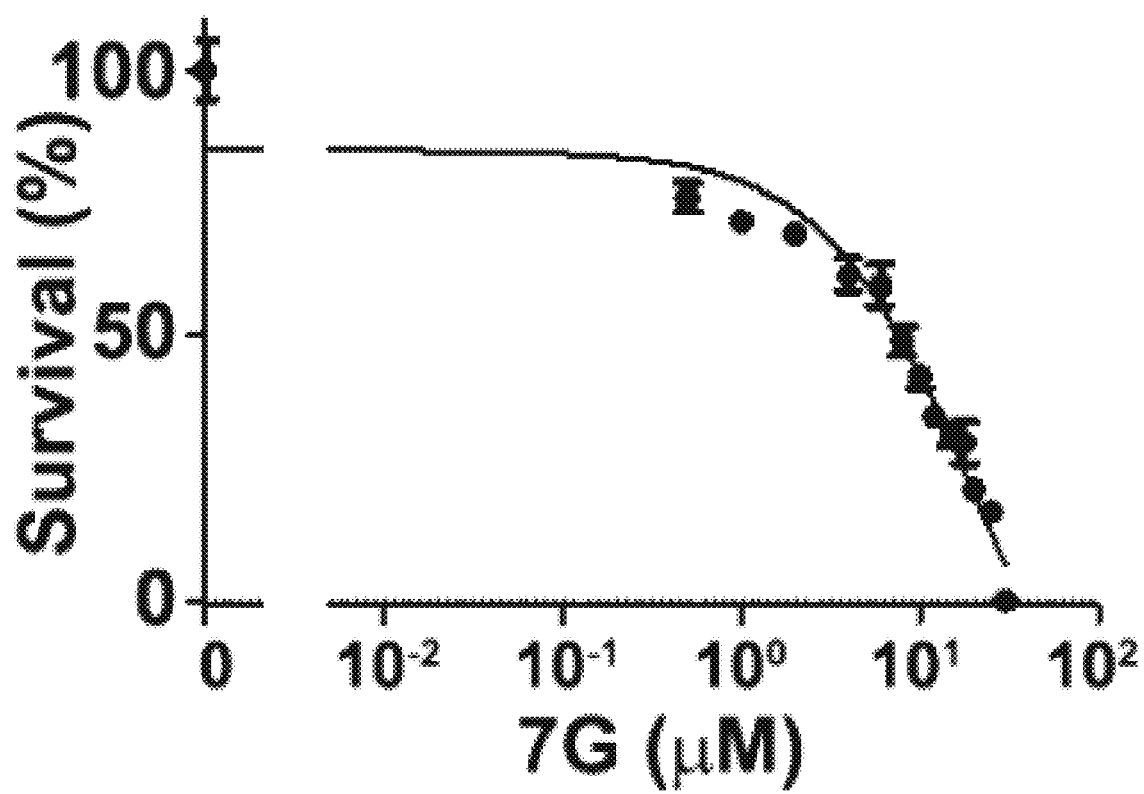
Figure 32B:
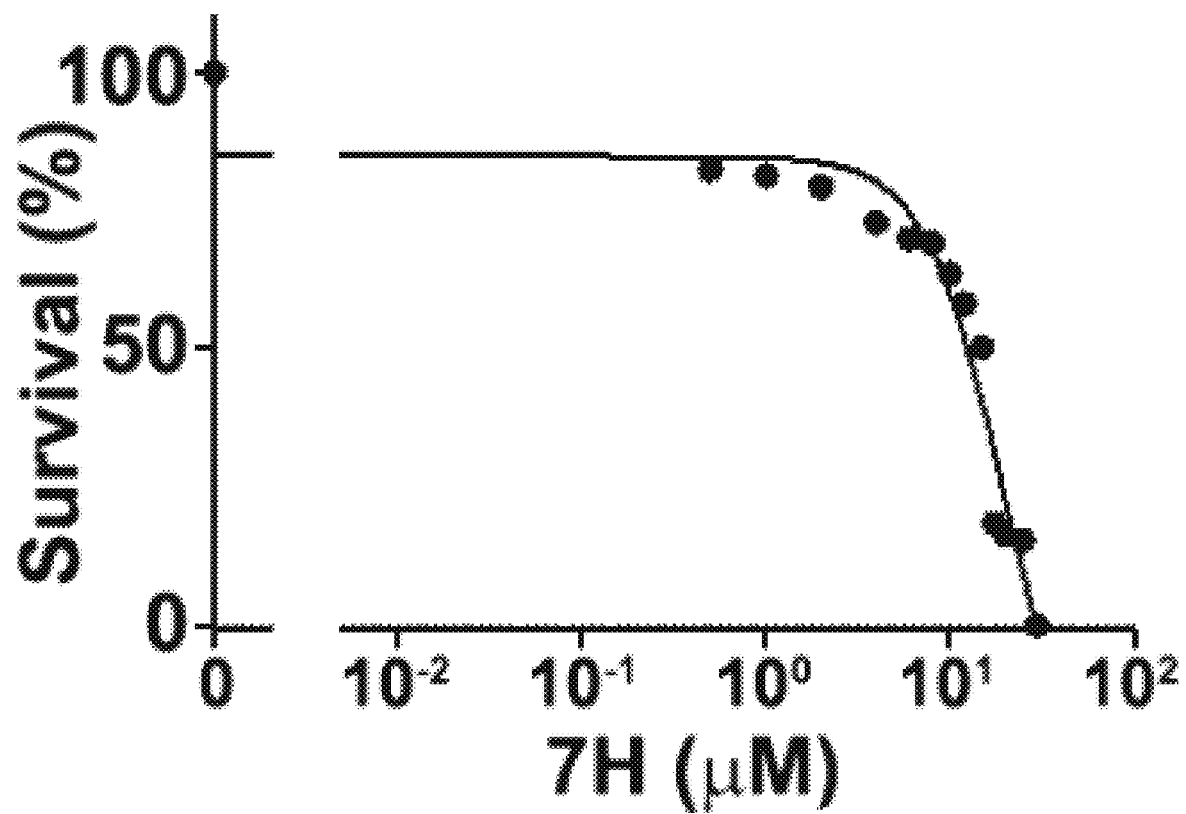
Figure 32B:
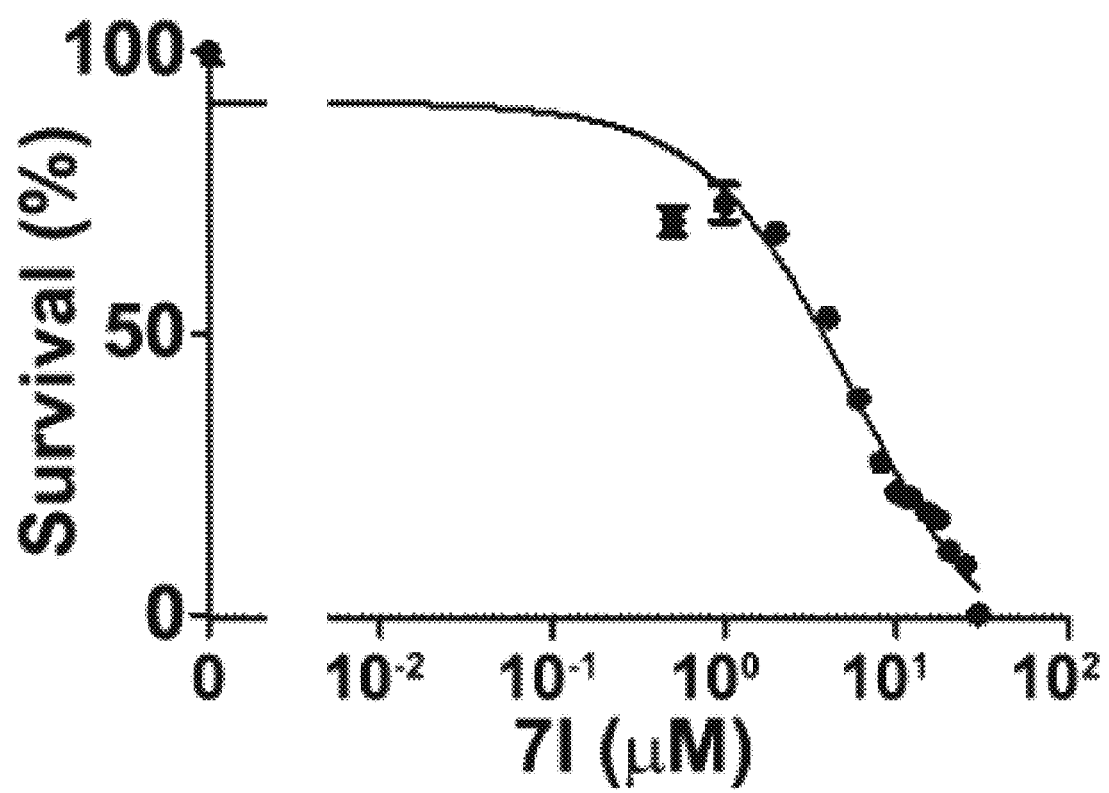
Figure 32B:
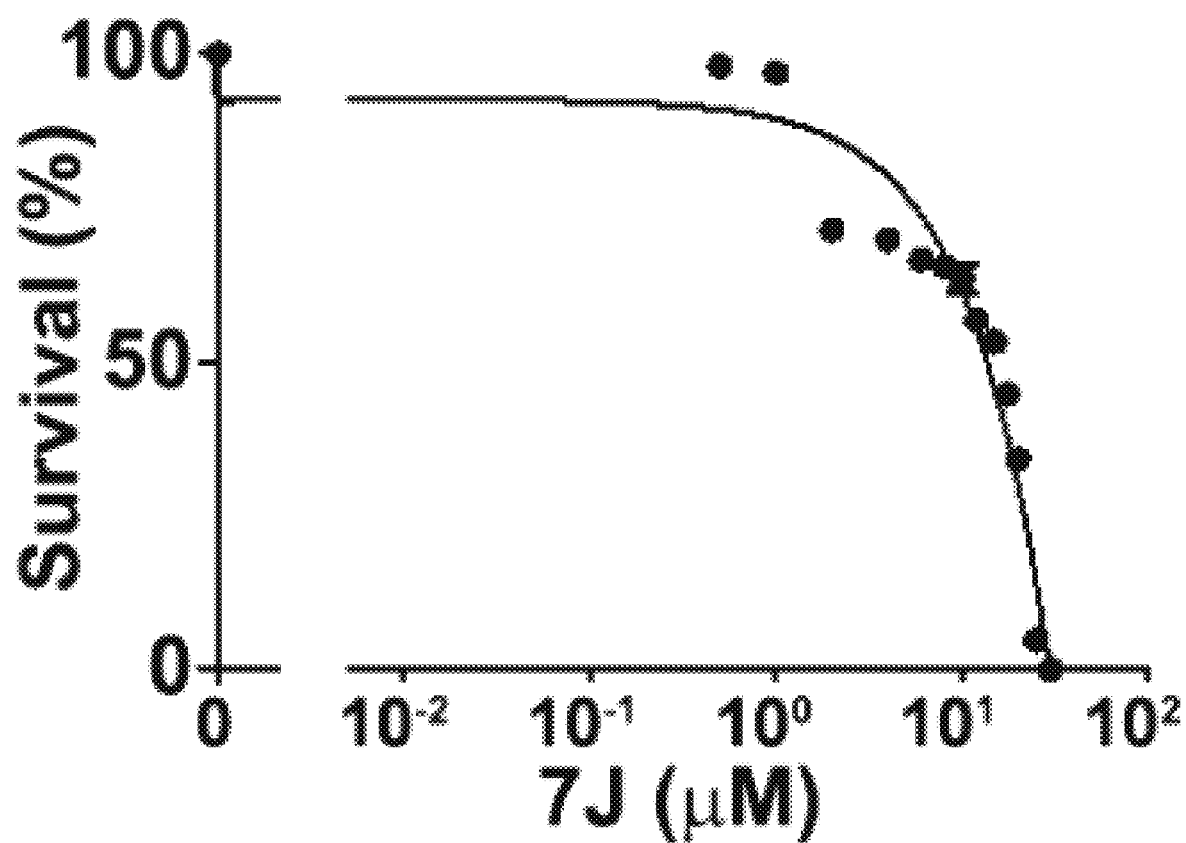
Figure 32B:
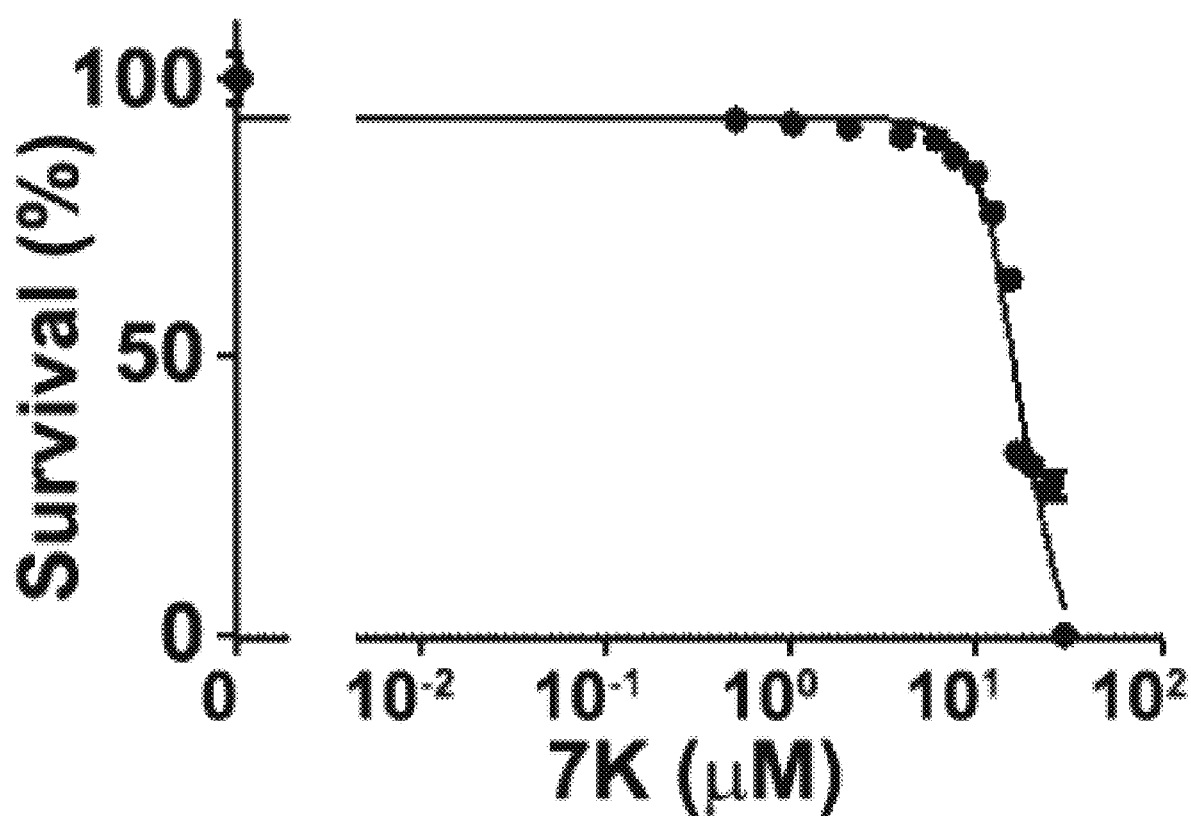

LQZ-7F-1 Structure Activity Relationship Analysis. Although the synthesis of 30 structural analogues did not yield an improved compound in terms of performance in cell based assays, the strategic alterations at specific positions of LQZ-7F-1 helped further elucidate critical aspects of the compound. As detailed in FIG. 31, there were three primary takeaways from the structure activity relationship analysis that was performed. First, the addition of the carbonyl group to the cyclopentane group (LQZ-7F-1) generated the most potent inhibitor in cytotoxicity and survivin inhibition assays. Secondly, the compounds that contained the oxadiazine ring in the ring backbone were more potent inhibitors of cell survival than those with a benzene ring at the same position. Finally, no functional group addition to the benzene ring of the backbone increased the potency of any of the inhibitors tested.

The data in this section serve as a first-generation optimization of the locked LQZ-7F survivin dimerization inhibitor backbone. In the experiments above, a structural analogue of LQZ-7F was found that has enhanced cytotoxicity in prostate cancer cells and inhibits survivin dimerization in a mammalian two hybrid assay greater than the parental compound. The compound, LQZ-7F-1, caused significant survivin degradation earlier than 8 hours in both PC-3 and C4-2. The loss of survivin caused by LQZ-7F-1 treatment is blocked by pretreatment with proteasome inhibitors, suggesting LQZ-7F-1 induced survivin loss is via proteasome degradation. LQZ-7F-1 increases cellular apoptosis of prostate cancer cells compared to control as measured by annexin V staining and increases in cleaved caspase 3 protein levels. Importantly, LQZ-7F-1 synergizes with docetaxel, warranting the exploration of a combination therapy in future xenograft efficacy studies. Finally, the carbonyl group of LQZ-7F-1, which was added to the cyclopentane in LQZ-7F, confers improved cellular responses in multiple assays as compared to other functional group substitutions at the same position.

LQZ-7F-1 is a Potent Survivin Inhibitor in the Nanomolar Range. LQZ-7F was a special analogue generated from LQZ-7 that had distinct backbone unlike other compounds identified in previous screenings. This backbone consisted of four locked ring structures that result in a less flexible compound backbone. The data here served as a first-generation optimization of the locked LQZ-7F survivin dimerization inhibitor backbone. LQZ-7F-1, a structural analogue of LQZ-7F, was found that has increased cytotoxicity in prostate cancer cells and inhibited survivin dimerization in a mammalian two hybrid assay greater than LQZ-7F. The compound, LQZ-7F-1, caused significant survivin degradation earlier than 8 hours in both PC-3 and C4-2. Similarly to LQZ-7-3, pretreatment with proteasome inhibitors rescued and restored survivin loss by LQZ-7F-1 to that of control levels. This further indicated that the class of survivin inhibitors presented here cause survivin degradation via the proteasome. The loss of survivin by LQZ-7F-1 also increased caspase 3 levels and lead to apoptosis of prostate cancer cells. As the data presented in the previous sections has indicated the possibility of survivin inhibitors being more successful in a combination therapy, it was promising to see strong synergism between docetaxel and LQZ-7F-1 In the structure activity relationship analysis, the carbonyl group of LQZ-7F-1 which was added to the cyclopentane in LQZ-7F showed significant increases in potency obtaining a nanomolar IC50. The similarity between LQZ-7F and LQZ-7F-1 leads us to hypothesize that LQZ-7F-1 may be an active metabolite product of LQZ-7F metabolism. This possibility is exciting and warrants further assessment in future studies. Overall, the strong performance of LQZ-7F-1 cell-based assay activity warrants further investigation as a lead compound in efficacy studies.

In this study, survivin was emphasized as an important cellular player in docetaxel resistance, and two primary lead compounds were identified for future efficacy studies as a single agent and combination therapy with docetaxel. There were not major obstacles encountered during the completion of this thesis besides minor technical adjustments required to optimize protocols. However, there may exist some potential limitations associated with the experiments presented here that warrant further discussion and evaluation going forward.

The use of 2D monolayer cell culture provides an easy, comparative method for the growth and analysis of cancer cells in culture. While 2D cultures have advanced the fields knowledge and allowed for greater understanding of cancer cell behaviors and mechanisms of resistance, the growth of cells on a flat surface has its limitations when trying to translate discoveries to in vivo systems. Currently, 2D cell cultures are often hyper-sensitive to anti-cancer agents and also fail to the model for the dynamic interactions between cancer cells and their microenvironment. Consequently, these cell line models may not be the best for transitioning results to the physiology of in vivo models and actual patients.

There is a still a lot of work to be done, however 3D cultures in the form of spheroids from cell lines and organoids from patient samples may better represent the dynamic interplay that occurs in a tumor. In these 3D cultures an extra-cellular matrix can surround the cells and allows for the interaction between the cancer cells and their microenvironment. The development of organoids from primary tumors or metastases from patients also allow for the study of cancer stem cells and microenvironment while also maintain tumor heterogeneity. 3D cultures generally have the problem that their complexity limits biological replicates and combination therapies are sometimes not practical, however more recently there has been the development of microwell-mesh 3D cultures that allow for the generation of roughly a hundred microtumors per well for screening anti-cancer compounds. In future studies using the survivin inhibitory compounds, the microwell-mesh 3D organoids technique derived from patients may represent innovative tool for therapeutic screening that better reflects the responses in animals and patients.

Finally, the other potential limitation associated with this study is the use of NSG mice for the in vivo xenograft efficacy study. These mice are immunodeficient meaning they lack mature T cells, B cells, and NK cells that make up a functioning immune system. Implantation of tumors in these mice are much easier as host rejection of human tumor cells becomes less likely however this comes with a tradeoff. Since there is a deficiency in the immune system these mouse models are unable to replicate the interplay between the cancer cells, the tumor microenvironment, and mature host immune cells seen in patients. Therefore, there exists the strong possibility that a compound that shows promise and efficacy in these mice may not necessarily work in patients. More recently, researchers have sought to overcome these challenges particularly in prostate cancer. The development of patient-derived xenograft models (PDX) may provide a critical alternative that will allow for clinically relevant and translation data. The PDX models preserve the tumor-microenvironment architecture and also the tumor heterogeneity. Unfortunately, very few PDX models have been successfully established for prostate cancer.

It is likely more appropriate for us going forward to implore an orthotopic syngeneic prostate cancer mouse model which possesses many advantages over subcutaneous injection of cancer cells or use of immunocompromised mice. First, orthotopic implantation involves injecting the cancer cells into the organ of origin which allows for more clinically accurate vasculature, tumor microenvironment, and response to therapy. There exists a number of established syngeneic mouse models for prostate cancer that allow for elegant experiments such as surgical castration to study castration resistant prostate cancer and even the use of fluorescent cancer cells to monitor there dissemination throughout the body over the course of the study. Syngeneic mouse models also allow for the use of immunocompetent mice and therefore help maintain the dynamic interplay between cancer cells and host immune cells. Finally, syngeneic mouse models are often times less expensive than genetically engineered models.

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

All publications, patents and patent applications referenced herein are hereby incorporated by reference in their entirety for all purposes as if each such publication, patent or patent application had been individually indicated to be incorporated by reference.

What is claimed:
1. A method of treating cancer, comprising administering to a subject in need thereof, a therapeutically effective amount of a composition comprising a survivin-targeting compound selected from the group consisting of: compounds of the following formulas

49
50
-continued
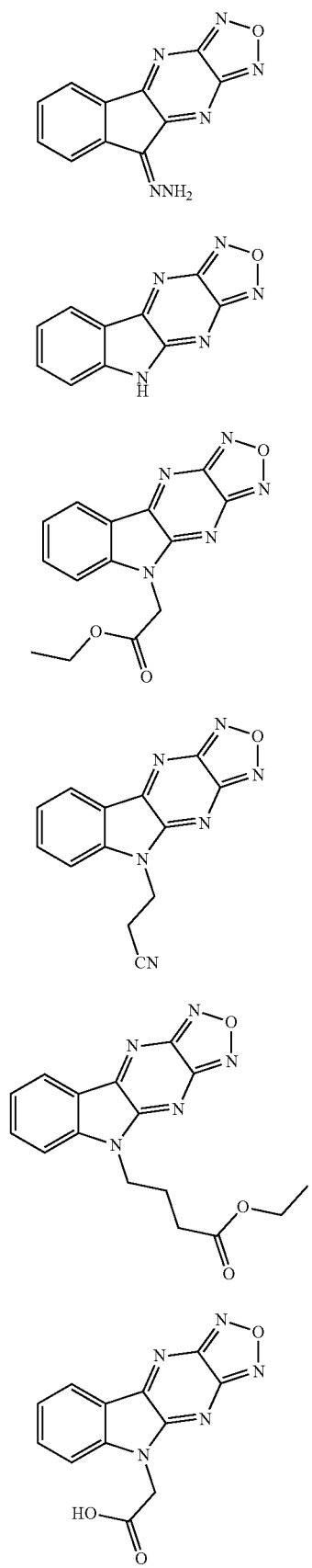
(a)
(b)
(c)
(d)
(e)
(f)
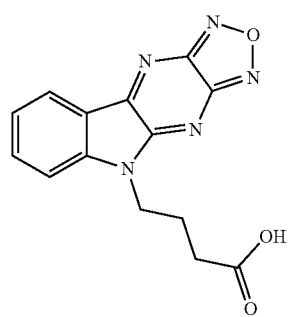
(g)
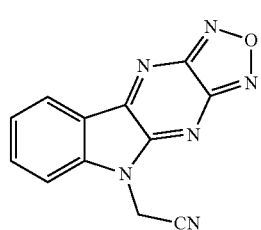
(h)
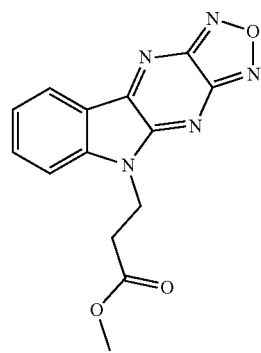
(i)
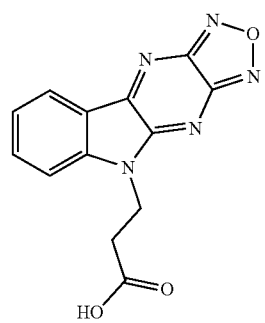
(j)

-continued
(l)
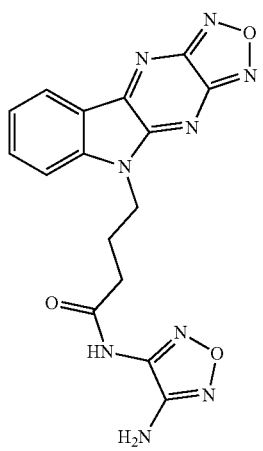
(n)
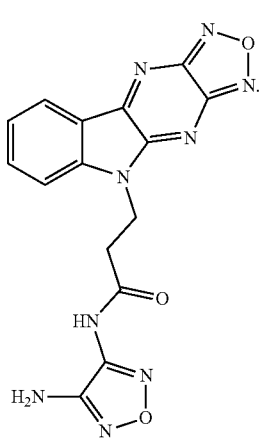
2. A method of treating cancer, comprising administering to a subject in need thereof, a therapeutically effective amount of a composition comprising a survivin-targeting compound selected from the group consisting of compounds of the following formulas
(a)
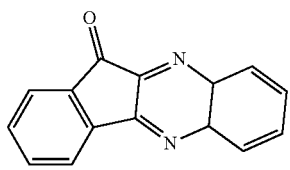
(b)
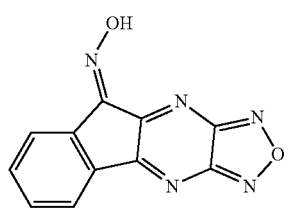
-continued
(d)
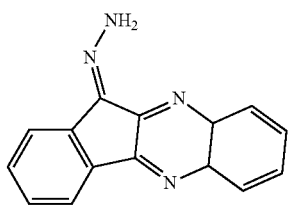
(e)
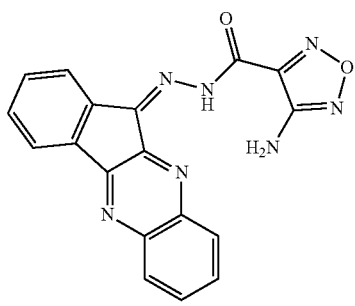
(g)
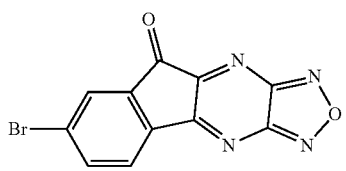
(h)
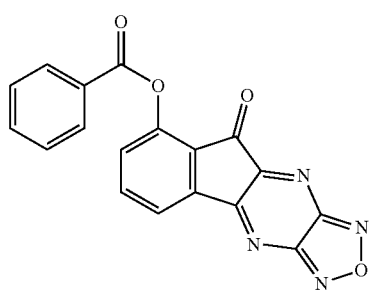
(i)
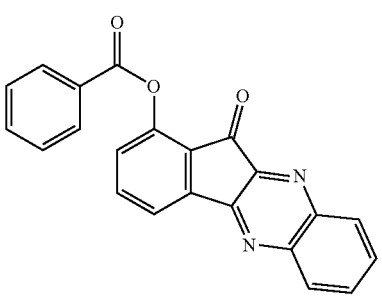
(j)
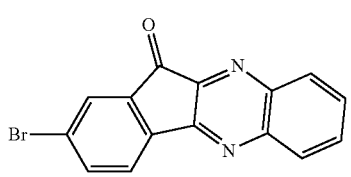

53
-continued
(k)
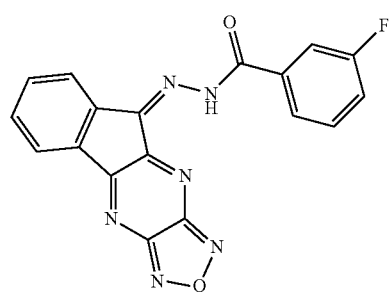
(l)
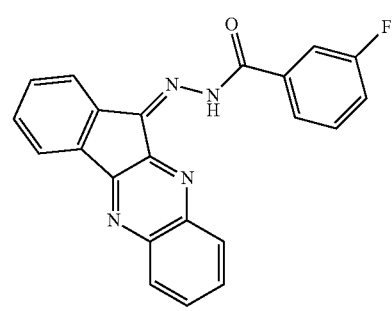
(m)
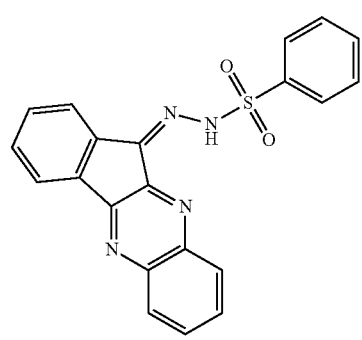
(n)
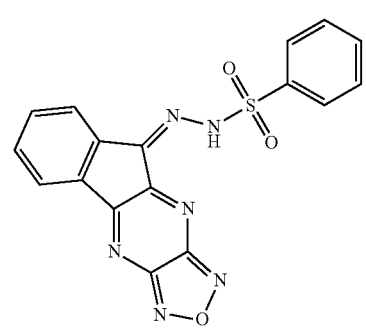
(o)
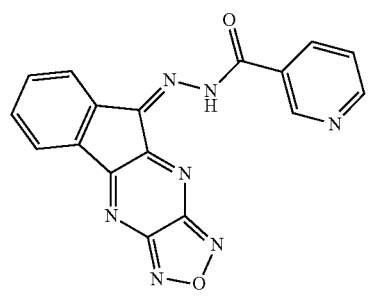
54
-continued
(p)
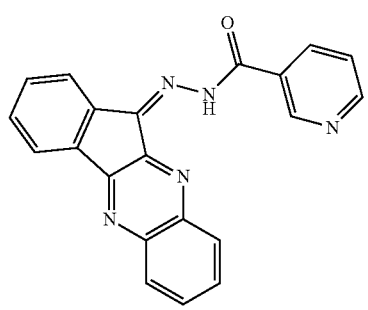
(q)
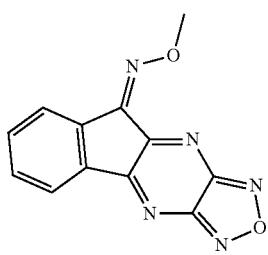
(r)
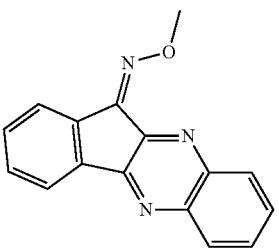
(s)
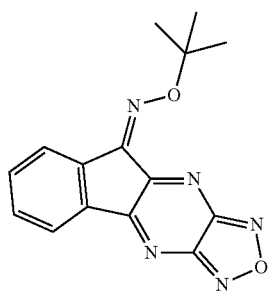
(t)
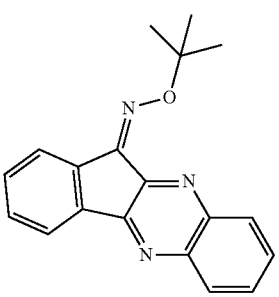

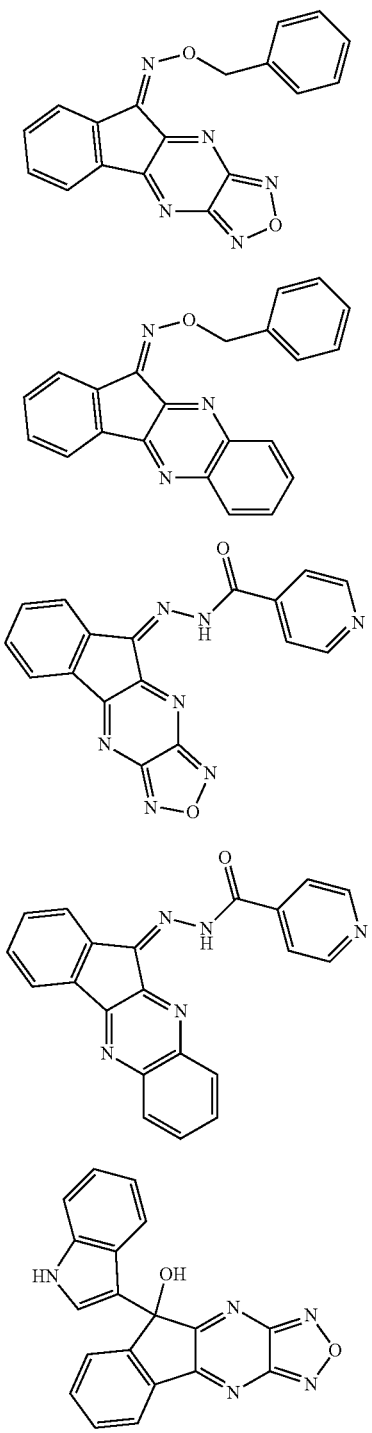
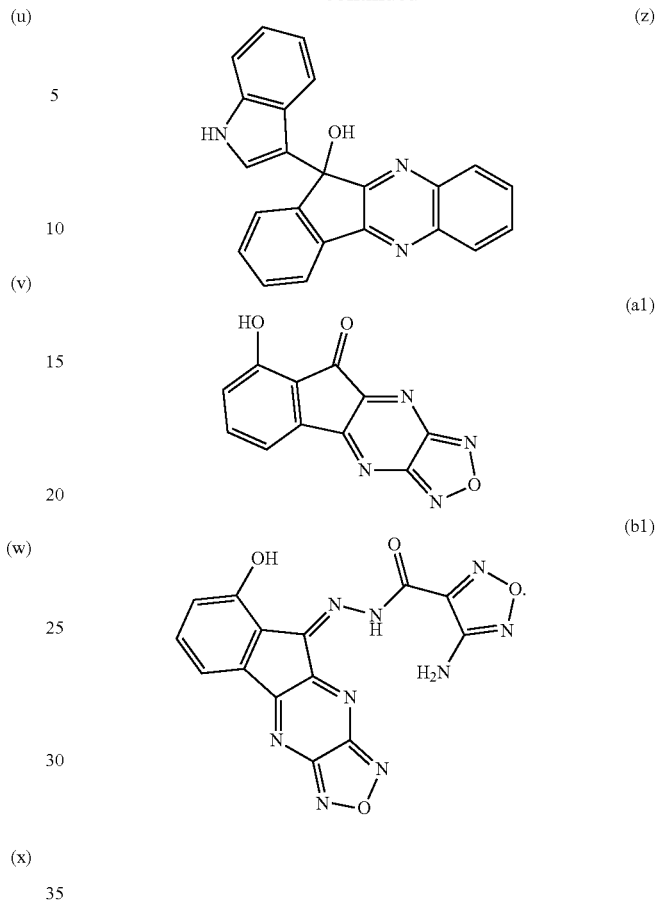

3. The method of claim 1 or claim 2, wherein the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

4. The method of claim 1 or claim 2, wherein the subject in need thereof is selected from the group consisting of subjects with at least one of the following diseases: breast cancer, colon cancer, lung cancer, pancreatic cancer, prostate cancer, ovarian cancer, and leukemia.

5. The method of claim 4, wherein the subject in need thereof has prostate cancer.

6. The method of claim 1 or claim 2, further comprising: administering to a subject in need thereof a pharmaceutically acceptable carrier.

* * * * *